(12) United States Patent
Cayer et al.

(10) Patent No.: US 11,247,209 B2
(45) Date of Patent: Feb. 15, 2022

(54) METHODS AND SYSTEMS FOR MICROFLUIDIC SCREENING

(71) Applicant: 1859, Inc., San Diego, CA (US)

(72) Inventors: Devon Cayer, Del Mar, CA (US); Andrew MacConnell, Del Mar, CA (US); Pavel Chubukov, Del Mar, CA (US); Ramesh Ramji, Del Mar, CA (US); Sean Stromberg, Del Mar, CA (US)

(73) Assignee: 1859, Inc., San Diego, CA (US)

( * ) Notice: Subject to any disclaimer, the term of this patent is extended or adjusted under 35 U.S.C. 154(b) by 0 days.

(21) Appl. No.: 17/090,719

(22) Filed: Nov. 5, 2020

(65) Prior Publication Data

US 2021/0107004 A1    Apr. 15, 2021

Related U.S. Application Data

(63) Continuation of application No. 17/067,534, filed on Oct. 9, 2020.

(60) Provisional application No. 62/954,348, filed on Dec. 27, 2019, provisional application No. 62/913,624, filed on Oct. 10, 2019.

(51) Int. Cl.
| | |
|---|---|
| *C12Q 1/686* | (2018.01) |
| *B01L 3/00* | (2006.01) |
| *C12N 15/10* | (2006.01) |
| *C12Q 1/6844* | (2018.01) |
| *C12Q 1/6876* | (2018.01) |
| *C40B 50/06* | (2006.01) |
| *C40B 50/16* | (2006.01) |
| *C40B 20/04* | (2006.01) |
| *C40B 30/08* | (2006.01) |

(52) U.S. Cl.
CPC .... *B01L 3/502761* (2013.01); *C12N 15/1093* (2013.01); *C12Q 1/686* (2013.01); *C12Q 1/6844* (2013.01); *C12Q 1/6876* (2013.01); *C40B 50/06* (2013.01); *C40B 50/16* (2013.01); *B01L 2200/0652* (2013.01); *B01L 2400/0403* (2013.01); *C40B 20/04* (2013.01); *C40B 30/08* (2013.01)

(58) Field of Classification Search
CPC .......... B01L 3/502761; C12N 15/1093; C12Q 1/6844; C12Q 1/686; C12Q 1/6876; C12Q 2563/179; C12Q 2523/319; C40B 50/26; C40B 50/16

See application file for complete search history.

(56) References Cited

U.S. PATENT DOCUMENTS

| | | | |
|---|---|---|---|
| 5,632,957 A | 5/1997 | Heller et al. | |
| 5,634,957 A | 6/1997 | Sykes et al. | |
| 5,750,341 A | 5/1998 | Macevicz | |
| 5,969,119 A | 10/1999 | Macevicz | |
| 6,306,597 B1 | 10/2001 | Macevicz | |
| 6,326,468 B1 | 12/2001 | Canne et al. | |
| 6,408,878 B2 | 6/2002 | Unger et al. | |
| 6,468,761 B2 | 10/2002 | Yang et al. | |
| 6,468,763 B1 | 10/2002 | Farinas | |
| 6,506,609 B1 | 1/2003 | Wada et al. | |
| 6,537,771 B1 | 3/2003 | Farinas et al. | |
| 6,589,729 B2 | 7/2003 | Chan et al. | |
| 6,592,821 B1 | 7/2003 | Wada et al. | |
| 6,635,487 B1 | 10/2003 | Lee et al. | |
| 6,681,788 B2 | 1/2004 | Parce et al. | |
| 6,720,148 B1 | 4/2004 | Nikiforov | |
| 6,752,966 B1 | 6/2004 | Chazan | |
| 6,759,191 B2 | 7/2004 | Farinas et al. | |
| 6,773,566 B2 | 8/2004 | Shenderov | |
| 6,773,567 B1 | 8/2004 | Wolk | |
| 6,777,184 B2 | 8/2004 | Nikiforov et al. | |
| 6,779,559 B2 | 8/2004 | Parce et al. | |
| 6,793,753 B2 | 9/2004 | Unger et al. | |
| 6,794,659 B2 | 9/2004 | Barbieri et al. | |
| 6,915,679 B2 | 7/2005 | Chien et al. | |
| 6,929,030 B2 | 8/2005 | Unger et al. | |
| 6,979,553 B2 | 12/2005 | Farinas et al. | |
| 7,023,007 B2 | 4/2006 | Gallagher | |
| 7,040,338 B2 | 5/2006 | Unger et al. | |
| 7,055,695 B2 | 6/2006 | Greenstein et al. | |
| 7,069,952 B1 | 7/2006 | McReynolds et al. | |
| 7,129,091 B2 | 10/2006 | Ismagilov et al. | |
| 7,161,356 B1 | 1/2007 | Chien | |
| 7,170,050 B2 | 1/2007 | Turner et al. | |
| 7,171,983 B2 | 2/2007 | Chien et al. | |
| 7,192,559 B2 | 3/2007 | Chow et al. | |

(Continued)

FOREIGN PATENT DOCUMENTS

| | | |
|---|---|---|
| EP | 1409989 A2 | 4/2004 |
| EP | 1558744 A2 | 8/2005 |

(Continued)

OTHER PUBLICATIONS

U.S. Appl. No. 17/090,665 First Action Interview dated Feb. 23, 2021.
PCT/US2020/055127 International Search Report and Written Opinion dated Feb. 1, 2021.
Brouzes et al.: Droplet microfluidic technology for single-cell high-throughput screening. PNAS. 106(34):14195-14200 (2009) www.pnas.org/cgi/doi/10.1073/pnas.0903542106.
Choi et al.: High-Throughput Analysis of Protein-Protein Interactions in Picoliter-Volume Droplets Using Fluorescence Polarization. Anal. Chem. 84(8):3849-3854 (2012) https://doi.org/10.1021/ac300414g.

(Continued)

*Primary Examiner* — David C Thomas
(74) *Attorney, Agent, or Firm* — Wilson Sonsini Goodrich & Rosati

(57) ABSTRACT

Provided are methods and systems useful for screening large libraries of effector molecules. Such methods and systems are particularly useful in microfluidic systems and devices. The methods and systems provided herein utilize encoded effectors to screen large libraries of effectors.

19 Claims, 40 Drawing Sheets

(56) References Cited

U.S. PATENT DOCUMENTS

| | | |
|---|---|---|
| 7,195,986 B1 | 3/2007 | Bousse et al. |
| 7,208,320 B2 | 4/2007 | Manz et al. |
| 7,211,390 B2 | 5/2007 | Rothberg et al. |
| 7,244,559 B2 | 7/2007 | Rothberg et al. |
| 7,244,567 B2 | 7/2007 | Chen et al. |
| 7,247,274 B1 | 7/2007 | Chow |
| 7,250,128 B2 | 7/2007 | Unger et al. |
| 7,252,928 B1 | 8/2007 | Hafeman et al. |
| 7,265,929 B2 | 9/2007 | Umeda et al. |
| 7,276,720 B2 | 10/2007 | Ulmer |
| 7,302,146 B2 | 11/2007 | Turner et al. |
| 7,303,727 B1 | 12/2007 | Dubrow et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,351,377 B2 | 4/2008 | Chazan et al. |
| 7,405,281 B2 | 7/2008 | Xu et al. |
| 7,445,926 B2 | 11/2008 | Mathies et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,479,186 B2 | 1/2009 | Quake et al. |
| 7,491,498 B2 | 2/2009 | Lapidus et al. |
| 7,494,555 B2 | 2/2009 | Unger et al. |
| 7,497,994 B2 | 3/2009 | Gandhi et al. |
| 7,501,245 B2 | 3/2009 | Quake et al. |
| 7,518,726 B2 | 4/2009 | Rulison et al. |
| 7,541,193 B2 | 6/2009 | Nguyen et al. |
| 7,544,473 B2 | 6/2009 | Brenner |
| 7,601,270 B1 | 10/2009 | Unger et al. |
| 7,655,470 B2 | 2/2010 | Ismagilov et al. |
| 7,670,559 B2 | 3/2010 | Chien et al. |
| 7,708,949 B2 | 5/2010 | Stone et al. |
| 7,727,371 B2 | 6/2010 | Kennedy et al. |
| 7,790,116 B2 | 9/2010 | Bousse et al. |
| 7,901,939 B2 | 3/2011 | Ismagliov et al. |
| 7,915,201 B2 | 3/2011 | Franch et al. |
| 7,943,030 B2 | 5/2011 | Shenderov |
| 7,968,287 B2 | 6/2011 | Griffiths et al. |
| 8,002,933 B2 | 8/2011 | Unger et al. |
| 8,034,629 B2 | 10/2011 | Chapin et al. |
| 8,048,627 B2 | 11/2011 | Dressman et al. |
| 8,104,515 B2 | 1/2012 | Unger et al. |
| 8,124,218 B2 | 2/2012 | Unger et al. |
| 8,206,901 B2 | 6/2012 | Freskgard et al. |
| 8,208,146 B2 | 6/2012 | Srinivasan et al. |
| 8,220,487 B2 | 7/2012 | Unger et al. |
| 8,252,539 B2 | 8/2012 | Quake et al. |
| 8,268,246 B2 | 9/2012 | Srinivasan et al. |
| 8,273,573 B2 | 9/2012 | Ismagilov et al. |
| 8,329,407 B2 | 12/2012 | Ismagilov et al. |
| 8,337,778 B2 | 12/2012 | Stone et al. |
| 8,361,412 B2 | 1/2013 | Yasuda et al. |
| 8,445,210 B2 | 5/2013 | Quake et al. |
| 8,496,875 B2 | 7/2013 | Greenstein et al. |
| 8,528,589 B2 | 9/2013 | Miller et al. |
| 8,557,742 B2 | 10/2013 | Blazej et al. |
| 8,562,807 B2 | 10/2013 | Srinivasan et al. |
| 8,592,215 B2 | 11/2013 | Quake et al. |
| 8,610,085 B2 | 12/2013 | Patt |
| 8,639,012 B2 | 1/2014 | Heng et al. |
| 8,658,367 B2 | 2/2014 | Quake et al. |
| 8,658,368 B2 | 2/2014 | Quake et al. |
| 8,658,430 B2 | 2/2014 | Miller et al. |
| 8,663,920 B2 | 3/2014 | Saxonov et al. |
| 8,685,344 B2 | 4/2014 | Sudarsan et al. |
| 8,692,998 B2 | 4/2014 | Gratton et al. |
| 8,702,938 B2 | 4/2014 | Srinivasan et al. |
| 8,722,583 B2 | 5/2014 | Gouliaev et al. |
| 8,761,486 B2 | 6/2014 | Heng et al. |
| 8,765,485 B2 | 7/2014 | Link et al. |
| 8,802,027 B2 | 8/2014 | Abate et al. |
| 8,857,462 B2 | 10/2014 | Miller et al. |
| 8,871,444 B2 | 10/2014 | Griffiths et al. |
| 8,889,083 B2 | 11/2014 | Ismagilov et al. |
| 8,907,312 B2 | 12/2014 | Heng et al. |
| 8,926,065 B2 | 1/2015 | Winger |
| 8,986,628 B2 | 3/2015 | Stone et al. |
| 9,011,662 B2 | 4/2015 | Wang et al. |
| 9,029,083 B2 | 5/2015 | Griffiths et al. |
| 9,038,919 B2 | 5/2015 | Link et al. |
| 9,056,299 B2 | 6/2015 | Romanowsky et al. |
| 9,068,916 B2 | 6/2015 | Heng |
| 9,091,654 B2 | 7/2015 | Heng et al. |
| 9,101,928 B2 | 8/2015 | Mehta et al. |
| 9,109,248 B2 | 8/2015 | Freskgard et al. |
| 9,150,852 B2 | 10/2015 | Samuels et al. |
| 9,207,249 B2 | 12/2015 | Greenstein et al. |
| 9,223,317 B2 | 12/2015 | Winger |
| 9,228,898 B2 | 1/2016 | Kiani et al. |
| 9,238,222 B2 | 1/2016 | Delattre et al. |
| 9,267,918 B2 | 2/2016 | Joaquim et al. |
| 9,273,308 B2 | 3/2016 | Link et al. |
| 9,284,600 B2 | 3/2016 | Freskgard et al. |
| 9,328,343 B2 | 5/2016 | Dressman et al. |
| 9,341,594 B2 | 5/2016 | Miller et al. |
| 9,358,539 B2 | 6/2016 | Abate et al. |
| 9,364,803 B2 | 6/2016 | Yurkovetsky et al. |
| 9,388,465 B2 | 7/2016 | Hindson et al. |
| 9,403,172 B2 | 8/2016 | Short et al. |
| 9,403,294 B2 | 8/2016 | Cauley, III |
| 9,422,067 B2 | 8/2016 | Abell et al. |
| 9,427,737 B2 | 8/2016 | Heredia et al. |
| 9,475,013 B2 | 10/2016 | Abate et al. |
| 9,486,757 B2 | 11/2016 | Romanowsky et al. |
| 9,487,775 B2 | 11/2016 | Franch et al. |
| 9,500,664 B2 | 11/2016 | Ness et al. |
| 9,535,000 B2 | 1/2017 | Sadri et al. |
| 9,551,637 B2 | 1/2017 | Fox et al. |
| 9,556,470 B2 | 1/2017 | Link et al. |
| 9,567,645 B2 | 2/2017 | Fan et al. |
| 9,574,189 B2 | 2/2017 | Franch et al. |
| 9,579,622 B2 | 2/2017 | Ismagilov et al. |
| 9,579,650 B2 | 2/2017 | Hong et al. |
| 9,588,117 B2 | 3/2017 | Chapman |
| 9,637,799 B2 | 5/2017 | Fan et al. |
| 9,651,039 B2 | 5/2017 | Mathies et al. |
| 9,659,508 B2 | 5/2017 | Fishler et al. |
| 9,683,251 B2 | 6/2017 | Janulaitis et al. |
| 9,689,024 B2 | 6/2017 | Hindson et al. |
| 9,696,257 B2 | 7/2017 | Fox et al. |
| 9,696,729 B2 | 7/2017 | Ismagilov et al. |
| 9,701,959 B2 | 7/2017 | Green et al. |
| 9,701,998 B2 | 7/2017 | Hindson et al. |
| 9,726,871 B2 | 8/2017 | Pristinski et al. |
| 9,733,168 B2 | 8/2017 | Miller et al. |
| 9,757,698 B2 | 9/2017 | Weitz et al. |
| 9,766,261 B2 | 9/2017 | Tracy et al. |
| 9,784,664 B2 | 10/2017 | Sadri et al. |
| 9,789,482 B2 | 10/2017 | Link et al. |
| 9,797,010 B2 | 10/2017 | Weitz et al. |
| 9,809,851 B2 | 11/2017 | Healy |
| 9,816,931 B2 | 11/2017 | Abate et al. |
| 9,822,356 B2 | 11/2017 | Ismagilov et al. |
| 9,829,451 B2 | 11/2017 | Gray et al. |
| 9,839,893 B2 | 12/2017 | Ismagilov et al. |
| 9,839,911 B2 | 12/2017 | Weitz et al. |
| 9,846,111 B2 | 12/2017 | Pristinski |
| 9,861,979 B2 | 1/2018 | Abate et al. |
| 9,878,325 B2 | 1/2018 | Weitz et al. |
| 9,885,035 B2 | 2/2018 | Franch et al. |
| 9,889,446 B2 | 2/2018 | Ismagilov et al. |
| 9,895,699 B2 | 2/2018 | Short et al. |
| 9,908,115 B2 | 3/2018 | Hobbs et al. |
| 9,919,277 B2 | 3/2018 | Griffiths et al. |
| 9,925,504 B2 | 3/2018 | Griffiths et al. |
| 9,933,565 B2 | 4/2018 | Swihart et al. |
| 9,968,933 B2 | 5/2018 | Ismagilov et al. |
| 9,981,230 B2 | 5/2018 | Link et al. |
| 10,012,592 B2 | 7/2018 | Abate et al. |
| 10,029,256 B2 | 7/2018 | Abate et al. |
| 10,036,697 B2 | 7/2018 | Fox et al. |

(56) References Cited

U.S. PATENT DOCUMENTS

| | | | |
|---|---|---|---|
| 10,052,605 B2 | 8/2018 | Griffiths et al. | |
| 10,053,723 B2 | 8/2018 | Hindson et al. | |
| 10,060,847 B2 | 8/2018 | Ling et al. | |
| 10,077,440 B2 | 9/2018 | Freskgard et al. | |
| 10,105,702 B2 | 10/2018 | Larson | |
| 10,105,703 B2 | 10/2018 | Ismagilov | |
| 10,118,174 B2 | 11/2018 | Ismagilov | |
| 10,124,351 B2 | 11/2018 | Yl et al. | |
| 10,125,393 B2 | 11/2018 | Esfandyarpour et al. | |
| 10,131,958 B1 | 11/2018 | Fan et al. | |
| 10,139,333 B2 | 11/2018 | Kotz et al. | |
| 10,151,003 B2 | 12/2018 | Fan et al. | |
| 10,151,429 B2 | 12/2018 | Weitz et al. | |
| 10,155,207 B2 | 12/2018 | Yurkovetsky et al. | |
| 10,180,385 B2 | 1/2019 | Fox et al. | |
| 10,208,356 B1 | 2/2019 | Fan et al. | |
| 10,215,771 B2 | 2/2019 | Weber et al. | |
| 10,221,442 B2 | 3/2019 | Hindson et al. | |
| 10,227,648 B2 | 3/2019 | Hindson et al. | |
| 10,253,364 B2 | 4/2019 | Hindson et al. | |
| 10,253,375 B1 | 4/2019 | Fan et al. | |
| 10,267,736 B2 | 4/2019 | Lo et al. | |
| 10,287,576 B2 | 5/2019 | Franch et al. | |
| 10,293,341 B2 | 5/2019 | Link et al. | |
| 10,316,345 B2 | 6/2019 | Tan et al. | |
| 10,323,279 B2 | 6/2019 | Hindson et al. | |
| 10,324,018 B2 | 6/2019 | Lo et al. | |
| 10,328,428 B2 | 6/2019 | Hong et al. | |
| 10,343,167 B2 | 7/2019 | Esmail et al. | |
| 10,350,594 B2 | 7/2019 | Hobbs et al. | |
| 10,371,699 B2 | 8/2019 | Griffiths et al. | |
| 10,428,369 B2 | 10/2019 | Miller et al. | |
| 10,429,291 B2 | 10/2019 | Fox et al. | |
| 10,525,464 B2 | 1/2020 | Wan et al. | |
| 10,551,603 B2 | 2/2020 | Pristinski et al. | |
| 10,710,078 B2 | 7/2020 | Merten et al. | |
| 10,745,742 B2* | 8/2020 | Bent | C12Q 1/6806 |
| 2006/0024678 A1 | 2/2006 | Buzby | |
| 2006/0024711 A1 | 2/2006 | Lapidus et al. | |
| 2006/0286566 A1 | 12/2006 | Lapidus et al. | |
| 2008/0087826 A1 | 4/2008 | Harris et al. | |
| 2008/0103058 A1 | 5/2008 | Siddiqi | |
| 2008/0206765 A1 | 8/2008 | Harris et al. | |
| 2008/0213770 A1 | 9/2008 | Williams et al. | |
| 2009/0024331 A1 | 1/2009 | Tomaney et al. | |
| 2009/0029385 A1 | 1/2009 | Christians et al. | |
| 2009/0035757 A1 | 2/2009 | Owen et al. | |
| 2009/0061439 A1 | 3/2009 | Buzby | |
| 2009/0068655 A1 | 3/2009 | Williams | |
| 2009/0215125 A1 | 8/2009 | Reed et al. | |
| 2010/0018584 A1 | 1/2010 | Bransky et al. | |
| 2011/0312599 A1 | 12/2011 | Azimi et al. | |
| 2012/0121480 A1 | 5/2012 | Frenz et al. | |
| 2012/0264646 A1 | 10/2012 | Link et al. | |
| 2013/0109575 A1 | 5/2013 | Kleinschmidt et al. | |
| 2013/0256534 A1 | 10/2013 | Micheels et al. | |
| 2013/0260447 A1 | 10/2013 | Link | |
| 2013/0296192 A1 | 11/2013 | Jacobson et al. | |
| 2014/0338753 A1 | 11/2014 | Sperling et al. | |
| 2015/0005199 A1* | 1/2015 | Hindson | C12N 15/1065 506/16 |
| 2015/0057163 A1 | 2/2015 | Rotem et al. | |
| 2015/0322494 A1 | 11/2015 | Garcia et al. | |
| 2015/0376609 A1 | 12/2015 | Hindson et al. | |
| 2016/0008778 A1 | 1/2016 | Weitz et al. | |
| 2016/0060621 A1 | 3/2016 | Agresti et al. | |
| 2016/0067706 A1 | 3/2016 | Molho, I et al. | |
| 2016/0122817 A1 | 5/2016 | Jarosz et al. | |
| 2016/0160259 A1 | 6/2016 | Du | |
| 2016/0231324 A1 | 8/2016 | Zhao et al. | |
| 2016/0288124 A1 | 10/2016 | Ismagilov et al. | |
| 2016/0312165 A1 | 10/2016 | Lowe, Jr. et al. | |
| 2017/0009274 A1 | 1/2017 | Abate et al. | |
| 2017/0028365 A1 | 2/2017 | Link et al. | |
| 2017/0028377 A1 | 2/2017 | Bernstein et al. | |
| 2017/0029813 A1 | 2/2017 | Weitz et al. | |
| 2017/0151536 A1 | 6/2017 | Weitz et al. | |
| 2017/0183616 A1 | 6/2017 | Thon et al. | |
| 2017/0189908 A1 | 7/2017 | Dzenitis et al. | |
| 2017/0198345 A1 | 7/2017 | Frenz et al. | |
| 2017/0225363 A1 | 8/2017 | Konstantinou et al. | |
| 2017/0232417 A1 | 8/2017 | Lebofsky et al. | |
| 2017/0233823 A1 | 8/2017 | Schroeder et al. | |
| 2017/0304785 A1 | 10/2017 | Link et al. | |
| 2017/0322401 A1 | 11/2017 | Pristinski et al. | |
| 2017/0336306 A1 | 11/2017 | Miller et al. | |
| 2017/0354937 A1 | 12/2017 | Weitz et al. | |
| 2017/0354969 A1 | 12/2017 | Lionberger et al. | |
| 2018/0030515 A1 | 2/2018 | Regev et al. | |
| 2018/0052154 A1 | 2/2018 | Stoner et al. | |
| 2018/0057875 A1 | 3/2018 | Weitz et al. | |
| 2018/0066305 A1 | 3/2018 | Weitz et al. | |
| 2018/0067113 A1 | 3/2018 | Kunding | |
| 2018/0071695 A1 | 3/2018 | Weitz et al. | |
| 2018/0071705 A1 | 3/2018 | Weitz et al. | |
| 2018/0078933 A1 | 3/2018 | Abate et al. | |
| 2018/0087078 A1 | 3/2018 | Weitz et al. | |
| 2018/0104693 A1 | 4/2018 | Merten et al. | |
| 2018/0112212 A1 | 4/2018 | Nicol et al. | |
| 2018/0117585 A1 | 5/2018 | Weitz et al. | |
| 2018/0119212 A1 | 5/2018 | Weitz et al. | |
| 2018/0133715 A1 | 5/2018 | Craig et al. | |
| 2018/0155777 A1 | 6/2018 | Weitz et al. | |
| 2018/0155778 A1 | 6/2018 | Weitz et al. | |
| 2018/0163713 A1 | 6/2018 | Morachis et al. | |
| 2018/0178174 A1 | 6/2018 | Link et al. | |
| 2018/0178213 A1 | 6/2018 | Ritchey et al. | |
| 2018/0193837 A1 | 7/2018 | Ismagilov et al. | |
| 2018/0216160 A1 | 8/2018 | Abate et al. | |
| 2018/0237836 A1 | 8/2018 | Abate et al. | |
| 2018/0238865 A1 | 8/2018 | Zur Megede et al. | |
| 2018/0250677 A1 | 9/2018 | Li et al. | |
| 2018/0265922 A1 | 9/2018 | Weitz et al. | |
| 2018/0272294 A1 | 9/2018 | Griffiths et al. | |
| 2018/0272295 A1 | 9/2018 | Link et al. | |
| 2018/0275058 A1 | 9/2018 | Stern et al. | |
| 2018/0280897 A1 | 10/2018 | Link et al. | |
| 2018/0284125 A1 | 10/2018 | Gordon et al. | |
| 2018/0291470 A1 | 10/2018 | Fan et al. | |
| 2018/0304268 A1 | 10/2018 | Ismagilov et al. | |
| 2018/0311669 A1 | 11/2018 | Basu et al. | |
| 2018/0320224 A1 | 11/2018 | Gaublomme et al. | |
| 2018/0321137 A1 | 11/2018 | Ismagilov et al. | |
| 2018/0333683 A1 | 11/2018 | Liu et al. | |
| 2018/0340171 A1 | 11/2018 | Belhocine et al. | |
| 2018/0353913 A1 | 12/2018 | Link et al. | |
| 2018/0363050 A1 | 12/2018 | Hutchison et al. | |
| 2019/0011349 A1 | 1/2019 | Bashir et al. | |
| 2019/0022645 A1 | 1/2019 | Hu et al. | |
| 2019/0024261 A1 | 1/2019 | Griffiths et al. | |
| 2019/0060900 A1 | 2/2019 | Breinlinger et al. | |
| 2019/0085391 A1 | 3/2019 | Hindson et al. | |
| 2019/0086034 A1 | 3/2019 | Weitz et al. | |
| 2019/0093103 A1 | 3/2019 | Vijayan et al. | |
| 2019/0094226 A1 | 3/2019 | Link et al. | |
| 2019/0118182 A1 | 4/2019 | Weitz et al. | |
| 2019/0125870 A1 | 5/2019 | Friedman et al. | |
| 2019/0127782 A1 | 5/2019 | Regev et al. | |
| 2019/0134581 A1 | 5/2019 | Yurkovetsky et al. | |
| 2019/0144854 A1 | 5/2019 | Ismagilov et al. | |
| 2019/0169666 A1 | 6/2019 | Hardenbol et al. | |
| 2019/0172196 A1 | 6/2019 | Du et al. | |
| 2019/0177789 A1 | 6/2019 | Hindson et al. | |
| 2019/0185800 A1 | 6/2019 | Weitz et al. | |
| 2019/0194726 A1 | 6/2019 | Ismagilov et al. | |
| 2019/0210018 A1 | 7/2019 | Vijayan et al. | |
| 2019/0218497 A1 | 7/2019 | Boedicker et al. | |
| 2019/0255531 A1 | 8/2019 | Hindson et al. | |
| 2019/0257687 A1 | 8/2019 | Pristinski | |
| 2019/0264199 A1 | 8/2019 | Williams et al. | |
| 2019/0276817 A1 | 9/2019 | Hindson et al. | |
| 2019/0302000 A1 | 10/2019 | Lo et al. | |
| 2019/0316197 A1 | 10/2019 | Hindson et al. | |
| 2019/0317085 A1 | 10/2019 | Griffiths et al. | |

(56) References Cited

U.S. PATENT DOCUMENTS

| | | |
|---|---|---|
| 2019/0324042 A1 | 10/2019 | Gormley et al. |
| 2019/0329209 A1 | 10/2019 | Sciambi et al. |
| 2019/0330701 A1 | 10/2019 | Abate et al. |
| 2019/0345488 A1 | 11/2019 | Soumillon et al. |
| 2019/0352708 A1 | 11/2019 | Gaige et al. |
| 2019/0358629 A1 | 11/2019 | Vijayan et al. |
| 2020/0001295 A1 | 1/2020 | Vijayan et al. |
| 2020/0324287 A1 | 10/2020 | Vijayan et al. |
| 2021/0106996 A1 | 4/2021 | Cayer et al. |

FOREIGN PATENT DOCUMENTS

| | | |
|---|---|---|
| EP | 1608748 A2 | 12/2005 |
| EP | 1677094 A2 | 7/2006 |
| EP | 1805324 A2 | 7/2007 |
| EP | 1842067 A2 | 10/2007 |
| EP | 1957644 A2 | 8/2008 |
| EP | 2236606 A2 | 10/2010 |
| EP | 2260130 A2 | 12/2010 |
| EP | 2267163 A1 | 12/2010 |
| EP | 2270235 A1 | 1/2011 |
| EP | 2278338 A2 | 1/2011 |
| EP | 2282214 A2 | 2/2011 |
| EP | 2283918 A2 | 2/2011 |
| EP | 2286125 A2 | 2/2011 |
| EP | 2315629 A1 | 5/2011 |
| EP | 2348124 A2 | 7/2011 |
| EP | 2364774 A2 | 9/2011 |
| EP | 2411148 A1 | 2/2012 |
| EP | 2446278 A2 | 5/2012 |
| EP | 2473263 A2 | 7/2012 |
| EP | 2532745 A2 | 12/2012 |
| EP | 2606333 A1 | 6/2013 |
| EP | 2635840 A2 | 9/2013 |
| EP | 2673614 A2 | 12/2013 |
| EP | 2675819 A1 | 12/2013 |
| EP | 2702175 A2 | 3/2014 |
| EP | 2755765 A2 | 7/2014 |
| EP | 2760578 A2 | 8/2014 |
| EP | 2798089 A2 | 11/2014 |
| EP | 2820158 A1 | 1/2015 |
| EP | 2839260 A1 | 2/2015 |
| EP | 2859324 A1 | 4/2015 |
| EP | 2906928 A2 | 8/2015 |
| EP | 2916954 A1 | 9/2015 |
| EP | 2925882 A1 | 10/2015 |
| EP | 2928606 A1 | 10/2015 |
| EP | 2970367 A1 | 1/2016 |
| EP | 2981349 A2 | 2/2016 |
| EP | 2986385 A2 | 2/2016 |
| EP | 2996809 A2 | 3/2016 |
| EP | 3002489 A1 | 4/2016 |
| EP | 3018206 A1 | 5/2016 |
| EP | 3031918 A1 | 6/2016 |
| EP | 3038834 A1 | 7/2016 |
| EP | 3041782 A1 | 7/2016 |
| EP | 3052236 A1 | 8/2016 |
| EP | 3056573 A1 | 8/2016 |
| EP | 3111215 A1 | 1/2017 |
| EP | 3132037 A1 | 2/2017 |
| EP | 3132844 A1 | 2/2017 |
| EP | 3153231 A1 | 4/2017 |
| EP | 3186191 A1 | 7/2017 |
| EP | 3189004 A1 | 7/2017 |
| EP | 3191605 A1 | 7/2017 |
| EP | 3229958 A1 | 10/2017 |
| EP | 3230717 A2 | 10/2017 |
| EP | 3230718 A1 | 10/2017 |
| EP | 3253479 A2 | 12/2017 |
| EP | 3253910 A1 | 12/2017 |
| EP | 3268125 A1 | 1/2018 |
| EP | 3283629 A1 | 2/2018 |
| EP | 3289362 A1 | 3/2018 |
| EP | 3290921 A1 | 3/2018 |
| EP | 3299463 A2 | 3/2018 |
| EP | 3299469 A1 | 3/2018 |
| EP | 3302801 A1 | 4/2018 |
| EP | 3305918 A2 | 4/2018 |
| EP | 3309262 A1 | 4/2018 |
| EP | 3314123 A1 | 5/2018 |
| EP | 3349896 A1 | 7/2018 |
| EP | 3368221 A1 | 9/2018 |
| EP | 3395957 A1 | 10/2018 |
| EP | 3397379 A1 | 11/2018 |
| EP | 3397973 A1 | 11/2018 |
| EP | 3412778 A1 | 12/2018 |
| EP | 3415235 A1 | 12/2018 |
| EP | 3436469 A1 | 2/2019 |
| EP | 3456846 A1 | 3/2019 |
| EP | 3467160 A1 | 4/2019 |
| EP | 3495503 A1 | 6/2019 |
| EP | 3501653 A1 | 6/2019 |
| EP | 3515598 A1 | 7/2019 |
| EP | 3519612 A1 | 8/2019 |
| EP | 3527978 A2 | 8/2019 |
| EP | 3538653 A1 | 9/2019 |
| EP | 3548181 A1 | 10/2019 |
| EP | 3549099 A1 | 10/2019 |
| EP | 3555290 A1 | 10/2019 |
| EP | 3562893 A1 | 11/2019 |
| EP | 3567116 A1 | 11/2019 |
| EP | 3569715 A1 | 11/2019 |
| WO | WO-9961888 A2 | 12/1999 |
| WO | WO-9961888 A3 | 12/2001 |
| WO | WO-03006133 A2 | 1/2003 |
| WO | WO-2004039825 A2 | 5/2004 |
| WO | WO-2004083427 A2 | 9/2004 |
| WO | WO-2006038035 A2 | 4/2006 |
| WO | WO-2006040551 A2 | 4/2006 |
| WO | WO-2007062664 A2 | 6/2007 |
| WO | WO-2009124296 A2 | 10/2009 |
| WO | WO-2009139898 A2 | 11/2009 |
| WO | WO-2010009365 A1 | 1/2010 |
| WO | WO-2010111231 A1 | 9/2010 |
| WO | WO-2010151776 A2 | 12/2010 |
| WO | WO-2011028764 A2 | 3/2011 |
| WO | WO-2012024633 A1 | 2/2012 |
| WO | WO-2012061444 A2 | 5/2012 |
| WO | WO-2012109600 A2 | 8/2012 |
| WO | WO-2012112804 A1 | 8/2012 |
| WO | WO-2012149042 A2 | 11/2012 |
| WO | WO-2013095737 A2 | 6/2013 |
| WO | WO-2013101783 A2 | 7/2013 |
| WO | WO-2013130674 A1 | 9/2013 |
| WO | WO-2013159117 A1 | 10/2013 |
| WO | WO-2013185023 A1 | 12/2013 |
| WO | WO-2014062719 A2 | 4/2014 |
| WO | WO-2014074367 A1 | 5/2014 |
| WO | WO-2014083205 A1 | 6/2014 |
| WO | WO-2014089372 A1 | 6/2014 |
| WO | WO-2014165559 A2 | 10/2014 |
| WO | WO-2014172586 A2 | 10/2014 |
| WO | WO-2014186440 A2 | 11/2014 |
| WO | WO-2015031849 A1 | 3/2015 |
| WO | WO-2015035246 A1 | 3/2015 |
| WO | WO-2015048798 A1 | 4/2015 |
| WO | WO-2015131142 A1 | 9/2015 |
| WO | WO-2015161223 A1 | 10/2015 |
| WO | WO-2016033434 A1 | 3/2016 |
| WO | WO-2016036536 A1 | 3/2016 |
| WO | WO-2016040476 A1 | 3/2016 |
| WO | WO-2016094308 A1 | 6/2016 |
| WO | WO-2016094459 A2 | 6/2016 |
| WO | WO-2016094522 A1 | 6/2016 |
| WO | WO-2016126865 A1 | 8/2016 |
| WO | WO-2016126871 A2 | 8/2016 |
| WO | WO-2016149096 A1 | 9/2016 |
| WO | WO-2016168584 A1 | 10/2016 |
| WO | WO-2016174229 A1 | 11/2016 |
| WO | WO-2016193758 A1 | 12/2016 |
| WO | WO-2016210077 A1 | 12/2016 |
| WO | WO-2017046565 A1 | 3/2017 |
| WO | WO-2017075549 A1 | 5/2017 |
| WO | WO-2017117440 A1 | 7/2017 |

(56) References Cited

FOREIGN PATENT DOCUMENTS

| | | |
|---|---|---|
| WO | WO-2017117490 A1 | 7/2017 |
| WO | WO-2017165791 A1 | 9/2017 |
| WO | WO-2017173105 A1 | 10/2017 |
| WO | WO-2018054975 A1 | 3/2018 |
| WO | WO-2018064640 A1 | 4/2018 |
| WO | WO-2018087539 A1 | 5/2018 |
| WO | WO-2018089641 A2 | 5/2018 |
| WO | WO-2018102748 A1 | 6/2018 |
| WO | WO-2018118971 A1 | 6/2018 |
| WO | WO-2018125901 A1 | 7/2018 |
| WO | WO-2018175411 A1 | 9/2018 |
| WO | WO-2018217625 A1 | 11/2018 |
| WO | WO-2019036505 A1 | 2/2019 |
| WO | WO-2019060830 A1 | 3/2019 |
| WO | WO-2019060857 A1 | 3/2019 |
| WO | WO-2019084207 A1 | 5/2019 |
| WO | WO-2019112567 A1 | 6/2019 |
| WO | WO-2019139650 A2 | 8/2019 |
| WO | WO-2019149955 A1 | 8/2019 |
| WO | WO-2019169060 A1 | 9/2019 |
| WO | WO-2019232473 A2 | 12/2019 |
| WO | WO-2021072306 A1 | 4/2021 |

OTHER PUBLICATIONS

Clausell-Tormos et al.: Droplet-Based Microfluidic Platforms for the Encapsulation and Screening of Mammalian Cells and Multicellular Organisms. 15(5):427-437 (2008).
Cochrane et al.: Activity-Based DNA-Encoded Library Screening. ACS Comb. Sci. 21(5):425-435 (2019) https://doi.org/10.1021/acscombsci.9b00037.
Co-pending U.S. Appl. No. 17/090,665, inventors Cayer; Devon et al., filed Nov. 5, 2020.
Co-pending U.S. Appl. No. 17/090,672, inventors Cayer; Devon et al., filed Nov. 5, 2020.
Co-pending U.S. Appl. No. 17/090,682, inventors Cayer; Devon et al., filed Nov. 5, 2020.
Co-pending U.S. Appl. No. 17/090,695, inventors Cayer; Devon et al., filed Nov. 5, 2020.
Co-pending U.S. Appl. No. 17/090,704, inventors Cayer; Devon et al., filed Nov. 5, 2020.
Co-pending U.S. Appl. No. 17/090,711, inventors Cayer; Devon et al., filed Nov. 5, 2020.
Davies et al.: Tetrazine-Triggered Release of Carboxylic-Acid-Containing Molecules for Activation of an Anti-inflammatory Drug. ChemBioChem. 20:1541-1546 (2019).
Debs et al.: Functional single-cell hybridoma screening using droplet-based microfluidics. PNAS. 109(29):11570-11575 (2012) www.pnas.org/cgi/doi/10.1073/pnas.1204514109.
Flood et al.: Expanding Reactivity in DNA-Encoded Library Synthesis via Reversible Binding of DNA to an Inert Quaternary Ammonium Support. ChemRxiv. (2019) https://chemrxiv.org/articles/Expanding_Reactivity_in_DNA-Encoded_Library_Synthesis_via_Reversible_Binding_of_DNA_to_an_Inert_Quaternary_Ammonium_Support/7966706.
Hackler et al.: Off-DNA DNA-Encoded Library Affinity Screening. ACS Comb. Sci. 22(1):25-34 (2019) https://doi.org/10.1021/acscombsci.9b00153.
Hsu et al.: Bioorthogonal Catalysis: A General Method To Evaluate Metal-Catalyzed Reactions in Real Time in Living Systems Using a Cellular Luciferase Reporter System. Bioconjugate Chem. 27:376-382 (2016).
MacConnell et al.: An Integrated Microfluidic Processor for DNA-Encoded Combinatorial Library Functional Screening. CS Comb. Sci. 19(3):181-192 (2017) https://doi.org/10.1021 /acscombsci.6b00192.
MacConnell et al.: DNA-Encoded Solid-Phase Synthesis: Encoding Language Design and Complex Oligomer Library Synthesis. ACS Comb. Sci. 17(9):518-534 (2015) https://doi.org/10.1021/acscombsci.5b00106.
MacConnell et al.: Poisson Statistics of Combinatorial Library Sampling Predict False Discovery Rates of Screening. ACS Comb. Sci. 19(8):524-532 (2017) https://doi.org/10.1021/acscombsci.7b00061.
Malone et al.: What is a "DNA-Compatible" Reaction?. ACS Comb. Sci. 18(4):182-187 (2016) https://doi.org/10.1021/acscombsci.5b00198.
Margulies et al.: Genome sequencing in microfabricated high-density picolitre reactors. Nature 437:376-380 (2005).
Mikkelsen et al.: Photolabile Linkers for Solid-Phase Synthesis. ACS Comb. Sci. 20(7):377-399 (2018).
Mondal et al.: Fragment Linking and Optimization of Inhibitors of the Aspartic Protease Endothiapepsin: Fragment-Based Drug Design Facilitated by Dynamic Combinatorial Chemistry. Chem. Int. Ed. 55:9422-9426 (2016).
Parker et al.: Ligand and Target Discovery by Fragment-Based Screening in Human Cells. CellPress 168:527-541 (2017) http://dx.doi.org/10.1016/j.cell.2016.12.029.
Price et al.: hvSABR: Photochemical Dose-Response Bead Screening in Droplets. Anal. Chem. 88(5):2904-2911 (2016) https://doi.org/10.1021/acs.analchem.5b04811.
Rozen et al.: From Azides to Nitro Compounds in a Few Seconds Using HOF•CH3CN. J. Am.Chem. 125:8118-8119 (2003) doi:10.1021/ja035616d.
Saikia et al.: Simultaneous multiplexed amplicon sequencing and transcriptome profiling in single cells. Nature Methods, pp. 1-15 (2018) doi:10.1038/S41592-018-0259-9.
Wade et al.: Application of Base Cleavable Safety Catch Linkers to Solid Phase Library Production. J. Comb. Chem. 2(3):266-275 (2000).
Wu et al.: 3'-O-modified nucleotides as reversible terminators for pyrosequencing. PNAS. 104(42):16462-16467 (2007).
U.S. Appl. No. 17/090,665 Restriction Requirement dated Dec. 28, 2020.
U.S. Appl. No. 17/090,672 Restriction Requirement dated Dec. 28, 2020.
U.S. Appl. No. 17/090,682 Restriction Requirement dated Dec. 28, 2020.
U.S. Appl. No. 17/090,695 Restriction Requirement dated Dec. 23, 2020.
U.S. Appl. No. 17/090,704 Restriction Requirement dated Jan. 28, 2021.
U.S. Appl. No. 17/090,711 First Action Interview dated Jan. 29, 2021.
Sepp et al.: Microbead display by in vitro compartmentalization: selection for binding using flow cytometry. FEBS Lett. 532(3):455-458 (2002).
Shang et al.: Emerging Droplet Microfluidics. Chem. Rev. 117:7964-8040 (2017).
U.S. Appl. No. 17/090,695 First Action Interview dated Feb. 10, 2021 .
Macosko et al.: Highly Parallel Genome-wide Expression Profiling of Individual Cells Using Nanoliter Droplets. Cell. 161(5):1202-1214 (2015).
U.S. Appl. No. 17/090,665 Office Action dated May 18, 2021.
U.S. Appl. No. 17/090,672 Office Action dated May 25, 2021.
U.S. Appl. No. 17/090,695 Office Action dated Mar. 29, 2021.
U.S. Appl. No. 17/090,711 Office Action dated Apr. 7, 2021.
U.S. Appl. No. 17/090,672 Pre-Interview Communication dated Mar. 8, 2021.
U.S. Appl. No. 17/090,682 First Action Interview dated May 25, 2021.
U.S. Appl. No. 17/090,704 Pre-Interview Communication dated Apr. 16, 2021.
U.S. Appl. No. 17/090,719 Pre-Interview Communication dated Mar. 12, 2021.

\* cited by examiner

| Serial No. | Description |
|---|---|
| 1 | Nikon Eclipse Ti Microscope Camera Port Adapter, Internal SM1 Threads, External SM2 Threads, 30 mm Cage Compatibility |
| 2 | SM1 (1.035"-40) Coupler, External Threads, 0.5" Long |
| 3 | Right-Angle Kinematic Elliptical Mirror Mount with Smooth Cage Rod Bores, 30 mm Cage System and SM1 Compatible, M4 and M6 Mounting Holes |
| 4 | 1" Protected Silver Elliptical Mirror, 450 nm - 20 μm |
| 5 | SM1 Lens Tube, 3.50" Thread Depth, One Retaining Ring Included |
| 6 | f=75 mm, Ø1" Achromatic Doublet, SM1- Threaded Mount, ARC: 400-700 nm |
| 7 | SM1 Lens Tube, 1.00" Thread Depth, One Retaining Ring Included |
| 8 | Ø1" Adjustable Lens Tube, 0.81" Travel Range |
| 9 | SM1-Threaded 30 mm Cage Plate, 0.50" Thick, 2 Retaining Rings, M4 Tap |
| 10 | 16-Position Motorized Pinhole Wheel for Confocal Imaging |
| 11 | SM05 Lens Tube, 0.50" Thread Depth, One Retaining Ring Included |
| 12 | Adapter with External SM05 Threads and Internal SM1 Threads |
| 13 | f=50 mm, Ø1" Achromatic Doublet, SM1- Threaded Mount, ARC: 400-700 nm |
| 14 | Kinematic Beam Turning 30 mm Cage Cube for Right-Angle Prism Mirror, Right Turning, M6 Tapped Holes |
| 15 | SM1 Lens Tube, 2.50" Thread Depth, One Retaining Ring Included |
| 16 | SM1 Zoom Housing for Ø1" Optics, Non-Rotating, 2" (50.8 mm) Travel |
| 17 | Kinematic Fluorescence Filter Cube, 30 mm Cage Compatible, Right-Turning, M6 Tapped Holes |
| 18 | 30 mm Cage System Removable Filter Holder for Ø1" Optics, Plate and Holder Included, Metric, M4 Tap |

FIG. 22B 50x slow (capture 1000 fps, playback 20 fps)
Scalebar = 100 μm

METHODS AND SYSTEMS FOR MICROFLUIDIC SCREENING

CROSS-REFERENCE

This application is a continuation of U.S. application Ser. No. 17/067,534 filed Oct. 9, 2020 which claims priority to U.S. Provisional Application No. 62/913,624, filed Oct. 10, 2019, and U.S. Provisional Application No. 62/954,348, filed Dec. 27, 2019, both of which are incorporated by reference herein in its entirety.

BACKGROUND

Drug development often requires a significant amount of testing and analysis to determine how specific chemical substances impact cellular and other biological components. As such, devices and specific methodologies that focus on correlating a relationship between specific chemical substances and biological components is an integral component for a drug developer, such as pharmaceutical companies.

SUMMARY

Provided herein are systems and methods for performing high-throughput assays using microfluidic systems and encoded effectors. The systems and methods described herein can be used to perform nearly any assay in a high-throughput manner and provide detailed information about the effect of various effector molecules on biological systems. The systems and methods provided herein utilize encoded effectors, which allow a user to readily ascertain which of the effectors has an effect on a biological sample.

Other systems have various drawbacks, including an inability to customize the addition of reagents at concentrations of interest at different unit operations during a screen. The systems and methods described herein address these drawbacks. For example, methods and systems described herein allow for the introduction of reagents at specified concentrations at different steps in a screening procedure. In some instances, adding reagents at defined concentrations allows uniform doses of effectors to be administered across a library being screened. This may allow for decreased false positives in a screen because low potency but highly-loaded effectors may be dosed against samples at a uniform concentration across a library screen. In some instances, the customizable additions of reagents allow for facile deconvolution of screening hits without a step of physical sorting of effectors that elicit a positive or negative response in the screen.

In another aspect are methods of monitoring biological samples in a microfluidic based screen without utilizing light (e.g. fluorescence) emitted from a sample. These methods may allow for more detailed information about a sample being analyzed than is available by other methods. Further provided herein are methods and systems for incorporating genetic or cellular information from a sample into the encoded effectors. This incorporation step can allow for an improved analysis of the response of a cell or other biological sample contacted with an effector than is available by other methods. In another aspect, information encoded in a sample, such as a DNA barcode, is incorporated from the sample into the encoding to allow determination of synergistic benefits of multiple effectors. This can be used for conducting a small-molecule fragment-based screen to generate compound leads.

The methods provided herein provide advantages over existing DNA encoded libraries being used for drug screening. In some embodiments, the methods enclosed herein are functional "activity-based" assays, not just "affinity-based" assays: they allows the screening of functional assays. In some embodiments, the methods herein are not limited to testing if a candidate drug binds to a disease target. In contrast, the methods herein may be capable of testing whether the candidate drug functions against that disease target. Such functions may comprise inhibition, disruption of protein-protein interactions, or activating an enzyme or allosteric pocket.

In some instances, the methods provided herein can screen in complex environments such as cell lysates, cells, or other multi-component mixtures in a single assay. In some embodiments, the functional activity test is orthogonal to all other components in a mixture and is specifically testing for functional activity of a target of interest. The screening modalities provided herein are diverse. Such modalities can screen for potency, selectivity, toxicity, liabilities, or other key metrics critical for drug discovery campaigns. The methods provided herein may allow for speed and diversity at 1000 times lower operational cost than other methods. In some instances, the speed, low reagent needs, and exceptional validation rates allow fast, iterative screening of potentially an unlimited set of chemically diverse compounds. The flexibility and speed allow for testing or screening of compounds in many different assays or formats for a single target, allowing multiple sampling of conditions, easy "restarts", fast "hit to lead" starts, and "immediate" validation of library designs.

In some instances, the methods provided herein do not require high sequencing depth, thus reducing costs for analysis. Additionally, the methods disclosed herein may allow for the quantification of yields of each chemistry step, allowing normalized dose-response curves and possibly quantitative analysis.

In some instances, the methods provided herein enable the use of DNA damaging chemistries that require organic solvents, or conditions that would otherwise be DNA damaging in the synthesis of encoded beads. For example, some chemistries needed to construct small-molecules may degrade or cause DNA to become non-amplifiable and thus the DNA barcode information can no longer be read. In some instances, this challenge is overcome by providing DNA encodings bound to scaffolds at high levels. In some embodiments, the scaffolds comprise 10 million or more encodings bound to a scaffold. Additionally, in some embodiments, as few as 10 encodings are required to be present in order to detect a positive hit.

Provided herein are methods for cell phenotypic screening. Cells directly within droplets can be tested and probed for a variety of different phenotypes. For example, an entire library can be screened for toxicity against a particular cell type, or an entire library can be screened for its ability to affect a particular disease target in its native cell context, or an entire library can be screened for its ability to affect a panel of targets (transcriptome, protein panel, etc.). This is allowed because a small molecule can be liberated off of the bead where it can then penetrate intracellularly a cell (or affect an extracellular target) and affect a particular disease target Further provided herein are methods for normalizing the results of screens of encoded effectors. Other methods of ascertaining the results from a screen suffer from high rates of false negative results, where an effector displays potency against a target sample, but due to damage to the encoding during the screen or low abundance of the encoding during the synthesis of the encoded effector, the "hit" is missed in the subsequent analysis. Provided herein are methods for normalizing the amount of encodings present after a screen has been performed in order to minimize false negative results due to low abundance of encodings of potent effectors.

Also provided herein are devices for performing the methods provided herein. In some instances, the method provided herein are performed on microfluidic devices or in microfluidic channels.

Further provided herein are devices useful for the performance of high-throughput screen using encoded libraries. These devices can allow for fixing a target sample, in some instances a single cell, in a fixed location in space with a single encoded effector. Such devices can allow for screening single compounds against cells to determine desired effects without the need to create in situ encapsulations separating each individual sample/effector combination.

Disclosed herein, in some embodiments is a method for screening an encoded effector, the method comprising: a) providing at least one cell and a scaffold in an encapsulation, wherein the scaffold comprises an encoded effector bound to the scaffold by a photocleavable linker and a nucleic acid encoding the effector; b) cleaving the photocleavable linker to release the encoded effector from the scaffold; and c) detecting a signal from the droplet, wherein the signal results from an interaction between the encoded effector and the at least one cell. In some embodiments, cleaving the photocleavable linker releases a pre-determined amount of the encoded effector into the droplet. In some embodiments, the photocleavable linker is cleaved using electromagnetic radiation. In some embodiments, cleaving the photocleavable linker comprises exposing the encapsulation to a light from a light source. In some embodiments, the light intensity of the light is from about 0.01 J/cm$^2$ to about 200 J/cm$^2$. In some embodiments, the method further comprising the step of lysing the one or more cells. In some embodiments, the method further comprising providing an activating reagent to activate the photocleavable linker, so as to enable the photocleavable linker to be cleaved from the encoded effector.

Disclosed herein, in some embodiments, is a system for screening an encoded effector, the system comprising: a) one or more cells; b) a scaffold, wherein an encoded effector is bound to the scaffold by a cleavable linker, wherein a nucleic acid encoding the effector is bound to the scaffold; and c) a microfluidic device configured to: i) receive the one or more cells and scaffold; ii) encapsulate the one or more cells and scaffold within an encapsulation; iii) cleave the cleavable linker from the encoded effector to release a predetermined amount of the encoded effector within the encapsulation; iv) incubate the encoded effector with the one or more cells for a period of time; v) detect a signal from the encapsulation, wherein the signal results from an interaction between the encoded effector and one or more cells; and vi) sort the encapsulation based on the detection of the signal. In some embodiments, the cleavable linker is a photocleavable linker. In some embodiments, the microfluidic device further comprises a first collection tube and second collection tube for sorting the encapsulation, wherein the encapsulation is placed in 1) the first collection tube if the signal is at or above a predetermined threshold or 2) the second collection tube if the signal is below a predetermined threshold. In some embodiments, the system further comprising a waveform pulse generator to move the encapsulation to the first or second collection tube by an electrical field gradient, by sound, by a diaphragm, by modifying geometry of the microfluidic channel, or by changing the pressure of a microfluidic channel of the microfluidic device. In some embodiments, the signal is detected based on detecting morphological changes in the one or more cells measured by recording a series of images of the droplet or detecting fluorescence emitted by a molecular beacon or probe. In some embodiments, the period of time is controlled by residence time as the encapsulation travels through a microfluidic channel of the microfluidic device.

Disclosed herein, is a method for amplifying a primer to maximize cellular nucleic acid capture comprising: a) providing an encapsulation comprising a nucleic acid encoded scaffold with one or more cells, an amplification mix, and a nicking enzyme, wherein a nucleic acid encoding is bound to the nucleic acid encoded scaffold; b) lysing the one or more cells to release one or more cellular nucleic acids; c) nicking the nucleic acid encoding with the nicking enzyme, thereby creating an encoded nucleic acid primer; d) amplifying the encoded nucleic acid primer via the nicking site and amplification mix; and e) labeling a released cellular nucleic acid with the encoded nucleic acid primer. In some embodiments, the specific site comprises a specific nucleotide sequence. In some embodiments, amplifying the encoded nucleic acid primer comprises 1) creating a copy of the nucleic acid encoding that extends from the nicking site, and 2) nicking the nucleic acid encoding copy to create another encoded nucleic acid primer. In some embodiments, amplifying the encoded nucleic acid primer comprises simultaneously 1) creating a copy of the nucleic acid encoding that extends from the nicking site, and 2) displacing the nucleic acid encoding copy to create another encoded nucleic acid primer. In some embodiments, the amplification mix comprises an amplification enzyme, such that the amplification enzyme enables for a copy of the nucleic acid encoding to be simultaneously created and displaced. In some embodiments, the amplification enzyme comprises a polymerase. In some embodiments, each nucleic acid encoding comprises a capture site that prescribes a target cellular coding or a target cellular nucleic acid to label a released cellular nucleic acid.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 22A-B shows an exemplary fluorescence detection device used with a microfluidic device described herein, and description of related components.

DETAILED DESCRIPTION

Screening Methods and Systems

Figure 1:
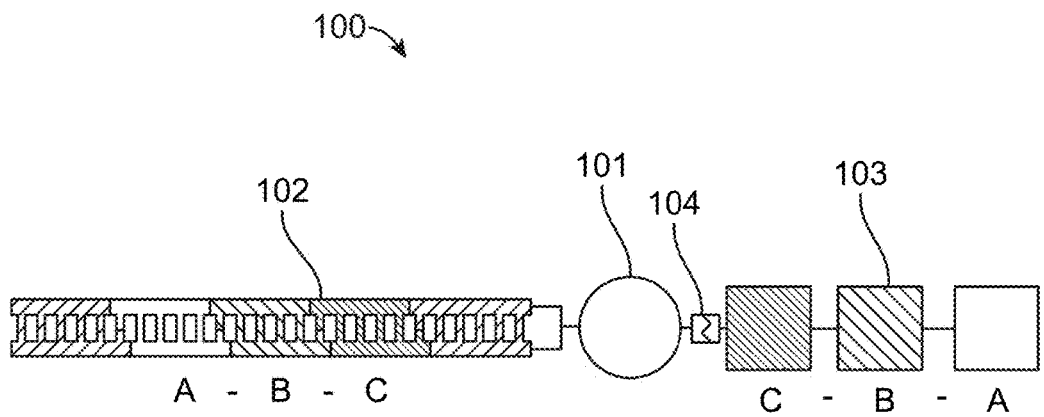
FIG. 1 provides a depiction of a nucleic acid encoded effector bound to a bead along with the nucleic acid encoding.

Provided herein are methods and systems for screening various effectors against samples in a high-throughput, low-material manner. The systems and methods, in some embodiments, utilize encoded effectors to probe various responses from samples. In some embodiments, encoded effectors are molecules whose structures can be measured by measuring a property of the corresponding encoding. Generally, samples are incubated with effectors in encapsulations. In response to an interaction with the effector, some type of signal can then be detected. Based on this signal, the effector can be determined to have efficacy against the sample in inducing a particular response. The systems and methods described herein, in some embodiments, utilize small encapsulations, such as droplets. In some instances, each individual encapsulation carries out an assay of the effector and the sample in a small volume. A large library of such effectors can be screened against the sample at the same time and in the same experiment, thus providing high-throughput methods for conducting screens. Effectors that produce a desired signal from a sample can then be sorted, and the encoding of the effector can be measured to deconvolute which effectors were efficacious in the assay.

Encoded Effectors

The systems and methods provided herein utilize encoded effectors. An encoded effector, in some embodiments, is an effector that has been linked with an encoding such that ascertaining a property of the encoding allows a researcher to readily determine the structure of the effector. An effector can be any type of molecule or substance whose effect on a sample is being investigated. In some embodiments, the effector is a compound, a protein, a peptide, an enzyme, a nucleic acid, or any other substance. In some instances, the encoding allows a user to determine the structure of the effector by determining a property of the encoding. Thus, each encoding moiety has a measurable property that, when measured, can be used to determine the structure of the effector which is encoded. Many different encoding modalities can be used, including without limitation nucleic acids and peptides. When the encoding modalities are nucleic acids, the sequence of the nucleic acid may provide information about the structure of its corresponding effector. In some instances, the encoded effectors are described by what kind of molecules is used in the encoding. For example, "nucleic acid encoded effectors" comprise an effector encoded by a nucleic acid.

In some instances, the effectors and their corresponding encodings are bound to a scaffold. This can allow the effector/encoding pair to remain linked in space. In some instances, when encoded effectors are placed into solutions or other environments, the link between the pairing is not lost. Many materials can be used as scaffolds, as any material capable of binding both the effector and the encoding may accomplish the desired goal of keeping the pair linked in space.

Various methods for preparing encoded effectors linked to scaffolds can be used. In some embodiments, the methods use orthogonal, compatible methodologies to create an effector and its encoding in a parallel synthesis scheme. This is sometimes referred to as "split and pool synthesis." For illustrative purposes only, an exemplary, non-limiting, workflow for the preparation of a scaffold containing an effector and encoding is described as follows: A first effector subunit is attached at an attachment point of a scaffold. The scaffold is then washed to remove unreacted and excess reagents from the scaffold. A first encoding subunit is then attached at another attachment point on the scaffold, and a wash step performed. Following this, a second effector subunit is then attached to the first effector subunit, followed by another wash step. Then, a second encoding subunit is attached to the first encoding subunit, followed by a wash step. This process is repeated as many times as desired to prepare the desired effectors and corresponding encodings. This process can be repeated on a massively parallel scale in small volumes to prepare vast libraries of compounds at low cost and with low amounts of reagents. In some instances, pre-synthesized compounds are loaded onto scaffolds which contain encodings. The encodings may be pre-synthesized and loaded onto the scaffolds or are synthesized directly onto the scaffolds using methods analogous to the split and pool synthesis described above. In some instances, each scaffold comprises numerous copies of a unique effector and its corresponding encoding.

An example of a nucleic acid encoded effector linked with a bead is shown in FIG. 1. A bead linked encoded effector 100 comprises a bead 101. Attached at one position is a nucleic acid encoding 102, which is covalently attached to the scaffold in this example. The nucleic acid encoding comprises encoding subunits A, B, and C. The encoding subunits correspond with effector subunits A, B, and C, which make up effector 103. The effector 103 is linked to the bead 101 through a linker 104. The linker 104 may be a cleavable linker, such a linker cleavable by electromagnetic radiation (photocleavable) or selectively cleavable by a cleaving reagent (chemically cleavable). Cleavable linkers can be used to liberate effectors from a bead or other scaffold to allow the effector to interact with a sample.

In some embodiments, the scaffolds further comprise impurities in the effector and/or its encoding. In some instances, impurities of the effector and its corresponding encoding occur due to damage during a screen, during manufacturing of the bead, effector, or encoding combination, or during storage. In some embodiments, impurities of the effector and its corresponding encoding are present due to defects in the methodologies used to synthesize the encoded effectors. In some embodiments, scaffolds as described herein can comprise a single encoder, an encoding and its impurities, or combinations thereof. In some embodiments, at least 5%, at least 10%, at least 20%, at least 30%, at least 40%, at least 50%, at least 60%, at least 70%, at least 80%, at least 90%, at least 95%, or at least 99% of the effectors attached to a scaffold comprise an identical structure. In some embodiments, at least 5%, at least 10%, at least 20%, at least 30%, at least 40%, at least 50%, at least 60%, at least 70%, at least 80%, at least 90%, at least 95%, or at least 99% of the encodings attached to a scaffold comprise an identical structure.

Screening System Components and Methods

Provided herein are methods and systems for screening encoded effectors on samples using encapsulations. In some embodiments, methods and systems for screening encoded effectors on samples are capable of being performed in a high-throughput manner. In some embodiments, the methods and systems provided herein allow for screening large libraries of encoded effectors using small volumes, minimal amounts of reagents, and small amounts of the effectors being screened. In some embodiments, the methods and systems provided herein allow for uniform dosing of effectors in a library against samples. In some embodiments, the methods and systems described herein allow for measurement of cellular features in a high throughput manner. In some embodiments, the methods and systems provided herein measure genomic, metabolomic, and/or proteomic data from cells screened against the encoded effectors. In some embodiments, the methods and systems provided herein allow for synergistic effects of using multiple effectors against a particular sample to be determined. In some embodiments, the methods and systems provided herein allow for a library of mutant proteins to be screened for a desired activity or improvement in activity.

Figure 2A:
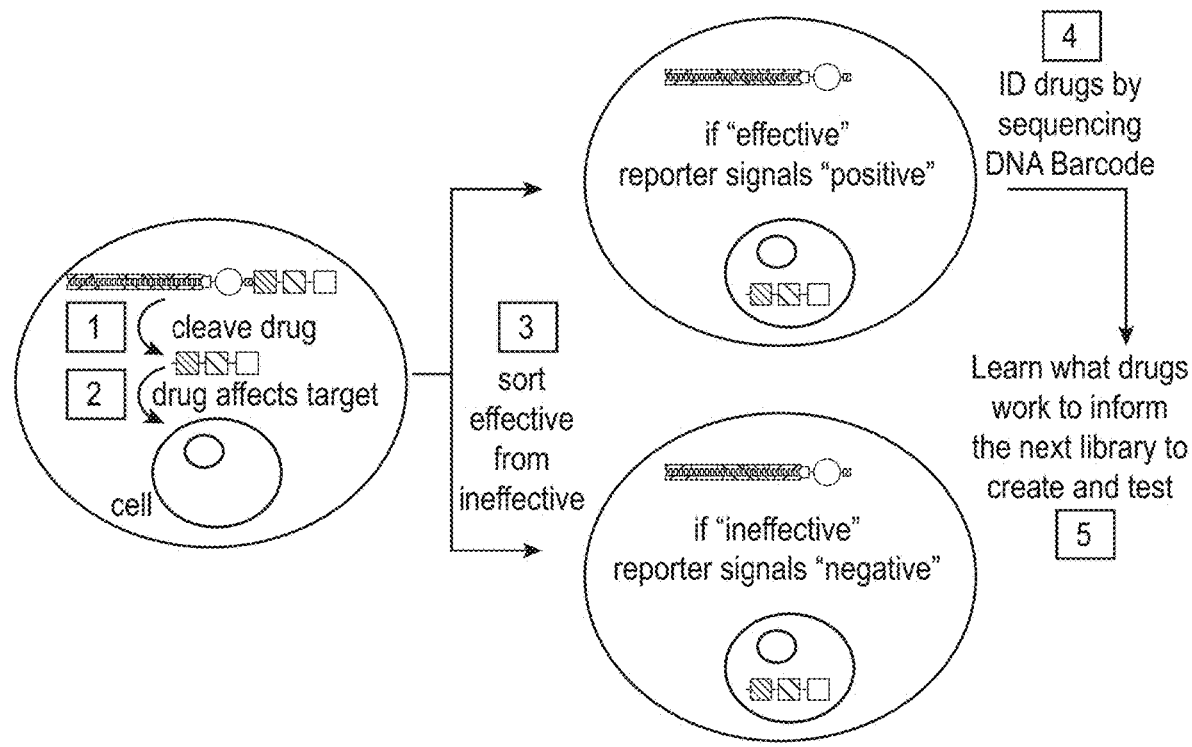
FIG. 2A shows an exemplary workflow of a screen using a nucleic acid encoded effector bound to a bead.

A non-limiting example workflow of a screen utilizing a single encoded effector bound to a scaffold is shown in FIG. 2A. The nucleic acid encoded effector bound to a scaffold is encapsulated with a target of interest, in this case a cell. In step 1, the effector, in this case a drug, is then cleaved from the bead within the encapsulation. In step 2, the effector is allowed to interact with the cell. If the drug has a desired effect on the cell, a reporter signal indicates that the drug is a positive hit. If there is no reporter signal detected, then the result for that drug is negative. In step 3, positive and negative results are sorted based on the detection of the signal. At the end of a screen, in step 4, the positive hits, which have been pooled together, are then sequenced (in the case of nucleic acid encodings) to reveal which effectors had the desired effect. In step 5, this information can then be used to guide synthesis of further libraries or identify lead molecules for further development.

Figure 2B:
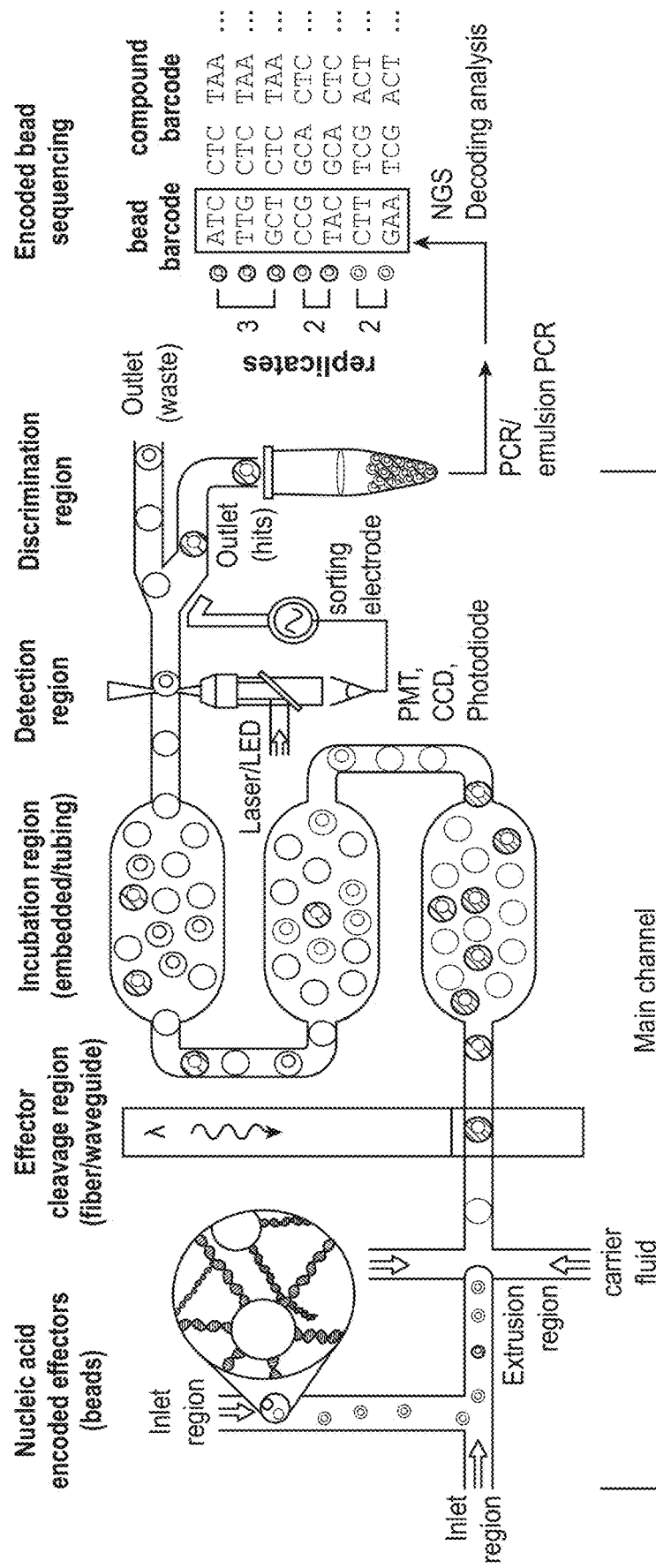
FIG. 2B shows an exemplary workflow of a screen using a microfluidic device.

FIG. 2B shows an additional exemplary, non-limiting workflow of an effector screen on a microfluidic device. In the exemplary workflow shown, a nucleic acid encoded effector bound to a bead is placed in an inlet and merged with an additional aqueous stream, which, in some embodiments, contains a sample to be tested. The merged fluids are driven through an "extrusion region" or "droplet formation region," wherein beads and sample are encapsulated within a carrier fluid immiscible with the aqueous fluids. An effector is then cleaved from bead at the effector cleavage region, which in some embodiments utilizes a light source to cleave a photocleavable linker. The encapsulations containing cleaved effectors are then allowed to continue flowing along the flow path of the device through the incubation region, which in some embodiments contains widened or enlarged chambers to control flow rate or residence time on the device. As the encapsulations travel through the incubation region, a detectable signal is generated if the released effectors have a desired activity. This signal is then detected in a detection region of the device. In some embodiments, this detectable signal is a fluorescent signal, though any detectable signal can be employed. This signal is then measured or detected at a detection region, which is in some embodiments equipped with a light source (e.g. a laser or LED) and a detector (e.g. a photomultiplier tube (PMT), a charged coupled device (CCD), or a photodiode) coupled to a sorting device (e.g. a dielectrophoresis electrode or any other sorting mechanism). In some embodiments, the detection region comprises an interrogation region, which is coupled to a sensor or an array of sensors. Based on the signal, the encapsulations are sorted into a waste outlet or a hit outlet. Following completion of the screen, the encodings of the hits are amplified (e.g. by PCR or emulsion PCR) and the encodings sequenced (e.g. by next generation sequencing). The sequenced encodings can then be decoded to reveal the effectors which had the desired activity. In some embodiments, each bead further comprises barcode unique to the bead itself (independent of the effector). Thus, in some embodiments, it is possible to ascertain if multiple beads bearing identical effectors were selected as hits within multiple encapsulations.

Figure 2C:
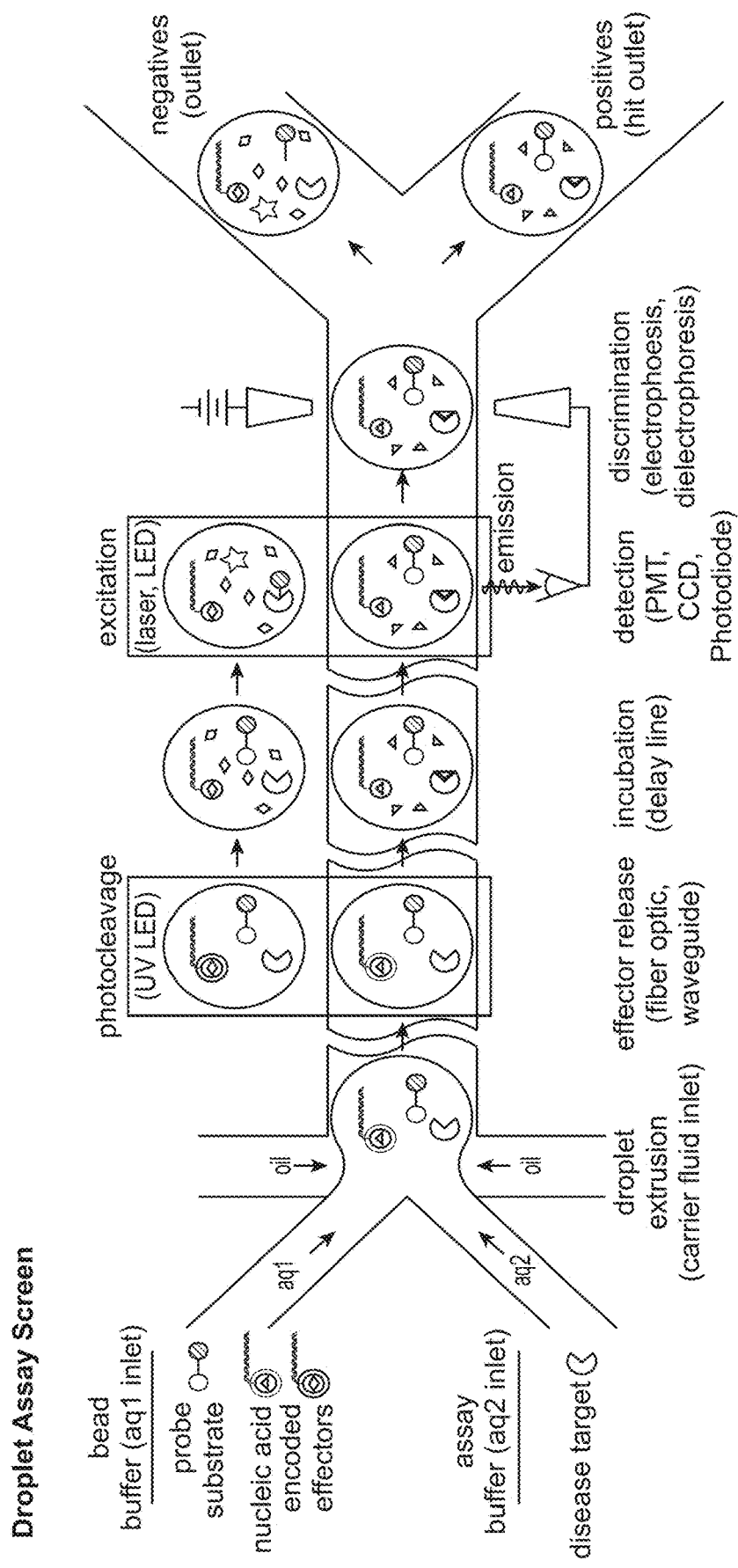
FIG. 2C shows an exemplary workflow for an encapsulation assay screen.
Figure 2D:
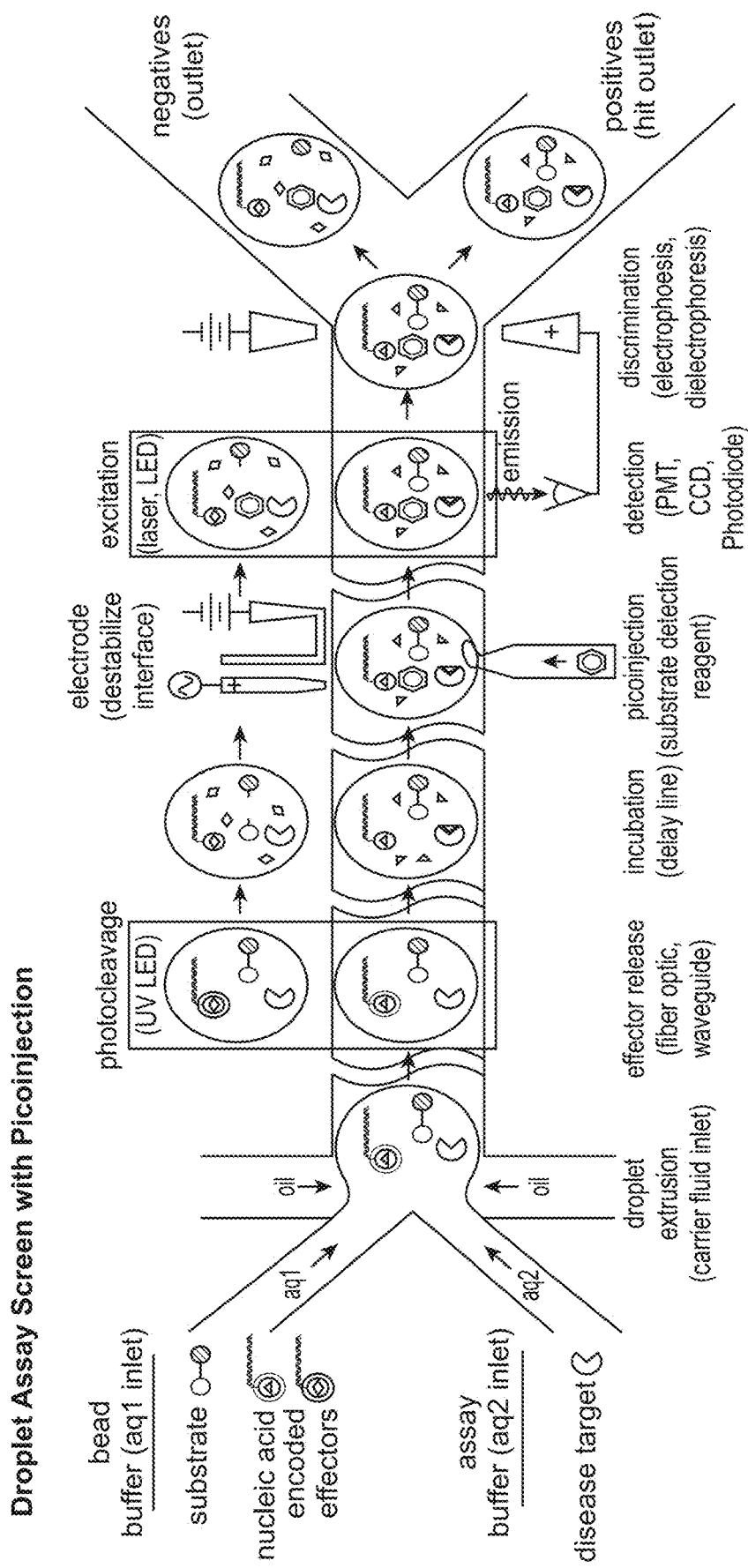
FIG. 2D shows an exemplary workflow for an encapsulation assay screen using pico-injection.

An exemplary, non-limiting droplet assay screen workflow is shown in FIG. 2C. A bead buffer comprising a probe substrate and nucleic acid encoded effectors bound to beads are merged with an assay buffer comprising a disease target (e.g. a protein such as an enzyme). An encapsulation comprising probe substrate, a bead bearing a nucleic acid encoded effector, and the disease target is then formed in an immiscible carrier fluid. The effector is then released from the bead and allowed to interact with the disease target. The sample is then incubated within a delay line (or any such suitable channel or reservoir configured to incubate the encapsulation for a desired time). In this embodiment, the probe substrate is cleaved by the disease target. Upon cleavage, a change in fluorescence properties of the substrate is observed, for example due to FRET interactions of the probe substrate. If the disease target is inhibited by the effector, the probe substrate will not be cleaved. After a desired incubation time, the fluorescence of the encapsulation is measured (e.g. by a PMT, CCD, or photodiode) after excitation (e.g. by a laser or LED) and the encapsulation is sorted (e.g. by electrophoresis or dielectrophoresis) based on the result. FIG. 2D shows a similar workflow but contains an additional step of adding a substrate detection reagent (e.g. by pico-injection or droplet merging) in order to allow detection of substrate that has or has not reacted with the disease target. In some embodiments, an electrode is employed at the pico-injection site in order to destabilize the interface of the encapsulation to facilitate incorporation of the pico-injected fluid into the encapsulation.

Provided herein are methods and systems for screening encoded effectors on samples using encapsulations, wherein the sample and an encoded effector are encapsulated. In some embodiments, the encoded effector and the sample are encapsulated by mixing a first solution comprising the encoded effector with a second solution comprising the sample. In some embodiments, the first and second solutions are mixed together with an oil. In some embodiments, mixing the first and second solutions with an oil forms an emulsion, wherein the first and second solutions combine to form droplets. In some embodiments, encapsulations are formed in a microfluidic device. In some embodiments, the encapsulation step comprises merging the first and second solution at a T-junction of microfluidic channels. In some embodiments, creating an encapsulation comprises converging aqueous streams in a microfluidic device. Creating an encapsulation can occur by numerous methods, any of which may be compatible with the methods described herein. In some embodiments, encapsulations are formed on microfluidic devices. In some embodiments, encapsulations flow through a microfluidic device.

In some embodiments, provided herein are methods and systems for screening a library of encoded effectors. In some embodiments, for any method or system described herein, the library of encoded effectors comprises at least about 1, 1,000, 10,000, 100,000, 250,000, 1,000,000, or 10,000,000 unique encoded effectors. In some embodiments, a plurality of scaffolds (as described herein) are encapsulated in a plurality of encapsulations (as described herein) with a sample in a microfluidic channel. In some embodiments, the plurality of scaffolds (e.g., beads) are bound to a library of unique encoded effectors. In some embodiments, each scaffold is bound to one or more unique encoded effectors. In some embodiments, the library of unique encoded effectors comprise at least about 250,000 unique encoded effectors. In some embodiments, the library of unique encoded effectors comprise about 1 unique encoded effector to about 10,000,000 unique encoded effectors. In some embodiments, the library of unique encoded effectors comprise about 1 unique encoded effector to about 1,000 unique encoded effectors, about 1 unique encoded effector to about 10,000 unique encoded effectors, about 1 unique encoded effector to about 100,000 unique encoded effectors, about 1 unique encoded effector to about 250,000 unique encoded effectors, about 1 unique encoded effector to about 1,000,000 unique encoded effectors, about 1 unique encoded effector to about 10,000,000 unique encoded effectors, about 1 unique encoded effector to about 200 unique encoded effectors, about 1,000 unique encoded effectors to about 10,000 unique encoded effectors, about 1,000 unique encoded effectors to about 100,000 unique encoded effectors, about 1,000 unique encoded effectors to about 250,000 unique encoded effectors, about 1,000 unique encoded effectors to about 1,000,000 unique encoded effectors, about 1,000 unique encoded effectors to about 10,000,000 unique encoded effectors, about 1,000 unique encoded effectors to about 200 unique encoded effectors, about 10,000 unique encoded effectors to about 100,000 unique encoded effectors, about 10,000 unique encoded effectors to about 250,000 unique encoded effectors, about 10,000 unique encoded effectors to about 1,000,000 unique encoded effectors, about 10,000 unique encoded effectors to about 10,000,000 unique encoded effectors, about 10,000 unique encoded effectors to about 200 unique encoded effectors, about 100,000 unique encoded effectors to about 250,000 unique encoded effectors, about 100,000 unique encoded effectors to about 1,000,000 unique encoded effectors, about 100,000 unique encoded effectors to about 10,000,000 unique encoded effectors, about 100,000 unique encoded effectors to about 200 unique encoded effectors, about 250,000 unique encoded effectors to about 1,000,000 unique encoded effectors, about 250,000 unique encoded effectors to about 10,000,000 unique encoded effectors, about 250,000 unique encoded effectors to about 200 unique encoded effectors, about 1,000,000 unique encoded effectors to about 10,000,000 unique encoded effectors, about 1,000,000 unique encoded effectors to about 200 unique encoded effectors, or about 10,000,000 unique encoded effectors to about 200 unique encoded effectors, including increments therein. In some embodiments, the library of unique encoded effectors comprise about 1 unique encoded effector, about 1,000 unique encoded effectors, about 10,000 unique encoded effectors, about 100,000 unique encoded effectors, about 250,000 unique encoded effectors, about 1,000,000 unique encoded effectors, about 10,000,000 unique encoded effectors, or about 200 unique encoded effectors. In some embodiments, the library of unique encoded effectors comprise at least about 1 unique encoded effector, about 1,000 unique encoded effectors, about 10,000 unique encoded effectors, about 100,000 unique encoded effectors, about 250,000 unique encoded effectors, about 1,000,000 unique encoded effectors, or about 10,000,000 unique encoded effectors. In some embodiments, the library of unique encoded effectors comprise at most about 1,000 unique encoded effectors, about 10,000 unique encoded effectors, about 100,000 unique encoded effectors, about 250,000 unique encoded effectors, about 1,000,000 unique encoded effectors, about 10,000,000 unique encoded effectors, or about 200 unique encoded effectors.

In some embodiments, each unique encoded effector is encoded with a corresponding encoding. In some embodiments, at least one encoding comprises a nucleic acid encoding. In some embodiments, at least one encoded effector is bound to a respective scaffold through a cleavable linker. In some embodiments, the cleavable linker comprises a photocleavable linker, or a chemically cleavable linker (e.g., linker cleaved through contact with a reagent). In some embodiments, one or more photocleavable linkers between an encoded effector and corresponding bead is cleaved. In some embodiments, cleaving a photocleavable linker releases the corresponding encoded effector from the bead. In some embodiments, a released encoded effector interacts with the corresponding sample within the respective encapsulation. In some embodiments, the interaction between the encoded effector and the sample creates a signal. In some embodiments, the signal is configured to be detected. In some embodiments, the plurality of encapsulations are sorted based on a corresponding signal being detected from each encapsulation. In some embodiments, the plurality of encapsulations are sorted based on a corresponding signal not being detected from each encapsulation. In some embodiments, the encoding(s) associated with the encapsulations having a detected signal(s) are barcoded, as an alternative sorting the encapsulation. In some embodiments, the encoding(s) associated with the encapsulations not having a detected signal(s) are barcoded, as an alternative sorting the encapsulation. In some embodiments, encapsulations are formed on microfluidic devices. In some embodiments, encapsulations flow through a microfluidic device.

Provided herein are methods and systems for screening encoded effectors on samples using encapsulations, wherein a signal is detected from the encapsulation. In some embodiments, the signal results from an interaction between an effector and the sample. In some embodiments, the signal is detected with a detector. In some embodiments, detecting the signal comprises providing the encapsulation through a microfluidic channel. In some embodiments, detecting the signal comprises providing the encapsulation through a microfluidic channel equipped with a detector. In some embodiments, the detector is configured to detect the signal.

Signals of the methods and systems provided herein can be any signal capable of detection in an encapsulation. In some embodiments, the signal is electromagnetic radiation, thermal radiation, a visual change in the sample, or combinations thereof. In some embodiments, the electromagnetic radiation is fluorescence or luminescence. In some embodiments, the electromagnetic radiation is in the visible spectrum. In some embodiments, the signal is absorbance of electromagnetic radiation.

Provided herein are methods and systems for screening encoded effectors on samples using encapsulations, wherein the encapsulation is sorted. In some embodiments, the encapsulation is sorted based on the detection of a signal. In some embodiments, the encapsulation is optionally sorted based on the detection of a signal.

Alternative Signal Detection

Provided herein are methods and systems for screening encoded effectors, wherein various alternative signal detection methods and systems may be used to identify activity by an effector or within an encapsulation. In some embodiments, the signal is a thermal radiation. In some embodiments, the thermal radiation is detected using an infrared camera. In some embodiments, the thermal radiation is a change in thermal radiation emitted by a sample. In some embodiments, the change in thermal radiation is due to metabolic activity in a sample. In some embodiments, the change in thermal radiation comprises a change in metabolic activity in the sample. In some embodiments, the change in thermal radiation comprises a change in metabolic activity in the sample due to an effect of the effector on the sample. In some embodiments the effect on the sample is a change in metabolic activity. In some embodiments, detecting the signal comprises detecting a change in metabolic activity in the sample by detecting a change in thermal radiation. In some embodiments, the sample is a cell and the signal is thermal radiation.

In some embodiments, the sample displays a change in emission of thermal radiation compared to a sample not encapsulated with the effector. In some embodiments, the change in thermal radiation is at least 10%, 20%, 30%, 40%, 50%, 60%, 70%, 80%, 90%, or 100% emission of thermal radiation. In some embodiments, the change in thermal radiation is at least 10%, 20%, 30%, 40%, 50%, 60%, 70%, 80%, 90%, or 100% emission of thermal radiation relative to sample not treated with the effector. In some embodiments, the change in thermal radiation is at least 2-fold, 3-fold, 4-fold, 5-fold, 6-fold, 7-fold, 8-fold, 9-fold, or 10-fold emission of thermal radiation relative to a sample not treated with the effector.

In some embodiments, the signal is luminescence. In some embodiments, detecting the signal comprises monitoring encapsulations for a period of time. In some embodiments, detecting the signal comprises monitoring luminescence from the sample over a period of time. In some embodiments, the luminescence is integrated over a period of time. In some embodiments, the luminescence is integrated over a period of at least 1 minute, at least 5 minutes, at least 30 minutes, at least 4 hours, or at least 12 hours. In some embodiments, the luminescence is integrated over a period of at most 1 minutes, at most 5 minutes, at most 30 minutes, at most 4 hours, or at most 12 hours. In some embodiments, the luminescence is integrated over a distance traveled by an encapsulation. In some embodiments, the luminescence is integrated over a distance travelled by an encapsulation through a microfluidic channel. In some embodiments, the luminescence is integrated over a distance of at least 1 µm, at least 10 µm, at least 50 µm, at least 100 µm, at least 250 µm, at least 500 µm, at least 1 mm, at least 10 mm, or at least 100 mm travelled by an encapsulation through a microfluidic channel. In some embodiments, the luminescence is integrated over a distance of at most 1 µm, at most 10 µm, at most 50 µm, at most 100 µm, at most 250 µm, at most 500 µm, at most 1 mm, at most 10 mm, or at most 100 mm travelled by an encapsulation through a microfluidic channel.

The signal from the sample may be a morphological or visual change in the sample which can be measured by imaging the encapsulation. In some embodiments, detecting the signal comprises recording images of the sample in the encapsulation. In some embodiments, detecting the signal comprises recording a series of images of the sample in the encapsulation. In some embodiments, detecting a signal comprises recording a series of images of samples in encapsulations and superimposing the series of images of the sample. In some embodiments, detecting a signal comprises detecting morphological or visual changes in the sample measured by recording a series of images of the encapsulation.

In some embodiments, morphology changes in a sample, such as one or more cells, can be detected by an imaging sensor, capturing trans illuminated light with a high-speed shutter, where composite video frames offers multiple full-cell images that can aid in shape determination. In some embodiments, morphology changes in a sample, such as one or more cells, can be detected by an imaging sensor, capturing trans illuminated light from a high-frequency pulsed light source, increasing temporal resolution and sharpening the perimeter of the cell. In one manifestation, morphology changes can be detected by fluorescence emission from a cell traversing a laser-light sheet excitation region. In some embodiments, the emission is captured by Avalanche Photodiode (APD) or charged coupled detector (CCD), in a one-dimensional array of pixels, binned by time, then restitched into a composite fluorescence-microscopy image.

In some embodiments, detecting the signal comprises recording images of the sample, wherein the sample is a cell. In some embodiments, recording images of the cell provides information about cell morphology, mitotic stage, levels of expressed proteins, levels of cellular components, cell health, or combinations thereof. In some embodiments, the encapsulation comprises a detection agent. In some embodiments, the detection agent is an intercalation dye. In some embodiments, the intercalation dye is ethidium bromide, propidium iodide, crystal violet, a dUTP-conjugated probe, DAPI (4',6-diamidino-2-phenylindole), 7-AAD (7-aminoactinomycin D), Hoechst 33258, Hoechst 33342, Hoechst 34580, combinations thereof, or derivatives thereof. In some embodiments, the detection agent highlights different regions of the cell. In some embodiments, the detection agent highlights a particular organelle. In some embodiments, the organelle is a mitochondrion, Golgi apparatus, endoplasmic reticulum, nucleus, ribosomes, cellular membrane, nucleolus, liposome, lipid vesicle, lysosome, or vacuole. In some embodiments, the organelle is a mitochondrion. In some embodiments, the organelle is the nucleus.

In some embodiments, detecting the signal comprises detecting the presence of a target nucleic acid. In some embodiments, the encapsulation further comprises a molecular beacon. In some embodiments, the molecular beacon is complementary to a portion of the target nucleic acid sequence of the sample. In some embodiments, the methods further comprise adding a molecular beacon to the encapsulation. In some embodiments, the target nucleic acid is detected by a molecular beacon. In some embodiments, the encapsulation further comprises a probe and a polymerase. In some embodiments, the encapsulation further comprises a TaqMan probe and a Taq polymerase. In some embodiments, the methods further comprise adding a TaqMan probe and a Taq polymerase to the encapsulation. In some embodiments, the TaqMan probe is complementary to a portion of the target nucleic acid sequence. In some embodiments, the TaqMan probe and Taq polymerase are added to the encapsulation at the same time. In some embodiments, the TaqMan probe and Taq polymerase are added sequentially. In some embodiments, the signal is fluorescence emitted by a molecular beacon. In some embodiments, the signal is fluorescence emitted by TaqMan probe. In some embodiments, the signal is fluorescence emitted by a molecular beacon or TaqMan probe.

Various molecular beacons can be used with the methods and systems described herein. In general, a molecular beacon comprises a nucleic acid binding region that binds to a complementary nucleic acid of interest. The molecular beacon can typically have a secondary structure wherein a fluorophore and a quencher are in proximity when the nucleic acid binding region is not bound to the complementary nucleic acid of interest. Upon binding of the nucleic acid binding region to the complementary nucleic acid of interest, the fluorophore and quencher may be separated in space such that a fluorescent signal can be detected. Thus, the amount of fluorescence detected can be used to quantify the amount of nucleic acid of interest present in a sample. In some embodiments, an inhibitor is used wherein activity between an effector and a sample inhibits or limits the intensity of a fluorescence signal.

In some embodiments, two or more signal detection methods are used in combination for detecting a signal. In some embodiments, detecting a signal comprises detecting morphological changes in the sample as well as detecting fluorescence emitted by a molecular beacon or probe. For example, in some embodiments, fluorescence emission from a molecular beacon in the encapsulation (e.g., droplet) can be measured by PMT or Avalanche Photodiode (APD). In some embodiments, simultaneous image capture by transillumination can identify other features in the encapsulation (e.g., droplet), such as encoded effectors and cells. In some embodiments, these streams of information together determine outcome at the sorting junction.

In some embodiments, detecting the presence of the target nucleic acid comprises amplifying the target nucleic acid. In some embodiments, the target nucleic acid is amplified by an isothermal amplification method. In some embodiments, the isothermal amplification method is loop-mediated isothermal amplification (LAMP), strand displacement amplification (SDA), helicase-dependent amplification (HAD), recombinase polymerase amplification (RPA), rolling circle replication (RCA) or nicking enzyme amplification reaction (NEAR). In some embodiments, the encapsulation further comprises reagents for isothermal amplification of the target nucleic acid. In some embodiments, the methods comprise adding reagents for isothermal amplification to the encapsulation. In some embodiments, the reagents for isothermal amplification are specific to the target nucleic acid sequence.

In some embodiments, the target nucleic acid is DNA. In some embodiments, the target nucleic acids are cellular DNA. In some embodiments, the target nucleic acids are genomic DNA. In some embodiments, the target nucleic acid is RNA. In some embodiments, the RNA is mRNA, ribosomal RNA, tRNA, non-protein-coding RNA (npcRNA), non-messenger RNA, functional RNA (fRNA), long non-coding RNA (lncRNA), pre-mRNAs, or primary miRNAs (pri-miRNAs). In some embodiments, the target nucleic acids are mRNA.

Scaffold and Beads

An exemplary embodiment of screening encoded effectors on samples using encapsulations comprises use of a scaffold. In some embodiments, the effector is bound to a scaffold. In some embodiments, the scaffold acts as a solid support and keeps the encoded effector molecules linked in space to their encodings. In some embodiments, the scaffold is a structure with a plurality of attachment points that allow linkage of one or more molecules. In some embodiments, the encoded effector is bound to a scaffold. In some embodiments, the scaffold is a solid support. In some embodiments, the scaffold is a bead, a fiber, nanofibrous scaffold, a molecular cage, a dendrimer, or a multi-valent molecular assembly.

In some embodiments, the scaffold is a bead. In some embodiments, the bead is a polymer bead, a glass bead, a metal bead, or a magnetic bead. In some embodiments, the bead is a polymer bead. In some embodiments, the bead is a glass bead. In some embodiments, the bead is a metal bead. In some embodiments, the bead is a magnetic bead.

The beads utilized in the methods provided herein may be made of any material. In some embodiments, the bead is a polymer bead. In some embodiments, the bead comprises a polystyrene core. In some embodiments, the beads are derivatized with polyethylene glycol. In some embodiments, the beads are grafted with polyethylene glycol. In some embodiments, the polyethylene glycol contains reactive groups for the attachment of other functionalities, such as effectors or encodings. In some embodiments, the reactive group is an amino or carboxylate group. In some embodiments, the reactive group is at the terminal end of the polyethylene glycol chain. In some embodiments, the bead is a TentaGel® bead.

The polyethylene glycol (PEG) attached to the beads may be any size. In some embodiments, the PEG is up to 20 kDa. In some embodiments, the PEG is up to 5 kDa. In some embodiments, the PEG is about 3 kDa. In some embodiments, the PEG is about 2 to 3 kDa.

In some embodiments, the PEG group is attached to the bead by an alkyl linkage. In some embodiments, the PEG group is attached to a polystyrene bead by an alkyl linkage. In some embodiments, the bead is a TentaGel® M resin.

In some embodiments, the bead comprises a PEG attached to a bead through an alkyl linkage and the bead comprises two bifunctional species. In some embodiments, the beads comprise surface modification on the outer surface of the beads that are orthogonally protected to reactive sites in the internal section of the beads. In some embodiments the beads comprise both cleavable and non-cleavable ligands. In some embodiments, the bead is a TentaGel® B resin.

Beads for use in the systems and methods as described herein can be any size. In some embodiments, the beads are at most 10 nm, at most 100 nm, at most 1 µm, at most 10 µm, or at most 100 µm in diameter. In some embodiments, the beads are at least 10 nm, at least 100 nm, at least 1 µm, at least 10 µm, or at least 100 µm in diameter. In some embodiments, the beads are about 10 µm to about 100 µm in diameter.

In some embodiments, the effector is covalently bound to the scaffold. In some embodiments, the effector is non-covalently bound to the scaffold. In some embodiments, the effector is bound to the scaffold through ionic interactions. In some embodiments, the effector is bound to the scaffold through hydrophobic interactions.

Cleavable Linker and Effector Release

Cleavable linkers can be used to attach effectors to scaffolds. In some embodiments, the effector is bound to a scaffold by a cleavable linker. In some embodiments, the cleavable linker is cleavable by electromagnetic radiation, an enzyme, a chemical reagent, heat, pH adjustment, sound, or electrochemical reactivity. In some embodiments, the cleavable linker is cleavable by electromagnetic radiation. In some embodiments, the cleavable linker is cleavable by electromagnetic radiation such as UV light. In some embodiments, the cleavable linker is a photocleavable linker. In some embodiments the photocleavable linker is cleavable by electromagnetic radiation. In some embodiments the photocleavable linker is cleavable through exposure to light. In some embodiments, the light comprises UV light. In some embodiments, the cleavable linker is cleavable by a cleaving reagent. In some embodiments, the cleavable linker must first be activated in order to be able to be cleaved. In some embodiments, the cleavable linker is activated through interaction with a reagent.

In some embodiments, the cleavable linker is a disulfide bond. In some embodiments, the cleavable linker is a disulfide bond and the cleavable reagent is a reducing agent. In some embodiments, the reducing agent is a disulfide reducing agent. In some embodiments, the disulfide reducing agent is a phosphine. In some embodiments, the reducing agent is 2-mercapto ethanol, 2-mercaptoethylamine, tris(2-carboxyethyl)phosphine (TCEP), dithiothreitol, a combination thereof, or a derivative thereof.

In some embodiments, the cleavable linker and cleaving reagent are biorthogonal reagents. Biorthogonal reagents are combinations of reagents that selectively react with each other, but do not have significant reactivity with other biological components. Such reagents allow for minimal cross-reactivity with other components of the reaction mixture, which allows for less off target events.

In some embodiments, the cleavable linker is a substituted trans-cyclooctene. In some embodiments, the cleavable linker is a substituted trans-cyclooctene and the cleaving reagent is a tetrazine. In some embodiments, the cleavable linker as the structure

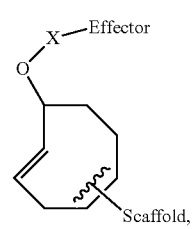

wherein X is —C(=O)NR—, —C(=O)O—, —C(=O)— or a bond, and R is H or alkyl. In some embodiments, the cleaving reagent is a tetrazine. In some embodiments, the cleaving reagent is dimethyl tetrazine (DMT). Further examples of tetrazine cleavable linkers and methods of use are described in Tetrazine-triggered release of carboxylic-acid-containing molecules for activation of an anti-inflammatory drug, ChemBioChem 2019, 20, 1541-1546, which is hereby incorporated by reference.

In some embodiments, the cleavable linker comprises an azido group attached to the same carbon as an ether linkage. In some embodiments, the cleavable linker has the structure

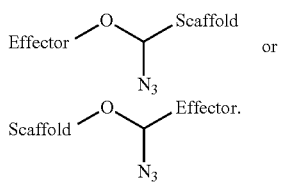

In some embodiments, the cleaving reagent is a reagent that reduces an azido group. In some embodiments, the cleaving reagent is a phosphine. In some embodiments, the cleaving reagent is hydrogen and a palladium catalyst.

In some embodiments, the cleavable linker is cleaved by a transition metal catalyst. In some embodiments, the cleavage reagent is a transition metal catalyst. In some embodiments, the transition metal catalyst is a ruthenium metal complex. In some embodiments, the cleavable linker is an O-allylic alkene. In some embodiments, the cleavable linker has the structure

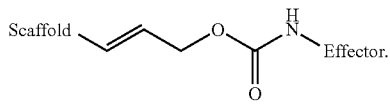

A non-limiting example of such a catalyst is described in Bioorthogonal catalysis: a general method to evaluate metal-catalyzed reaction in real time in living systems using a cellular luciferase reporter system, *Bioconjugate Chem.* 2016, 27, 376-382, which is hereby incorporated by reference. In some embodiments, the transition metal complex is a palladium complex. In some embodiments, the cleavable linker has the structure

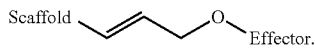

Such cleavable linkers are described in 3'-O-modified nucleotides as reversible terminators for pyrosequencing, PNAS Oct. 16, 2007, 104 (42) 16462-16467, which is hereby incorporated by reference.

In some embodiments, the number of effectors cleaved from the scaffold is controlled. In some embodiments, the number of effectors cleaved from a scaffold is controlled by controlling the amount of stimulus used to cleave the cleavable linker. In this context, a "stimulus" is any method or chemical used to specifically cleave a cleavable linker. In some embodiments, the stimulus is a chemical reaction with a cleaving reagent. In some embodiments, the stimulus is electromagnetic radiation. In some embodiments, the stimulus is a change in pH. In some embodiments, the change in pH is acidification. In some embodiments, the change in pH is basification.

In some embodiments, methods described herein comprise cleaving the cleavable linker with a cleaving reagent. In some embodiments, the methods comprise adding the cleaving reagent to an encapsulation comprising an effector bound to a scaffold through a cleavable linker. In some embodiments, the methods comprise adding the cleaving reagent to an encapsulation comprising an encoding bound to a scaffold through a cleavable linker.

In some embodiments, the number of effectors cleaved from the scaffold is controlled by controlling the concentration of the cleaving reagent. In some embodiments, the concentration of the cleavage reagent is controlled in an encapsulation containing an encoded effector bound to a scaffold. In some embodiments, the concentration of chemical reagent used to cleave the cleavable linker is at least 100 pM, at least 500 pM, at least 1 nM, at last 10 nM, at least 100 nM, at least 1 µM, at least 10 µM, at least 100 µM, at least 1 mM. at least 10 mM, at least 100 mM, or at least 500 mM. In some embodiments, the concentration of cleaving reagent used to cleave the cleavable linker is at most 100 pM, at most 500 pM, at most 1 nM, at most 10 nM, at most 100 nM, at most 1 µM, at most 10 µM, at most 100 µM, at most 1 mM, at most 10 mM, at most 100 mM, or at most 500 mM.

In some embodiments, the cleaving reagent is added to a plurality of encapsulations. In some embodiments, the concentration of cleaving reagent added to the plurality of encapsulations is substantially uniform among individual encapsulations of the plurality. In some embodiments, the concentration of cleaving reagent used to cleave the cleavable linker in a plurality of encapsulations is at least 10%, 20%, 30%, 40%, 50%, 60%, 70%, 80%, or 90% identical in each individual encapsulation. In some embodiments, concentration of cleaving reagent used to cleave the cleavable linker in a plurality of encapsulations differs by no more than 2-fold, 3-fold, 4-fold, 5-fold, 6-fold, 7-fold, 8-fold, 9-fold, 10-fold, 15-fold, 20-fold, 50-fold, or 100-fold among each individual encapsulation of the plurality.

In some embodiments, the cleaving reagent is added to the encapsulation by pico-injection. In some embodiments, the encapsulation is passed through a microfluidic channel comprising a pico-injection site. In some embodiments, pico-injections are timed such that the rate of pico-injection matches the rate at which encapsulation cross the pico-injection site. In some embodiments, at least 80%, 85%, 90%, 95%, 98%, or 99% of encapsulations passing a pico-injection site receive a pico-injection. In some embodiments, the pico-injections are at least 2-fold, at least 5-fold, at least 10-fold, at least 20-fold, at least 30-fold, at least 50-fold, at least 100-fold, at least 500-fold, or at least 1000-fold smaller in volume than the passing droplets. In some embodiments, the cleaving reagent is added to the encapsulation by droplet merging.

In some embodiments, the cleaving reagent is added from a stock solution to the encapsulation. In some embodiments, the stock solution is at least 2×, 5×, 0×, 20×, 30×, 50×, 100×, 500×, or 1000× more concentrated than the desired final concentration in the encapsulation.

In some embodiments, methods and systems described herein comprise cleaving a photocleavable linker between an encoded effector and a scaffold. In some embodiments, the methods and systems described herein comprise exposing an encapsulation to electromagnetic radiation comprising an effector bound to a scaffold through a photocleavable linker. In some embodiments, the methods and systems described herein comprise exposing an encapsulation to light (for e.g., UV light) comprising an effector bound to a scaffold through a photocleavable linker. In some embodiments, the encapsulation is exposed to the light using a microfluidic device.

In some embodiments, the photocleavable linker is cleaved by exposure to light (e.g., UV light). In some embodiments, the concentration of the number of effector molecules released from a scaffold is controlled by controlling the intensity and/or duration of exposure to UV light. In some embodiments, the light intensity of a light (e.g., UV light) that an encapsulation (e.g., droplet) described herein is exposed to is at least about 0.1 $J/cm^2$ to about 200 $J/cm^2$. In some embodiments, the light intensity of a light (e.g., UV light) that an encapsulation (e.g., droplet) described herein is exposed to is about 0.1 $J/cm^2$ to about 200 $J/cm^2$. In some embodiments, the light intensity of a light (e.g., UV light) that an encapsulation (e.g., droplet) described herein is exposed to is about 0.1 $J/cm^2$ to about 5 $J/cm^2$, about 0.1 $J/cm^2$ to about 25 $J/cm^2$, about 0.1 $J/cm^2$ to about 100 $J/cm^2$, about 0.1 $J/cm^2$ to about 150 $J/cm^2$, about 0.1 $J/cm^2$ to about 200 $J/cm^2$, about 5 $J/cm^2$ to about 25 $J/cm^2$, about 5 $J/cm^2$ to about 100 $J/cm^2$, about 5 $J/cm^2$ to about 150 $J/cm^2$, about 5 $J/cm^2$ to about 200 $J/cm^2$, about 25 $J/cm^2$ to about 100 $J/cm^2$, about 25 $J/cm^2$ to about 150 $J/cm^2$, about 25 $J/cm^2$ to about 200 $J/cm^2$, about 100 $J/cm^2$ to about 150 $J/cm^2$, about 100 $J/cm^2$ to about 200 $J/cm^2$, or about 150 $J/cm^2$ to about 200 $J/cm^2$, including increments therein. In some embodiments, the light intensity of a light (e.g., UV light) that an encapsulation (e.g., droplet) described herein is exposed to is about 0.1 $J/cm^2$, about 5 $J/cm^2$, about 25 $J/cm^2$, about 100 $J/cm^2$, about 150 $J/cm^2$, or about 200 $J/cm^2$. In some embodiments, the light intensity of a light (e.g., UV light) that an encapsulation (e.g., droplet) described herein is exposed to is at least about 0.1 $J/cm^2$ about 5 $J/cm^2$, about 25 $J/cm^2$, about 100 $J/cm^2$, or about 150 $J/cm^2$. In some embodiments, the light intensity of a light (e.g., UV light) that an encapsulation (e.g., droplet) described herein is exposed to is at most about 5 $J/cm^2$, about 25 $J/cm^2$, about 100 $J/cm^2$, about 150 $J/cm^2$, or about 200 $J/cm^2$.

In some embodiments, the light (e.g., UV light) that an encapsulation (e.g., droplet) described herein is exposed to is at least about 5 mV. In some embodiments, the light (e.g., UV light) that an encapsulation (e.g., droplet) described herein is exposed to is from about 5 mV to about 10,000 mV. In some embodiments, the light (e.g., UV light) that an encapsulation (e.g., droplet) described herein is exposed to is about 100 mV, 200 mV, 400 mV, 600 mV, 800 mV, 1000 mv, 1250 mV, 1500 mV, 2000 mV, 4000 mV, 5000 mV. In some embodiments, the light that an encapsulation (e.g., droplet) is exposed to is a calibrated amount of light.

In some embodiments, the cleavable linker is cleaved by electromagnetic radiation. In some embodiments, the concentration of the number of effector molecules released from a scaffold is controlled by controlling the intensity or duration of electromagnetic radiation.

Any suitable photoreactive or photocleavable linker can be used as a cleavable linker cleaved by electromagnetic radiation (e.g., exposure to UV light). A non-limiting list of linkers cleavable by electromagnetic radiation includes (i) o-nitrobenzyloxy linkers, (ii) o-nitrobenzylamino linkers, (iii) α-substituted o-nitrobenzyl linkers, (iv) o-nitroveratryl linkers, (v) phenacyl linkers, (vi) p-alkoxyphenacyl linkers, (vii) benzoin linkers, (viii) pivaloyl linkers, and (ix) other photolabile linkers. Further examples of photocleavable linkers are described in Photolabile linkers for solid-phase synthesis, ACS Comb Sci. 2018 Jul. 9; 20(7):377-99, which is hereby incorporated by reference. In some embodiments, the cleavable linker is an o-nitrobenzyloxy linker, an o-nitrobenzylamino linker, an α-substituted o-nitrobenzyl linker, an o-nitroveratryl linker, a phenacyl linker, p-alkoxyphenacyl linker, a benzoin linker, or a pivaloyl linker.

Figure 17A:
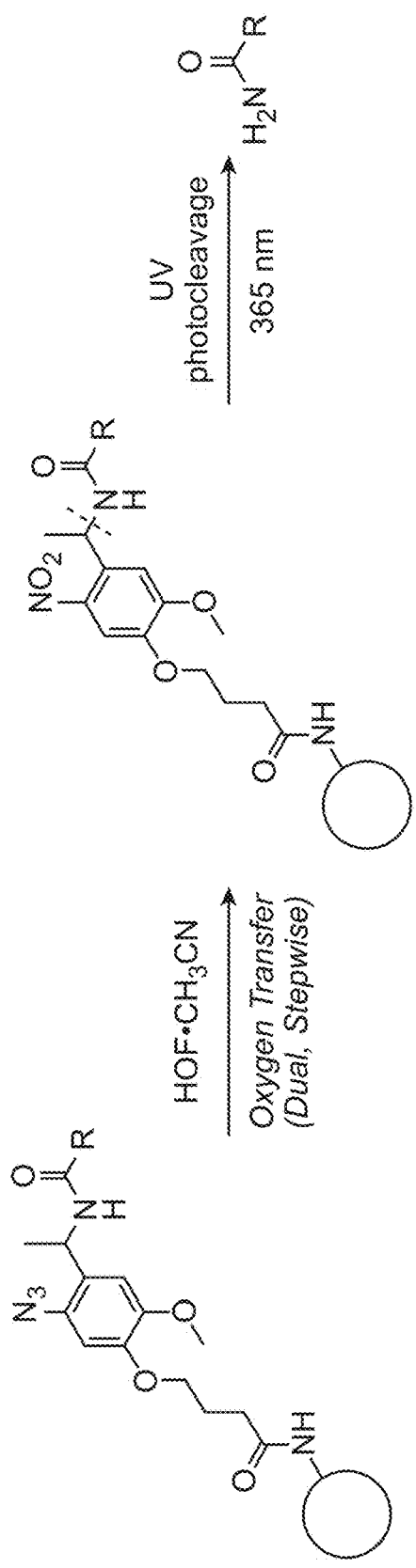
FIG. 17A-B shows exemplary molecules being activated for photocleavage.
Figure 17B:
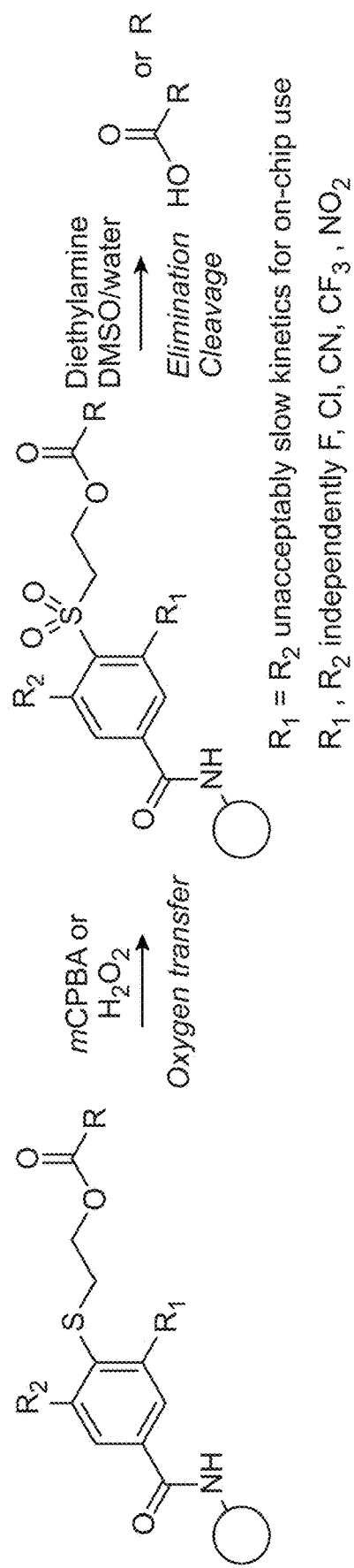

In some embodiments, the photocleavable linker requires to be first activated through exposure to a reagent before being able to be cleaved through exposure to electromagnetic radiation (e.g., UV light). In some embodiments, the desired number of effectors released can be further controlled by selectively exposing reagents to encapsulations (e.g., droplets). In some embodiments, providing photocleavable linkers that need to be activated before being cleaved through exposure to UV light enables for improved bead-handling, synthesis, storage, and preparation due to minimized or eliminated encoded effector release through incident UV exposure. FIG. 17A provides an exemplary molecule configured to be transformed upon interaction with a reagent, such that it becomes activated for UV photocleavage (reference: J. AM. CHEM. SOC. 2003, 125, 8118-8119; 10.1021/ja035616d). As depicted, the azide group functionally reduces the sensitivity of the photocleavable-linker moiety, such that linker is more stable, thus advantageous for handling and storing under ambient lighting. As depicted in FIG. 17A, the azide can be converted upon reagent treatment (HOF—CH3CN) to generate the photo-sensitive Nitro-benzyl motif (molecule depicted in the middle), wherein the product photocleavable-linker can be calibrated to release a known quantity of effector upon UV-exposure. FIG. 17B provides another exemplary molecule configured to be transformed upon interaction with a reagent, such that it becomes activated for UV photocleavage (reference: J. Comb. Chem. 2000, 2, 3, 266-275). As depicted, the thio-phenol ester provides a stable covalent linker to compound (R). Specific oxidation of the thio-phenol (shown in middle molecule) can generate an "activated" linker-moiety. Kinetic control of the oxidation step may allow for quantitative "activation" to prescribe compound release. In some embodiments, base treatment causes linker scission through elimination, thereby generating a free acid compound, or with subsequent decarboxylation generates just a compound.

In some embodiments, the cleavable linker is cleaved by an enzyme. In some embodiments, the cleavable linker is cleaved by a protease, a nuclease, or a hydrolase. In some embodiments, the cleavable linker is a peptide. In some embodiments, the cleavable linker is a cleavable nucleic acid sequence. In some embodiments, the cleavable linker is a carbohydrate. In some embodiments, the number of effector molecules cleaved from the scaffold is controlled by controlling the concentration of the enzyme. In some embodiments, the rate at which effector molecules are cleaved from the scaffold is controlled by controlling the concentration of the enzyme.

In some embodiments, the methods comprise cleaving the cleavable linker. In some embodiments, the methods comprise cleaving the cleavable linker with a cleaving reagent. In some embodiments, the cleaving reagent is added to the encapsulation by pico-injection. In some embodiments, the cleaving reagent is added to the encapsulation by pico-injection at a concentration configured to release a predetermined amount of effector. In some embodiments, the cleaving reagent is added to the encapsulation by pico-injection at a concentration configured to release a desired amount of effector.

In some embodiments, methods described herein comprise first activating the cleavable linker to enable the cleavable linker to be cleaved. In some embodiments, upon activating the cleavable linker, the cleavable linker can be cleaved using methods described herein, such as through photocleavage, interaction with an enzyme, using a cleaving reagent, and so on. In some embodiments, the cleavable linker is activated through interaction with an activating reagent. In some embodiments, the methods comprise adding the activating reagent to an encapsulation comprising an effector bound to a scaffold. In some embodiments, the methods comprise adding the activating reagent to an encapsulation comprising an encoding bound to a scaffold. In some embodiments, the activating reagent comprises any reagent described herein as a cleaving reagent. In some embodiments, the activating reagent comprises a disulfide reducing reagent. In some embodiments, the activating reagent comprises tetrazine.

In some embodiments, the activating reagent is added to the encapsulation by pico-injection. In some embodiments, the encapsulation is passed through a microfluidic channel comprising a pico-injection site. In some embodiments, pico-injections are timed such that the rate of pico-injection matches the rate at which encapsulation cross the pico-injection site. In some embodiments, at least 80%, 85%, 90%, 95%, 98%, or 99% of encapsulations passing a pico-injection site receive a pico-injection. In some embodiments, the pico-injections are at least 2-fold, at least 5-fold, at least 10-fold, at least 20-fold, at least 30-fold, at least 50-fold, at least 100-fold, at least 500-fold, or at least 1000-fold smaller in volume than the passing droplets. In some embodiments, the activating reagent is added to the encapsulation by droplet merging.

In some embodiments, the concentration of the activating reagent used to activate the cleavable linker is at most 100 picomolar (pM), at most 500 pM, at most 1 nanomolar (nM), at most 10 nM, at most 100 nM, at most 1 micromolar ($\mu$M), at most 10 $\mu$M, at most 100 $\mu$M, at most 1 millimolar (mM), at most 10 mM, at most 100 mM, or at most 500 mM.

In some embodiments, the activating reagent is added from a stock solution to the encapsulation. In some embodiments, the stock solution is at least 2×, 5×, 0×, 20×, 30×, 50×, 100×, 500×, or 1000× more concentrated than the desired final concentration in the encapsulation.

In some embodiments, effectors are released from scaffolds. In some embodiments, releasing effectors from scaffolds allows the effectors to move freely in solution. This free movement may allow the effector to interact with the sample or target being interrogated. In some embodiments, these effectors are released in a controlled fashion. This controlled fashion may allow for a predetermined and/or known dose of effectors to be released form the scaffold. Such a procedure may allow for improved quantification and analysis of hits from a screen, as dose response can be measured. Additionally, releasing a known amount of effectors across a library of effectors being screened may remove bias from the sample set. Bias can occur in library screens using encoded scaffolds when individual scaffolds possess attachments of effectors that vary in amount among the scaffolds of the library. For example, one scaffold may contain 10 copies of an effector molecule, and another scaffold may contain 1000 copies of an effector molecule. Consequently, different concentrations of effector being screened against a sample or target may be released, making a determination of the efficacy of individual effectors difficult to ascertain. By releasing a uniform amount of effectors from each scaffold in a screen, a uniform dose across the screen is employed, removing bias from lower potency, higher concentration effectors.

In some embodiments, the effectors are released to a desired concentration. In some embodiments, the effectors are released to a desired concentration within an encapsulation. In some embodiments, the desired concentration is at least 100 pM, at least 500 pM, at least 1 nM, at least 10 nM, at least 100 nM, at least 1 $\mu$M, at least 10 $\mu$M, at least 100 $\mu$M, at least 1 mM. at least 10 mM, at least 50 mM, at least 100 mM, or at least 250 mM. In some embodiments, the desired concentration is at most 100 pM, at most 500 pM, at most 1 nM, at most 10 nM, at most 100 nM, at most 1 $\mu$M, at most 10 $\mu$M, at most 100 $\mu$M, at most 1 mM, at most 10 mM, at most 50 mM, at most 100 mM, or at most 250 mM.

In some embodiments, the effectors are released to a predetermined concentration. In some embodiments, the effectors are released to a predetermined concentration within an encapsulation. In some embodiments, the predetermined concentration is at least 100 pM, at least 500 pM, at least 1 nM, at least 10 nM, at least 100 nM, at least 1 pM, at least 10 pM, at least 100 pM, at least 1 mM. at least 10 mM, at least 50 mM, at least 100 mM, or at least 250 mM. In some embodiments, the predetermined concentration is at most 100 pM, at most 500 pM, at most 1 nM, at most 10 nM, at most 100 nM, at most 1 $\mu$M, at most 10 $\mu$M, at most 100 $\mu$M, at most 1 mM, at most 10 mM, at most 50 mM, at most 100 mM, or at most 250 mM.

In some embodiments, effector molecules are released from scaffolds in a plurality of encapsulations. In some embodiments, the concentration of effector molecules released from scaffolds in a plurality of encapsulations is uniform among the encapsulations. In some embodiments, the concentration of effector molecules released from scaffolds in a plurality of encapsulations is substantially uniform among the encapsulations. In some embodiments, the concentration of effector molecules released from scaffolds in a plurality of encapsulations is at least 10%, 20%, 30%, 40%, 50%, 60%, 70%, 80%, or 90% identical in each individual encapsulation. In some embodiments, the concentration of effector molecules released from scaffolds in a plurality of encapsulations differs by no more than 2-fold, 3-fold, 4-fold, 5-fold, 6-fold, 7-fold, 8-fold, 9-fold, 10-fold, 15-fold, 20-fold, 50-fold, or 100-fold among each individual encapsulation of the plurality.

In some embodiments, the methods described herein comprise incubating the encapsulation for a period of time. In some embodiments, the methods comprise incubating the encapsulation for a period of time to allow the effector and sample to interact. In some embodiments, the encapsulations are incubated for a period of time to allow the effector and the sample to react. In some embodiments, the period of time is at least 1 millisecond, 1 second, 1 minute, at least 10 minutes, at least 1 hour, at least 4 hours, or at least 24 hours. In some embodiments, the period of time is at most 1 minutes, at most 10 minutes, at most 1 hour, at most for hours, or at most 24 hours. In some embodiments, the incubation time is measured after releasing effectors from a scaffold.

In some embodiments, the period of time is controlled by a residence time as the encapsulation travels through a microfluidic channel. In some embodiments, the residence time is controlled by a flow valve, a geometry of the microfluidic channel, the length of the microfluidic channel, by removing the encapsulations from the microfluidic channel, or combinations thereof.

The effectors of the methods and systems provided herein can be any type of molecule. In some embodiments, an effector is a biochemical, chemical, or biological moiety. In some embodiments, an effector is a cell, a protein, peptide, small molecule, small molecule fragment, or a nucleic acid. An effector is any molecule that is capable interacting with a target. The term "effector" is used broadly to encompass any moiety whose effect on a sample is being interrogated.

In some embodiments, the effectors have a handle that allows for attachment to a scaffold. A handle is a reactive functional group that can be used to tether the effector to an attachment site on a scaffold. This handle may be any functional group capable of forming a bond. Handles may include, without limitation, sulfhydryl groups, CLICK chemistry reagents, amino groups, carboxylate groups, or numerous other groups.

In some embodiments, effectors are comprised of individual subunits. These individual subunits may be joined using various chemical reactions to form the full effector. In some embodiments, iterative chemical processes are used to generate the effectors, similar to methodologies used in solid-phase peptide synthesis. Similar methods can be used to create non-peptide effectors, wherein a first reaction is performed to link two subunits, the two linked subunits are subjected to a second reaction to activate the linked subunits, and a third subunit is then attached, and so on. Any type of such an iterative chemical synthesis scheme may be employed to create the effectors used in the methods and systems provided herein.

In some embodiments, the effectors elicit a response from the target being interrogated. The response elicited can take any form and depends on the sample being interrogated. As a non-limiting example, when the sample comprises a cell, the response may be a change in expression pattern, apoptosis, expression of a particular molecule, or a morphological change in the cell. As another non-limiting example, when the sample comprises a protein, the effector may inhibit protein activity, enhance protein activity, alter protein folding, or measure protein activity.

In some embodiments, the effector is a protein. In some embodiments, the protein may be a naturally occurring or mutant protein. In some embodiments, the protein is a fragment of a naturally occurring protein. In some embodiments, the protein is an antibody. In some embodiments, the protein is an antibody-fragment. In some embodiments, the protein is an enzyme. In some embodiments, the protein is a recombinant protein. In some embodiments, the protein is a signaling protein, an enzyme, a binding protein, an antibody or antibody fragment, a structural protein, a storage protein, or a transport protein, or any mutant thereof In some embodiments, the effector is a peptide. In some embodiments, the effector is a non-natural peptide. In some embodiments, the effector is a polymer. In some embodiments, the peptide is 5 amino acids to 50 amino acids in length. In some embodiments, the peptide is 5 amino acids to 10 amino acids, 5 amino acids to 15 amino acids, 5 amino acids to 20 amino acids, 5 amino acids to 30 amino acids, 5 amino acids to 50 amino acids, 10 amino acids to 15 amino acids, 10 amino acids to 20 amino acids, 10 amino acids to 30 amino acids, 10 amino acids to 50 amino acids, 15 amino acids to 20 amino acids, 15 amino acids to 30 amino acids, 15 amino acids to 50 amino acids, 20 amino acids to 30 amino acids, 20 amino acids to 50 amino acids, or 30 amino acids to 50 amino acids in length. In some embodiments, the peptide is 5 amino acids, 10 amino acids, 15 amino acids, 20 amino acids, 30 amino acids, or 50 amino acids in length. In some embodiments, the peptide comprises at least 5 amino acids, 10 amino acids, 15 amino acids, 20 amino acids, or 30 amino acids. In some embodiments, the peptide comprises at most 10 amino acids, 15 amino acids, 20 amino acids, 30 amino acids, or 50 amino acids. In some embodiments, the peptide comprises unnatural amino acids. In some embodiments, the peptide comprises a non-peptide region. In some embodiments, the peptide is a cyclic peptide. In some embodiments, the peptide has a secondary structure that mimics a protein.

In some embodiments, the effector is a compound. In some embodiments, the compound is an organic molecule. In some embodiments, the compound is an inorganic molecule. In some embodiments, the compounds used as effectors contain organic and inorganic atoms. In some embodiments, the compound is a drug-like small molecule. In some embodiments, the compound is an organic compound. In some embodiments, the compound comprises one or more inorganic atoms, such as one or more metal atoms. In some embodiments, the effector is a small molecule. In some embodiments, the effector is a macro molecule.

In some embodiments, the compound is a completed chemical that is synthesized by connecting a plurality of chemical monomers to each other. In some embodiments, the effector is a pre-synthesized compound loaded onto a bead after synthesis.

In some embodiments, the compound is a small molecule fragment. Small molecule fragments are small organic molecules which are small in size and low in molecular weight. In some embodiments, the small molecule fragments are less than 500 Dalton (Da), less than 400 Da, less than 300 Da, less than 200 Da, or less than 100 Da in molecular weight (MW).

In some embodiments, the effector is an effector nucleic acid. In some embodiments, the effector nucleic acid is 5 nucleotides to 50 nucleotides in length. In some embodiments, the effector nucleic acid is 5 nucleotides to 10 nucleotides, 5 nucleotides to 15 nucleotides, 5 nucleotides to 20 nucleotides, 5 nucleotides to 30 nucleotides, 5 nucleotides to 50 nucleotides, 10 nucleotides to 15 nucleotides, 10 nucleotides to 20 nucleotides, 10 nucleotides to 30 nucleotides, 10 nucleotides to 50 nucleotides, 15 nucleotides to 20 nucleotides, 15 nucleotides to 30 nucleotides, 15 nucleotides to 50 nucleotides, 20 nucleotides to 30 nucleotides, 20 nucleotides to 50 nucleotides, or 30 nucleotides to 50 nucleotides in length. In some embodiments, the effector nucleic acid comprises 5 nucleotides, 10 nucleotides, 15 nucleotides, 20 nucleotides, 30 nucleotides, or 50 nucleotides. In some embodiments, the effector nucleic acid comprises at least 5 nucleotides, 10 nucleotides, 15 nucleotides, 20 nucleotides, or 30 nucleotides. In some embodiments, the effector nucleic acid is at most 10 nucleotides, 15 nucleotides, 20 nucleotides, 30 nucleotides, or 50 nucleotides in length. In some embodiments, the effector nucleic acid comprises unnatural nucleotides. In some embodiments, the nucleic acid is an aptamer. In some embodiments, the effector nucleic acid comprises DNA, RNA, or combinations thereof.

Enzyme Evolution Screen

The methods and systems herein are further useful for screening effector proteins for the possession of various activities. In these embodiments, the effector is a protein. A variety of mutant variants of a protein can be screened by linking plasmids or other nucleic acids coding for the expression of a protein to scaffolds. The "coding" referred to in this aspect refers to the genetic code, and "encoding" refers to an alternative strategy for elucidating the structure of the protein. In some instances, each nucleic acid has a barcode that is unique to the specific mutant protein which can be sequenced to reveal the mutations therein without conducting a full sequence read on the whole plasmid or other nucleic acid which codes for the protein. The barcode thus acts as its own encoding to delineate the structure and sequence of the protein without relying on the full coding sequence. In this aspect, a library of mutant proteins can be screened against samples with the components provided herein in encapsulation-based assays.

In a non-limiting example, a scaffold containing the nucleic acid encoding the protein of interest is encapsulated. The protein can then be expressed in the encapsulation using an expression system, such as any in vitro transcription/translation system. In some embodiments, one or more detection reagents can be added to the encapsulation for which the protein may exhibit a certain desired activity. In some instances, these detection reagents may be present during the expression of the protein or may be added later. These detection reagents may be used to assess any desired activity, including protein binding, enzymatic activity, or the detection reagents may be capable of probing protein structure. In some embodiments, each detection reagent comprises one or more chemical compounds or molecules, which the expressed protein (e.g., an enzyme of interest) can bind together. In some embodiments, at least two detection reagents are provided, each comprising a molecular probe, such that the expressed protein (e.g., an enzyme) can bind the molecular probes from the respective detection reagents together. In some embodiments, at least two detection reagents are provided, each comprising one or more chemical compounds, such that the expressed protein (e.g., an enzyme) can bind one or more of the chemical compounds from the respective detection reagents together. In some embodiments, the binding of the molecular probes or chemical compounds by the protein leads to the production of a signal. In some embodiments, the binding of the molecular probes or chemical compounds by the protein is a certain desired activity that leads to the production of a signal.

If the protein in an encapsulation has the certain desired activity, the activity can lead to the production of a signal. The signal can be any of the signals described herein. In some embodiments, the signal is a fluorescent signal created due to the ligation of two molecules of interest. In some embodiments, the molecules of interest have FRET pairings affixed to them, or fluorophore/quencher pairings affixed to them, or any other type of moieties that lead to a change in signal due to brining the two moieties into proximity to each other. In some embodiments, the two moieties are brought into proximity to each other due to the formation of a bond between the molecules of interest. The signal produced can then be detected, indicating that the protein being screened has the desired activity. The encapsulation can then be sorted based on the detectable signal, such as the signals presence, absence, or level. In some embodiments, the encoded effector is a protein and the encoding comprises a barcoded nucleic acid which further codes for the expression of the protein.

Provided herein are methods for screening nucleic acid encoded proteins against a sample. In some embodiments, the methods comprise providing an encapsulation comprising a nucleic acid encoding attached to a scaffold, the nucleic acid encoding comprising an encoding barcode and a coding section for the expression of an encoded effector protein. In some embodiments, the encapsulation further comprises an expression system for the production of the encoded protein. In some embodiments, the encoded protein is expressed within the encapsulation. In some embodiments, detection reagents are introduced to the encapsulation. In some embodiments the detection reagents are present in the encapsulation during protein expression. In some embodiments, the detection reagents produce a signal upon interaction with the encoded protein if the encoded protein has a certain activity. In some embodiments, the signal produced due to this interaction is measured. In some embodiments, the encapsulation is sorted based on the measurement of the signal. In some embodiments, the nucleic acid encoding is sequenced. In some embodiments, this nucleic acid encoding is sequenced by next-generation sequencing.

The nucleic acid encoding which comprises a coding section for the expression of the encoded protein may be of any form that allows for the expression to occur. In some embodiments, the nucleic acid encoding comprising a coding section for the expression of an encoded effector protein is a linear nucleic acid. In some embodiments, the nucleic acid encoding comprising a coding section for the expression of an encoded effector protein is a plasmid. In some embodiments, the nucleic acid encoding comprising a coding section for the expression of an encoded effector protein is single stranded. In some embodiments, the nucleic acid encoding comprising a coding section for the expression of an encoded effector protein is double stranded.

In some embodiments, the nucleic acid encoding comprising a coding section for the expression of an encoded effector protein comprises a barcode. In some embodiments, the barcode acts as the encoding for the encoded effector protein. In some embodiments, the barcode is upstream of the coding section for the expression of the encoded effector protein. In some embodiments, the barcode is downstream of the coding section for the expression of the encoded effector protein. In some embodiments, the nucleic acid encoding comprising a coding section for the expression of an encoded effector protein further comprises a sequencing primer. In some embodiments, the sequencing primer is upstream of the barcode. In some embodiments, the sequencing primer is downstream of the barcode.

In some embodiments, the effector is a nucleic acid encoded protein. In some embodiments, the corresponding nucleic acid encoding comprises a coding section for the expression of the encoded protein. In some embodiments, the nucleic acid encoded protein is an enzyme or mutant thereof. In some embodiments, the enzyme or mutant thereof is being screened for an enzymatic activity.

In some embodiments, the enzymatic activity is oxidation, reduction, ligation, polymerization, bond cleavage, bond formation, or isomerization. In some embodiments, the enzymatic activity is covalent bond formation. In some embodiments, the enzyme is an amino acid dehydrogenase, a natural amine dehydrogenase, an opine dehydrogenase, or an imine reductase. In some embodiments, the enzymatic activity is an enantiospecific activity. In some embodiments, the enzymatic activity is a stereospecific activity.

A variety of protein characteristics can be probed or screened for using the methods and systems provided herein. In some embodiments, the certain characteristic being screened for comprises an enzymatic activity, a binding ability, a catalytic activity, a physical property, an inhibitory activity, or a structure. In some embodiments, the certain characteristic being screened for comprises a binding ability. In some embodiments, the certain characteristic being screened for comprises a catalytic activity. In some embodiments, the certain characteristic being screened for comprises a physical property. In some embodiments, the certain characteristic being screened for comprises an inhibitory activity. In some embodiments, the certain characteristic being screened for comprises a secondary, tertiary, or quaternary structure.

In some embodiments, the enzymatic activity is the ability to form a bond between molecular probes from a first detection reagent and a second detection reagent. In some embodiments, the enzymatic activity comprises forming a bond between molecular probes from a first detection reagent and a second detection reagent. In some embodiments, the enzymatic activity is the ability to form a bond between one or more chemical compounds from a first detection reagent and a second detection reagent. In some embodiments, the enzymatic activity comprises forming a bond between one or more chemical compounds from a first detection reagent and a second detection reagent. In some embodiments, the bond is a covalent bond. In some embodiments, the bond is an irreversible covalent bond. In some embodiments, the first detection reagent and the second detection reagent exhibit a fluorescent signal when the molecules from the first and second detection reagents are bound together. In some embodiments, the first detection reagent and the second detection reagent exhibit a changed fluorescent signal when molecular probes from the first and second detection reagents are bound together compared to when the molecular probes from the first detection reagent and second detection reagent are not bound together. In some embodiments, the first detection reagent and the second detection reagent exhibit a fluorescent signal when the one or more chemical compounds from the first and second detection reagents are bound together. In some embodiments, the first detection reagent and the second detection reagent exhibit a changed fluorescent signal when one or more chemical compounds from the first and second detection reagents are bound together compared to when the one or more chemical compounds from the first detection reagent and second detection reagent are not bound together. In some embodiments, the fluorescent signal is due to fluorescence resonance energy transfer (FRET), bioluminescent resonance energy transfer (BRET), lanthanide chelate excite time resolved fluorescence resonance energy transfer (LANCE TR-FRET), or an amplified luminescent proximity homogeneous assay. In some embodiments, the first and second reagents are chemical compounds.

In some embodiments, the molecular probes from the first and second detection reagents comprise a FRET pair or a fluorophore/quencher pair. In some embodiments, the molecular probes from the first and second detection reagents comprise fluorophores or quenchers independently selected from 4-(4-dimethylaminophenyl azo), 5-((3-aminoethyl)amino)-1-napthalene sulfonic acid, 5-((2-aminoethyl)amino)-1-napthalene sulfonic acid (EDANS), 4-(dimethylaminoazo)benzene-4-carboxylic acid (DABCYL), and fluorescein-isothiocyanate (FITC), or derivatives thereof. In some embodiments, the FRET pair or fluorophore/quencher pair comprise different fluorophores. In some embodiments, the FRET pairing is duplicate copies of the same fluorophore.

In some embodiments, the one or more chemical compounds from the first and second detection reagents comprise a FRET pair or a fluorophore/quencher pair. In some embodiments, the one or more chemical compounds from the first and second detection reagents comprise fluorophores or quenchers independently selected from 4-(4-dimethylaminophenyl azo), 5-((3-aminoethyl)amino)-1-napthalene sulfonic acid, 5-((2-aminoethyl)amino)-1-napthalene sulfonic acid (EDANS), 4-(dimethylaminoazo)benzene-4-carboxylic acid (DABCYL), and fluorescein-isothiocyanate (FITC), or derivatives thereof. In some embodiments, the FRET pair or fluorophore/quencher pair comprise different fluorophores. In some embodiments, the FRET pairing is duplicate copies of the same fluorophore.

In some embodiments, the ability to form a bond is an imine reduction. In some embodiments, the imine reduction is enantiospecific. In some embodiments, the imine reduction is stereospecific. In some embodiments, the imine reduction favors an S-enantiomer at a substituted carbon adjacent to the reduced imine bond. In some embodiments, the imine reduction favors an R-enantiomer at a substituted carbon adjacent to the reduced imine bond. In some embodiments, the imine reduction is an intramolecular reaction. In some embodiments, the imine reduction is diastereospecific.

In some embodiments, a library of nucleic acid encoded proteins are screened against the sample. In some embodiments, the methods comprise performing any of the described screens against a library of nucleic acid encoded proteins, wherein the library of nucleic acid encoded proteins comprises a plurality of different mutant versions of the nucleic acid encoded protein. In some embodiments, each mutant version of the nucleic acid encoded protein is encoded by a unique barcode.

The methods and systems provided herein sometimes comprise the addition of detection reagents to the encapsulation. In some embodiments, the detection reagents are added by pico-injection. In some embodiments, the detection reagents are added by droplet merging. In some embodiments, the detection reagents are added before the signal is detected. In some embodiments, the detection reagents are added after the signal is detected. In some embodiments, the detection reagents facilitate the detection of the signal.

In some embodiments, the encapsulation further comprises a reporter enzyme. In some embodiments, the reporter enzyme reacts with another reagent to produce a functional readout. In some embodiments, a bond between the first and second molecular probes creates a new molecule that inhibits the reporter enzyme.

Additional reagents may also be used to add barcodes to nucleic acids of the sample or the encoding. In some embodiments, the additional reagents add a nucleic acid barcode to one or more contents of the encapsulation. In some embodiments, the nucleic acid barcode is added to the encoding. In some embodiments, the nucleic acid barcode is added to nucleic acids from the sample.

Encodings for Effectors

The effectors provided herein can be linked with encodings. In some embodiments, the effectors are linked with an encoding. In some instances, the encoding allows a user to determine the structure of the effector by determining a property of the encoding. Thus, each encoding moiety has a measurable property that, when measured, can be used to determine the structure of the effector which is encoded.

In some embodiments, the encoding is a nucleic acid. In some embodiments, the sequence of the nucleic acid provides information about the structure of the effector. In some embodiments, the encoding comprises a nucleic acid barcode. In some embodiments, the barcode is unique to a specific effector. In some embodiments, the encoding comprises a sequencing primer. In some embodiments, sequencing the nucleic acid encoding allows the user to ascertain the structure of the corresponding effector.

In some embodiments, the encoding is DNA. In some embodiments, the encoding is double stranded DNA. In some embodiments, the encoding is single stranded DNA. In some embodiments, the encoding is RNA. In some embodiments, the encoding is single stranded RNA. In some embodiments, the encoding is double stranded RNA.

In some embodiments, the encoding nucleic acid comprises at least 20 nucleotides, at least 40 nucleotides, at least 60 nucleotides, at least 80 nucleotides, at least 100 nucleotides, at least 200 nucleotides, or at least 500 nucleotides. In some embodiments, the encoding nucleic acid comprises 20 nucleotides to 100 nucleotides in length. In some embodiments, the encoding nucleic acid is 20 nucleotides to 40 nucleotides, 20 nucleotides to 60 nucleotides, 20 nucleotides to 80 nucleotides, 20 nucleotides to 100 nucleotides, 40 nucleotides to 60 nucleotides, 40 nucleotides to 80 nucleotides, 40 nucleotides to 100 nucleotides, 60 nucleotides to 80 nucleotides, 60 nucleotides to 100 nucleotides, or 80 nucleotides to 100 nucleotides in length. In some embodiments, the encoding nucleic acid comprises about 20 nucleotides, about 40 nucleotides, about 60 nucleotides, about 80 nucleotides, or about 100 nucleotides. In some embodiments, the encoding nucleic acid comprises at least 20 nucleotides, 40 nucleotides, 60 nucleotides, or 80 nucleotides. In some embodiments, the encoding nucleic acid is at most 40 nucleotides, 60 nucleotides, 80 nucleotides, or 100 nucleotides in length.

In some embodiments, the encoding is made up of individual subunits that encode a corresponding effector subunit. Consequently, an entire encoding can specify which individual subunits have been linked or combined to form the effector. In some embodiments, each subunit may comprise up to 5, 10, 15, 20, 25, 30, 40, 50, or more individual nucleotides. The full encoding sequence can comprise any number of these individual subunits. In some embodiments, the full encoding sequence comprises 1, 2, 3, 4, 5, 6, 7, 8, 9, 10, or more encoding subunits. These encoding subunits can be ligated together using many known methods, including enzymatic ligation, template-free synthesis, templated polymerase extension, chemical ligation, recombination, or solid phase nucleic acid synthesis techniques.

In some embodiments, the encoding is a molecular weight barcode. In some embodiments, the molecular weight barcode is at least 1,000, at least 5,000, at least 10,000, or at least 15,000 Daltons in molecular weight. In some embodiments, the molecular weight barcode is a peptide. In some embodiments, the molecular weight barcode peptide comprises 5 amino acids to 10 amino acids, 5 amino acids to 15 amino acids, 5 amino acids to 20 amino acids, 5 amino acids to 30 amino acids, 5 amino acids to 50 amino acids, 10 amino acids to 15 amino acids, 10 amino acids to 20 amino acids, 10 amino acids to 30 amino acids, 10 amino acids to 50 amino acids, 15 amino acids to 20 amino acids, 15 amino acids to 30 amino acids, 15 amino acids to 50 amino acids, 20 amino acids to 30 amino acids, 20 amino acids to 50 amino acids, or 30 amino acids to 50 amino acids. In some embodiments, the molecular weight barcode peptide comprises 5 amino acids, 10 amino acids, 15 amino acids, 20 amino acids, 30 amino acids, or 50 amino acids. In some embodiments, the molecular weight barcode peptide comprises at least 5 amino acids, 10 amino acids, 15 amino acids, 20 amino acids, or 30 amino acids. In some embodiments, the peptide comprises at most 10 amino acids, 15 amino acids, 20 amino acids, 30 amino acids, or 50 amino acids. In some embodiments, the molecular weight barcode peptides comprise unnatural amino acids.

In some embodiments, the encoding is loaded onto a scaffold. In some embodiments, the scaffold comprises a high loading of the encoding. In some embodiments, the scaffold comprises about 1,000,000 copies to about 50,000,000 copies of the encoding. In some embodiments, the scaffold comprises about 1,000,000 copies to about 2,000,000 copies, about 1,000,000 copies to about 5,000,000 copies, about 1,000,000 copies to about 10,000,000 copies, about 1,000,000 copies to about 15,000,000 copies, about 1,000,000 copies to about 20,000,000 copies, about 1,000,000 copies to about 50,000,000 copies, about 2,000,000 copies to about 5,000,000 copies, about 2,000,000 copies to about 10,000,000 copies, about 2,000,000 copies to about 15,000,000 copies, about 2,000,000 copies to about 20,000,000 copies, about 2,000,000 copies to about 50,000,000 copies, about 5,000,000 copies to about 10,000,000 copies, about 5,000,000 copies to about 15,000,000 copies, about 5,000,000 copies to about 20,000,000 copies, about 5,000,000 copies to about 50,000,000 copies, about 10,000,000 copies to about 15,000,000 copies, about 10,000,000 copies to about 20,000,000 copies, about 10,000,000 copies to about 50,000,000 copies, about 15,000,000 copies to about 20,000,000 copies, about 15,000,000 copies to about 50,000,000 copies, or about 20,000,000 copies to about 50,000,000 copies of the encoding. In some embodiments, the scaffold comprises about 1,000,000 copies, about 2,000,000 copies, about 5,000,000 copies, about 10,000,000 copies, about 15,000,000 copies, about 20,000,000 copies, or about 50,000,000 copies of the encoding. In some embodiments, the scaffold comprises at least about 1,000,000 copies, about 2,000,000 copies, about 5,000,000 copies, about 10,000,000 copies, about 15,000,000 copies, or about 20,000,000 copies. In some embodiments, the scaffold comprises at most about 2,000,000 copies, about 5,000,000 copies, about 10,000,000 copies, about 15,000,000 copies, about 20,000,000 copies, or about 50,000,000 copies of the encoding.

In some embodiments, the encoding is nucleic acid comprising a barcode sequence. In some embodiments, the encoding comprises a DNA barcode. In some embodiments, there is at least 1 DNA barcode per bead, at least 10 copies of the DNA barcode per bead, at least 100 copies, at least 1,000 copies, at least 100,000 copies, at least 1 million copies, or at least 10 million copies of the DNA barcode per bead. In some embodiments, the scaffold comprises at least 10 million copies of the DNA barcode per bead.

In some embodiments, DNA barcodes are used to identify a scaffold. In some instances, the scaffold is a bead. In some instances, only 1 DNA barcode out of 10 million DNA barcodes is required to identify the bead. In some instances, only 5 DNA barcodes, 10 DNA barcodes, 20 DNA barcodes, 50 DNA barcodes, 100 DNA barcodes, 1000 DNA barcodes, 10,000 DNA barcodes, 100,000 DNA barcodes, or 1 million DNA barcodes out of 10 million barcodes is required to identify the bead.

Sample

Samples of any type can be utilized with the methods and systems provided herein. In some embodiments, the sample is a biological sample. In some embodiments, the sample comprises one or more cells, one or more proteins, one or more enzymes, one or more nucleic acids, one or more cellular lysates, or one or more tissue extracts.

In some embodiments, the sample is a cell. In some embodiments, the cell is a eukaryotic cell. In some embodiments, the cell is a prokaryotic cell. In some embodiments, the cell is a mammalian cell. In some embodiments, the cell is a bacterial cell. In some embodiments, the cell is a human cell. In some embodiments, the cell is a cancer cell. In some embodiments, the cell is SH-SY5Y, Human neuroblastoma; Hep G2, Human Caucasian hepatocyte carcinoma; 293 (also known as HEK 293), Human Embryo Kidney; RAW 264.7, Mouse monocyte macrophage; HeLa, Human cervix epithelioid carcinoma; MRC-5 (PD 19), Human fetal lung; A2780, Human ovarian carcinoma; CACO-2, Human Caucasian colon adenocarcinoma; THP 1, Human monocytic leukemia; A549, Human Caucasian lung carcinoma; MRC-5 (PD 30), Human fetal lung; MCF7, Human Caucasian breast adenocarcinoma; SNL 76/7, Mouse SIM strain embryonic fibroblast; C2C12, Mouse C3H muscle myoblast; Jurkat E6.1, Human leukemic T cell lymphoblast; U937, Human Caucasian histiocytic lymphoma; L929, Mouse C3H/An connective tissue; 3T3 L1, Mouse Embryo; HL60, Human Caucasian promyelocytic leukaemia; PC-12, Rat adrenal phaeochromocytoma; HT29, Human Caucasian colon adenocarcinoma; OE33, Human Caucasian oesophageal carcinoma; OE19, Human Caucasian oesophageal carcinoma; NIH 3T3, Mouse Swiss NIH embryo; MDA-MB-231, Human Caucasian breast adenocarcinoma; K562, Human Caucasian chronic myelogenous leukemia; U-87 MG, Human glioblastoma astrocytoma; MRC-5 (PD 25), Human fetal lung; A2780cis, Human ovarian carcinoma; B9, Mouse B cell hybridoma; CHO-K1, Hamster Chinese ovary; MDCK, Canine Cocker Spaniel kidney; 1321N1, Human brain astrocytoma; A431, Human squamous carcinoma; ATDC5, Mouse 129 teratocarcinoma AT805 derived; RCC4 PLUS VECTOR ALONE, Renal cell carcinoma cell line RCC4 stably transfected with an empty expression vector, pcDNA3, conferring neomycin resistance; HUVEC (5200-05n), Human Pre-screened Umbilical Vein Endothelial Cells (HUVEC); neonatal; Vero, Monkey African Green kidney; RCC4 PLUS VHL, Renal cell carcinoma cell line RCC4 stably transfected with pcDNA3-VHL; Fao, Rat hepatoma; J774A.1, Mouse BALB/c monocyte macrophage; MC3T3-E1, Mouse C57BL/6 calvaria; J774.2, Mouse BALB/c monocyte macrophage; PNT1A, Human post pubertal prostate normal, immortalised with SV40; U-2 OS, Human Osteosarcoma; HCT 116, Human colon carcinoma; MA104, Monkey African Green kidney; BEAS-2B, Human bronchial epithelium, normal; NB2-11, Rat lymphoma; BHK 21 (clone 13), Hamster Syrian kidney; NSO, Mouse myeloma; Neuro 2a, Mouse Albino neuroblastoma; SP2/0-Ag14, Mouse x Mouse myeloma, non-producing; T47D, Human breast tumor; 1301, Human T-cell leukemia; MDCK-II, Canine Cocker Spaniel Kidney; PNT2, Human prostate normal, immortalized with SV40; PC-3, Human Caucasian prostate adenocarcinoma; TF1, Human erythroleukaemia; COS-7, Monkey African green kidney, SV40 transformed; MDCK, Canine Cocker Spaniel kidney; HUVEC (200-05n), Human Umbilical Vein Endothelial Cells (HUVEC); neonatal; NCI-H322, Human Caucasian bronchioalveolar carcinoma; SK.N.SH, Human Caucasian neuroblastoma; LNCaP.FGC, Human Caucasian prostate carcinoma; OE21, Human Caucasian oesophageal squamous cell carcinoma; PSN1, Human pancreatic adenocarcinoma; ISHIKAWA, Human Asian endometrial adenocarcinoma; MFE-280, Human Caucasian endometrial adenocarcinoma; MG-63, Human osteosarcoma; RK 13, Rabbit kidney, BVDV negative; EoL-1 cell, Human eosinophilic leukemia; VCaP, Human Prostate Cancer Metastasis; tsA201, Human embryonal kidney, SV40 transformed; CHO, Hamster Chinese ovary; HT 1080, Human fibrosarcoma; PANC-1, Human Caucasian pancreas; Saos-2, Human primary osteogenic sarcoma; Fibroblast Growth Medium (116K-500), Fibroblast Growth Medium Kit; ND7/23, Mouse neuroblastoma x Rat neuron hybrid; SK-0V-3, Human Caucasian ovary adenocarcinoma; COV434, Human ovarian granulosa tumor; Hep 3B, Human hepatocyte carcinoma; Vero (WHO), Monkey African Green kidney; Nthy-ori 3-1, Human thyroid follicular epithelial; U373 MG (Uppsala), Human glioblastoma astrocytoma; A375, Human malignant melanoma; AGS, Human Caucasian gastric adenocarcinoma; CAKI 2, Human Caucasian kidney carcinoma; COLO 205, Human Caucasian colon adenocarcinoma; COR-L23, Human Caucasian lung large cell carcinoma; IM R 32, Human Caucasian neuroblastoma; QT 35, Quail Japanese fibrosarcoma; WI 38, Human Caucasian fetal lung; HMVII, Human vaginal malignant melanoma; HT55, Human colon carcinoma; TK6, Human lymphoblast, thymidine kinase heterozygote; SP2/0-AG14 (AC-FREE), Mouse x mouse hybridoma non-secreting, serum-free, animal component (AC) free; AR42J, or Rat exocrine pancreatic tumor, or any combination thereof In some embodiments, the sample is a protein. In some embodiments, the sample is a recombinant protein. In some embodiments, the sample is a mutant protein. In some embodiments, the sample is an enzyme. In some embodiments, the sample is a mutant enzyme. In some embodiments, the enzyme is a protease, a hydrolase, a kinase, a recombinase, a reductase, a dehydrogenase, an isomerase, a synthetase, an oxidoreductase, a transferase, a lyase, a ligase, or any mutant thereof.

In some embodiments, the sample is a single cell. In some embodiments, sample is 2 or more cells. In some embodiments, the sample is at least 2, at least 3, at least 4, at least 5, at least 10, at least 100, at least 1000, or at least 10000 cells.

In some embodiments, the cells comprise transfected nucleic acids. In some embodiments, the cells comprise stably integrated nucleic acids.

Ion Channel Screen

In some embodiments, the cells comprise ion channels. In some embodiments, the ion channels are endogenous to the cells. In some embodiments, the ion channels are non-endogenous to the cells. In some embodiments, the ion channels are mutant ion channels. In some embodiments, the ion channels comprise a mutation. In some embodiments, the mutation sensitizes the ion channel to optical stimulation. In some embodiments, the optical stimulation is stimulation with electromagnetic radiation. In some embodiments, the optical stimulation is stimulation with visible light.

In some embodiments, the methods comprise stimulating ion channels. Stimulating ion channels may comprise activating or deactivating an ion channel. In some embodiments, the ion channels are stimulated by electrostimulation, optical stimulation, or chemical stimulation. In some embodiments, the stimulation is electrostimulation. In some embodiments, electrostimulation comprises delivering an electric field to an ion channel. In some embodiments, the electrostimulation is performed by an electrode. In some embodiments, the electrostimulation is performed by an electrode on a microfluidic device. In some embodiments, the electrode is within a flow path of a microfluidic device. In some embodiments, the electrode is within a flow path of an encapsulation. In some embodiments, the electrode is outside of a flow path of a microfluidic device. In some embodiments, the electrode is outside a flow path of an encapsulation.

In some embodiments, provided herein, is a method for screening ion channel modulators. In some embodiments, the ion channel modulator is an inhibitor. In some embodiments, the ion channel modulator is an agonist. In some embodiments, the method comprises providing an encapsulation. In some embodiments, the encapsulation comprises a cell expressing an ion channel protein. In some embodiments, the encapsulation comprises a set of voltage sensor probes. In some embodiments, the encapsulation comprises an encoded effector and its corresponding encoding. In some embodiments, the encapsulation comprises a cell expressing an ion channel protein, a set of voltage sensor probes, and an encoded effector and its corresponding encoding. In some embodiments, the method comprises stimulating an ion channel of the cell. In some embodiments, the method comprises detecting a signal from at least one member of the set of voltage sensor probes. In some embodiments, the method comprises sorting the encapsulation. In some embodiments, the method comprises sorting the encapsulation based on the presence, absence, level, or change of the signal. In some embodiments, the method comprises measuring a property of the encoding to ascertain the identity of the effector. In some embodiments, the encoding is a nucleic acid and the property measured to ascertain the identity of the effector is the nucleic acid sequence of the encoding.

The ion channel protein may be any such protein. In some embodiments, the ion channel protein comprises a sodium, calcium, chloride, proton, or potassium ion channel protein. In some embodiments, the ion channel protein comprises a sodium ion channel protein. In some embodiments, the ion channel protein comprises a potassium ion channel protein. In some embodiments, the ion channel protein comprises a calcium ion channel protein. In some embodiments, the ion channel protein comprises a chloride ion channel protein. In some embodiments, the ion channel protein comprises a proton ion channel protein.

In some embodiments, the ion channel protein comprises a voltage gated ion channel protein. Any voltage gated ion channel protein may be used. In some embodiments, the voltage gated ion channel protein comprises a sodium, calcium, chloride, proton, or potassium voltage gated ion channel protein. In some embodiments, the voltage gated ion channel protein comprises a voltage gated calcium ion channel protein. In some embodiments, the voltage gated ion channel protein comprises a voltage gated sodium ion channel protein. In some embodiments, the voltage gated ion channel protein comprises a voltage gated potassium ion channel protein. In some embodiments, the voltage gated ion channel protein comprises a voltage gated chloride ion channel protein. In some embodiments, the voltage gated ion channel protein comprises a voltage gated proton ion channel protein.

In some embodiments, the ion channel protein is endogenous to the cell. In some embodiments, the ion channel protein is an exogenous ion channel protein. In some embodiments, the ion channel protein is incorporated into the cell through a vector. In some embodiments, the ion channel protein stably expressed in the cell through the addition of a vector. In some embodiments, a gene encoding the ion channel protein is transiently transfected into the cell. In some embodiments, a gene encoding the ion channel is stably incorporated into the cell. In some embodiments, the ion channel protein is overexpressed.

In some embodiments, the voltage gated ion channel protein comprises a voltage-gated calcium channel protein (VGCC). Any VGCC or any mutant, fragment, or conjugate thereof may be used. In some embodiments, the VGCC comprises an L-type calcium channel (e.g. $Ca_v1.1$, $Ca_v1.2$, $Ca_v1.3$, or $Ca_v1.4$), a P-type calcium channel (e.g. $Ca_v2.1$), an N-type calcium channel (e.g. $Ca_v2.2$), an R-type calcium channel (e.g. $Ca_v2.3$), or a T-type calcium channel (e.g. $Ca_v3.1$, $Ca_v3.2$, or $Ca_v3.3$), or any mutant, fragment, or conjugate thereof. In some embodiments, the VGCC comprises an L-type calcium channel. In some embodiments, the VGCC comprises a P-type calcium channel. In some embodiments, the VGCC comprises an N-type calcium channel. In some embodiments, the VGCC comprises an R-type calcium channel. In some embodiments, the VGCC comprises a T-type calcium channel.

In some embodiments, the ion channel protein comprises a voltage gated sodium channel protein ($Na_v$) or any mutant, fragment, or conjugate thereof. Any voltage gated sodium channel protein may be used. In some embodiments, the voltage gated sodium channel protein comprises $Na_v1.1$, $Na_v1.2$, $Na_v1.3$, $Na_v1.4$, $Na_v1.5$, $Na_v1.6$, $Na_v1.7$, $Na_v1.8$, $Na_v1.9$, $Na_v2.1$, $Na_v2.2$, $Na_v2.3$, or $Na_v3.1$, or any mutant, fragment, or conjugate thereof.

In some embodiments, the ion channel protein comprises a voltage gated potassium channel protein (VGKC) or any mutant, fragment, or conjugate thereof. Any VGKC protein may be used. The VGKC protein may have any alpha subunit. In some embodiments, the VGKC comprises a delayed rectifier potassium channel (e.g. $K_v1.1$, $K_v1.2$, $K_v1.3$, $K_v1.5$, $K_v1.6$, $K_v1.7$, $K_v1.8$, $K_v2.1$, $K_v2.1$, $K_v3.1$, $K_v3.2$, $K_v7.1$, $K_v7.2$, $K_v7.3$, $K_v7.4$, $K_v7.5$, or $K_v10.1$). In some embodiments, the VGKC comprises an A-type potassium channel (E.g. $K_v1.4$, $K_v3.3$, $K_v3.4$, $K_v4.1$, $K_v4.1$, $K_v4.2$, or $K_v4.3$). In some embodiments, the VGKC comprises an outward-rectifying potassium channel (e.g. $K_v10.2$). In some embodiments, the VGKC comprises an inwardly-rectifying potassium channel (e.g. an ether-a-go-go potassium channel, such as $K_v11.1$, $K_v11.2$, or $K_v11.3$). In some embodiments, the VGKC comprises a slowly activating potassium channel (e.g. $K_v12.1$, $K_v12.2$, or $K_v12.3$). In some embodiments, the VGKC comprises a modifier/silencer potassium channel (e.g. $K_v5.1$, $K_v6.1$, $K_v6.2$, $K_v6.3$, $K_v6.4$, $K_v8.1$, $K_v8.2$, $K_v9.1$, $K_v9.2$, or $K_v9.3$). Any mutant, fragment, or conjugate of any of the preceding potassium channels may be used.

In some embodiments, the ion channel protein comprises a voltage gated chloride channel protein. Any voltage gated chloride channel protein may be used. In some embodiments, the voltage gated chloride channel protein is from the CLCN family (e.g. CLCN1, CLCN2, CLCN3, CLCN4, CLCN5, CLCN6, CLCN7, CLCNKA, CLCNKB). In some embodiments, the voltage gated chloride channel protein is from the epithelial chloride channel family (e.g. CLCA1, CLCA2, CLCA3, or CLCA4). In some embodiments, the voltage gated chloride channel protein is from the chloride intracellular channel (CLIC) family (e.g. CLIC1, CLIC2, CLIC3, CLIC4, CLIC5, or CLIC6).

In some embodiments, the ion channel protein comprises a voltage gated proton channel. Any voltage gated proton channel protein may be used. In some embodiments, the voltage gated proton channel comprise voltage-gated hydrogen channel 1 protein.

In some embodiments, the ion channel protein comprises a channelrhodopsin or any mutant, fragment, or conjugate thereof. In some embodiments, wherein the channelrhodopsin is ChrimsonR or any mutant, fragment, or conjugate thereof. In some embodiments, the channelrhodopsin is a ChrimsonR mutant comprising a K176R mutation, S267M mutation, Y268F mutation, Y261F mutation, or any combination thereof.

The set of voltage sensor probes may comprise any suitable probe. In some embodiments, the set of voltage sensor probes comprise a FRET pair. In some embodiments, the set of voltage sensor probes comprises a voltage-sensitive oxonol, a fluorescent coumarin, or both. In some embodiments, the set of voltage sensor probes comprises a voltage-sensitive oxonol. In some embodiments, the set of voltage sensor probes comprises a fluorescent coumarin. In some embodiments, the set of voltage sensor probes comprises a DiSBAC compound, a coumarin phospholipid, or any combination or derivative thereof. In some embodiments, the set of voltage sensor probes comprises a DiSBAC compound. In some embodiments, the set of voltage sensor probes comprises a coumarin phospholipid. the set of voltage sensors comprises a $DiSBAC_2$, $DiSBAC_4$, $DiSBAC_6$, CC1-DMPE, CC2-DMPE, or any combination or derivative thereof. In some embodiments, the set of voltage sensors comprises a $DiSBAC_2(3)$, $DiSBAC_2(5)$, $DiSBAC_4(3)$, DiS- BAC$_4$(5), DiSBAC$_6$(3), DiSBAC$_6$(5), CC-DMPE, CC2-DMPE, or any combination or derivative thereof. In some embodiments, the set of voltage sensors comprises DiSBAC$_6$ and CC2-DMPE.

The encapsulation may further comprise a voltage assay background suppression compound. In some embodiments, the voltage assay background suppression compound comprises VABSC-1.

In some embodiments, the stimulation is optical stimulation. In some embodiments, the optical stimulation is electromagnetic radiation. In some embodiments, the optical stimulation is visible light. In some embodiments, the optical stimulation is UV, VIS, or near-infrared radiation. In some embodiments, the optical stimulation is UV radiation. In some embodiments, the optical stimulation is visible light. In some embodiments, the optical stimulation is near-infrared radiation.

In some embodiments, the wavelength of light for optical stimulation is about 660 nm. In some embodiments, the wavelength of light for optical stimulation is about 100 nm to about 1,000 nm. In some embodiments, the wavelength of light for optical stimulation is about 100 nm to about 200 nm, about 100 nm to about 400 nm, about 100 nm to about 450 nm, about 100 nm to about 500 nm, about 100 nm to about 550 nm, about 100 nm to about 600 nm, about 100 nm to about 650 nm, about 100 nm to about 700 nm, about 100 nm to about 750 nm, about 100 nm to about 800 nm, about 100 nm to about 1,000 nm, about 200 nm to about 400 nm, about 200 nm to about 450 nm, about 200 nm to about 500 nm, about 200 nm to about 550 nm, about 200 nm to about 600 nm, about 200 nm to about 650 nm, about 200 nm to about 700 nm, about 200 nm to about 750 nm, about 200 nm to about 800 nm, about 200 nm to about 1,000 nm, about 400 nm to about 450 nm, about 400 nm to about 500 nm, about 400 nm to about 550 nm, about 400 nm to about 600 nm, about 400 nm to about 650 nm, about 400 nm to about 700 nm, about 400 nm to about 750 nm, about 400 nm to about 800 nm, about 400 nm to about 1,000 nm, about 450 nm to about 500 nm, about 450 nm to about 550 nm, about 450 nm to about 600 nm, about 450 nm to about 650 nm, about 450 nm to about 700 nm, about 450 nm to about 750 nm, about 450 nm to about 800 nm, about 450 nm to about 1,000 nm, about 500 nm to about 550 nm, about 500 nm to about 600 nm, about 500 nm to about 650 nm, about 500 nm to about 700 nm, about 500 nm to about 750 nm, about 500 nm to about 800 nm, about 500 nm to about 1,000 nm, about 550 nm to about 600 nm, about 550 nm to about 650 nm, about 550 nm to about 700 nm, about 550 nm to about 750 nm, about 550 nm to about 800 nm, about 550 nm to about 1,000 nm, about 600 nm to about 650 nm, about 600 nm to about 700 nm, about 600 nm to about 750 nm, about 600 nm to about 800 nm, about 600 nm to about 1,000 nm, about 650 nm to about 700 nm, about 650 nm to about 750 nm, about 650 nm to about 800 nm, about 650 nm to about 1,000 nm, about 700 nm to about 750 nm, about 700 nm to about 800 nm, about 700 nm to about 1,000 nm, about 750 nm to about 800 nm, about 750 nm to about 1,000 nm, or about 800 nm to about 1,000 nm. In some embodiments, the wavelength of light for optical stimulation is about 100 nm, about 200 nm, about 400 nm, about 450 nm, about 500 nm, about 550 nm, about 600 nm, about 650 nm, about 700 nm, about 750 nm, about 800 nm, or about 1,000 nm. In some embodiments, the wavelength of light for optical stimulation is at least about 100 nm, about 200 nm, about 400 nm, about 450 nm, about 500 nm, about 550 nm, about 600 nm, about 650 nm, about 700 nm, about 750 nm, or about 800 nm. In some embodiments, the wavelength of light for optical stimulation is at most about 200 nm, about 400 nm, about 450 nm, about 500 nm, about 550 nm, about 600 nm, about 650 nm, about 700 nm, about 750 nm, about 800 nm, or about 1,000 nm.

In some embodiments, the intensity of light for optical stimulation is about 500 mJ/s/cm$^2$. In some embodiments, intensity of light for optical stimulation is about 50 to about 1,000 mJ/S/cm$^2$. In some embodiments, intensity of light for optical stimulation is about 50 to about 100, about 50 to about 250, about 50 to about 500, about 50 to about 750, about 50 to about 1,000, about 100 to about 250, about 100 to about 500, about 100 to about 750, about 100 to about 1,000, about 250 to about 500, about 250 to about 750, about 250 to about 1,000, about 500 to about 750, about 500 to about 1,000, or about 750 to about 1,000 mJ/S/cm$^2$. In some embodiments, intensity of light for optical stimulation is about 50, about 100, about 250, about 500, about 750, or about 1,000 mJ/S/cm$^2$. In some embodiments, intensity of light for optical stimulation is at least about 50, about 100, about 250, about 500, or about 750. In some embodiments, intensity of light for optical stimulation is at most about 100, about 250, about 500, about 750, or about 1,000 mJ/S/cm$^2$.

In some embodiments, the frequency of optical stimulation is about 10 Hz. In some embodiments, the frequency of optical stimulation is about 1 Hz to about 100 Hz. In some embodiments, the frequency of optical stimulation is about 1 Hz to about 2 Hz, about 1 Hz to about 5 Hz, about 1 Hz to about 10 Hz, about 1 Hz to about 20 Hz, about 1 Hz to about 50 Hz, about 1 Hz to about 100 Hz, about 2 Hz to about 5 Hz, about 2 Hz to about 10 Hz, about 2 Hz to about 20 Hz, about 2 Hz to about 50 Hz, about 2 Hz to about 100 Hz, about 5 Hz to about 10 Hz, about 5 Hz to about 20 Hz, about 5 Hz to about 50 Hz, about 5 Hz to about 100 Hz, about 10 Hz to about 20 Hz, about 10 Hz to about 50 Hz, about 10 Hz to about 100 Hz, about 20 Hz to about 50 Hz, about 20 Hz to about 100 Hz, or about 50 Hz to about 100 Hz. In some embodiments, the frequency of optical stimulation is about 1 Hz, about 2 Hz, about 5 Hz, about 10 Hz, about 20 Hz, about 50 Hz, or about 100 Hz. In some embodiments, the frequency of optical stimulation is at least about 1 Hz, about 2 Hz, about 5 Hz, about 10 Hz, about 20 Hz, or about 50 Hz. In some embodiments, the frequency of optical stimulation is at most about 2 Hz, about 5 Hz, about 10 Hz, about 20 Hz, about 50 Hz, about 100 Hz, about 150 Hz, or about 200 Hz.

In some embodiments, stimulation is chemical stimulation. In some embodiments, the chemical stimulation comprises contacting the ion channel with a toxin. In some embodiments, the toxin is an ion channel toxin. In some embodiments, the toxin is added to an encapsulation by pico-injection. In some embodiments, the toxin is added to an encapsulation by conditional pico-injection. In some embodiments, chemical stimulation comprises contacting the ion channel with an ion channel toxin. In some embodiments, the ion channel toxin comprises veratridine, OD-1, or another ion channel toxin, or any combination thereof. In some embodiments, the ion channel toxin comprises veratridine. In some embodiments, the ion channel toxin comprises OD-1.

In some embodiments, the ion channel toxin as added to the encapsulation by pico-injection, droplet fusion, or through a pre-arranged architecture of a microfluidic device which contains the encapsulation. In some embodiments, the ion channel toxin as added to the encapsulation by pico-injection. In some embodiments, the ion channel toxin as added to the encapsulation by droplet fusion. In some embodiments, the ion channel toxin as added to the encapsulation through a pre-arranged architecture of a microfluidic device which contains the encapsulation.

The ion channel may be stimulated by electrical stimulation. In some embodiments, stimulating the ion channel is performed by at least one electrode. In some embodiments, the at least one electrode is in the flow path of the encapsulation. In some embodiments, the at least one electrode is outside the flow path of the encapsulation. In some embodiments, electrostimulation is performed by non-contact electrodes to generate electric fields, dielectrophoretic forces, or embedded metal-contact electrodes. In some embodiments, electrostimulation is performed by non-contact electrodes to generate electric fields. In some embodiments, electrostimulation is performed dielectrophoretic forces. In some embodiments, electrostimulation is performed by embedded metal-contact electrodes.

In some embodiments, electrostimulation is dictated by geometry of a microfluidic device containing the encapsulation. In some embodiments, the frequency of electrostimulation is about 10 Hz. In some embodiments, the frequency of electrostimulation is about 1 Hz to about 100 Hz. In some embodiments, the frequency of electrostimulation is about 1 Hz to about 2 Hz, about 1 Hz to about 5 Hz, about 1 Hz to about 10 Hz, about 1 Hz to about 20 Hz, about 1 Hz to about 50 Hz, about 1 Hz to about 100 Hz, about 2 Hz to about 5 Hz, about 2 Hz to about 10 Hz, about 2 Hz to about 20 Hz, about 2 Hz to about 50 Hz, about 2 Hz to about 100 Hz, about 5 Hz to about 10 Hz, about 5 Hz to about 20 Hz, about 5 Hz to about 50 Hz, about 5 Hz to about 100 Hz, about 10 Hz to about 20 Hz, about 10 Hz to about 50 Hz, about 10 Hz to about 100 Hz, about 20 Hz to about 50 Hz, about 20 Hz to about 100 Hz, or about 50 Hz to about 100 Hz. In some embodiments, the frequency of electrostimulation is about 1 Hz, about 2 Hz, about 5 Hz, about 10 Hz, about 20 Hz, about 50 Hz, or about 100 Hz. In some embodiments, the frequency of electrostimulation is at least about 1 Hz, about 2 Hz, about 5 Hz, about 10 Hz, about 20 Hz, or about 50 Hz. In some embodiments, the frequency of electrostimulation is at most about 2 Hz, about 5 Hz, about 10 Hz, about 20 Hz, about 50 Hz, about 100 Hz, about 150 Hz, or about 200 Hz.

The stimulation of the ion channels can be performed numerous times, or only a single time. In some embodiments, the ion channel of the cell is stimulated about 1 time to about 20 times. In some embodiments, the ion channel of the cell is stimulated about 1 time to about 2 times, about 1 time to about 3 times, about 1 time to about 5 times, about 1 time to about 7 times, about 1 time to about 10 times, about 1 time to about 20 times, about 2 times to about 3 times, about 2 times to about 5 times, about 2 times to about 7 times, about 2 times to about 10 times, about 2 times to about 20 times, about 3 times to about 5 times, about 3 times to about 7 times, about 3 times to about 10 times, about 3 times to about 20 times, about 5 times to about 7 times, about 5 times to about 10 times, about 5 times to about 20 times, about 7 times to about 10 times, about 7 times to about 20 times, or about 10 times to about 20 times. In some embodiments, the ion channel of the cell is stimulated about 1 time, about 2 times, about 3 times, about 5 times, about 7 times, about 10 times, or about 20 times. In some embodiments, the ion channel of the cell is stimulated at least about 1 time, about 2 times, about 3 times, about 5 times, about 7 times, or about 10 times. In some embodiments, the ion channel of the cell is stimulated at most about 2 times, about 3 times, about 5 times, about 7 times, about 10 times, or about 20 times. In some embodiments, the ion channel is stimulated a single time. In embodiments where stimulation occurs by the addition of an ion channel toxin or other ion channel inhibitor, the ion channel toxin need only be added at a single step.

In some embodiments, provided herein, are methods for stimulating an ion channel. In some embodiments, the methods comprise providing a cell in an encapsulation. In some embodiments, the methods comprise stimulating an ion channel of the cell by electrostimulation, optical stimulation, or chemical stimulation. In some embodiments, the methods comprise detecting a signal from the cell by capturing images of the cell in the encapsulation.

In some embodiments, the method comprises detecting a signal from at least one member of the set of voltage sensor probes. In some embodiments, the signal is electromagnetic radiation. In some embodiments, the electromagnetic radiation is luminescence or fluorescence. In some embodiments, the electromagnetic radiation is fluorescence. In some embodiments, the electromagnetic radiation is emitted due to a FRET interaction. In some embodiments, the signal is an increase, decrease, or change in electromagnetic radiation as compared to an identical encapsulation without the encoded effector. In some embodiments, the signal is an increase, decrease, or change in electromagnetic radiation as compared to the encapsulation before the stimulation of the ion channel.

In some embodiments, the method comprises the step of sorting the encapsulation based on the presence, absence, level, or change of the signal. In some embodiments, the method further comprises measuring a property of the encoding to ascertain the identity of the effector.

In some embodiments, the sample is a protein. In some embodiments, the sample is a recombinant protein. In some embodiments, the sample is a mutant protein. In some embodiments, the sample is an enzyme. In some embodiments, the sample is a mutant enzyme. In some embodiments, the enzyme is a protease, a hydrolase, a kinase, a recombinase, a reductase, a dehydrogenase, an isomerase, a synthetase, an oxidoreductase, a transferase, a lyase, a ligase, or any mutant thereof.

The sample may further comprise a nucleic acid which codes for the expression of a target protein and the target protein itself. These sample nucleic acids may be barcoded. The presence of a barcode on the nucleic acids may allow for the transfer of the barcode to nucleic acid encodings of effectors that are co-encapsulated with the target protein and the nucleic acid which codes for the expression of the target protein. This in turn allows for a determination of which combinations of effectors were encapsulated together and produced a synergistic effect against the target protein. Such methods can be used to conduct fragment-based screens to identify lead molecules of interest in further drug discovery.

Fragment Based Screen and Enzyme Evolution Method

In some embodiments, the sample is a target protein and a nucleic acid coding the expression of a target protein. In some embodiments, the nucleic acid coding the expression of the target protein further comprises a barcode region. In some embodiments, the nucleic acid coding the expression of a target protein is bound to a scaffold. In some embodiments, the barcode from the nucleic acid that codes for the target protein can be transferred to nucleic acid encodings of effectors. In some embodiments, the sample target protein and nucleic acid coding the expression of the target protein are co-encapsulated with an in vitro transcription/translation system. In some embodiments, the in vitro transcription/translation system is used to amplify the target protein.

In some embodiments, two or more nucleic acid encoded effectors with their corresponding nucleic acid encodings are introduced into the encapsulation comprising the target protein and nucleic acid encoding the expression of the target protein. In some embodiments, the barcode is transferred to the nucleic acids encoding the effectors. In some embodiments, the encapsulation is incubated for a period of time to allow the two or more effectors to interact with the target protein. In some embodiments, a signal is produced by the interaction of the two or more effectors and the target protein. In some embodiments, the encapsulation is sorted based on the measurement of the signal. In some embodiments, the nucleic acid encodings which now comprise the barcode from nucleic acid coding for the target protein are sequenced. In some embodiments, the sequencing allows for identifying combinations of effectors that conferred efficacy against the target protein.

In some embodiments, the target protein coded by the nucleic acid is a signaling protein, an enzyme, a binding protein, an antibody or antibody fragment, a structure protein, a storage protein, or a transport protein. In some embodiments, the target protein is an enzyme. In some embodiments, the target protein is trypsin, macrophage metalloelastase 12 (MMP-12), extracellular signal-related kinase 1 (ERK1), or extracellular signal-regulated kinase 2 (ERK2).

In embodiments wherein the sample is a target protein and a nucleic acid coding the expression of the target protein, the nucleic acid may comprise a sequence complementary to the nucleic acid encoding an effector. This complementarity can be utilized for amplification of the barcode onto the nucleic acid encoding the effector. In embodiments wherein the sample is a target protein and a nucleic acid coding the expression of the target protein, the nucleic acid may contain a promoter sequence. In some embodiments, the promoter sequence allows for amplification of the nucleic acid sequence and/or the nucleic acid sequence encoding the effector after the barcode has been transferred.

In vitro transcription/translation systems are systems which can express proteins from nucleic acids which code for the protein without requiring any living tissue or cells. In some embodiments, the in vitro transcription/translation system is used to express the target protein within an encapsulation. In some embodiments, the in vitro transcription/translation system is used to express the target protein within an encapsulation to a target concentration. In some embodiments, the in vitro transcription/translation system is used to amplify the target protein within an encapsulation. In some embodiments, the in vitro transcription/translation system is used to amplify the target protein within an encapsulation to a desired concentration.

Encapsulation

An encapsulation can refer to the formation of a compartment within a larger system. In preferred embodiments, the encapsulation is a droplet within a microfluidic channel. In some embodiments, the encapsulation is a droplet, an emulsion, a macrowell, a microwell, bubble, or a microfluidic confinement. Once an encapsulation is formed, any component inside the encapsulation can remain in the encapsulation until the encapsulation is destroyed or broken down. In some embodiments, the encapsulations used herein remain stable for at least 4 hours, at least 12 hours, at least 1 day, at least 2 days, at least 3 days, or at least 1 week. In some embodiments, the encapsulations are stable for the duration of the screen to be performed so that no intermingling of reagents between encapsulations occurs.

In some embodiments, the encapsulation is a droplet. In some embodiments, the droplet is at most 1 picoliter, at most 10 picoliters, at most 100 picoliters, at most 1 nanoliter, at most 10 nanoliters, at most 100 nanoliters, or at most 1 microliter in volume. In some embodiments, the droplet is at least 1 picoliter, at least 10 picoliters, at least 100 picoliters, at least 1 nanoliter, at least 10 nanoliters, at least 100 nanoliters, or at least 1 microliter in volume. In some embodiments, the droplet is between about 200 picoliters and about 10 nanoliters.

In some embodiments, the droplet is an aqueous droplet in a larger body of oil. In some embodiments, the droplets are placed in an oil emulsion. In some embodiments, the oil comprises a silicone oil, a fluorosilicone oil, a hydrocarbon oil, a mineral oil, a paraffin oil, a halogenated oil, a fluorocarbon oil, or any combination thereof. In some embodiments, the oil comprises a silicone oil. In some embodiments, the oil comprises a fluorosilicone oil. In some embodiments, the oil comprises a hydrocarbon oil. In some embodiments, the oil comprises a mineral oil. In some embodiments, the oil comprises a paraffin oil. In some embodiments, the oil comprises a halogenated oil. In some embodiments, the oil comprises a fluorocarbon oil.

In embodiments wherein there are a plurality of encapsulations, each individual encapsulation may be any size. In some embodiments, each encapsulation is approximately the same size. In some embodiments, each encapsulation is within 5%, 10%, 15%, 20%, or 25% of the average size encapsulation within the plurality. In some embodiments, at least 80%, 85%, 90%, or 95% of the encapsulations are within about 5%, 10%, 15%, 20%, or 25% of the average size encapsulation within the plurality.

The encapsulations may be formed by any method. In some embodiments, an encapsulation is formed by flowing an aqueous stream into an immiscible carrier fluid. In some embodiment, the aqueous stream flows into an immiscible carrier fluid at a junction of microfluidic channels. In some embodiments, the junction is a T-junction. In some embodiments, the junction is a meeting of two perpendicular microfluidic channels. The junction may be a meeting of any number of microfluidic channels. The junction may be at any angle. The aqueous stream may be formed by an upstream junction of two or more aqueous streams. In some embodiments, sample solutions and effector solutions are joined upstream of the aqueous stream junction with the immiscible carrier fluid.

The size of the droplets may be controlled by modulating a variety of parameters. These parameters include the geometry of the junction of two microfluidic channels, the flow rate of the two streams, the type of oil used, the presence of surfactants, the pressure applied to the flow streams, or any combination thereof.

In some embodiments, a single encoded effector is present in an encapsulation. In some embodiments, a single scaffold comprising an encoded effector and its encoding are present in an encapsulation. In some embodiments, a plurality of scaffolds, each scaffold comprising a different encoded effector and its respective encoding, are present in an encapsulation.

In some embodiments, encapsulations comprise biological samples. In some embodiments, encapsulations comprise single cells. In some embodiments, encapsulations comprise one or more cells. In some embodiments, the encapsulations comprise nucleic acids. In some embodiments, the encapsulations comprise proteins. In some embodiments, the encapsulations comprise.

Sorting

The methods and systems provided herein may comprise sorting steps. The sorting step can be accomplished in a variety of ways. One way of sorting the "hit" effectors from the non-hit effectors is to physically separate the hits from non-hits in space. This can be accomplished in a variety of manners. In some embodiments, sorting the encapsulations comprises providing the encapsulation through a microfluidic channel. In some embodiments, the microfluidic channel is equipped with a detector. In some embodiments, the "hit" effectors are placed into one collection vessel if the "hit" criteria is met, and the "non-hit" effectors are placed into another collection vessel. As described herein, in some embodiments, such "hit" effectors are sorted based on the presence or absence of a signal resulting from an interaction with the effector (or another component) and the sample, a reagent, or combinations thereof. In some embodiments, the sorting is based on the level of a signal detected. In some embodiments, the sorting is based on the presence of a signal detected. In some embodiments, the sorting is based on the absence of a signal.

In some embodiments, sorting droplets is accomplished by activity-based screening. Activity based sorting is accomplished by the ability to sort based on detecting a response emitted by the droplet as it passes by a detecting region on the microfluidic chip. As an example, certain small-molecules inhibit particular enzymes which can be screened by an activity-based assay that detects for that inhibition. Thus, sorting is based on the "activity" of the enzyme and thus screening for small-molecules that functionally inhibit the enzyme rather than simply bind to the enzyme. It is a more relevant screen and is much more similar to conventional HTS screening which screens for activity.

In some embodiments, sorting the encapsulations comprises placing the encapsulations (e.g., droplets) into a first collection tube if the signal is at or above a predetermine threshold. In some embodiments, sorting the encapsulation comprises placing the droplet into a second collection tube if the signal is below a predetermined threshold. In some embodiments, sorting the encapsulation comprises placing the droplet into a first collection tube if the signal is at or above a predetermine threshold or placing the droplet into a second collection tube if the signal is below a predetermined threshold. In some embodiments, sorting the encapsulation comprises placing encapsulations in two or more collection tubes, or bins. In some embodiments, "hit" effectors or positive "hits' are stored in two or more collection tubes or bins. In some embodiments, the "hit" effectors, or positive "hits" are sorted based on the signal or activity measured.

Figure 26A:
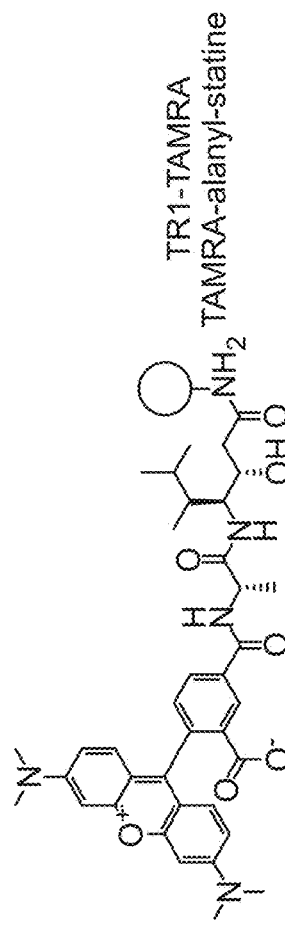
FIG. 26A shows an exemplary bead attached with a TR1-TAMRA fluorophore.
Figure 26B:
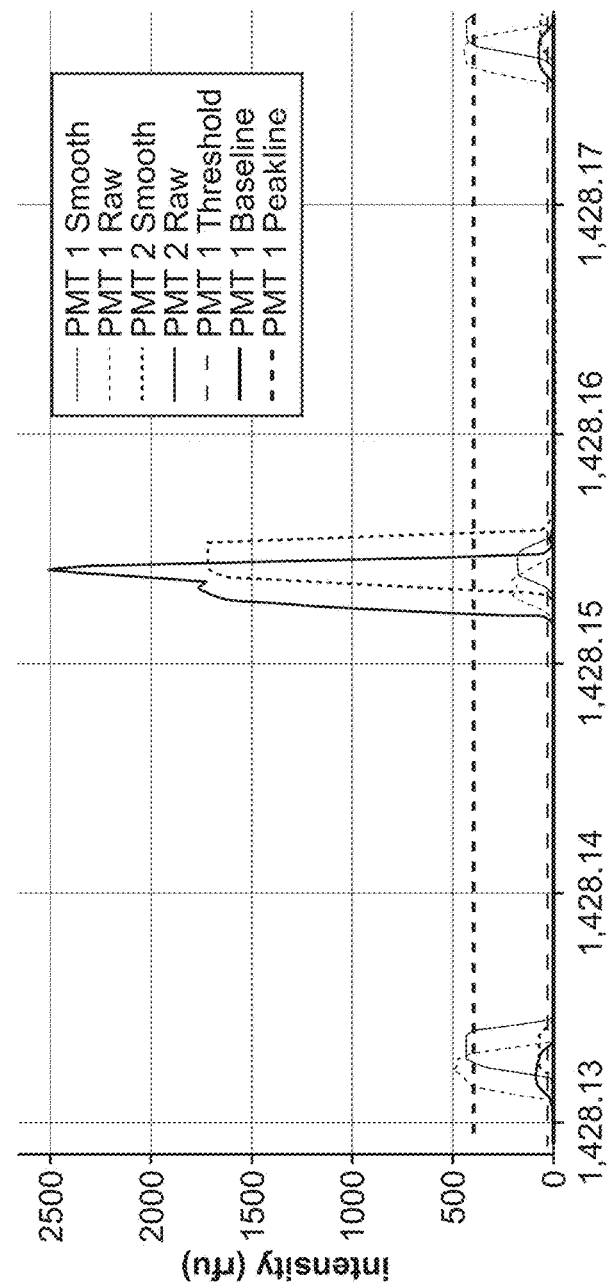
FIG. 26B shows an exemplary intensity peak detected for the TR1-TAMRA after it has been released from the bead.
Figure 27A:
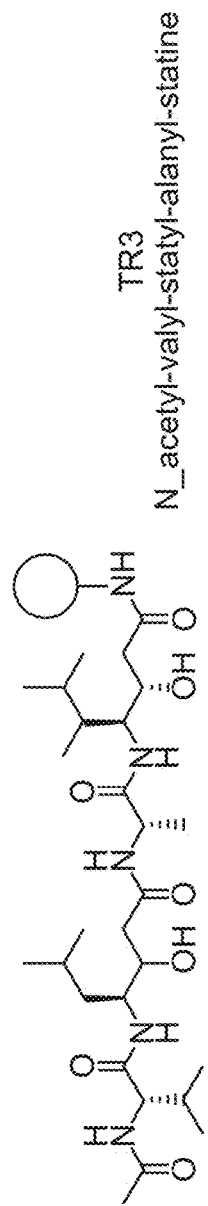
FIG. 27A shows an exemplary bead attached with a TR3 inhibitor.
Figure 27B:
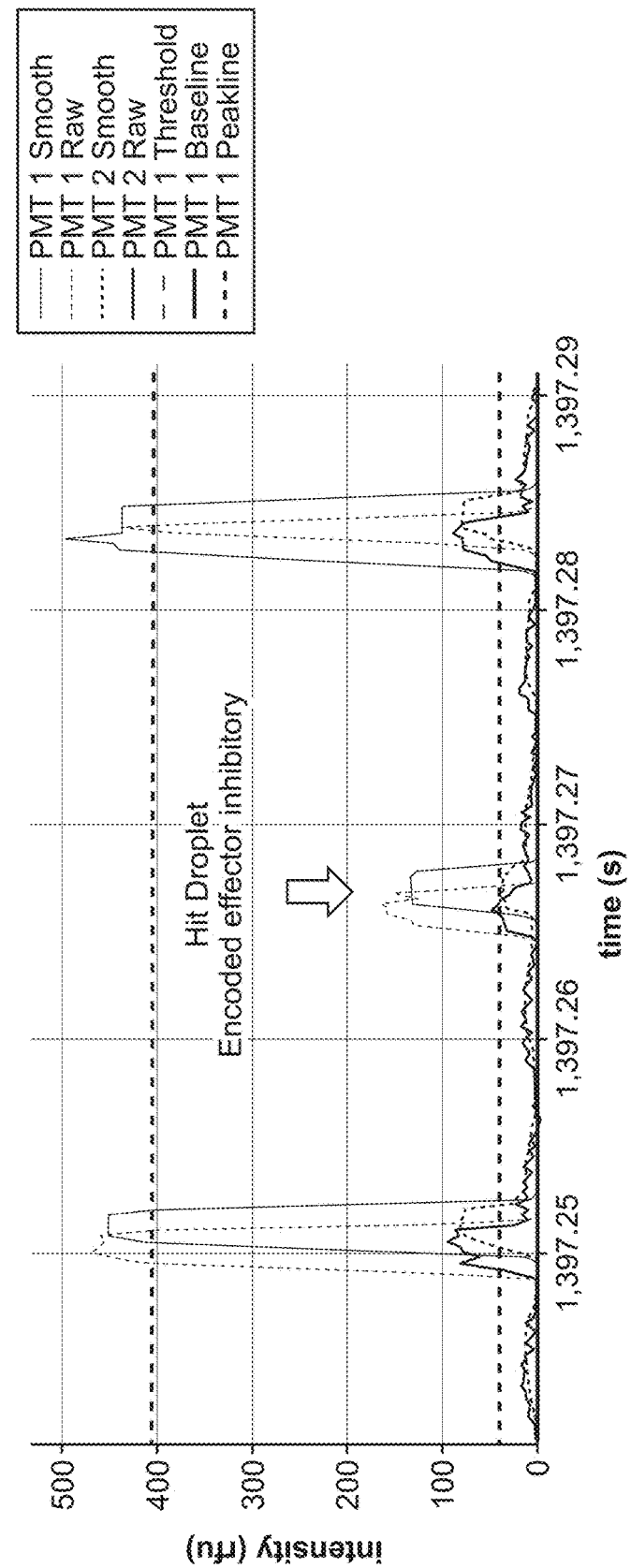
FIG. 27B shows an exemplary intensity inhibited corresponding to activity by the TR3 inhibitor after it has been released from the bead.
Figure 27C:
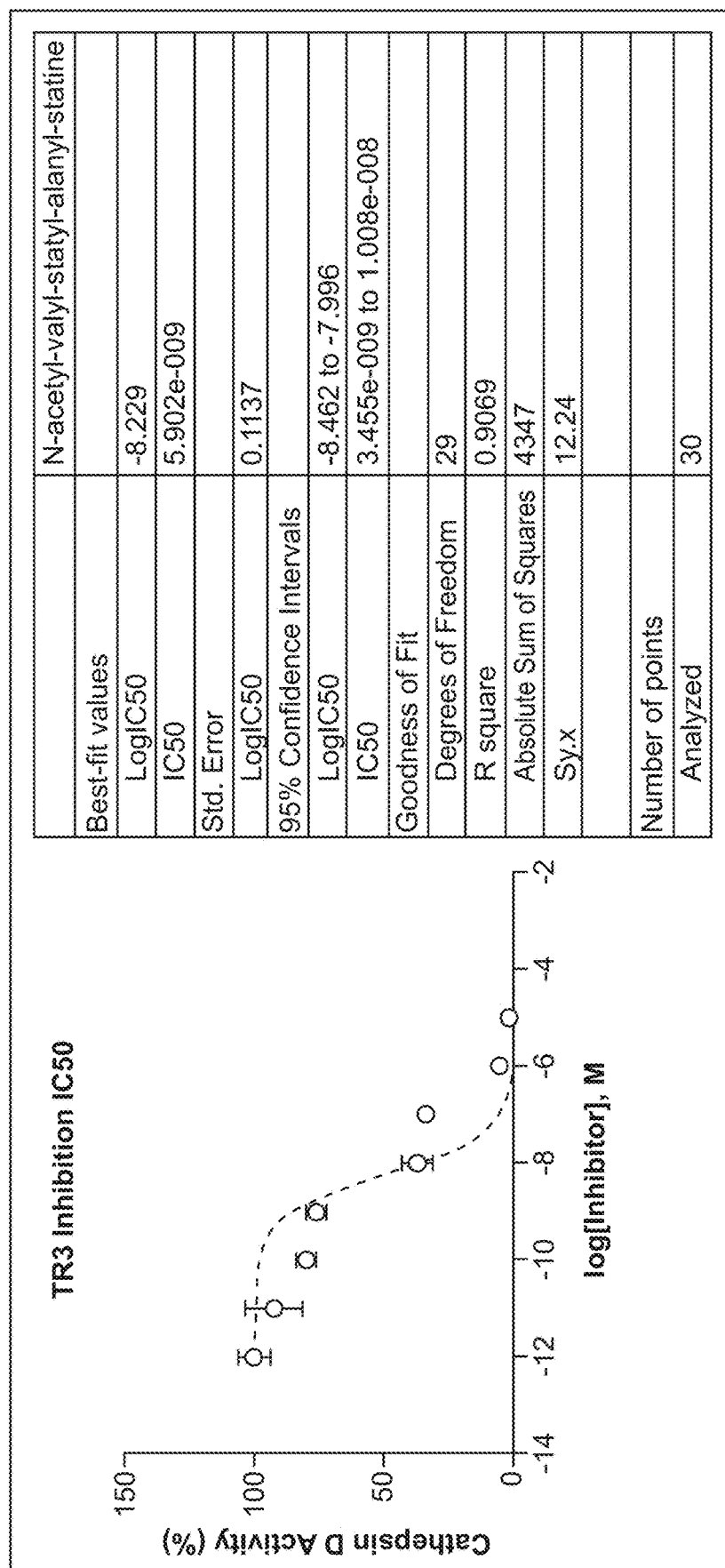
FIG. 27C shows an exemplary variation of Cathepsin D activity based on increasing concentration of a TR3 inhibitor.
Figure 28A:
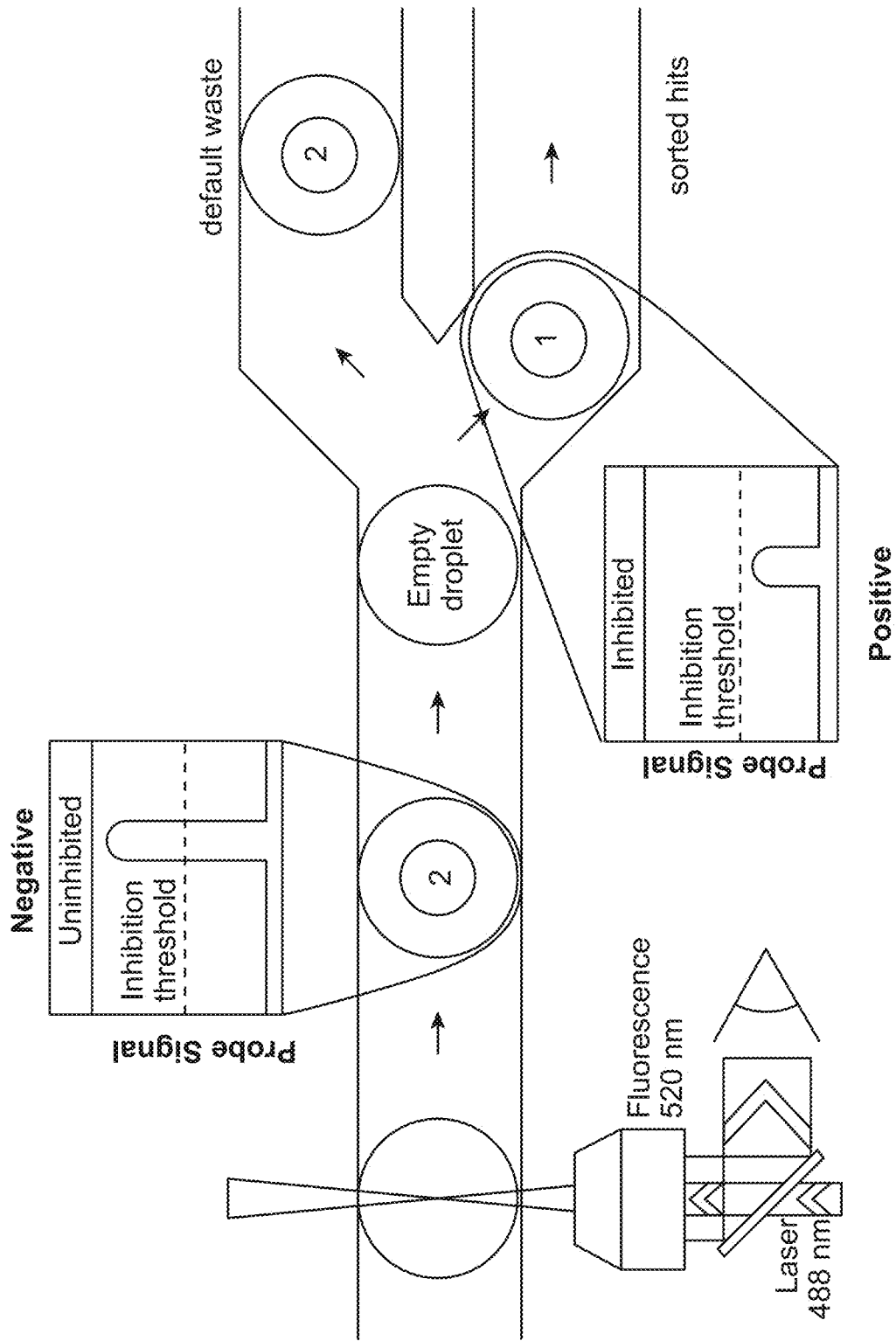
FIG. 28A provides an exemplary depiction of a sorting schematic for beads that exhibit an intensity below an inhibition threshold.
Figure 28B:
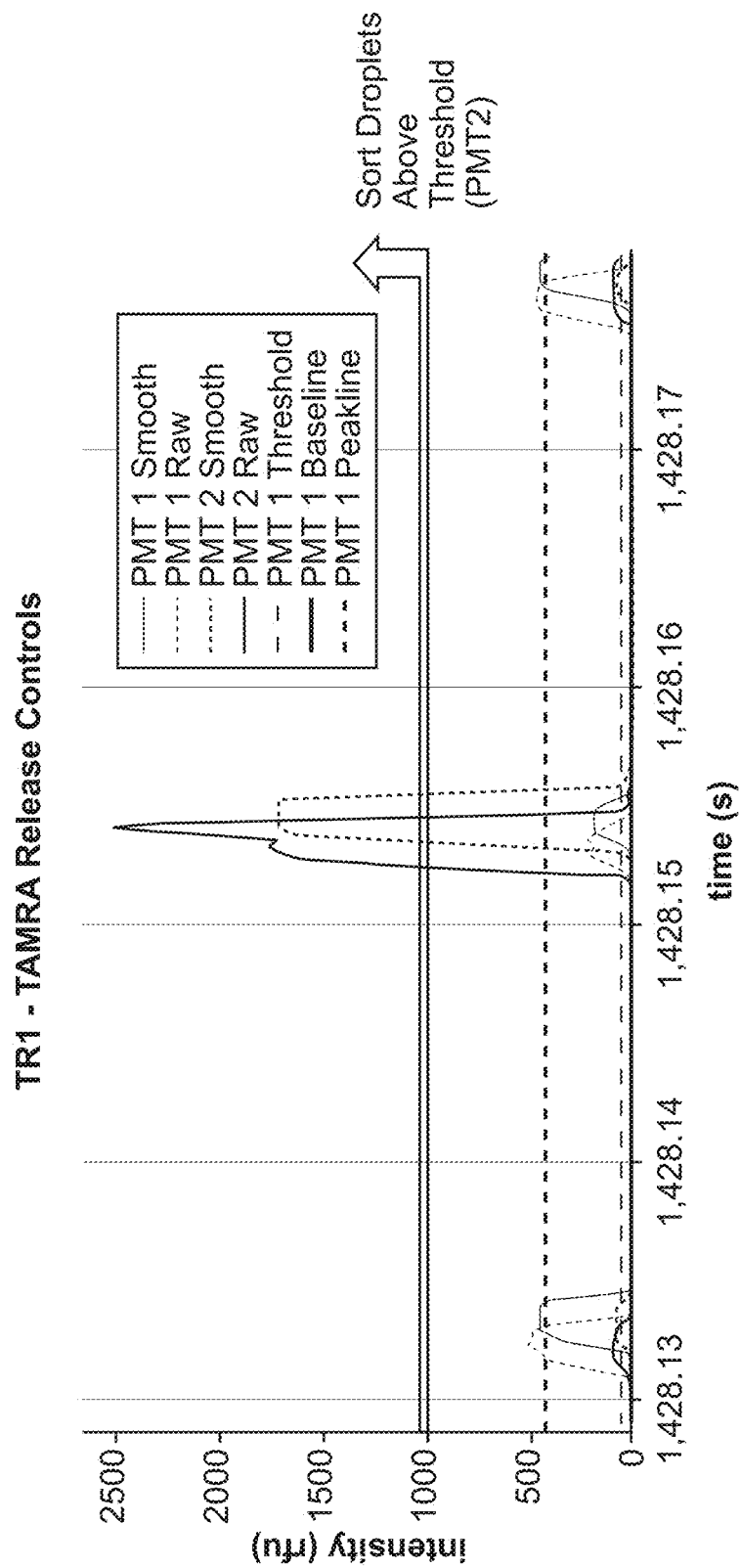
FIG. 28B shows an exemplary intensity peak detected for the TR1-TAMRA that is above a threshold for positive sorting.
Figure 28C:
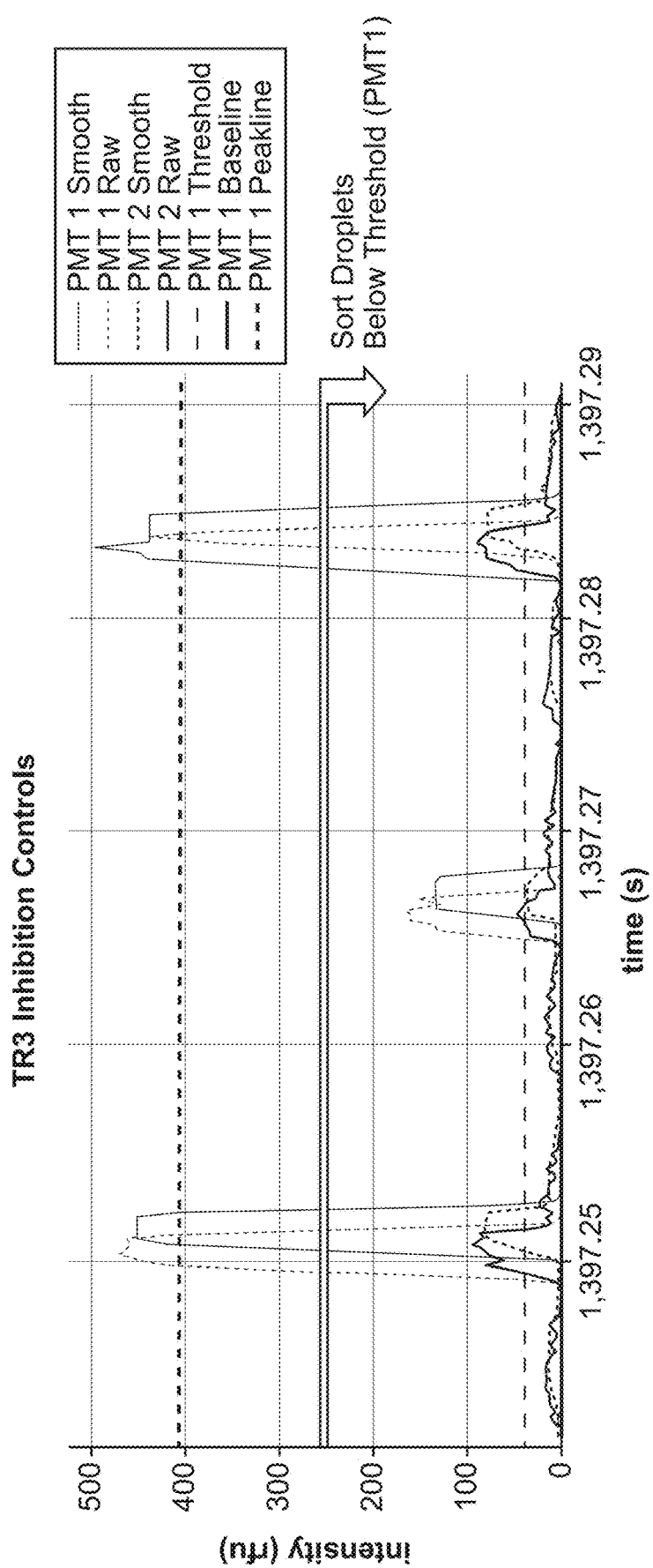
FIG. 28C shows an exemplary intensity peak inhibited for the TR3 inhibitor that is below a threshold for positive sorting.
Figure 28D:
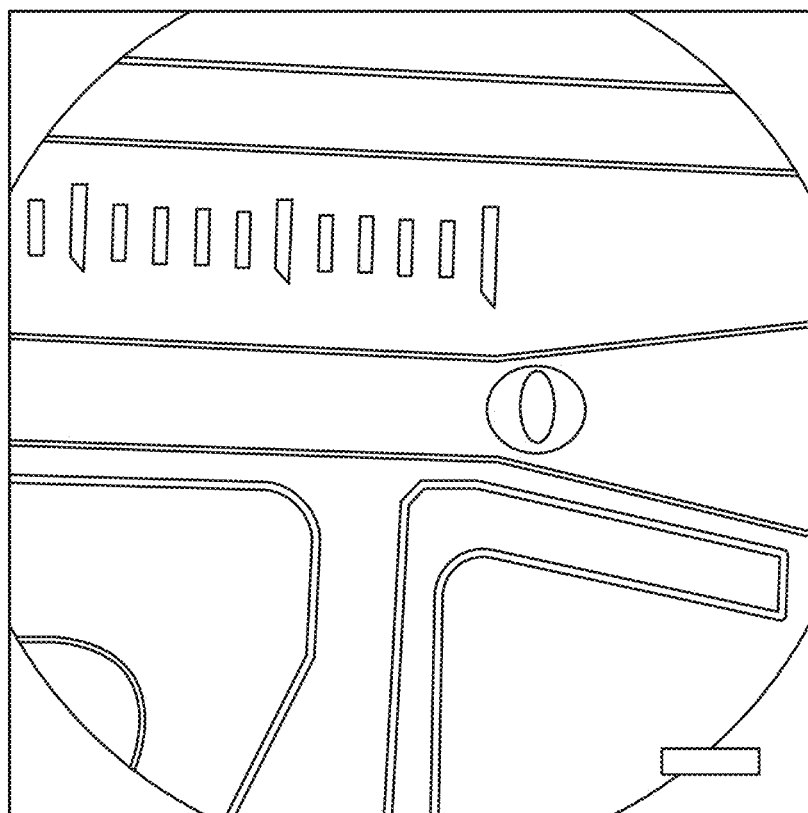
FIG. 28D shows an exemplary a device being used for sorting encapsulations.

FIGS. 26A to 28C depict sorting droplets based on two types of detection signals. FIGS. 26A-B depict the use of a bead attached with fluorophore TR1-TAMRA, which upon release from the bead, provides a detectable intensity level (FIG. 26B). By contrast, FIGS. 27A-B depict the use of a bead attached with an inhibitor TR3, which upon release inhibits or minimizes the intensity of fluorescence detected (FIG. 27B). FIG. 27C depicts a decrease in Cathepsin D activity with increasing concentration of the TR3 inhibitor. FIG. 28A provides an exemplary depiction of droplets being sorted based on a certain inhibition threshold being met, wherein for those droplets exhibiting a fluorescence intensity level below a certain threshold will be a "positive" hit, and those droplets exhibiting fluorescence intensity levels above the threshold, will be a "negative" hit. FIG. 28C provides an exemplary threshold level for such inhibitory activity. In some embodiments, the threshold for sorting will be based on a minimum fluorescence intensity level being measured (e.g., as occurring through use of TAMRA fluorophore). FIG. 28B provides an exemplary threshold level for such fluorescence detection activity. FIG. 28D provides an exemplary illustration of a device as used in a method or system described herein.

In some embodiments, sorting the encapsulation comprises using a waveform pulse generator to move the encapsulation to a collection tube by an electrical field gradient, by sound, by a diaphragm, by modifying geometry of microfluidic channel, or by changing the pressure of the microfluidic channel. In some embodiments, the waveform pulse generator moves the encapsulation by an electrical field gradient. In some embodiments, the waveform pulse generator moves the encapsulation by sound. In some embodiments, the waveform pulse generator moves the encapsulation by a diaphragm. In some embodiments, the waveform pulse generator modifies the geometry of the microfluidic channel. In some embodiments, the waveform pulse generator changes the pressure of the microfluidic channel.

Various methods for determining which effectors had the desired effect may be used. In some instances, physical sorting of "hit" effectors is used to determine which effectors had the desired effect. In some instances, selective addition of a detectable label to encapsulations comprising a "hit" effector is used. In some instances, a detectable label is used to determine which effectors had the desired effect by linking detectable label with the encoding. For example, the addition of a nucleic acid barcode to nucleic acid encodings of effectors can accomplish tagging the "hit" effectors in a way that can be ascertained by sequencing. If only "hit" effectors encodings are tagged with the nucleic acid barcode, then these samples can be picked out during a subsequent sequencing step, as effectors which lacked the desired activity will lack the barcode. The barcode may additionally comprise a unique primer sequence to allow for amplification of only the "hit" effector encodings. In this way, all encapsulations can be pooled together, regardless of activity or efficacy, and the resulting hits can still be ascertained.

Barcode Non-Sorting Method

In some embodiments provided herein, the methods do not comprise a physical sorting step. In these embodiments, deconvolution of which effectors had the desired effect on a sample is accomplished in a different manner. In some embodiments, the method further comprises the step of adding additional reagents to the encapsulation which add a barcode to the encoding. In some embodiments, the method further comprises the step of adding additional reagents to the encapsulation which add a barcode to a nucleic acid encoding. In some embodiments, the additional reagents add a barcode to the encoding by annealing the barcode to the encoding, ligating the barcode to the encoding, or amplifying the barcode onto the encoding. In some embodiments, the additional reagents comprise a tagging nucleic acid comprising a sequence complementary to a sequence on the nucleic acid encoding which acts as a primer for the nucleic acid encoding and the barcode. In some embodiments, the additional reagents comprise enzymes to add the barcode to the nucleic acid encoding.

Provided herein, in some embodiments, are methods for screening an encoded effector without a physical sorting step. In some embodiments, the method comprises providing a sample, a nucleic acid encoded effector, and a nucleic acid encoding in an encapsulation. In some embodiments, a signal is detected in the encapsulation. In some embodiments, the signal results from an interaction between the effector and the sample. In some embodiments, a first capping mix is added to the droplet based on the detection, absence, or level of the signal. In some embodiments, the first capping mix adds a first nucleic acid cap to the nucleic acid encoding. In some embodiments, a second capping mix is added to the encapsulation. In some embodiments, the second capping mix is only added if the first capping mix is not added to the encapsulation. In some embodiments, the first nucleic acid cap and the second nucleic acid cap have different sequences. In some embodiments, only the first nucleic acid cap or only the second nucleic acid cap is added to the nucleic acid encoding.

The first and second nucleic acid caps can have different significance and indicate different things when added to nucleic acid encodings. In some embodiments, the first nucleic acid cap indicates that the effector had a desired activity. In some embodiments, the desired activity resulted in the signal being above a pre-determined threshold. In some embodiments, the desired activity resulted in the signal being below a pre-determined threshold. In some embodiments, the desired activity resulted in the presence of the signal. In some embodiments, the desired activity resulted in the absence of the signal.

In some embodiments, the second nucleic acid cap indicates that the effector lacked a desired activity. In some embodiments, the lack of desired activity resulted in the signal being below a pre-determined threshold. In some embodiments, the lack of desired activity resulted in the signal being above a pre-determined threshold. In some embodiments, the lack of desired activity resulted in the absence of the signal. In some embodiments, the lack of desired activity resulted in the presence of the signal.

The nucleic acid caps can be added to nucleic acid encodings by a variety of methods. In some embodiments, the nucleic acid cap is added to the nucleic acid encoding by ligation, hybridization, extension of the nucleic acid encoding, or combinations thereof. In some embodiments, the nucleic acid cap is added to the nucleic acid encoding by ligation. In some embodiments, the nucleic acid cap is added to the nucleic acid encoding by hybridization. In some embodiments, the nucleic acid cap is added to the nucleic acid encoding by extension of the nucleic acid encoding. In some embodiments, the nucleic acid cap is added to the nucleic acid encoding by chemically crosslinking the nucleic acids. In some embodiments, the nucleic acid cap is added to the nucleic acid encoding by chemical crosslinking with psoralen. In some embodiments, a complementary sequence the nucleic acid cap is located on the terminal end of the nucleic acid encoding to allow for the addition of the nucleic acid cap. In some embodiments, the nucleic acid caps comprise a barcode sequence.

In some embodiments, the capping mix comprises additional reagents for adding the nucleic acid cap to the encoding. In some embodiments, the additional reagents comprise an enzyme. In some embodiments, the enzyme is a polymerase, a ligase, a restriction enzyme, or a recombinase. In some embodiments, the enzyme is a polymerase.

Bead Capture of Nucleic Acids

In addition to measuring activity from detectable signals, additional information can be gathered from a screen by incorporating nucleic acids from the sample onto encodings. In some embodiments, the method comprises transferring one or more nucleic acids from the sample to the encoding. The transfer of nucleic acids from the sample to the encoding allows substantial information about the sample, and information about the effect the effector has on the sample to be ascertained, particularly when the sample is a cell. The transfer of the nucleic acids from the sample can allow for quantification of expressed protein by quantifying the amount of target mRNA, as well as provide global proteomic and genomic data about the cell. This data can be collected and compared to cells that did not receive a dose of the indicated effector In one aspect, provided herein, is a method for detecting sample nucleic acids in a nucleic acid encoded effector screen. In some embodiments, the method comprises providing one or more cells, a nucleic acid encoded effector, and a nucleic acid encoding in an encapsulation. In some embodiments, the encapsulation is incubated for a period of time to allow for the effector and the cell to interact. In some embodiments, as described herein, the interaction between the effector and the cell produces a signal. In some embodiments, the period of time is sufficient to allow for changes in transcription and/or translation to occur in the cell in response to the effector. In some embodiments, the method comprises transferring cellular nucleic acids to the nucleic acid encoding. In some embodiments, the cellular nucleic acids are quantified by sequencing the nucleic acid encodings after the cellular nucleic acids have been transferred. In this way, an expression fingerprint of the cell can be generated in response to treatment with the effector. As described herein, in some embodiments, the method further comprises detecting a signal produced through interaction between the effector and one or more cells, and sorting the encapsulation based on the detection of the signal.

In order to release the cellular nucleic acids, the cell may be lysed. In some embodiments, the method further comprises the step of lysing the cell. In some embodiments, lysing the cell comprises adding lysis buffer to the encapsulation. In some embodiments, the lysis buffer is added by pico-injection. In some embodiments, the lysis buffer comprises a salt. In some embodiments, the lysis buffer comprises a detergent. In some embodiments, the detergent is SDS, Triton, or Tween. In some embodiments, the lysis buffer comprises a chemical which causes cell lysis.

Any type of cellular nucleic acid can be transferred to the nucleic acid encoding. In some embodiments, the method comprises transferring one or more cellular nucleic acids from the sample to the nucleic acid encoding. In some embodiments, the nucleic acids are mRNA. In some embodiments, the nucleic acids are mRNA that express a protein of interest. In some embodiments, the nucleic acids are genomic DNA. In some embodiments, the nucleic acids are added as antibody-DNA constructs. In some embodiments, the nucleic acids added are proximity ligation products. In some embodiments, the nucleic acids added are proximity extension products. In some embodiments, a plurality of different cellular nucleic acids are attached to nucleic acid encodings.

In some embodiments, the nucleic acids transferred to the encoding comprise a complementary sequence to a sequence on the encoding. This may allow for the ligation of the sample nucleic acid with the encoding nucleic acid via various methods. These methods include, without limitation, annealing, ligating, chemically cross-linking, or amplifying the cellular contents on to the nucleic acid encoding the effector. In some embodiments, the nucleic acid encodings comprise a sequence complementary to the nucleic acid of interest to be transferred to the encoding. This complementary sequence allows for the nucleic acids to hybridize with the encoding, which in turn allows for extension of the encoding with the cellular nucleic acid and vice versa.

In some embodiments, additional reagents are added to the encapsulation to facilitate the transfer of the nucleic acids to the encoding. In some embodiments, the additional reagents comprise an enzyme that facilitates the transfer of the nucleic acids. In some embodiments, the reagents for transferring the nucleic acids to the encoding are added during encapsulation step. In some embodiments, the reagents for transferring the nucleic acids to the encoding are added during an incubation step. In some embodiments, the reagents for transferring the nucleic acids to the encoding are added after an incubation step.

In some embodiments, the additional reagents to facilitate the transfer of the nucleic acids comprise an enzyme. In some embodiments, the enzyme is a polymerase, a ligase, a restriction enzyme, or a recombinase. In some embodiments, the enzyme is a polymerase. In some embodiments, the additional reagents comprise a chemical cross-linking reagent. In some embodiments, the chemical cross-linking reagent is psoralen.

Adding Reagents to an Encapsulation

Methods and systems described herein may include adding one or more reagents to an encapsulation. In some embodiments, additional reagents can be added during a screen to encapsulations by pico-injection. In some embodiments, additional reagents are added by pico-injection. In some embodiments, each encapsulation passing by a pico-injection site receive a pico-injection. In some embodiments, at least 80%, at least 85%, at least 90%, at least 95%, at least 97%, at least 98%, or at least 99% of encapsulations passing a pico-injection site receive pico-injections. In some embodiments, at least 80% of encapsulations passing a pico-injection site receive pico-injections. In some embodiments, at least 85% of encapsulations passing a pico-injection site receive pico-injections. In some embodiments, at least 90% of encapsulations passing a pico-injection site receive pico-injections. In some embodiments, at least 95% of encapsulations passing a pico-injection site receive pico-injections. In some embodiments, at least 97% of encapsulations passing a pico-injection site receive pico-injections. In some embodiments, at least 98% of encapsulations passing a pico-injection site receive pico-injections. In some embodiments, at least 99% of encapsulations passing a pico-injection site receive pico-injections.

In some embodiments, pico-injections are performed at the same frequency at which encapsulations pass by a pico-injection site. In some embodiments, pico-injections are performed at substantially the same frequency at which encapsulations pass by a pico-injection site. In some embodiments, the frequency at which encapsulations pass by a pico-injection site is determined by monitoring the encapsulations. In some embodiments, the frequency at which encapsulations pass by a pico-injection site is determined by monitoring the encapsulations in flow. In some embodiments, the encapsulations are monitored by taking images in real time. In some embodiments, the encapsulations are monitored with a detector.

In some embodiments, the pico-injections are conditional. Conditional pico-injections may only occur after a certain condition is met. In some embodiments, a conditional pico-injection only occurs when a signal is detected. In some embodiments, a reagent is injected by pico-injection if a signal is detected. In some embodiments, a reagent is added to an encapsulation by pico-injections if a signal is detected. In some embodiments, the signal must be above a predetermined threshold.

In some embodiments, a method for screening an encoded effector comprises providing an encapsulation comprising a sample and one or more scaffolds, wherein the scaffold comprises: an encoded effector bound to the scaffold by a cleavable linker and a nucleic acid encoding the effector; adding one or more reagents to the encapsulation through pico-injection or by droplet merging; cleaving the cleavable linker to release a pre-determined amount of the effector; detecting one or more signals from the encapsulation, wherein the signal results from an interaction between the encoded effector and the sample; and sorting the encapsulation based on the detection of the signal.

In some embodiments, one or more reagents added to an encapsulation comprises one or more fluorophores, one or more antibodies, one or more chemical compounds, or any combination thereof.

Post-Sorting of Encapsulations

After a sorting step or barcoding step based on the detection of the signal of interest, the results are deconvoluted in order to determine which effectors displayed the activity of interest against the target sample. In some embodiments, the methods described herein comprise the step of ascertaining which encodings are present in the samples sorted based on the detection of the signal. In some embodiments wherein the encoding is a nucleic acid, the methods described herein further comprise the step of sequencing the encodings. In some embodiments, the encodings are sequenced by next generation sequencing. In some embodiments, the sequences are compared to a reference to ascertain which effectors displayed the activity of interest in the screen.

In some embodiments, sequencing the nucleic acid encoding comprises sequencing the encoding while the encoding is still attached to the scaffold. In some embodiments, sequencing the nucleic acid encoding comprises cleaving the nucleic acid encoding from the scaffold. In some embodiments, sequencing the nucleic acid encoding comprises cleaving the nucleic acid encoding from the scaffold prior to sequencing. In some embodiments, cleaving the nucleic acid encoding from the scaffold comprises cleaving a cleavable linker with a cleaving reagent. In some embodiments, cleaving the nucleic acid encoding from the scaffold comprises cleaving a cleavable linker with electromagnetic radiation. In some embodiments, any of the cleavable linkers and cleaving reagents described herein work for this purpose. In some embodiments, a nicking enzyme or a restriction enzyme can be used to cleave. In some embodiments enzymatic, chemical reagent, photocleavage can be used to cleave the encodings.

In some embodiments, the nucleic acid encoding comprises a sequencing primer. The sequencing primer allows for facile amplification of the nucleic acid encoding. In some embodiments comprising a library of encoded effectors, the sequencing primer is the same for each encoding. In some embodiments comprising a library of encoded effectors, the sequencing primer differs among the encodings. In some embodiments, the sequencing primer is upstream of the encoding. In some embodiments, the sequencing primer is downstream of the encoding.

In some embodiments, the methods provided herein are performed using microfluidic devices. Microfluidic devices may perform the encapsulation steps. Additionally, microfluidic devices may be equipped with pico-injectors and other components which allow for the methods provided herein to be performed. In some embodiments, pico-injectors are in place along microfluidic channels defining a flow path through the microfluidic device. In some embodiments, the pico-injectors are positioned such that reagents are added at desired times while performing the methods provided herein.

In some embodiments, the methods and systems provided herein utilize libraries of encoded effectors. Libraries of encoded effectors comprise a plurality of different effectors, each uniquely encoded by a known encoding modality, such as those described above. Libraries may contain any number of encoded effectors. In some embodiments, the libraries comprise at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or $10^{16}$ unique effectors. In some embodiments, the libraries comprise at least about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or $10^{16}$ unique effectors.

In some embodiments, libraries of encoded effectors are linked to scaffolds. These scaffolds may be referred to as "scaffold encoded libraries." Scaffold encoded libraries comprise a plurality of encoded effector molecules linked to the scaffold. The scaffold acts as a solid support and keeps the encoded effector molecules linked in space to their encodings. In some embodiments, the libraries comprise at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or $10^{16}$ scaffolds. In some embodiments, the libraries comprise at least about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or $10^{16}$ scaffolds.

Any of the methods or systems described herein for a single encoded effector may be utilized by a library of encoded effectors. In some embodiments, provided herein, is a method of screening a library of encoded effectors, the method comprising using any of the methods previously described herein with a library of encoded effectors.

In some embodiments, libraries of encoded effectors comprise a plurality of different encoded effectors. In some embodiments, libraries comprise multiple copies of substantially identical effectors or scaffold encoded effectors.

Microfluidic Devices

The methods and systems provided herein may be performed on a microfluidic device. Device architecture and methods may be accomplished in a variety of ways. An analyzer or sorter device according to the disclosure comprises at least one analysis unit having an inlet region in communication with a main channel at a droplet extrusion region (e.g., for introducing droplets of a sample into the main channel), a detection region within or coincident with all or a portion of the main channel or droplet extrusion region, and a detector associated with the detection region. In certain embodiments the device may have two or more droplet extrusion regions. For example, embodiments are provided in which the analysis unit has a first inlet region in communication with the main channel at a first droplet extrusion region, a second inlet region in communication with the main channel at a second droplet extrusion region (for example, downstream from the first droplet extrusion region), and so forth.

In some embodiments, a microfluidic device described herein is configured for a droplet generation frequency of about 5 Hz to about 200 Hz. In some embodiments, a microfluidic device described herein is configured for a throughput of about 5 Hz to about 15 Hz, about 5 Hz to about 25 Hz, about 5 Hz to about 50 Hz, about 5 Hz to about 80 Hz, about 5 Hz to about 100 Hz, about 5 Hz to about 150 Hz, about 5 Hz to about 200 Hz, about 15 Hz to about 25 Hz, about 15 Hz to about 50 Hz, about 15 Hz to about 80 Hz, about 15 Hz to about 100 Hz, about 15 Hz to about 150 Hz, about 15 Hz to about 200 Hz, about 25 Hz to about 50 Hz, about 25 Hz to about 80 Hz, about 25 Hz to about 100 Hz, about 25 Hz to about 150 Hz, about 25 Hz to about 200 Hz, about 50 Hz to about 80 Hz, about 50 Hz to about 100 Hz, about 50 Hz to about 150 Hz, about 50 Hz to about 200 Hz, about 80 Hz to about 100 Hz, about 80 Hz to about 150 Hz, about 80 Hz to about 200 Hz, about 100 Hz to about 150 Hz, about 100 Hz to about 200 Hz, or about 150 Hz to about 200 Hz, including increments therein. In some embodiments, a microfluidic device described herein is configured for a droplet generation frequency of about 5 Hz, about 15 Hz, about 25 Hz, about 50 Hz, about 80 Hz, about 100 Hz, about 150 Hz, or about 200 Hz. In some embodiments, a microfluidic device described herein is configured for a droplet generation frequency of at least about 5 Hz, about 15 Hz, about 25 Hz, about 50 Hz, about 80 Hz, about 100 Hz, or about 150 Hz. In some embodiments, a microfluidic device described herein is configured for a droplet generation frequency of at most about 15 Hz, about 25 Hz, about 50 Hz, about 80 Hz, about 100 Hz, about 150 Hz, or about 200 Hz.

Sorter embodiments of the device also have a discrimination region or branch point in communication with the main channel and with branch channels, and a flow control responsive to the detector. There may be a plurality of detection regions and detectors, working independently or together, e.g., to analyze one or more properties of a sample or encapsulation. The branch channels may each lead to an outlet region and to a well or reservoir. There may also be a plurality of inlet regions, each of which introduces droplets of a different sample (e.g., of cells, of virions or of molecules such as molecules of an enzyme or a substrate) into the main channel. Each of the one or more inlet regions may also communicate with a well or reservoir.

As each droplet passes into the detection region, it is examined for a predetermined characteristic or activity (i.e., using the detector) and a corresponding signal is produced, for example indicating that "yes" the characteristic or activity is present, or "no" it is not. The signal may correspond to a characteristic qualitatively or quantitatively. That is, the amount of the signal can be measured and can correspond to the degree to which a characteristic or activity is present. For example, the strength of the signal may indicate the size of a molecule, or the potency or amount of an enzyme expressed by a cell, or a positive or negative reaction such as binding or hybridization of one molecule to another, a chemical reaction of a substrate catalyzed by an enzyme, or the activation or inhibition of an enzyme, or any other type of response. In response to the signal, data can be collected and/or a flow control can be activated to divert a droplet into one branch channel or another. Thus, samples within a droplet at a discrimination region can be sorted into an appropriate branch channel according to a signal produced by the corresponding examination at a detection region. In some embodiments, optical detection of molecular, cellular, viral, or other sample characteristics is used, for example directly or by use of a reporter associated with a characteristic chosen for sorting. However, other detection techniques may also be employed.

A variety of channels for sample flow and mixing can be microfabricated on a single chip and can be positioned at any location on the chip as the detection and discrimination or sorting points, e.g., for kinetic studies. A plurality of analysis units of the disclosure may be combined in one device. Microfabrication applied according to the disclosure eliminates the dead time occurring in conventional gel electrophoresis or flow cytometric kinetic studies, and achieves a better time-resolution. Furthermore, linear arrays of channels on a single chip, i.e., a multiplex system, can simultaneously detect and sort a sample by using an array of photo multiplier tubes (PMT) for parallel analysis of different channels. This arrangement can be used to improve throughput or for successive sample enrichment, and can be adapted to provide a very high throughput to the microfluidic devices that exceeds the capacity permitted by conventional flow sorters. Circulation systems can be used in cooperation with these and other features of the disclosure. Microfluidic pumps and valves are one way of controlling fluid and sample flow. See, for example, U.S. patent application Ser. No. 60/186,856.

Microfabrication permits other technologies to be integrated or combined with flow cytometry on a single chip, such as PCR, moving cells using optical tweezer/cell trapping, transformation of cells by electroporation, TAS, and DNA hybridization. Detectors and/or light filters that are used to detect viral (or cell) characteristics of the reporters can also be fabricated directly on the chip.

A device of the disclosure can be microfabricated with a sample solution reservoir or well at the inlet region, which is typically in fluid communication with an inlet channel. A reservoir may facilitate introduction of molecules or cells into the device and into the sample inlet channel of each analysis unit. An inlet region may have an opening such as in the floor of the microfabricated chip, to permit entry of the sample into the device. The inlet region may also contain a connector adapted to receive a suitable piece of tubing, such as liquid chromatography or HPLC tubing, through which a sample may be supplied. Such an arrangement facilitates introducing the sample solution under positive pressure in order to achieve a desired pressure at the droplet extrusion region.

A device of the disclosure may have an additional inlet region, in direct communication with the main channel at a location upstream of the droplet extrusion region, through which a pressurized stream or "flow" of a fluid is introduced into the main channel. In some embodiments, this fluid is one which is not miscible with the solvent or fluid of the sample. For example, in some embodiments, the fluid is a non-polar solvent, such as decane (e.g., tetradecane or hexadecane), and the sample (e.g., of cells, virions or molecules) is dissolved or suspended in an aqueous solution so that aqueous droplets of the sample are introduced into the pressurized stream of non-polar solvent at the droplet extrusion region.

Substrate and flow channels may be accomplished in a variety of ways. A typical analysis unit of the disclosure comprises a main inlet that is part of and feeds or communicates directly with a main channel, along with one or more sample inlets in communication with the main channel at a droplet extrusion region situated downstream from the main inlet (each different sample inlet may communicate with the main channel at a different droplet extrusion region). The droplet extrusion region generally comprises a junction between the sample inlet and the main channel such that a pressurized solution of a sample (i.e., a fluid containing a sample such as cells, virions or molecules) is introduced to the main channel in droplets. In some embodiment, the sample inlet intersects the main channel such that the pressurized sample solution is introduced into the main channel at an angle perpendicular to a stream of fluid passing through the main channel. For example, in some embodiments, the sample inlet and main channel intercept at a T-shaped junction; i.e., such that the sample inlet is perpendicular (90 degrees) to the main channel. However, the sample inlet may intercept the main channel at any angle, and need not introduce the sample fluid to the main channel at an angle that is perpendicular to that flow. In some embodiments the angle between intersecting channels is in the range of from about 60 to about 120 degrees. Particular exemplary angles are 45, 60, 90, and 120 degrees. In some embodiments, the angle between the intersecting channels is in the range of about 5 to about 60 degrees. In some embodiments, the angle between the intersecting channels is in the range of about 5 to about 60 degrees. In some embodiments, the angle between the intersecting channels is in the range of about 5 to about 10, about 5 to about 15, about 5 to about 20, about 5 to about 25, about 5 to about 30, about 5 to about 40, about 5 to about 50, about 5 to about 60, about 10 to about 15, about 10 to about 20, about 10 to about 25, about 10 to about 30, about 10 to about 40, about 10 to about 50, about 10 to about 60, about 15 to about 20, about 15 to about 25, about 15 to about 30, about 15 to about 40, about 15 to about 50, about 15 to about 60, about 20 to about 25, about 20 to about 30, about 20 to about 40, about 20 to about 50, about 20 to about 60, about 25 to about 30, about 25 to about 40, about 25 to about 50, about 25 to about 60, about 30 to about 40, about 30 to about 50, about 30 to about 60, about 40 to about 50, about 40 to about 60, or about 50 to about 60 degrees. In some embodiments, the angle between the intersecting channels is in the range of about 5, about 10, about 15, about 20, about 25, about 30, about 40, about 50, or about 60 degrees. In some embodiments, the angle between the intersecting channels is in the range of at least about 5, about 10, about 15, about 20, about 25, about 30, about 40, or about 50. In some embodiments, the angle between the intersecting channels is in the range of at most about 10, about 15, about 20, about 25, about 30, about 40, about 50, or about 60 degrees. In some embodiments, the angle between the intersecting channels is in the range of about 120 to about 175 degrees. In some embodiments, the angle between the intersecting channels is in the range of about 120 to about 130, about 120 to about 140, about 120 to about 150, about 120 to about 160, about 120 to about 170, about 120 to about 175, about 130 to about 140, about 130 to about 150, about 130 to about 160, about 130 to about 170, about 130 to about 175, about 140 to about 150, about 140 to about 160, about 140 to about 170, about 140 to about 175, about 150 to about 160, about 150 to about 170, about 150 to about 175, about 160 to about 170, about 160 to about 175, or about 170 to about 175 degrees. In some embodiments, the angle between the intersecting channels is in the range of about 120, about 130, about 140, about 150, about 160, about 170, or about 175 degrees. In some embodiments, the angle between the intersecting channels is in the range of at least about 120, about 130, about 140, about 150, about 160, or about 170 degrees. In some embodiments, the angle between the intersecting channels is in the range of at most about 130, about 140, about 150, about 160, about 170, or about 175 degrees.

The droplet extrusion or droplet formation region may also comprise two microfluidic channels carrying immiscible carrier fluid that are introduced on opposite sides of a main microfluidic channel. In some embodiments, the two microfluidic channels are substantially collinear. In some embodiments, such a junction resembles and X-shape. In some embodiments, the main microfluidic channel contains the sample or assay fluid.

The main channel in turn communicates with two or more branch channels at another junction or "branch point", forming, for example, a T-shape or a Y-shape. Other shapes and channel geometries may be used as desired. In sorting embodiments, the region at or surrounding the junction can also be referred to as a discrimination region or a sorting region. Precise boundaries for the discrimination region are not required, but are preferred.

A detection region may be within, communicating or coincident with a portion of the main channel at or downstream of the droplet extrusion region and, in sorting embodiments, at or upstream of the discrimination region or branch point. Precise boundaries for the detection region are not required, but are preferred. The discrimination region may be located immediately downstream of the detection region or it may be separated by a suitable distance consistent with the size of the molecules, the channel dimensions and the detection system. It will be appreciated that the channels may have any suitable shape or cross-section (for example, tubular or grooved), and can be arranged in any suitable manner so long as flow can be directed from inlet to outlet and from one channel into another.

The channels of the disclosure may be microfabricated, for example by etching a silicon chip using conventional photolithography techniques, or using a micromachining technology called "soft lithography". These and other microfabrication methods may be used to provide inexpensive miniaturized devices, and in the case of soft lithography, can provide robust devices having beneficial properties such as improved flexibility, stability, and mechanical strength. When optical detection is employed, the devices provided herein may also provide minimal light scatter from molecule or cell (including virion) suspension and chamber material. In some embodiments, devices provided herein are relatively inexpensive and easy to set up. They can also be disposable, which greatly relieves many of the concerns of gel electrophoresis (for molecules), and of sterilization and permanent adsorption of particles into the flow chambers and channels of conventional FACS machines (for cells, virions and other particle suspensions).

A microfabricated device of the disclosure may be fabricated from a silicon microchip or silicon elastomer. In some embodiments, the dimensions of the chip are those of typical microchips, ranging between about 0.5 cm to about 5 cm per side and about 1 micron to about 1 cm in thickness. The device may contain at least one analysis unit having a main channel with a droplet extrusion region and a coincident detection region. The device may also contain at least one inlet region (which may contain an inlet channel) and one or more outlet regions (which may have fluid communication with a branch channel in each region). In a sorting embodiment, at least one detection region cooperates with at least one discrimination region to divert flow via a detector-originated signal. It shall be appreciated that the "regions" and "channels" are in fluid communication with each other and therefore may overlap; i.e., there may be no clear boundary where a region or channel begins or ends. A microfabricated device can be transparent and can be covered with a material having transparent properties, such as a glass coverslip, to permit detection of a reporter, for example, by an optical device such as an optical microscope.

The dimensions of the detection region are influenced by the nature of the sample under study and, in particular, by the size of the molecules or cells (including virions) under study. For example, viruses can have a diameter from about 20 nm to about 500 nm, although some extremely large viruses may reach lengths of about 2000 nm (i.e., as large or larger than some bacterial cells). By contrast, biological cells are typically many times larger. For example, mammalian cells can have a diameter of about 1 to 50 microns, more typically 10 to 30 microns, although some mammalian cells (e.g., fat cells) can be larger than 120 microns. Plant cells are generally 10 to 100 microns.

Detection regions used for detecting molecules and cells (including virions) have a cross-sectional area large enough to allow a desired molecule to pass through without being substantially slowed down relative to the flow carrying it. To avoid "bottlenecks" and/or turbulence, and promote single-file flow, the channel dimensions, particularly in the detection region, should generally be at least about twice, or at least about five times as large per side or in diameter as the diameter of the largest molecule, cell or droplet that will be passing through it.

For particles (e.g., cells, including virions) or molecules that are in encapsulations (i.e., deposited by the droplet extrusion region) within the flow of the main channel, the channels of the device may be rounded, with a diameter between about 2 and 100 microns. In some embodiments, the round channels of the device are about 60 microns in diameter or about 30 microns at the crossflow area or droplet extrusion region. This geometry facilitates an orderly flow of droplets in the channels. Similarly, the volume of the detection region in an analysis device may be in the range of between about 10 femtoliters (fl) and 5000 fl, about 40 or 50 fl to about 1000 or 2000 fl, or on the order of about 200 fl. In some embodiments, the channels of the device, and particularly the channels of the inlet connecting to a droplet extrusion region, are between about 2 and 50 microns, or about 30 microns.

In one embodiment, droplets at these dimensions tend to conform to the size and shape of the channels, while maintaining their respective volumes. Thus, as droplets move from a wider channel to a narrower channel they become longer and thinner, and vice versa. In some embodiments, droplets are at least about four times as long as they are wide. This droplet configuration, which can be envisioned as a lozenge shape, flows smoothly and well through the channels. Longer droplets, produced in narrower channels, provides a higher shear, meaning that droplets can more easily be sheared or broken off from a flow, i.e. using less force. Droplets may also tend to adhere to channel surfaces, which can slow or block the flow, or produce turbulence. Droplet adherence is overcome when the droplet is massive enough in relation to the channel size to break free. Thus, droplets of varying size, if present, may combine to form uniform droplets having a so-called critical mass or volume that results in smooth or laminar droplet flow. Droplets that are longer than they are wide, for example about four times longer than they are wide, generally have the ability to overcome channel adherence and move freely through the microfluidic device. Thus, in an exemplary embodiment with 60 micron channels, atypical free-flowing droplet is about 60 microns wide and 240 microns long. Droplet dimensions and flow characteristics can be influenced as desired, in part by changing the channel dimensions, e.g. the channel width.

In some embodiments, the devices provided herein generate round, monodisperse droplets. In some embodiments, the droplets have a diameter that is smaller than the diameter of the microchannel; i.e., less than 60 m. Monodisperse droplets may be particularly preferable, e.g., in high throughput devices and other embodiments where it is desirable to generate droplets at high frequency.

To prevent sample (e.g., cells, virions and other particles or molecules) or other material from adhering to the sides of the channels, the channels (and coverslip, if used) may have a coating which minimizes adhesion. Such a coating may be intrinsic to the material from which the device is manufactured, or it may be applied after the structural aspects of the channels have been microfabricated. "TEFLON" is an example of a coating that has suitable surface properties. Alternatively, the channels may be coated with a surfactant.

Non-limiting examples of surfactants that may be used include, but are not limited to, surfactants such as sorbitan-based carboxylic acid esters (e.g., the "Span" surfactants, Fluka Chemika), including sorbitan monolaurate (Span20), sorbitan monopalmitate (Span40), sorbitan monostearate (Span60) and sorbitan monooleate (Span80). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used.

A silicon substrate containing the microfabricated flow channels and other components may be covered and sealed, including with a transparent cover, e.g., thin glass or quartz, although other clear or opaque cover materials may be used. When external radiation sources or detectors are employed, the detection region may be covered with a clear cover material to allow optical access to the cells. For example, anodic bonding to a "PYREX" cover slip can be accomplished by washing both components in an aqueous $H_2SO_4$/$H_2O_2$ bath, rinsing in water, and then, for example, heating to about 350° C. while applying a voltage of 450V.

Switching and flow control can be accomplished in a variety of ways. Some embodiments of the disclosure use pressure drive flow control, e.g., utilizing valves and pumps, to manipulate the flow of cells virions, particles, molecules, enzymes or reagents in one or more directions and/or into one or more channels of a microfluidic device. However, other methods may also be used, alone or in combination with pumps and valves, such as electro-osmotic flow control, electrophoresis and dielectrophoresis. In certain embodiments of the disclosure, the flow moves in one "forward" direction, e.g. from the main inlet region through the main and branch channels to an outlet region. In other embodiments the direction of flow is reversible. Application of these techniques according to the disclosure provides more rapid and accurate devices and methods for analysis or sorting, for example, because the sorting occurs at or in a discrimination region that can be placed at or immediately after a detection region. This provides a shorter distance for molecules or cells to travel, they can move more rapidly and with less turbulence, and can more readily be moved, examined, and sorted in single file, i.e., one at a time. In a reversible embodiment, potential sorting errors can be avoided, for example by reversing and slowing the flow to re-read or resort a molecule, cell or virion (or pluralities thereof) before irretrievably committing the cell or cells to a particular branch channel.

Without being bound by any theory, electro-osmosis is believed to produce motion in a stream containing ions, e.g. a liquid such as a buffer, by application of a voltage differential or charge gradient between two or more electrodes. Neutral (uncharged) molecules or cells (including virions) can be carried by the stream. Electro-osmosis is particularly suitable for rapidly changing the course, direction or speed of flow. Electrophoresis is believed to produce movement of charged objects in a fluid toward one or more electrodes of opposite charge, and away from one on or more electrodes of like charge. In embodiments of the disclosure where an aqueous phase is combined with an oil phase, aqueous droplet encapsulations are encapsulated or separated from each other by oil. In some embodiments, the oil phase is not an electrical conductor and may insulate the encapsulations from the electro-osmotic field. In these embodiment, electro-osmosis may be used to drive the flow of encapsulations if the oil is modified to carry or react to an electrical field, or if the oil is substituted for another phase that is immiscible in water but which does not insulate the water phase from electrical fields.

Dielectrophoresis produces dielectric objects, which have no net charge, but have regions that are positively or negatively charged in relation to each other. Alternating, non-homogeneous electric fields in the presence of encapsulations, including droplets, and/or particles, such as cells or virions, cause the encapsulations and/or particles to become electrically polarized and thus to experience dielectrophoretic forces. Depending on the dielectric polarizability of the particles and the suspending medium, dielectric particles will move either toward the regions of high field strength or low field strength. For example, the polarizability of living cells and virions depends on their composition, morphology, and phenotype and is highly dependent on the frequency of the applied electrical field. Thus, cells and virions of different types and in different physiological states generally possess distinctly different dielectric properties, which may provide a basis for cell separation, e.g., by differential dielectrophoretic forces. Likewise, the polarizability of encapsulations, including droplets, also depends upon their size, shape and composition. For example, droplets that contain salts can be polarized. Individual manipulation of single encapsulations requires field differences (inhomogeneities) with dimensions close to the encapsulations.

Manipulation is also dependent on permittivity (a dielectric property) of the encapsulations and/or particles with the suspending medium. Thus, polymer particles, living cells and virions show negative dielectrophoresis at high-field frequencies in water. For example, dielectrophoretic forces experienced by a latex sphere in a 0.5 MV/m field (10V for a 20 micron electrode gap) in water are predicted to be about 0.2 piconewtons (pN) for a 3.4 micron latex sphere to 15 pN for a 15 micron latex sphere. These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the disclosure. Dielectrophoresis is particularly suitable for moving objects that are electrical conductors. AC current may be used to prevent permanent alignment of ions. Megahertz frequencies are suitable to provide a net alignment, attractive force, and motion over relatively long distances.

Radiation pressure can also be used in the disclosure to deflect and move objects, e.g. encapsulations, droplets, and particles (molecules, cells, virions, etc.) contained therein, with focused beams of light such as lasers. Flow can also be obtained and controlled by providing a pressure differential or gradient between one or more channels of a device or in a method of the disclosure.

In some embodiments, molecules, cells or virions (or droplets containing molecules, cells or virions) can be moved by direct mechanical switching, e.g., with on-off valves or by squeezing the channels. Pressure control may also be used, for example, by raising or lowering an output well to change the pressure inside the channels on the chip. Different switching and flow control mechanisms can be combined on one chip or in one device and can work independently or together as desired.

Detection and discrimination for sorting can be accomplished in a variety of ways. The detector can be any device or method for interrogating a molecule, a cell or a virion as it passes through the detection region. Typically, molecules, cells or virions (or droplets containing such particles) are to be analyzed or sorted according to a predetermined characteristic that is directly or indirectly detectable, and the detector is selected or adapted to detect that characteristic. One detector is an optical detector, such as a microscope, which may be coupled with a computer and/or other image processing or enhancement devices to process images or information produced by the microscope using known techniques. For example, molecules can be analyzed and/or sorted by size or molecular weight. Enzymes can be analyzed and/or sorted by the extent to which they catalyze chemical reaction of a substrate (conversely, substrate can be analyzed and/or sorted by the level of chemical reactivity catalyzed by an enzyme). Cells and virions can be sorted according to whether they contain or produce a particular protein, by using an optical detector to examine each cell or virion for an optical indication of the presence or amount of that protein. The protein may itself be detectable, for example by a characteristic fluorescence, or it may be labeled or associated with a reporter that produces a detectable signal when the desired protein is present, or is present in at least a threshold amount. There is no limit to the kind or number of characteristics that can be identified or measured using the techniques of the disclosure, which include without limitation surface characteristics of the cell or virion and intracellular characteristics, provided only that the characteristic or characteristics of interest for sorting can be sufficiently identified and detected or measured to distinguish cells having the desired characteristic(s) from those which do not. For example, any label or reporter as described herein can be used as the basis for analyzing and/or sorting molecules or cells (including virions), i.e. detecting molecules or cells to be collected.

In some embodiments, the samples (or encapsulations containing them) are analyzed and/or separated based on the intensity of a signal from an optically-detectable reporter bound to or associated with them as they pass through a detection window or "detection region" in the device. In some embodiments, the samples are analyzed and/or separated based on the intensity of a signal from a detectable reporter. Molecules or cells or virions having an amount or level of the reporter at a selected threshold or within a selected range are diverted into a predetermined outlet or branch channel of the device. The reporter signal may be collected by a microscope and measured by a photo multiplier tube (PMT). A computer digitizes the PMT signal and controls the flow via valve action or electro-osmotic potentials. Alternatively, the signal can be recorded or quantified as a measure of the reporter and/or its corresponding characteristic or marker, e.g., for the purpose of evaluation and without necessarily proceeding to sort the molecules or cells.

In one embodiment, the chip is mounted on an inverted optical microscope. Fluorescence produced by a reporter is excited using a laser beam focused on molecules (e.g., DNA, protein, enzyme or substrate) or cells passing through a detection region. Fluorescent reporters include, e.g., rhodamine, fluorescein, Texas red, Cy 3, Cy 5, phycobiliprotein, green fluorescent protein (GFP), YOYO-1 and PicoGreen, to name a few. In molecular fingerprinting applications, the reporter labels are optionally fluorescently labeled single nucleotides, such as fluorescein-dNTP, rhodamine-dNTP, Cy3-dNTP, etc.; where dNTP represents dATP, dTTP, dUTP or dCTP. The reporter can also be chemically-modified single nucleotides, such as biotin-dNTP. In other embodiments, the reporter can be fluorescently or chemically labeled amino acids or antibodies (which bind to a particular antigen, or fragment thereof, when expressed or displayed by a cell or virus).

Thus, in one aspect of the disclosure, the device can analyze and/or sort cells or virions based on the level of expression of selected cell markers, such as cell surface markers, which have a detectable reporter bound thereto, in a manner similar to that currently employed using fluorescence-activated cell sorting (FACS) machines. Proteins or other characteristics within a cell, and which do not necessarily appear on the cell surface, can also be identified and used as a basis for sorting. In another aspect of the disclosure, the device can determine the size or molecular weight of molecules such as polynucleotides or polypeptides (including enzymes and other proteins) or fragments thereof passing through the detection region. Alternatively, the device can determine the presence or degree of some other characteristic indicated by a reporter. If desired, the cells, virions or molecules can be sorted based on this analysis. The sorted cells, virions or molecules can be collected from the outlet channels and used as needed.

To detect a reporter or determine whether a molecule, cell or virion has a desired characteristic, the detection region may include an apparatus for stimulating a reporter for that characteristic to emit measurable light energy, e.g., a light source such as a laser, laser diode, high-intensity lamp, (e.g., mercury lamp), and the like. In embodiments where a lamp is used, the channels may be shielded from light in all regions except the detection region. In embodiments where a laser is used, the laser can be set to scan across a set of detection regions from different analysis units. In addition, laser diodes may be microfabricated into the same chip that contains the analysis units. Alternatively, laser diodes may be incorporated into a second chip (i.e., a laser diode chip) that is placed adjacent to the microfabricated analysis or sorter chip such that the laser light from the diodes shines on the detection region(s).

In some embodiments, an integrated semiconductor laser and/or an integrated photodiode detector are included on the silicon wafer in the vicinity of the detection region. This design provides the advantages of compactness and a shorter optical path for exciting and/or emitted radiation, thus minimizing distortion.

Sorting schemes can be accomplished in a variety of ways. According to the disclosure, molecules (such as DNA, protein, enzyme or substrate) or particles (i.e., cells, including virions) are sorted dynamically in a flow stream of microscopic dimensions based on the detection or measurement of a characteristic, marker or reporter that is associated with the molecules or particles. More specifically, encapsulations of a solution (for example an aqueous solution or buffer), containing a sample of molecules, cells or virions, are introduced through a droplet extrusion region into a stream of fluid (for example, a non-polar fluid such as decane or other oil) in the main channel. The individual droplet encapsulations are then analyzed and/or sorted in the flow stream, thereby sorting the molecules, cells or virions contained within the droplets.

The flow stream in the main channel is typically, but not necessarily continuous and may be stopped and started, reversed or changed in speed. Prior to sorting, a liquid that does not contain samples molecules, cells or virions can be introduced into a sample inlet region (such as an inlet well or channel) and directed through the droplet extrusion region, e.g., by capillary action, to hydrate and prepare the device for use. Likewise, buffer or oil can also be introduced into a main inlet region that communicates directly with the main channel to purge the device (e.g., or "dead" air) and prepare it for use. If desired, the pressure can be adjusted or equalized, for example, by adding buffer or oil to an outlet region.

The pressure at the droplet extrusion region can also be regulated by adjusting the pressure on the main and sample inlets, for example, with pressurized syringes feeding into those inlets. By controlling the pressure difference between the oil and water sources at the droplet extrusion region, the size and periodicity of the droplets generated may be regulated. Alternatively, a valve may be placed at or coincident to either the droplet extrusion region or the sample inlet connected thereto to control the flow of solution into the droplet extrusion region, thereby controlling the size and periodicity of the droplets. Periodicity and droplet volume may also depend on channel diameter, the viscosity of the fluids, and shear pressure.

The droplet forming liquid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with the population of molecules, cells or virions to be analyzed and/or sorted can be used. The fluid passing through the main channel and in which the droplets are formed is preferably one that is not miscible with the droplet forming fluid. In some embodiments, the fluid passing through the main channel is a non-polar solvent, for example decane (e.g., tetradecane or hexadecane) or another oil.

The fluids used in the disclosure may contain additives, such as agents which reduce surface tensions (surfactants). Exemplary surfactants include Tween, Span, fluorinated oils, and other agents that are soluble in oil relative to water. Surfactants may aid in controlling or optimizing droplet size, flow and uniformity, for example by reducing the shear force needed to extrude or inject droplets into an intersecting channel. This may affect droplet volume and periodicity, or the rate or frequency at which droplets break off into an intersecting channel.

Channels of the disclosure may be formed from silicon elastomer (e.g. RTV), urethane compositions, of from silicon-urethane composites such as those available from Polymer Technology Group (Berkeley, Calif.), e.g. PurSi™ and CarboSil™. The channels may also be coated with additives or agents, such as surfactants, TEFLON, or fluorinated oils such as octadecafluoroctane (98%, Aldrich) or fluorononane. TEFLON is particularly suitable for silicon elastomer (RTV) channels, which are hydrophobic and advantageously do not absorb water, but they may tend to swell when exposed to an oil phase. Swelling may alter channel dimensions and shape, and may even close off channels, or may affect the integrity of the chip, for example by stressing the seal between the elastomer and a coverslip. Urethane substrates do not tend to swell in oil but are hydrophilic, they may undesirably absorb water, and tend to use higher operating pressures. Hydrophobic coatings may be used to reduce or eliminate water absorption. Absorption or swelling issues may also be addressed by altering or optimizing pressure or droplet frequency (e.g. increasing periodicity to reduce absorption). RTV-urethane hybrids may be used to combine the hydrophobic properties of silicon with the hydrophilic properties of urethane.

Embodiments of the disclosure are also provided in which there are two or more droplet formation regions introducing droplets of samples into the main channel. For example, a first droplet extrusion region may introduce droplets of a first sample into a flow of fluid (e.g., oil) in the main channel and a second droplet extrusion region may introduce droplets of a second sample into the flow of fluid in main channel, and so forth. Optionally, the second droplet extrusion region is downstream from the first droplet extrusion region (e.g., about 30 µm). In one embodiment, the fluids introduced into the two or more different droplet extrusion regions comprise the same fluid or the same type of fluid (e.g., different aqueous solutions). For example, in one embodiment droplets of an aqueous solution containing an enzyme are introduced into the main channel at the first droplet extrusion region and droplets of aqueous solution containing a substrate for the enzyme are introduced into the main channel at the second droplet extrusion region. The introduction of droplets through the different extrusion regions may be controlled, e.g., so that the droplets combine (allowing, for example, the enzyme to catalyze a chemical reaction of the substrate). Alternatively, the droplets introduced at the different droplet extrusion regions may be droplets of different fluids which may be compatible or incompatible. For example, the different droplets may be different aqueous solutions, or droplets introduced at a first droplet extrusion region may be droplets of one fluid (e.g., an aqueous solution) whereas droplets introduced at a second droplet extrusion region may be another fluid (e.g., alcohol or oil).

The concentration (i.e., number) of scaffolds, molecules, cells or virions in a droplet can influence sorting efficiently and therefore may be optimized. In particular, the sample concentration should be dilute enough that most of the droplets contain no more than a singles scaffold, molecule, cell or virion, with only a small statistical chance that a droplet will contain two or more molecules, cells or virions. In some embodiments, the sample concentration should be such that a single cell is encapsulated with a single scaffold. This is to ensure that for the large majority of measurements, the level of reporter measured in each droplet as it passes through the detection region corresponds to a single molecule, cell or virion and not to two or more molecules, cells or virions. Additionally, ensuring that a single cell or virion is encapsulated with only a single encoded effector scaffold ensures that positive "hits" are correctly correlated with the correct effectors.

The parameters which govern this relationship are the volume of the droplets and the concentration of molecules, cells or virions in the sample solution. The probability that a droplet will contain two or more scaffolds, molecules, cells, or virions ($P \leq 2$) can be expressed as $$P \leq 2 = 1 - \{1 + [\text{virion}] \times V\} \times e - [\text{virion}] \times V$$

where "[virion]" is the concentration of molecules, cells or virions in units of number of molecules, cells or virions per cubic micron ($\mu m^3$), and V is the volume of the droplet in units of $\mu m^3$.

It will be appreciated that $P \leq 2$ can be minimized by decreasing the concentration of scaffolds, molecules, cells or virions in the sample solution. However, decreasing the concentration of molecules, cells or virions in the sample solution also results in an increased volume of solution processed through the device and can result in longer run times. Accordingly, it is desirable to minimize to presence of multiple molecules, cells or virions in the droplets (thereby increasing the accuracy of the sorting) and to reduce the volume of sample, thereby permitting a sorted sample in a reasonable time in a reasonable volume containing an acceptable concentration of molecules, cells or virions.

The maximum tolerable P≤2 depends on the desired "purity" of the sorted sample. The "purity" in this case refers to the fraction of sorted molecules, cells or virions that possess a desired characteristic (e.g., display a particular antigen, are in a specified size range or are a particular type of molecule, cell or virion). The purity of the sorted sample is inversely proportional to P≤2. For example, in applications where high purity is not needed or desired a relatively high P≤2 (e.g., P≤2=0.2) may be acceptable. For most applications, maintaining P≤2 at or below about 0.1, or at or below about 0.01, provides satisfactory results.

A sample solution containing a mixture or population of molecule, cells or virions in a suitable carrier fluid (such as a liquid or buffer described above) is supplied to the sample inlet region, and droplets of the sample solution are introduced, at the droplet extrusion region, into the flow passing through the main channel. The force and direction of flow can be controlled by any desired method for controlling flow, for example, by a pressure differential, by valve action or by electro-osmotic flow (e.g., produced by electrodes at inlet and outlet channels). This permits the movement of the cells into one or more desired branch channels or outlet regions.

A "forward" sorting algorithm, according to the disclosure, includes embodiments where droplets from a droplet extrusion region flow through the device to a predetermined branch or outlet channel (which can be called a "waste channel"), until the level of measurable reporter of a molecule, cell or virion within a droplet is above a pre-set threshold. At that time, the flow is diverted to deliver the droplet (and the scaffold, molecule, cell, and/or virion contained therein) to another channel. For example, in an electro-osmotic embodiment, where switching is virtually instantaneous and throughput is limited by the highest voltage, the voltages are temporarily changed to divert the chosen droplet to another predetermined outlet channel (which can be called a "collection channel"). Sorting, including synchronizing detection of a reporter and diversion of the flow, can be controlled by various methods including computer or microprocessor control. Different algorithms for sorting in the microfluidic device can be implemented by different computer programs, such as programs used in conventional FACS devices. For example, a programmable card can be used to control switching, such as a Lab PC 1200 Card, available from National Instruments, Austin, Tex. Algorithms as sorting procedures can be programmed using C++, LAB VIEW, or any suitable software.

A "reversible" sorting algorithm can be used in place of a "forward" mode, for example in embodiments where switching speed may be limited. For example, a pressure-switched scheme can be used instead of electro-osmotic flow and does not require high voltages and may be more robust for longer runs. However, mechanical constraints may cause the fluid switching speed to become rate-limiting. In a pressure-switched scheme the flow is stopped when a molecule or cell or virion of interest is detected within a droplet. By the time the flow stops, the droplet containing the molecule, cell or virion may be past the junction or branch point and be part of the way down the waste channel. In this situation, a reversible embodiment can be used. The system can be run backwards at a slower (switchable) speed (e.g., from waste to inlet), and the droplet is then switched to a different branch or collection channel. At that point, a potentially mis-sorted droplet (and the molecule, cell or virion therein) is "saved", and the device can again be run at high speed in the forward direction. This "reversible" sorting method is not possible with standard FACS machines. FACS machines mostly sort aerosol droplets which cannot be reversed back to the chamber, in order to be redirected. The aerosol droplet sorters are virtually irreversible. Reversible sorting is particularly useful for identifying molecules, cells or virions that are rare (e.g., in molecular evolution and cancer cytological identification) or few in number, which may be misdirected due to a margin of error inherent to any fluidic device. The reversible nature of the device of the disclosure permits a reduction in this possible error.

In addition, a "reversible" sorting method permits multiple time course measurements of a molecule, cell or virion contained within a single droplet. This allows for observations or measurements of the same molecule, cell or virion at different times, because the flow reverses the cell back into the detection window again before redirecting the cell into a different channel. Thus, measurements can be compared or confirmed, and changes in properties over time can be examined, for example in kinetic studies.

When trying to separate scaffolds, molecules, cells or virions in a sample at a very low ratio to the total number of scaffolds, molecules, cells or virions, a sorting algorithm can be implemented that is not limited by the intrinsic switching speed of the device. Consequently, the droplets flow at the highest possible static (non-switching) speed from the inlet channel to the waste channel. Unwanted droplets (i.e., containing unwanted molecules, cells or virions) can be directed into the waste channel at the highest speed possible, and when a droplet containing a desired molecule, cell or virion is detected, the flow can be slowed down and then reversed, to direct the droplet back into the detection region, from where it can be redirected (i.e. to accomplish efficient switching). Hence the droplets (and the molecules, cells or virions contained therein) can flow at the highest possible static speed.

Provided herein are methods for controlling for variables such as temperature, pH and concentration. This may be accomplished by converging two aqueous streams to form droplets, where, for example, the first aqueous stream would contain 2× the concentration of component "A" desired in the droplet and the second aqueous stream would contain 2× the concentration of component "B" desired in the droplet, thus when the streams merge they would form a 1× solution of both "A" and "B". Different ratios of aqueous streams converging with different concentrations of reagents may also be sued to reach desired final concentrations of samples, scaffolds, and/or reagents. The concentrations in droplets are controlled by knowing what the concentrations are of components in each aqueous stream. This concept can be applied to pH, salt, concentration, etc. For temperature control a transparent stage may be used to heat the chip to a desired temperature.

Both the fluid comprising the droplets and the fluid carrying the droplets (i.e., the aqueous and non-polar fluids) may have a relatively low Reynolds Number, for example $10^{-2}$. The Reynolds Number represents an inverse relationship between the density and velocity of a fluid and its viscosity in a channel of given length. More viscous, less dense, slower moving fluids over a shorter distance will have a lower Reynolds Number, and are easier to divert, stop, start, or reverse without turbulence. Because of the small sizes and slow velocities, microfabricated fluid systems are often in a low Reynolds number regime (Re<<1). In this regime, inertial effects, which cause turbulence and secondary flows, are negligible; viscous effects dominate the dynamics. These conditions are advantageous for sorting, and are provided by microfabricated devices of the disclosure. Accordingly, the microfabricated devices of the disclosure are optionally operated at a low or very low Reynold's number.

In one aspect provided herein is a microfluidic device designed for droplet based encoded library screening. In some embodiments, the device comprises a first microfluidic channel comprising an aqueous fluid. In some embodiments, the device comprises a second microfluidic channel comprising a fluid immiscible with the aqueous stream. In some embodiments, the device comprises a junction at which the first microfluidic channel is in fluid communication with the second microfluidic channel. In some embodiments, the junction of the first and second microfluidic channels defines a device plane. In some embodiments, the junction is configured to form droplets of the aqueous fluid within the fluid from the second microfluidic channel. In some embodiments, the second microfluidic channel is configured to continue past the junction thereby defining an assay flow path. In some embodiments, the fluid from the second microfluidic channel with the droplets therein moves past the junction in a third microfluidic channel that defines an assay flow path. The assay flow path may also be called an incubation region. In some embodiments, the device comprises a cleavage region for cleaving effectors from scaffolds disposed within the assay flow path. In some embodiments, the device comprises a detection region. In some embodiments, the device comprises a sorting region. In some embodiments, the device comprises a stimulation region.

In some embodiments, the device comprises a third microfluidic channel. The third microfluidic channel may be in fluidic communication with the first microfluidic channel upstream of the junction of the first and second microfluidic channels. This third microfluidic channel may be used to mix an additional aqueous fluid with the first aqueous fluid prior to droplet formation, thus allowing the mixing of different sets of reagents shortly before the droplets are formed.

The junction of the first and second microfluidic channels is configured to create aqueous droplets encapsulated in the immiscible fluid of the second microfluidic channel. This junction may be of any configuration. In some embodiments, the junction is a T-junction. In some embodiments, the junction is at an oblique angle. In some embodiments, the junction further comprises a supplementary microfluidic channel. In some embodiments, the supplementary microfluidic channel comprises a second fluid immiscible with the aqueous stream. In some embodiments, the second fluid immiscible with the aqueous stream is the same as the fluid immiscible with the aqueous stream from the second microfluidic channel. In some embodiments, the second fluid immiscible with the aqueous stream is different from the fluid immiscible with the aqueous stream from the second microfluidic channel. In some embodiments, the second microfluidic channel and the supplementary microfluidic channel are positioned on opposite sides of the first microfluidic channel. In some embodiments, the second microfluidic channel and the supplementary microfluidic channel are configured to add their respective fluids immiscible with the aqueous stream simultaneously.

After the junction, the flow path of the second microfluidic channel may continue along the same trajectory for a least a short distance. After droplet formation, the channel downstream of the junction forms an assay flow path. The assay flow path is the path of the microfluidic channel where the screening assay is performed in the droplet. As the droplet continues along this assay flow path, additional unit operations can be performed on the droplet in sequences that allow an assay with a detectable readout to occur within the droplet. In some embodiments, the assay flow path comprises a cleavage region. In some embodiments, the assay flow path comprises a detection region. In some embodiments, the assay flow path comprises a sorting region. In some embodiments, the assay flow path comprises a stimulation region.

The assay flow path may be in any shape. In some embodiments, the assay flow path acts as an incubation region, allowing the assay to be performed over a desired length of time. In some embodiments, the assay flow path comprises a serpentine path region. The serpentine path region may contain a plurality of curves or turns. Such a pathway allows for an extended flow path to able to be embedded on a device of a small size. Additionally, the curves of the flow path may be used to orient various detectors, stimulators, sorters, or other components in a manner that minimizes background signal, cross-talk, or bleed through of various inputs into the droplets as they travel along the path. In some embodiments, this is accomplished by orienting the various inputs of unit operations along the curves or turns of the serpentine path. This minimizes the amount of the input that can travel along the flow path. For example, configuring a light source to input the light at a location along a curve or turn of the flow path minimizes the light that will travel along the path and reach droplets not the target of the emission.

The serpentine path region can be any length of the microfluidic device and can comprise any number of curves or turns. In some embodiments, the serpentine flow path region comprises about 10 curves to about 100 curves. In some embodiments, the serpentine flow path region comprises about 10 curves to about 20 curves, about 10 curves to about 30 curves, about 10 curves to about 40 curves, about 10 curves to about 50 curves, about 10 curves to about 100 curves, about 20 curves to about 30 curves, about 20 curves to about 40 curves, about 20 curves to about 50 curves, about 20 curves to about 100 curves, about 30 curves to about 40 curves, about 30 curves to about 50 curves, about 30 curves to about 100 curves, about 40 curves to about 50 curves, about 40 curves to about 100 curves, or about 50 curves to about 100 curves. In some embodiments, the serpentine flow path region comprises about 10 curves, about 20 curves, about 30 curves, about 40 curves, about 50 curves, or about 100 curves. In some embodiments, the serpentine flow path region comprises at least about 10 curves, about 20 curves, about 30 curves, about 40 curves, or about 50 curves. In some embodiments, the serpentine flow path region comprises at most about 20 curves, about 30 curves, about 40 curves, about 50 curves, or about 100 curves.

In some embodiments, the assay flow path comprises one or more chambers disposed within the assay flow path. In some embodiments, one or more of the chambers comprise an entrance and exit microfluidic channel. In some embodiments, the entrance microfluidic channel is at an upstream position and the exit microfluidic channel is at a downstream position of the chamber. In some embodiments, the entrance microfluidic channels and exit microfluidic channels act as connecting channels between chambers. In some embodiments, each droplet travelling through the assay flow path travels through the one or more chambers. In some embodiments, the chambers are configured to adjust the flow rate of the droplets as they flow through the assay flow path. In some embodiments, the chambers are configured to adjust the residence time of the droplets as they flow through the assay flow path. In some embodiments, the one or more chambers do not comprise an entrance and exit microfluidic channel (e.g., there are no connecting channels between the chambers). In some embodiments, the one or more chambers are connected to each other. In some embodiments, the one or more chambers are arranged to form serpentine assay flow path.

Additional design considerations may be taken into mind when selecting desired chamber and assay flow path geometry. For example, characteristics of the immiscible carrier fluid can influence suitability of a chamber or channel geometry for a particular assay being performed on a device. For example, immiscible carrier fluids with high viscosity contribute to greater resistance to flow on the device, and thus are less compatible with device flow path geometries which utilize substantial lengths of narrow channels or chambers. However, widening of channels or chambers on the device can increase dispersion of droplets travelling through the chambers or channels, thereby yielding a high variance of incubation times for individual droplets travelling through the device. Thus, in some embodiments, it is preferable that a device be operated with a low-viscosity immiscible carrier fluid, such as 3-ethoxyperfluoro(2-methylhexane). In some embodiments, the device is designed to optimize characteristics such as residence time, modest flow pressures, and dispersion ratio with a particular immiscible carrier fluid. In some embodiments, the device is designed for optimal performance with low-density (e.g. less than 1.00 g/mL) immiscible carrier fluid with low viscosity. In some embodiments, the device is designed for optimal performance with 3-ethoxyperfluoro(2-methylhexane) as the immiscible carrier fluid.

In some embodiments, the chambers are configured to prevent the trapping of droplets as the droplets travel through the flow path. In embodiments wherein a carrier fluid denser than the aqueous droplets is used (e.g. 3-ethoxyperfluoro(2-methylhexane)), aqueous droplets may rise to the top of the widened, heightened chambers and become trapped within the chamber as the droplets and carrier fluid flow through the device. To counteract this, in some embodiments, the chambers and entrance and or exit microfluidic channels are configured to have only a small difference in channel height between the chambers and the connecting channels. In some embodiments, the height between the chambers and the exit channels does not change until after the width of the channel has been narrowed along the flow path. By adjusting the height only after narrowing the width of the channel, droplets are more prone to flowing along the desired path and not becoming trapped.

In some embodiments, the height of the chambers is only slightly greater than the height of the connecting channels. In some embodiments, the height of the chamber is about 1.1× to about 3× greater than the height of the connecting channel. In some embodiments, the height of the chamber is about 3× to about 2.5×, about 3× to about 2×, about 3× to about 1.9×, about 3× to about 1.8×, about 3× to about 1.7×, about 3× to about 1.6×, about 3× to about 1.5×, about 3× to about 1.4×, about 3× to about 1.3×, about 3× to about 1.2×, about 3× to about 1.1×, about 2.5× to about 2×, about 2.5× to about 1.9×, about 2.5× to about 1.8×, about 2.5× to about 1.7×, about 2.5× to about 1.6×, about 2.5× to about 1.5×, about 2.5× to about 1.4×, about 2.5× to about 1.3×, about 2.5× to about 1.2×, about 2.5× to about 1.1×, about 2× to about 1.9×, about 2× to about 1.8×, about 2× to about 1.7×, about 2× to about 1.6×, about 2× to about 1.5×, about 2× to about 1.4×, about 2× to about 1.3×, about 2× to about 1.2×, about 2× to about 1.1×, about 1.9× to about 1.8×, about 1.9× to about 1.7×, about 1.9× to about 1.6×, about 1.9× to about 1.5×, about 1.9× to about 1.4×, about 1.9× to about 1.3×, about 1.9× to about 1.2×, about 1.9× to about 1.1×, about 1.8× to about 1.7×, about 1.8× to about 1.6×, about 1.8× to about 1.5×, about 1.8× to about 1.4×, about 1.8× to about 1.3×, about 1.8× to about 1.2×, about 1.8× to about 1.1×, about 1.7× to about 1.6×, about 1.7× to about 1.5×, about 1.7× to about 1.4×, about 1.7× to about 1.3×, about 1.7× to about 1.2×, about 1.7× to about 1.1×, about 1.6× to about 1.5×, about 1.6× to about 1.4×, about 1.6× to about 1.3×, about 1.6× to about 1.2×, about 1.6× to about 1.1×, about 1.5× to about 1.4×, about 1.5× to about 1.3×, about 1.5× to about 1.2×, about 1.5× to about 1.1×, about 1.4× to about 1.3×, about 1.4× to about 1.2×, about 1.4× to about 1.1×, about 1.3× to about 1.2×, about 1.3× to about 1.1×, or about 1.2× to about 1.1× greater than the height of the connecting channel. In some embodiments, the height of the chamber is about 3×, about 2.5×, about 2×, about 1.9×, about 1.8×, about 1.7×, about 1.6×, about 1.5×, about 1.4×, about 1.3×, about 1.2×, or about 1.1×. In some embodiments, the height of the chamber is at least about 3×, about 2.5×, about 2×, about 1.9×, about 1.8×, about 1.7×, about 1.6×, about 1.5×, about 1.4×, about 1.3×, or about 1.2× greater than the height of the connecting channel. In some embodiments, the height of the chamber is at most about 2.5×, about 2×, about 1.9×, about 1.8×, about 1.7×, about 1.6×, about 1.5×, about 1.4×, about 1.3×, about 1.2×, or about 1.1× greater than the height of the connecting channel. In some embodiments, the height of the chamber is from about 1.1× to about 1.8× greater than the height of the connecting channel. In some embodiments, the height of the chamber is from about 1.4× to about 1.8× greater than the height of the connecting channel. In some embodiments, the height of the chamber is about 1.1× greater than the height of the connecting channel. In some embodiments, the height of the chamber is about 1.2× greater than the height of the connecting channel. In some embodiments, the height of the chamber is about 1.3× greater than the height of the connecting channel. In some embodiments, the height of the chamber is about 1.4× greater than the height of the connecting channel. In some embodiments, the height of the chamber is about 1.5× greater than the height of the connecting channel. In some embodiments, the height of the chamber is about 1.6× greater than the height of the connecting channel. In some embodiments, the height of the chamber is about 1.7× greater than the height of the connecting channel. In some embodiments, the height of the chamber is about 1.8× greater than the height of the connecting channel. In some embodiments, the height of the chamber is about 1.9× greater than the height of the connecting channel. In some embodiments, the height of the chamber is about 2× greater than the height of the connecting channel.

In some embodiments, the height of the chamber is about 50 microns to about 120 microns. In some embodiments, the height of the chamber is about 120 microns to about 100 microns, about 120 microns to about 90 microns, about 120 microns to about 80 microns, about 120 microns to about 70 microns, about 120 microns to about 60 microns, about 120 microns to about 50 microns, about 100 microns to about 90 microns, about 100 microns to about 80 microns, about 100 microns to about 70 microns, about 100 microns to about 60 microns, about 100 microns to about 50 microns, about 90 microns to about 80 microns, about 90 microns to about 70 microns, about 90 microns to about 60 microns, about 90 microns to about 50 microns, about 80 microns to about 70 microns, about 80 microns to about 60 microns, about 80 microns to about 50 microns, about 70 microns to about 60 microns, about 70 microns to about 50 microns, or about 60 microns to about 50 microns. In some embodiments, the height of the chamber is about 120 microns, about 100 microns, about 90 microns, about 80 microns, about 70 microns, about 60 microns, or about 50 microns. In some embodiments, the height of the chamber is at least about 120 microns, about 100 microns, about 90 microns, about 80 microns, about 70 microns, or about 60 microns. In some embodiments, the height of the chamber is at most about 100 microns, about 90 microns, about 80 microns, about 70 microns, about 60 microns, or about 50 microns. In some embodiments, the height of the chamber is about 80 microns.

In some embodiments, the height of the chamber is about 300 microns to about 1,000 microns. In some embodiments, the height of the chamber is about 1,000 microns to about 750 microns, about 1,000 microns to about 600 microns, about 1,000 microns to about 500 microns, about 1,000 microns to about 450 microns, about 1,000 microns to about 400 microns, about 1,000 microns to about 350 microns, about 1,000 microns to about 300 microns, about 750 microns to about 600 microns, about 750 microns to about 500 microns, about 750 microns to about 450 microns, about 750 microns to about 400 microns, about 750 microns to about 350 microns, about 750 microns to about 300 microns, about 600 microns to about 500 microns, about 600 microns to about 450 microns, about 600 microns to about 400 microns, about 600 microns to about 350 microns, about 600 microns to about 300 microns, about 500 microns to about 450 microns, about 500 microns to about 400 microns, about 500 microns to about 350 microns, about 500 microns to about 300 microns, about 450 microns to about 400 microns, about 450 microns to about 350 microns, about 450 microns to about 300 microns, about 400 microns to about 350 microns, about 400 microns to about 300 microns, or about 350 microns to about 300 microns. In some embodiments, the height of the chamber is about 1,000 microns, about 750 microns, about 600 microns, about 500 microns, about 450 microns, about 400 microns, about 350 microns, or about 300 microns. In some embodiments, the height of the chamber is at least about 1,000 microns, about 750 microns, about 600 microns, about 500 microns, about 450 microns, about 400 microns, or about 350 microns. In some embodiments, the height of the chamber is at most about 750 microns, about 600 microns, about 500 microns, about 450 microns, about 400 microns, about 350 microns, or about 300 microns. In some embodiments, the height of the chamber is about 500 microns.

In some embodiments, the width of the connecting channel is about 50 microns to about 120 microns. In some embodiments, the width of the connecting channel is about 120 microns to about 100 microns, about 120 microns to about 90 microns, about 120 microns to about 80 microns, about 120 microns to about 70 microns, about 120 microns to about 60 microns, about 120 microns to about 50 microns, about 100 microns to about 90 microns, about 100 microns to about 80 microns, about 100 microns to about 70 microns, about 100 microns to about 60 microns, about 100 microns to about 50 microns, about 90 microns to about 80 microns, about 90 microns to about 70 microns, about 90 microns to about 60 microns, about 90 microns to about 50 microns, about 80 microns to about 70 microns, about 80 microns to about 60 microns, about 80 microns to about 50 microns, about 70 microns to about 60 microns, about 70 microns to about 50 microns, or about 60 microns to about 50 microns. In some embodiments, the width of the connecting channel is about 120 microns, about 100 microns, about 90 microns, about 80 microns, about 70 microns, about 60 microns, or about 50 microns. In some embodiments, the width of the connecting channel is at least about 120 microns, about 100 microns, about 90 microns, about 80 microns, about 70 microns, or about 60 microns. In some embodiments, the width of the connecting channel is at most about 100 microns, about 90 microns, about 80 microns, about 70 microns, about 60 microns, or about 50 microns. In some embodiments, the width of the connecting channel is about 80 microns.

In some embodiments, the height of the connecting channel is about 35 microns to about 75 microns. In some embodiments, the height of the connecting channel is about 75 microns to about 65 microns, about 75 microns to about 55 microns, about 75 microns to about 50 microns, about 75 microns to about 45 microns, about 75 microns to about 40 microns, about 75 microns to about 35 microns, about 65 microns to about 55 microns, about 65 microns to about 50 microns, about 65 microns to about 45 microns, about 65 microns to about 40 microns, about 65 microns to about 35 microns, about 55 microns to about 50 microns, about 55 microns to about 45 microns, about 55 microns to about 40 microns, about 55 microns to about 35 microns, about 50 microns to about 45 microns, about 50 microns to about 40 microns, about 50 microns to about 35 microns, about 45 microns to about 40 microns, about 45 microns to about 35 microns, or about 40 microns to about 35 microns. In some embodiments, the height of the connecting channel is about 75 microns, about 65 microns, about 55 microns, about 50 microns, about 45 microns, about 40 microns, or about 35 microns. In some embodiments, the height of the connecting channel is at least about 75 microns, about 65 microns, about 55 microns, about 50 microns, about 45 microns, or about 40 microns. In some embodiments, the height of the connecting channel is at most about 65 microns, about 55 microns, about 50 microns, about 45 microns, about 40 microns, or about 35 microns. In some embodiments, the height of the connecting channel is about 50 microns.

In some embodiments, the chambers are configured to reduce the flow rate of the droplets as the droplets travel through the device. In some embodiments, the flow rate is reduced due to an increase in the cross-sectional area of the chamber relative to the microfluidic channel upstream of the chamber. For example, a chamber having 10× the cross-sectional area compared to the microfluidic channel upstream of the chamber would have a flow rate through the chamber of 10% of the flow rate compared to the flow rate through the upstream microfluidic channel. In some embodiments, the flow rate through the chambers is about 1% to about 25% of the flow rate through the microfluidic channel upstream of the chambers. In some embodiments, the flow rate through the chambers is about 25% to about 20%, about 25% to about 15%, about 25% to about 12%, about 25% to about 10%, about 25% to about 8%, about 25% to about 5%, about 25% to about 3%, about 25% to about 1%, about 20% to about 15%, about 20% to about 12%, about 20% to about 10%, about 20% to about 8%, about 20% to about 5%, about 20% to about 3%, about 20% to about 1%, about 15% to about 12%, about 15% to about 10%, about 15% to about 8%, about 15% to about 5%, about 15% to about 3%, about 15% to about 1%, about 12% to about 10%, about 12% to about 8%, about 12% to about 5%, about 12% to about 3%, about 12% to about 1%, about 10% to about 8%, about 10% to about 5%, about 10% to about 3%, about 10% to about 1%, about 8% to about 5%, about 8% to about 3%, about 8% to about 1%, about 5% to about 3%, about 5% to about 1%, or about 3% to about 1% of the flow rate through the microfluidic channel upstream of the chambers. In some embodiments, the flow rate through the chambers is about 25%, about 20%, about 15%, about 12%, about 10%, about 8%, about 5%, about 3%, or about 1% of the flow rate through the microfluidic channel upstream of the chambers. In some embodiments, the flow rate through the chambers is at least about 25%, about 20%, about 15%, about 12%, about 10%, about 8%, about 5%, or about 3%. In some embodiments, the flow rate through the chambers is at most about 20%, about 15%, about 12%, about 10%, about 8%, about 5%, about 3%, or about 1% of the flow rate through the microfluidic channel upstream of the chambers. In some embodiments, the flow rate through the chambers is about 10% of the flow rate through the microfluidic channel upstream of the chambers. In some embodiments, the flow rate through the microfluidic channel upstream of the chambers varies at different points of the device. In such embodiments, the flow rate used for the flow rate comparison to the chambers is the fastest flow rate after the droplet formation junction (e.g. the microfluidic channel portion with the smallest cross-sectional area).

In some embodiments, the chambers are configured such that the droplets formed on the microfluidic device have substantially the same residence time travelling through the device. In some embodiments, the microfluidic device is configured such that the droplets form on the device have substantially the same residence time travelling through the device. In some embodiments, this is measured by the dispersion ratio. The dispersion ratio is calculated according to the following formula: $6\sigma/T_{avg}$; wherein $T_{avg}$ is the average residence time of a droplet travelling through the device and $\sigma$ is the standard deviation of residence time of droplets travelling through the device. In some embodiments, the device has a dispersion ratio of at most about 10%, about 8%, about 6%, about 5%, about 4%, about 3%, about 2%, or about 1%. In some embodiments, the device has a dispersion ratio of at most about 10%. In some embodiments, the device has a dispersion ratio of at most about 8%. In some embodiments, the device has a dispersion ratio of at most about 6%. In some embodiments, the device has a dispersion ratio of at most about 5%. In some embodiments, the device has a dispersion ratio of at most about 4%. In some embodiments, the device has a dispersion ratio of at most about 3%. In some embodiments, the device has a dispersion ratio of at most about 2%. In some embodiments, the device has a dispersion ratio of at most about 1%.

Figure 9A:
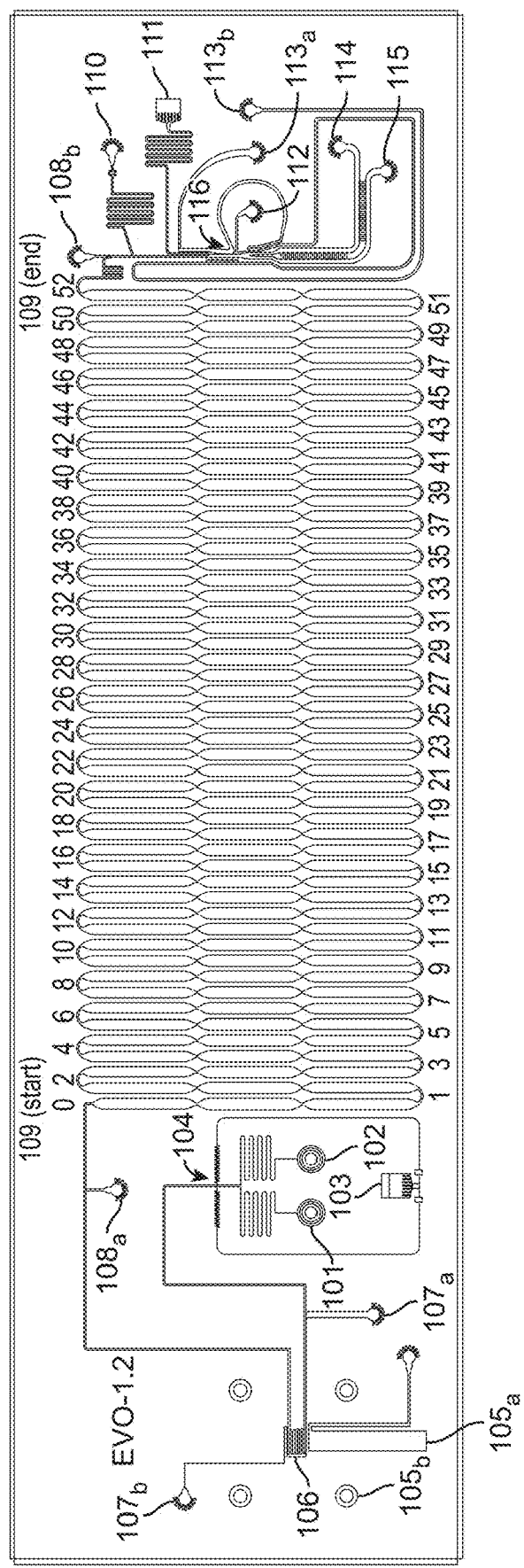
FIG. 9A provides a depiction of an exemplary microfluidic device provided with the methods and systems described herein.
Figure 10:
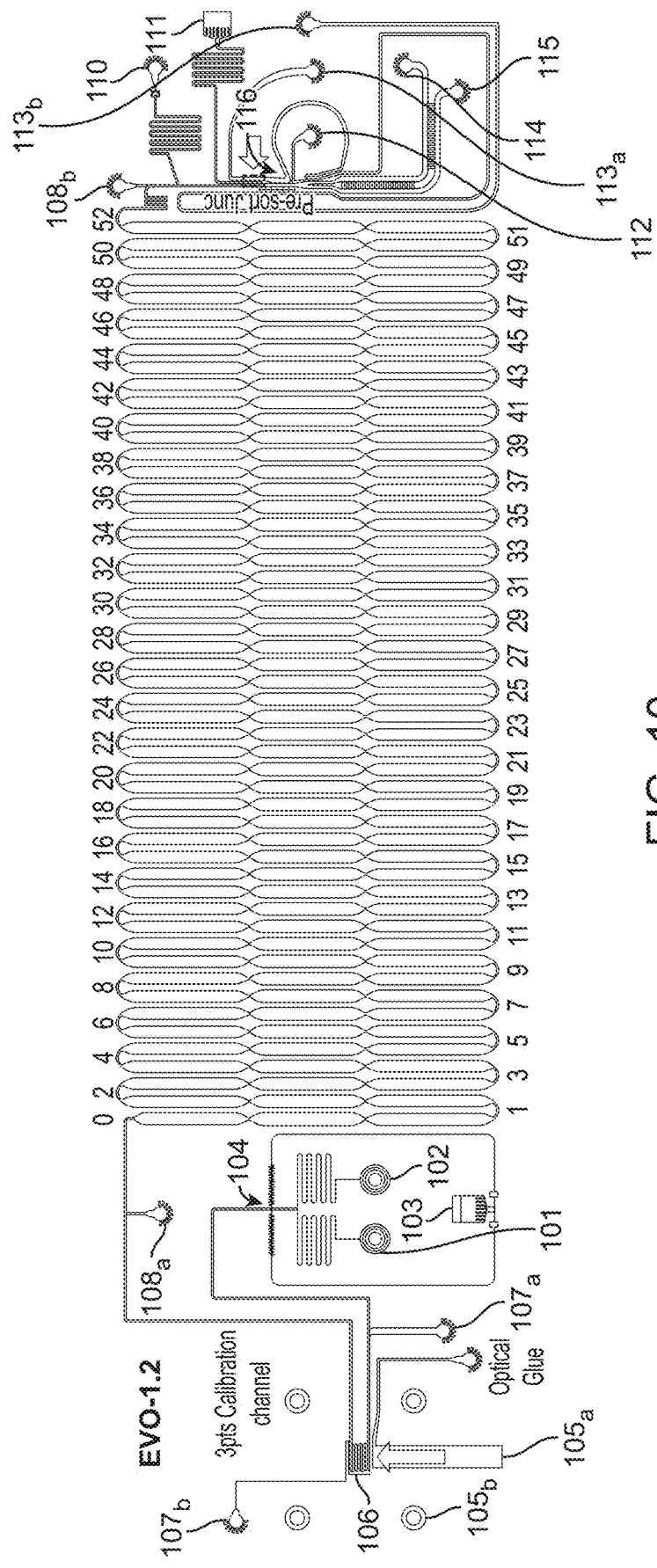
FIG. 10 provides another exemplary depiction of the microfluidic device provided in FIG. 9A.
Figure 18:
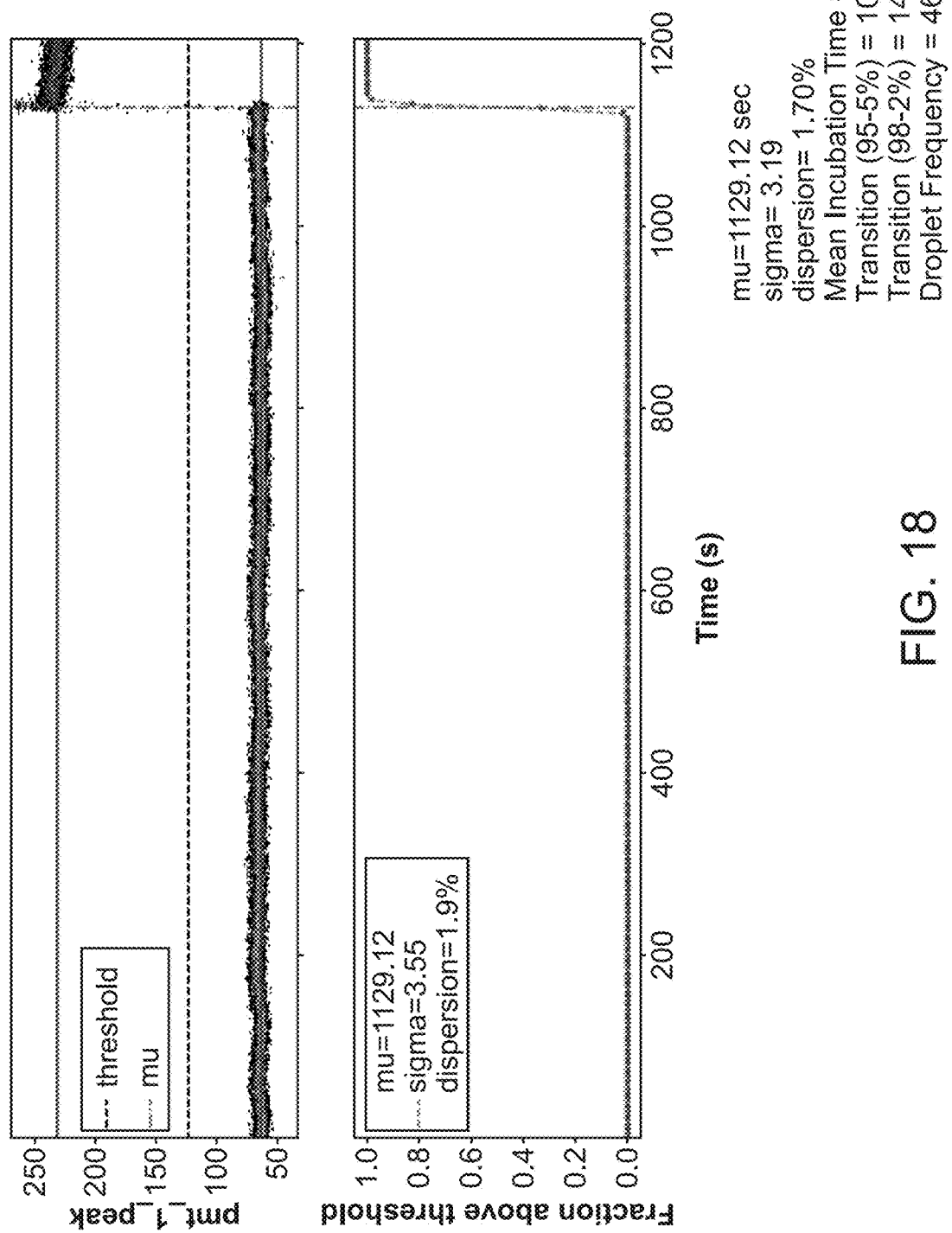
FIG. 18 shows exemplary data for uniform incubation in the microfluidic device shown in FIG. 9A
Figure 19:
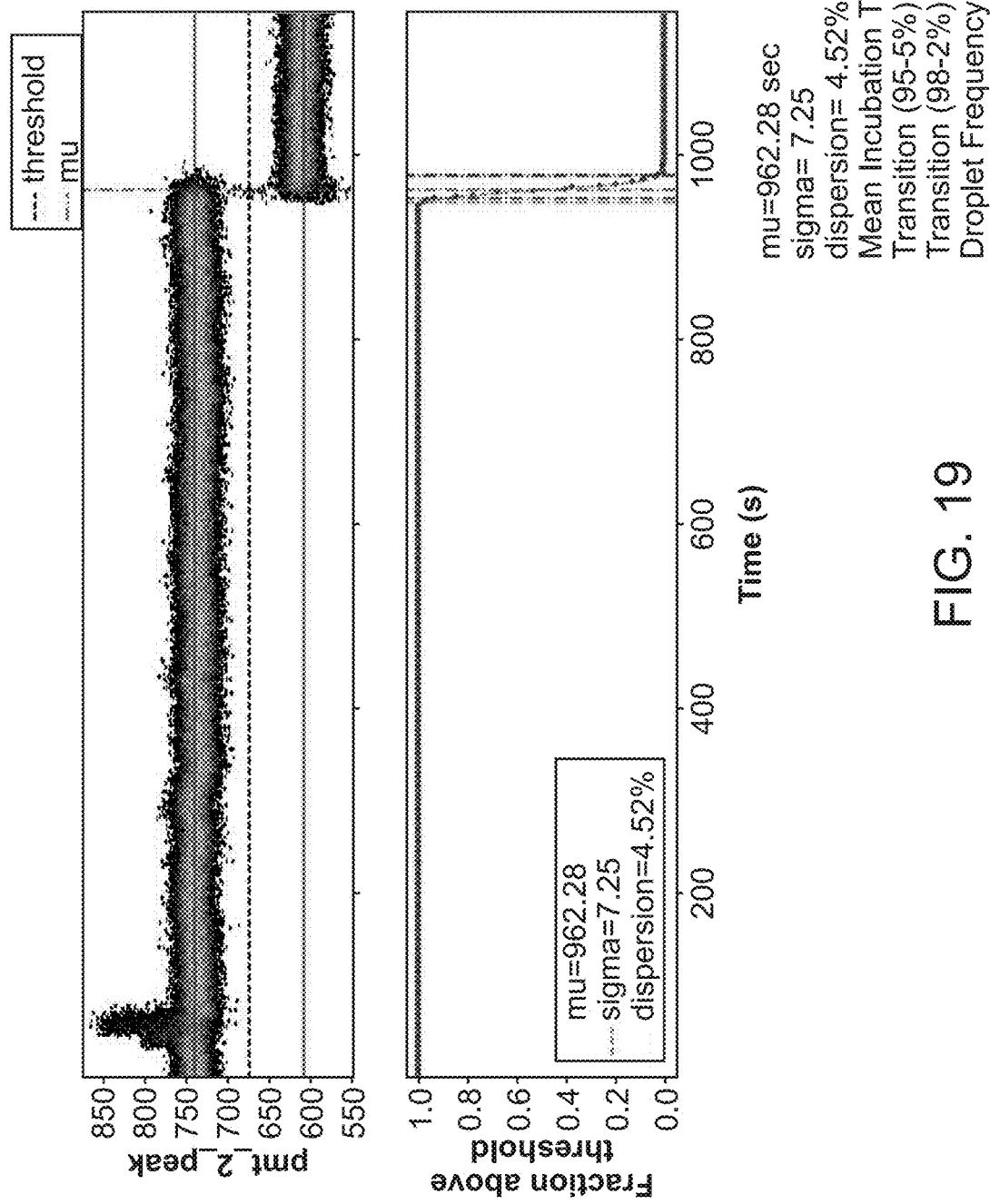
FIG. 19 shows exemplary data for uniform incubation in the microfluidic device shown in FIG. 11.

FIG. 18. provides an exemplary data set depicting a level of uniformity for incubation period using a microfluidic device as depicted FIGS. 9A and 10. Specifically, two aqueous inputs were provided to inlets 101, 102, wherein one aqueous input contained a buffer solution and fluorophore ("fluorophore solution"), and the other aqueous input contained just the buffer solution ("buffer solution"). The fluorophore solution and buffer solution were provided with setpoint pressures that were offset by about 3%, such that one solution would flow through the assay flow channel with a higher concentration than the other. Initially, the buffer solution was provided with the higher pressure, after which the setpoint pressures were switched such that the fluorophore solution was provided at a higher pressure. As depicted in FIG. 18, the PMT count for a first period of time is less than 100 rfu after which there is a sudden increase. The dispersion amongst the data set was calculated to be only 1.7%, with a sigma of 3.19. As such, this displays a level of uniform incubation period as the fluorophore solution provided detection signals within 2% dispersion, and without significant lag when switching the concentrations. As such, this correlates to encapsulations moving along the assay flow path at a relatively uniform rate. FIG. 19 provides a similar analysis using the microfluidic device from FIG. 11, wherein the fluorophore solution was provided with a higher pressure initially, before being switched to a lower pressure. The dispersion amongst the data point was calculated to be slightly higher at 4.52%, with a sigma of 7.25. As such, this similarly displays a level of uniformity for the incubation period as the fluorophore solution provided detection signals with less than 5% dispersion.

In some embodiments, the device further comprises one or more collection chambers. In some embodiments, the one or more collection chambers are configured to receive a subset of the plurality of droplets passing through the assay flow path. In some embodiments, the collection chambers are configured to incubate the subset for an extended period of time. In some embodiments, the collection chambers are configured to lengthen the residence time for the subset of plurality of droplets.

In some embodiments, the device further comprises one or more shunts positioned along the flow path of the device. A shunt may be positioned at any location of the device. The shunt may be used for a variety of purposes. In some embodiments, a shunt is used to insert additional immiscible carrier fluid into the microfluidic channel in order to affect droplet spacing. In some embodiments, a shunt is used to divert droplets of carrier fluid off of the microfluidic device. In some embodiments, a shunt is used in initiation of the device. In some embodiments, a shunt is used in equilibration of the device. In some embodiments, the device is equilibrated In some embodiments, the assay flow path comprises a first shunt. In some embodiments, the first shunt is positioned in an upstream area of the assay flow path. In some embodiments, the first shunt is positioned upstream of the serpentine area of the assay flow path. In some embodiments, the first shunt is positioned upstream of the one or more chambers. In some embodiments, the first shunt is opened during an equilibration phase of using the device. In some embodiments, carrier fluid is run through the device in a reverse direction from normal operation during an equilibration stage of the device and allowed to exit the device through the first shunt. In some embodiments, aqueous droplets are simultaneously introduced into the microfluidic device upstream of the first shunt and allowed to exit the device through the first shunt. In some embodiments, the shunt is closed once pressures of input fluids on the device have been adjusted to desired levels in order to run the system as desired (e.g. flow rates, pressures, droplet size, droplet spacing, etc.).

In some embodiments, the first shunt configured to allow droplets to bypass at least a portion of the assay flow path. In some embodiments, an alternate flow path is coupled to the first shunt. The alternate flow path can have any property and can be used to affect the assay flow path in any manner. For example, the alternate flow path can be used to change the incubation time or residence time of droplets on the microfluidic device, add an additional reagent steam (e.g. a droplet merging junction or pico-injection site), or to incubate droplets off the device entirely.

The cleavage region may comprise a mechanism for liberating an effector that is linked to a bead by a cleavable linker. In some embodiments, the cleavage region comprises a pico-injection site or droplet merging site to introduce reagents to cleave the effector from a scaffold. In some embodiments, the cleavage region comprises a light source configured to cleave effectors from scaffolds disposed within the assay flow path. In some embodiments, the light source is a source of UV light. In some embodiments, the light source is a waveguide. In some embodiments, the light source is a fiberoptic cable. In some embodiments, the light source is a light source configured to cleave effectors from scaffolds disposed within the assay flow path. In some embodiments, the light source is configured to have an optical axis substantially parallel with the device plane. In some embodiments, the light source illuminates a passing droplet at a curve in the assay flow path. In some embodiments, the light source is configured to have an optical axis substantially perpendicular to the device plane. In some embodiments, the light source is aligned with the microfluidic channel of the cleavage region by pillars mounted on the device. In some embodiments, the light source is configured to emit light over an area covering multiple portions of the microfluidic channel passing through the cleavage region. In some embodiments, the cleavage region comprises a serpentine flow path.

The cleavage region can be at any point along the microfluidic device depending upon the needs of the assay being employed on the device. In some embodiments, the cleavage region is upstream of the detection region, the sorting region, and the stimulation region. In some embodiments, the cleavage region is upstream of the detection region. In some embodiments, the cleavage region is upstream of the sorting region. In some embodiments, the cleavage region is upstream of the stimulation region. In some embodiments, the cleavage region is upstream of the detection region and the sorting region.

In some embodiments, the device comprises an additional inlet and outlet positioned on the microfluidic channel upstream and downstream of the cleavage region. In some embodiments, the inlet and outlets are positioned immediately before and immediately after the cleavage region.

In some embodiments, these inlets and outlets are configured to allow for a calibration of the cleavage region. The calibration allows for control over device-to-device variability in how much light the samples passing through the cleavage region are exposed to. Such variability can come from small changes to a variety of parameters of the device, including the coupling of the light source to the device. Variability in exposure intensity time and duration can lead to variability in amount of compound released from beads, which can cause errors in ultimate screening assay readouts.

Figure 12A:
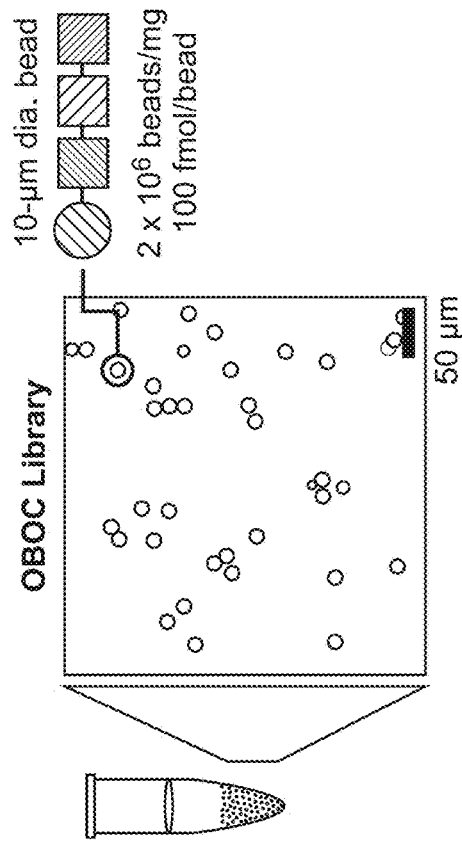
FIG. 12A provides a depiction of a library of beads attached with an encoded-effector modified with fluorophore.
Figure 12B:
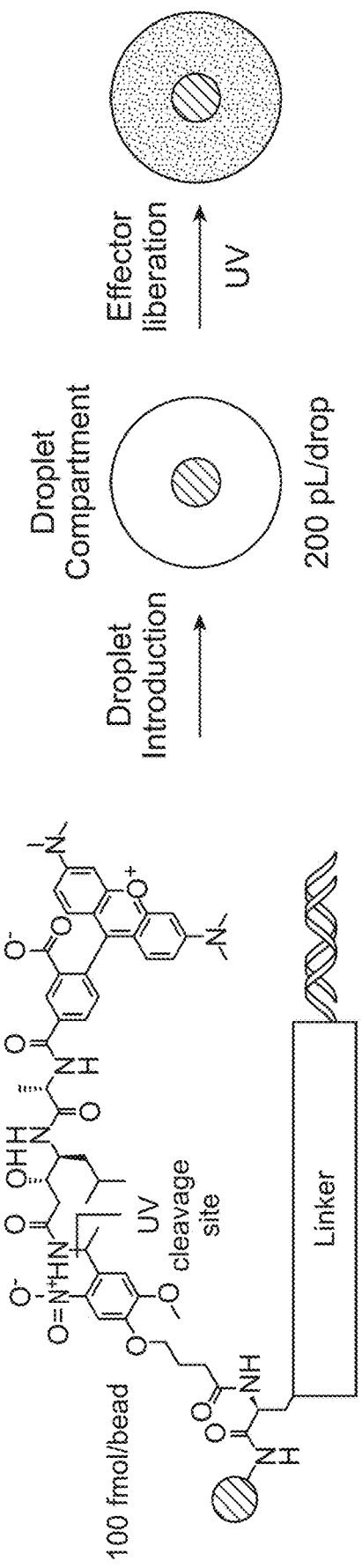
FIG. 12B provides a depiction of an encoded-effector modified with a fluorophore dye being liberated from a bead upon being exposed to UV light.
Figure 12C:
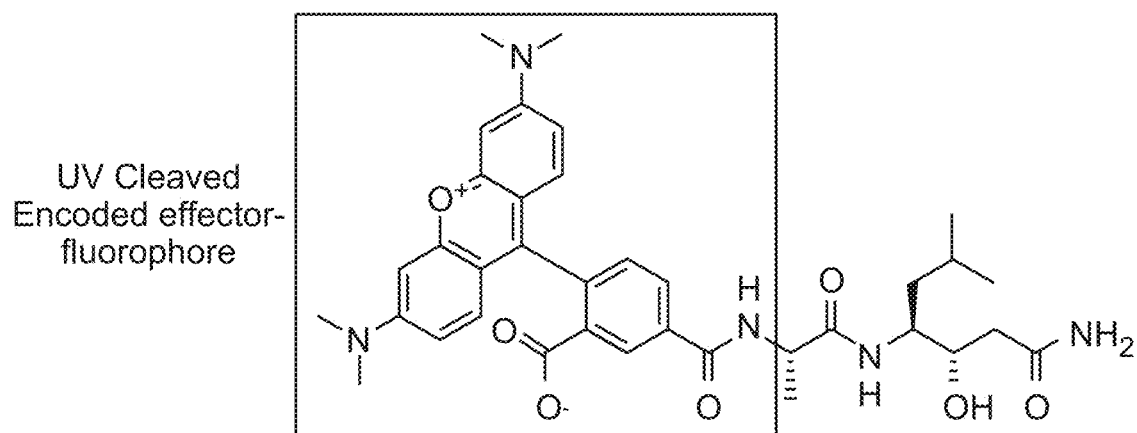
FIG. 12C provides a depiction of the released encoded effector-fluorophore from FIG. 12B.
Figure 12D:
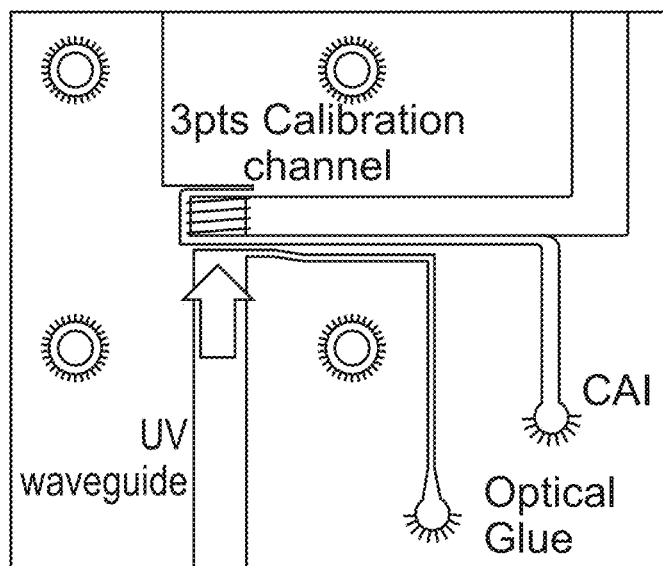
FIG. 12D provides a depiction of the cleavage region of a microfluidic device described herein.
Figure 12E:
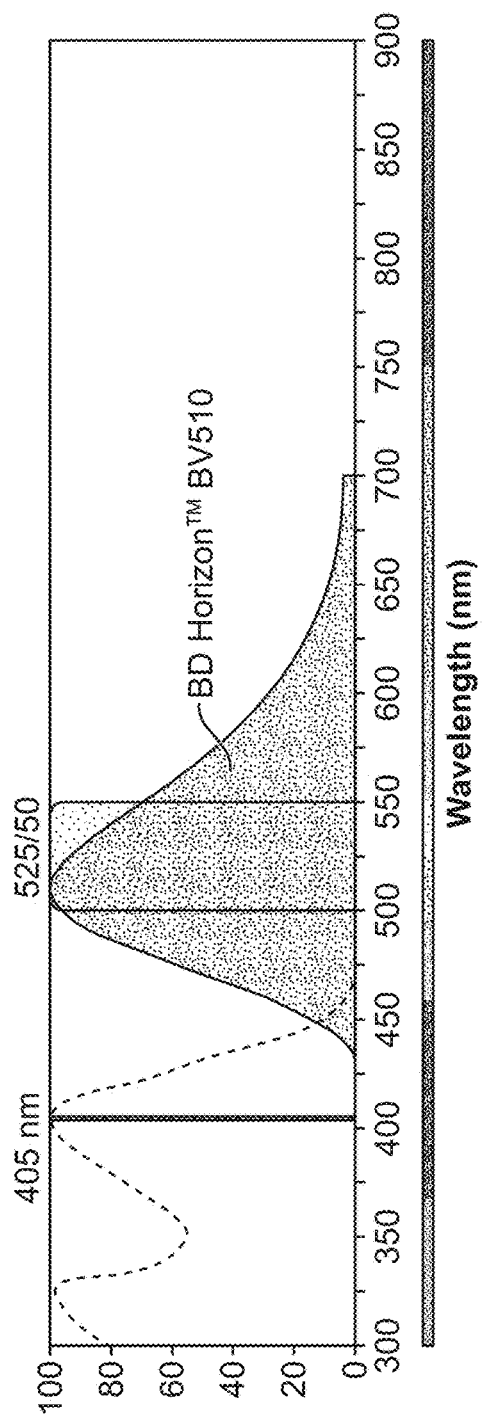
FIG. 12E shows a depiction of a correlation between UV light and a calibrant fluid.

In some embodiments, the inlets and outlets are used for the calibration procedure. In some embodiments, the calibration procedure comprises flowing a solution comprising a fluorescent dye through the cleavage region. FIG. 12D provides an exemplary depiction of the cleavage region for a microfluidic device described herein, wherein the calibration inlet and UV waveguide for exposing the encapsulations (e.g., droplets) to light are shown. In some embodiments, the calibrant channel is filled with UV-sensitive fluorophore to measure the UV intensity in the cleavage region. In some embodiments, the UV waveguide directs light from a UV LED coupled fiberoptic into a confined area. In some embodiments, the UV LED power is then set, based on a calibrant dye being measured. FIG. 12E provides exemplary data correlating a calibrant dye with a given light exposure (BD Horizon™ BV510).

Figure 12F:
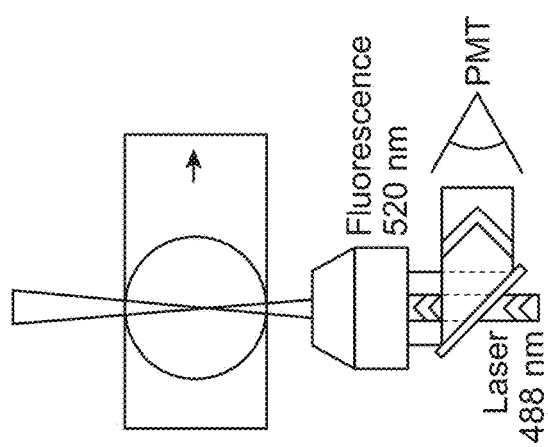
FIG. 12F shows a depiction of an exemplary device for confocal laser and PMT emission capture.
Figure 13A:
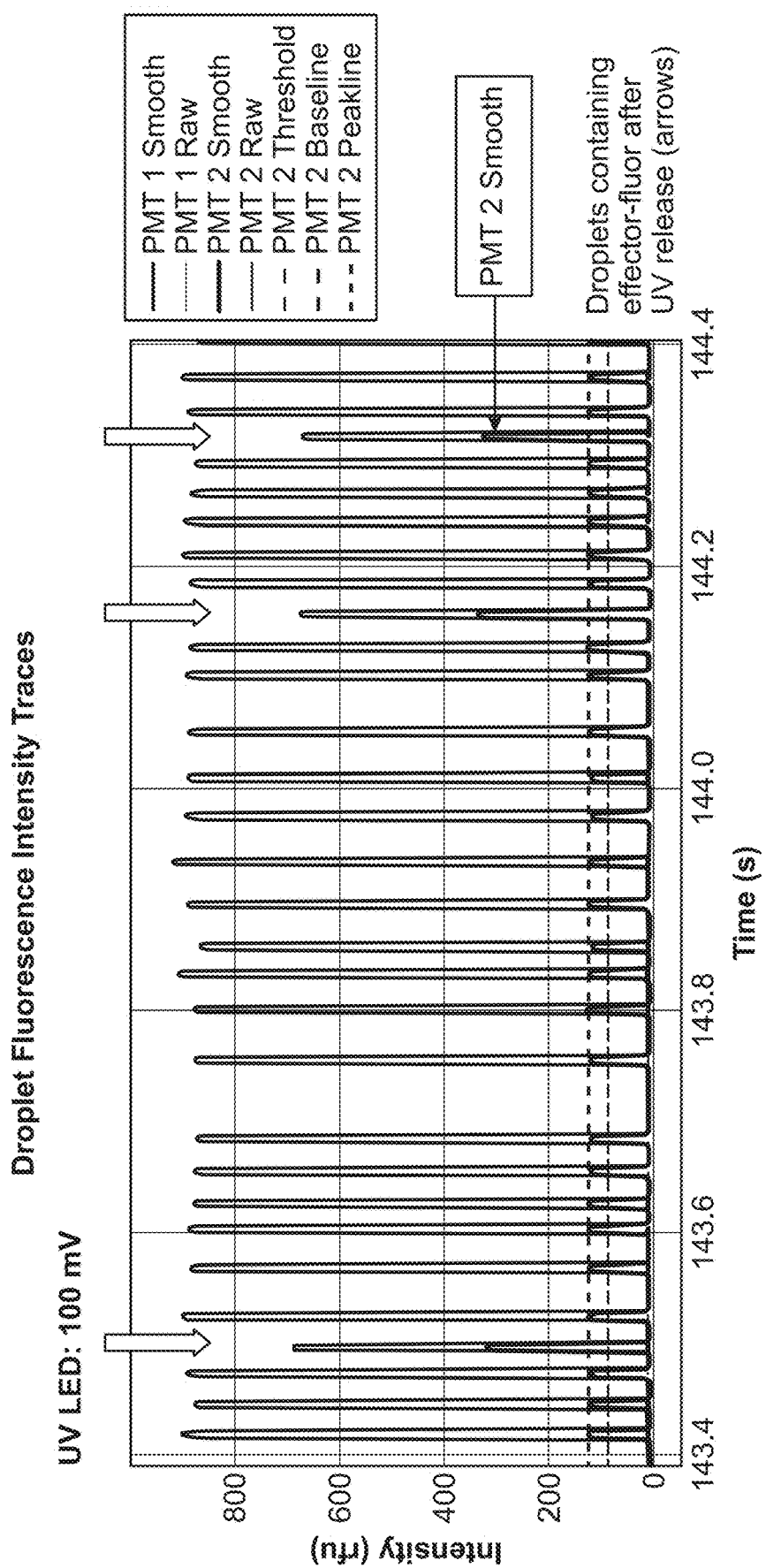
FIG. 13A shows measured intensity peaks of a fluorophore dye using 100 mV UV light.
Figure 13B:
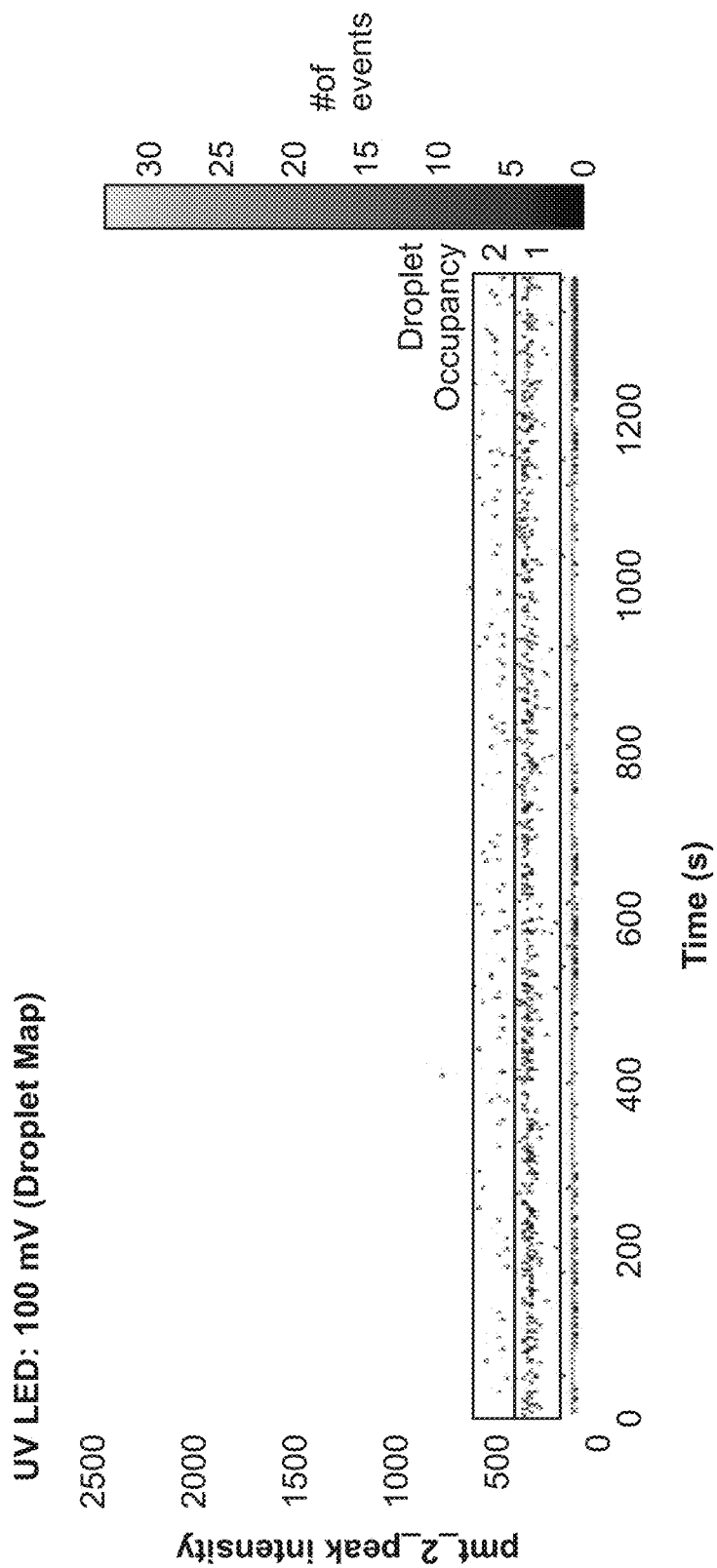
FIG. 13B shows a droplet map corresponding to intensity peaks of a fluorophore dye using 100 mV UV light.
Figure 14A:
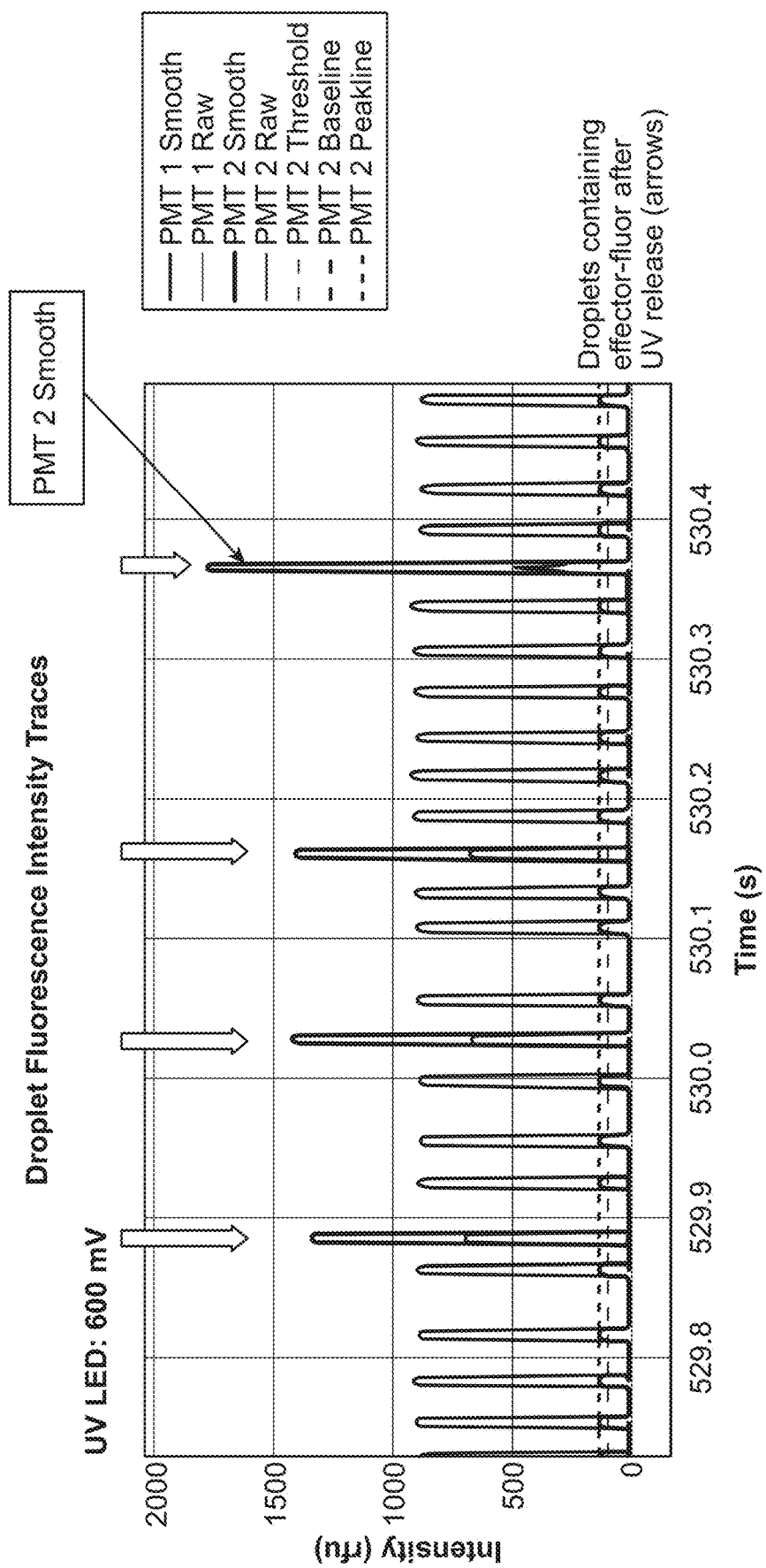
FIG. 14A shows measured intensity peaks of a fluorophore dye using 600 mV UV light.
Figure 14B:
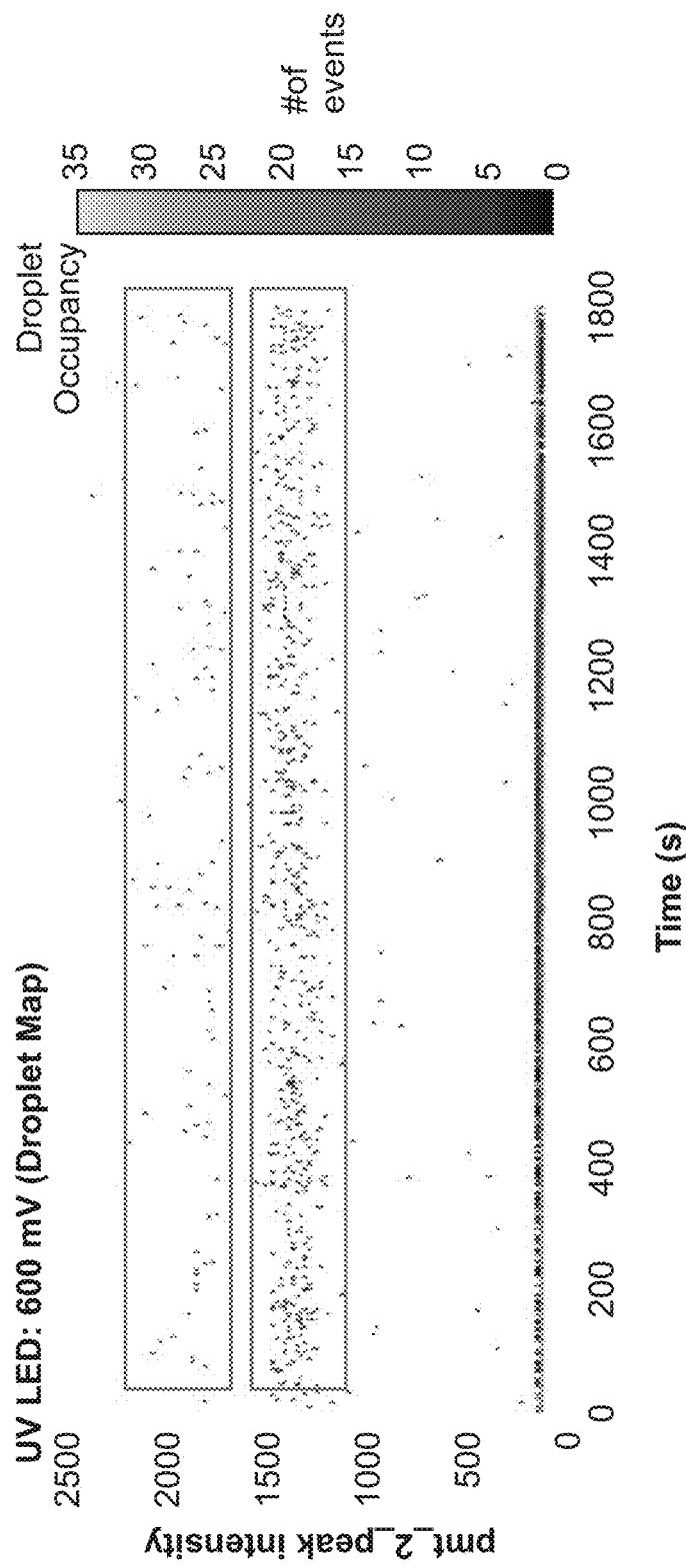
FIG. 14B shows a droplet map corresponding to intensity peaks of a fluorophore dye using 600 mV UV light.
Figure 15A:
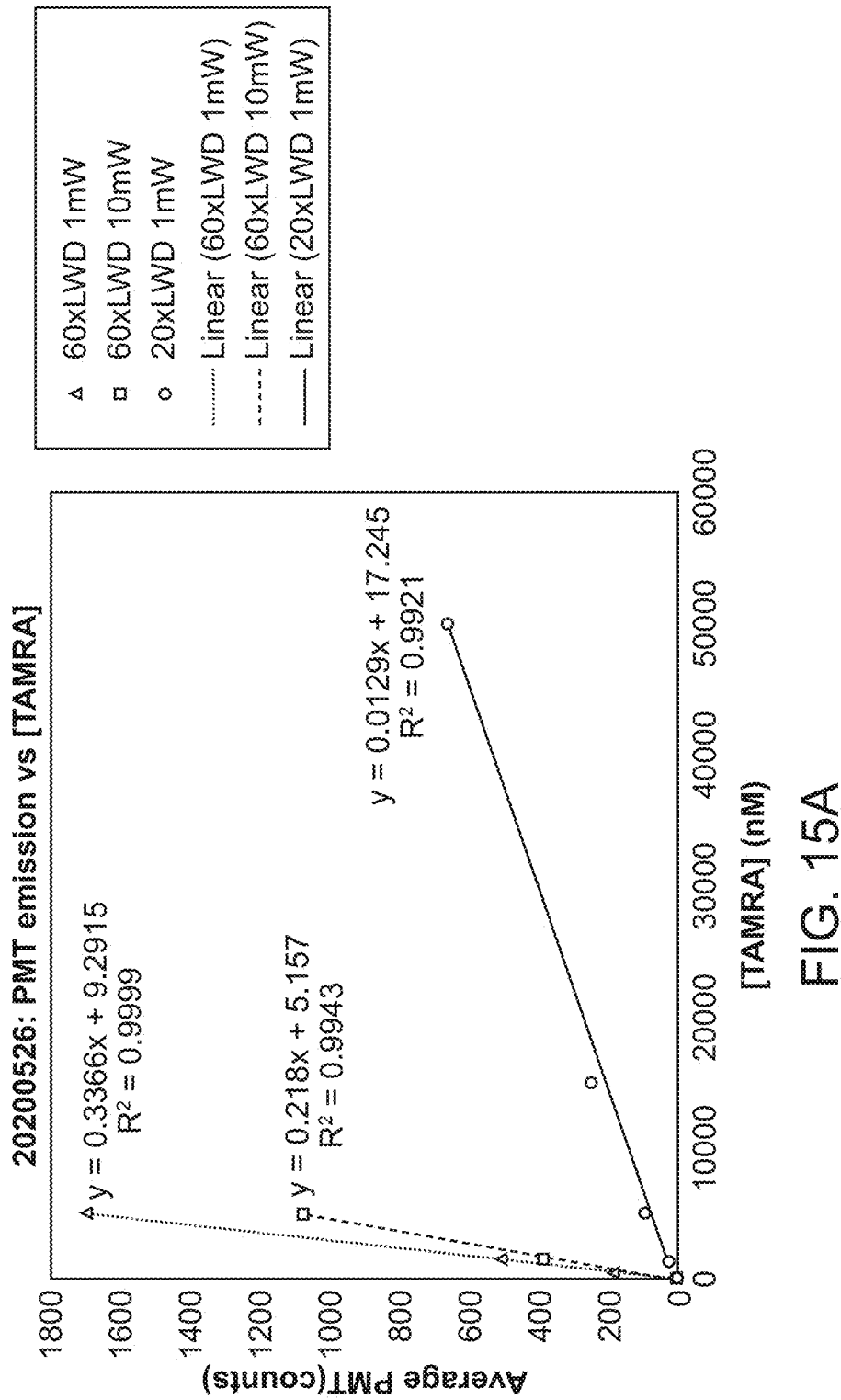
FIG. 15A provides a known correlation between UV power and PMT count of a fluorophore dye.
Figure 15B:
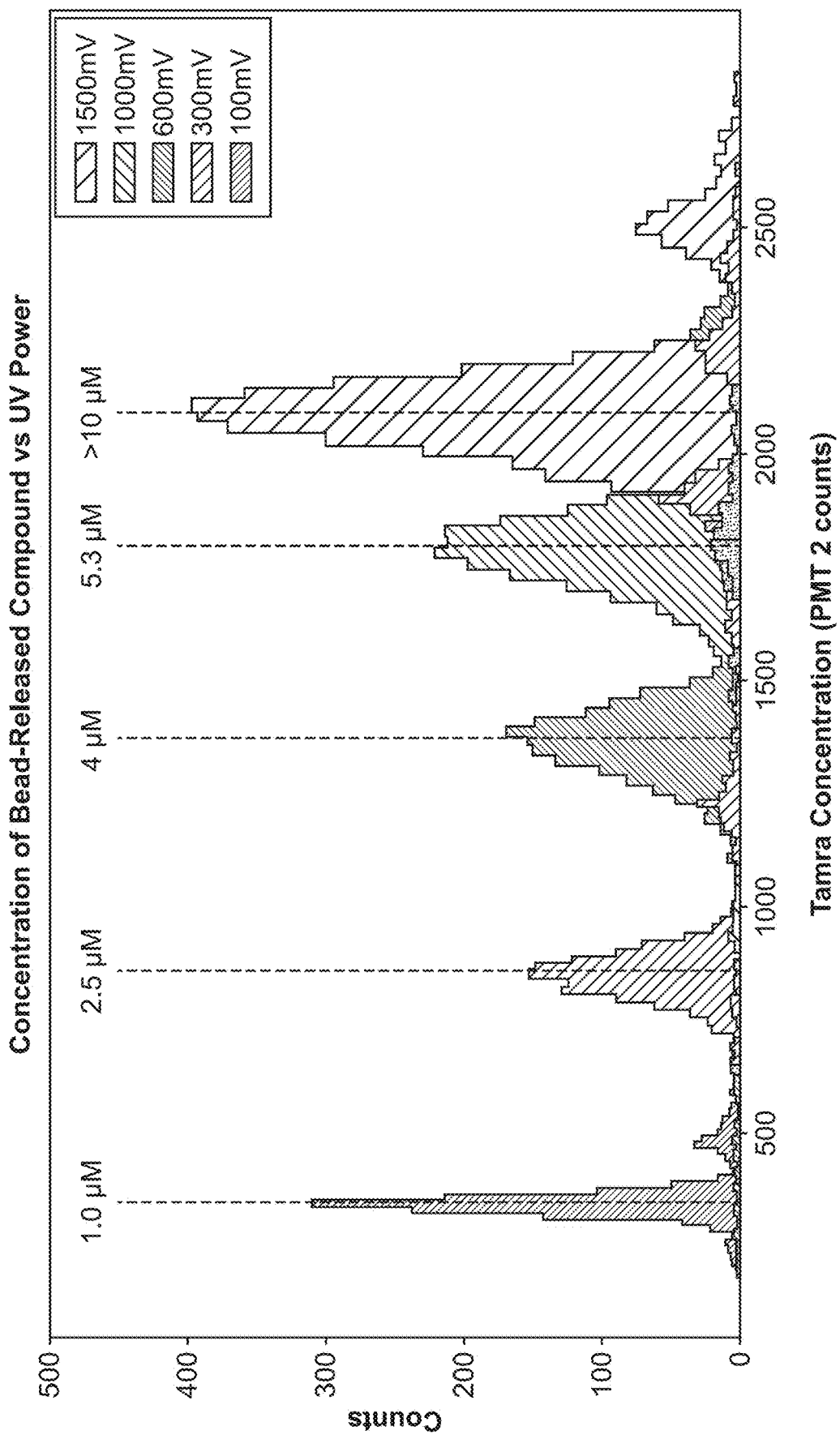
FIG. 15B provides a histogram of distributed intensity values of encoded effector-fluorophore compared with UV power exposure.

In some embodiments, encoded effector-fluorophore beads are introduced into encapsulations (e.g., droplets) using a microfluidic device as described herein. FIG. 12A provides an exemplary solution of beads with an encoded-effector modified with a fluorophore, wherein the solution can comprise a library of beads. As shown in FIG. 12B, the effector-fluorophore may be connected by a photo-cleavable, or pro-photo-cleavable linker. In some embodiments, the encoded-fluorophore beads are introduced into droplets at approximately 200 pL in volume. In some embodiments, the droplets are introduced into the cleavage region and exposed to the UV light. As shown in FIG. 12B, when exposed to the UV light, the effector is liberated (i.e. cleaving the photocleavable linker), such that the effector is released from the bead (FIG. 12C). The droplets then continue to flow through the microfluidic device, as described herein, until reaching an "interrogation region" of the microfluidic device, wherein the droplets are subject to laser excitation (e.g., confocal laser excitation, FIG. 12F), thereby exciting the released effector-fluorophore. The emission from the encoded effector-fluorophore is then collected by PMT detectors, as shown in FIGS. 13A and 14A (represented by PMT 2 Smooth), which represent the effector release based on exposure from 100 mV and 600 mV light respectively, thereby measuring the released effector-fluorophore concentration. FIGS. 13B and 14B provide the peak emission measured for each droplet based on exposure from 100 mV and 600 mV light respectively, plotted as a heatmap over time to observe the stability of the signal. As shown, increasing the UV LED power increases the exposure, thereby enabling the ability to control the final concentration of released effector-fluorophore. FIG. 15B provides a histogram with compressed droplet maps (e.g., from FIGS. 13B and 14B), so as to depict normally distributed intensity values. The median value is correlated to known Fluorophore concentration calibrations (e.g., FIG. 15A), so as to determine the final concentration of the effector-fluorophore after UV release. As such, the emission intensity, as measured with a calibrant fluid, can be correlated to a resultant effector-release concentration, thereby providing a predictive quantitative release.

Figure 22A:
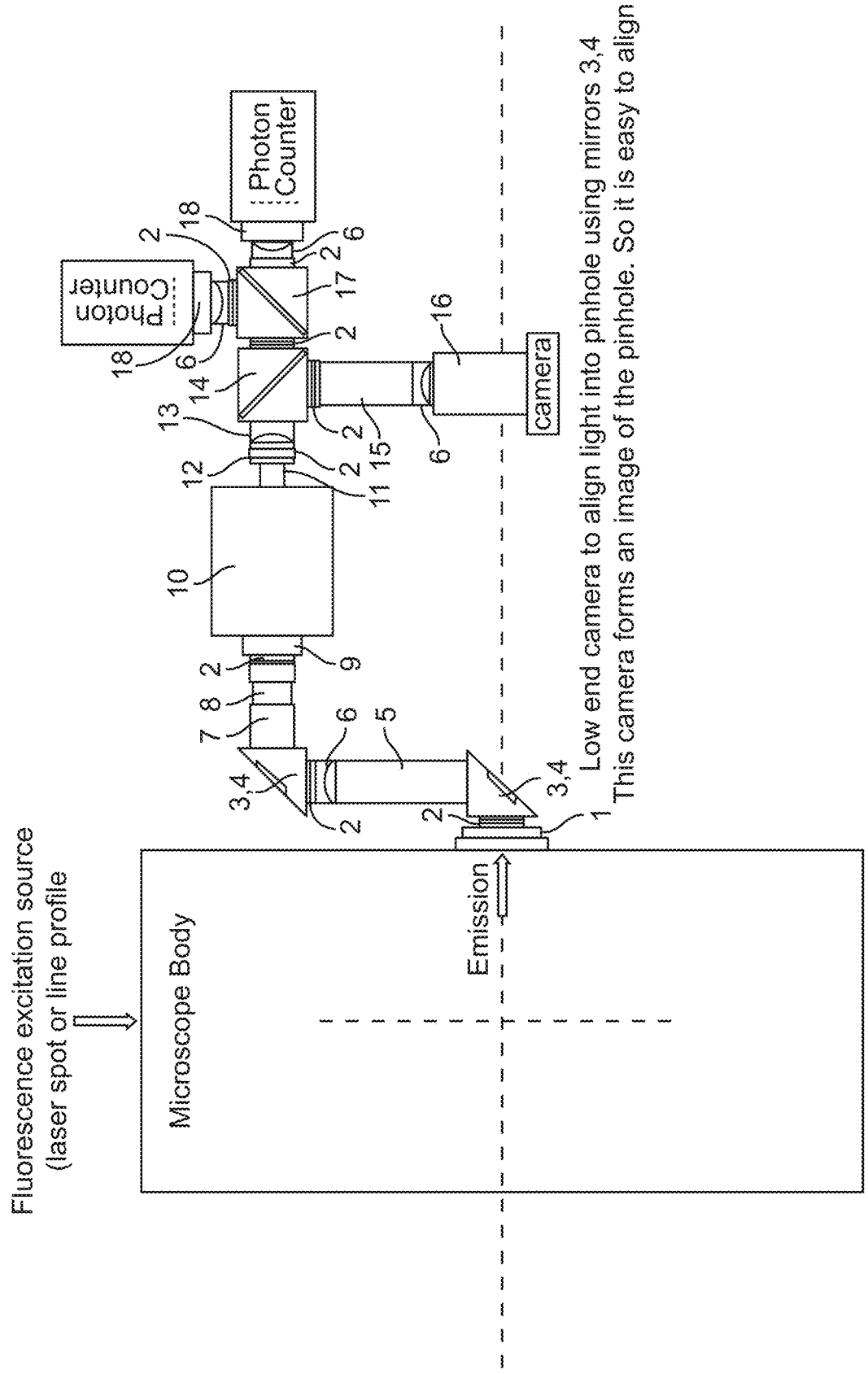

The detection region is configured with a detector capable of detecting any desired readout of an assay to be performed on the device. In some embodiments, the detection region comprises a fluorometer. In some embodiments, the fluorometer comprises a photomultiplier tube detector, a light source, an excitation filter and an emission filter. In some embodiments, the fluorometer is configured to have an optical axis substantially parallel to the device plane. In some embodiments, the fluorometer is configured to have an optical axis substantially perpendicular to the device plane. In some embodiments, the fluorometer illuminates a passing droplet at a curve in the assay flow path. In some embodiments, the detection region comprises confocal detection and laser scanning. In some embodiments, the detection region comprises a confocal laser scanning device, as shown in FIGS. 22A-B (providing a top view of the device). FIG. 12F provides an exemplary schematic of encapsulation detection via confocal laser scanning. In some embodiments, the detection region comprises laser scanning. In some embodiments, the detection region comprises fluorescence. In some embodiments, the detection region comprises any combination of detection means described herein.

In some embodiments, the detection region comprises an objective or fiber for emitting an excitation light into the detection region. In some embodiments, the detection region comprises an objective, fiber, or charged coupled device configured to collect emission from the detection region. In some embodiments, a single objective is configured to direct excitation and collect emission from the detection region. In some embodiments, the objective configured to collect emission from the detection region (which may be the same as the excitation objective) is an inverted objective lens. In some embodiments, the objective configured to collect emission from the detection region (which may be the same as the excitation objective) is configured to collect, collimate, and direct the emitted light through optical fibers. In some embodiments, the optical fibers are coupled to a detector configured to quantify the emission. In some embodiments, the detector configured to quantify the emission is a photomultiplier tube, charged coupled device, or photodiode.

In some embodiments, the detection region is capable of being moved on the chip. In some embodiments, the detection region comprises an excitation light source that is not coupled to the device. In some embodiments, the detection region comprises an objective that is not coupled to the device. In some embodiments, having a light source or detector for the detection region not coupled to the device allows for the system to be adjusted based on assay need. For example, the system can be adjusted to increase or decrease the time between detection and sorting. Additionally, the system can be adjusted so that a single light source may be used for calibration and initialization of the device prior to performing a screening assay on the device.

In some embodiments, the detection region is configured to detect two or more wavelengths of fluorescence. This allows for the detection of the abundance of a plurality of fluorescent probes. In some embodiments, the droplet being assayed may comprise a control fluorophore and an assay fluorophore. The assay fluorophore gives a readout of the assay, e.g. a positive or negative result of the assay. The control fluorophore, if present, may be detected and quantified. In some embodiments, the control fluorophore is placed into the aqueous fluid of the first microfluidic channel at a known concentration. When the droplet comprising the aqueous fluid of the first microfluidic channel reaches the detection region, the amount of control fluorophore fluorescence detected can be used to quantify the size of the droplet. This can be used to normalize the results of the assay fluorophore readout. In some embodiments, the detection region is configured to measure two or more assay fluorophores.

In some embodiments, the device comprises a single detection region. In some embodiments, the detection region is downstream of the cleavage region. In some embodiments, the detection region is downstream of the stimulation region. In some embodiments, the detection region is upstream of the sorting region.

In some embodiments, the device comprises multiple detection regions. When the device comprises multiple detection regions, they may be placed anywhere on the device. In some embodiments, the detection region is configured to be in communication with another region. For example, the detection region may be in communication with the sorting region to allow sorting to occur based on the detection of a signal. In some embodiments, a detection region is configured to be in communication with a pico-injector. When a detection region is in communication with a pico-injector, reagents or other assay components can be selectively added only when certain conditions are met, such as the presence or absence of a signal.

In some embodiments, the device comprises a stimulation region. In some embodiments, the stimulation region comprises one or more actuators for stimulating an ion channel. Any method of stimulating an ion channel may be employed by the actuators when the device is configured to perform an ion channel modulation assay. In some embodiments, the stimulation region comprises one or more actuators for stimulating an ion channel. In some embodiments, the one or more actuators for stimulating the ion channel comprises at least one light source, at least one electrode, or at least one pico-injection site equipped with an ion channel toxin. In some embodiments, the one or more actuators comprises at least one light source. In some embodiments, the one or more actuators comprises at least one electrode. In some embodiments, the one or more actuators comprises an injection site for an ion channel toxin.

In some embodiments, the one or more actuators comprises at least one electrode. Any type of electrode capable of delivering an electromagnetic current to the encapsulation may be employed. In some embodiments, the electrode lies along a wall of the assay flow path and delivers an electric field to the passing stream. In some embodiments, the electric field is pulsed to match the frequency at which droplets pass the electrode.

In some embodiments, the one or more actuators comprises a pair of electrodes on opposite walls of the assay flow path such that when a droplet passes the pair of electrodes the droplet contacts the electrodes, thereby allowing a current to flow through the droplet. In some embodiments, the device comprises multiple pairs of electrodes so configured. In some embodiments, the stimulation region comprises about 1 pair to about 20 pairs of electrodes so configured. In some embodiments, the stimulation region comprises about 1 pair to about 2 pairs, about 1 pair to about 3 pairs, about 1 pair to about 5 pairs, about 1 pair to about 7 pairs, about 1 pair to about 10 pairs, about 1 pair to about 20 pairs, about 2 pairs to about 3 pairs, about 2 pairs to about 5 pairs, about 2 pairs to about 7 pairs, about 2 pairs to about 10 pairs, about 2 pairs to about 20 pairs, about 3 pairs to about 5 pairs, about 3 pairs to about 7 pairs, about 3 pairs to about 10 pairs, about 3 pairs to about 20 pairs, about 5 pairs to about 7 pairs, about 5 pairs to about 10 pairs, about 5 pairs to about 20 pairs, about 7 pairs to about 10 pairs, about 7 pairs to about 20 pairs, or about 10 pairs to about 20 pairs of electrodes so configured. In some embodiments, the stimulation region comprises about 1 pair, about 2 pairs, about 3 pairs, about 5 pairs, about 7 pairs, about 10 pairs, or about 20 pairs of electrodes so configured. In some embodiments, the stimulation region comprises at least about 1 pair, about 2 pairs, about 3 pairs, about 5 pairs, about 7 pairs, or about 10 pairs of electrodes so configured. In some embodiments, the stimulation region comprises at most about 2 pairs, about 3 pairs, about 5 pairs, about 7 pairs, about 10 pairs, or about 20 pairs of electrodes so configured.

Any number of actuators may be employed on the microfluidic device. In some embodiments, the stimulation region comprises about 1 actuator to about 20 actuators. In some embodiments, the stimulation region comprises about 1 actuator to about 2 actuators, about 1 actuator to about 3 actuators, about 1 actuator to about 5 actuators, about 1 actuator to about 7 actuators, about 1 actuator to about 10 actuators, about 1 actuator to about 20 actuators, about 2 actuators to about 3 actuators, about 2 actuators to about 5 actuators, about 2 actuators to about 7 actuators, about 2 actuators to about 10 actuators, about 2 actuators to about 20 actuators, about 3 actuators to about 5 actuators, about 3 actuators to about 7 actuators, about 3 actuators to about 10 actuators, about 3 actuators to about 20 actuators, about 5 actuators to about 7 actuators, about 5 actuators to about 10 actuators, about 5 actuators to about 20 actuators, about 7 actuators to about 10 actuators, about 7 actuators to about 20 actuators, or about 10 actuators to about 20 actuators. In some embodiments, the stimulation region comprises about 1 actuator, about 2 actuators, about 3 actuators, about 5 actuators, about 7 actuators, about 10 actuators, or about 20 actuators. In some embodiments, the stimulation region comprises at least about 1 actuator, about 2 actuators, about 3 actuators, about 5 actuators, about 7 actuators, or about 10 actuators. In some embodiments, the stimulation region comprises at most about 2 actuators, about 3 actuators, about 5 actuators, about 7 actuators, about 10 actuators, or about 20 actuators.

In some embodiments, the device comprises multiple stimulation regions. Stimulation regions may be distributed in any orientation throughout the microfluidic device. In some embodiments, the stimulation region is downstream of the cleavage region. In some embodiments, the stimulation region is upstream of the detection region. In some embodiments, the stimulation region is upstream of the sorting region.

In some embodiments, the device comprises an additional inlet configured to insert carrier fluid into the flow path of the microfluidic device. Optimal spacing of droplets is an important consideration in order to accurately sort desired droplets. Factors which can affect accurate sorting of droplets include droplet size, average separation of droplets, total oil fraction of the flow, ionic strength of the droplets, and contents of the droplets. Individual assays performed on the devices provided herein may require optimization of spacing, which is allowed by the presence of the additional inlet. In some embodiments, the additional inlet inserts additional carrier fluid into the flow path of the microfluidic device to increase spacing of the droplets. In some embodiments, the additional inlet inserts additional carrier fluid into the flow path of the microfluidic device to focus the droplets. In some embodiments, the additional carrier fluid is the immiscible fluid from the second microfluidic channel. In some embodiments, the additional carrier fluid is different from the immiscible fluid from the second microfluidic channel. In some embodiments, the additional inlet operates at a constant flow. In some embodiments, the additional inlet operates at a variable flow. In preferred embodiments, the additional inlet is positioned shortly upstream of the detection region. In some embodiments, the additional inlet operates at a flow rate selected to optimally space the droplets. In some embodiments, the device comprises two additional inlets. In some embodiments, the device comprises a first additional inlet configured to deliver spacing oil and a second additional inlet configured to deliver focusing oil.

In some embodiments, the devices comprise a sorting region. Any method of sorting the droplets in the device may be used. In some embodiments, the sorting region is in communication with the detection region. In some embodiments, the sorting region comprises a sorting apparatus that sorts the droplets based on the detection of the presence, absence, or level of a signal detected by the detection region. In some embodiments, the sorting region comprises a sorting electrode. In some embodiments, the sorting electrode is an electrophoresis electrode. In some embodiments, the sorting electrode is a dielectrophoresis electrode. In some embodiments, the sorting region comprises a valve configured for sorting. In some embodiments, the sorting region comprises a deflectable membrane configured for sorting. In some embodiments, the sorting region comprises an acoustic wave generator configured for sorting. In some embodiments, the sorting region comprises an inlet for fluid configured to guide a passing droplet down a sorted path.

In some embodiments, the device comprises microfluidic channels which are fully enclosed. In some embodiments, the device comprises microfluidic channels encompassed on all sides of the microfluidic channel, except for any inlets and outlets into the device. In some embodiments, the device comprises a cover slip configured to enclose the channels. In some embodiments, the cover slip is coated with a hydrophobic material (e.g. PDMS). The cover slip may be of any size (e.g. 5 micron, 10 micron, 15 micron, 20 micron, 30 micron, 40 micron, 50 micron or greater).

Control of flow of fluids through the device may be accomplished in any manner. In preferred embodiments, the flow of fluids is controlled by a device capable of delivering fluid through the device for a prolonged period of time and/or in a continuous fashion (e.g. a pneumatic pump or a peristaltic pump). Such pumps have several advantages over other pumps, such as syringe pumps, including the ability to run the system for a prolonged period of time at constant pressure, thus allowing for continuous feed of material through the device and control over residence time of droplets travelling through the device. In some embodiments, the flow of fluids is controlled by a continuous pump. In some embodiments, the flow of fluids is controlled by a pneumatic pump. In some embodiments, the fluids are delivered to the device from a reservoir of fluid off of the device. This allows the device to draw a much larger amount of fluid than would be possible from an on-device reservoir. Any of the sample fluids, immiscible fluids, spacing oil, focusing oil, or other fluid delivered onto the chip can be delivered in this manner.

In some embodiments, the pump is configured to deliver fluids through the device for a continuous period of at least 4 hours, at least 8 hours, at least 12 hours, at least 16 hours, or at least 24 hours. In some embodiments, the pump is configured to deliver fluids through the device for a continuous period of at least 12 hours. In some embodiments, the pump is configured to deliver fluids through the device for a continuous period of at least 24 hours.

Figure 9B:
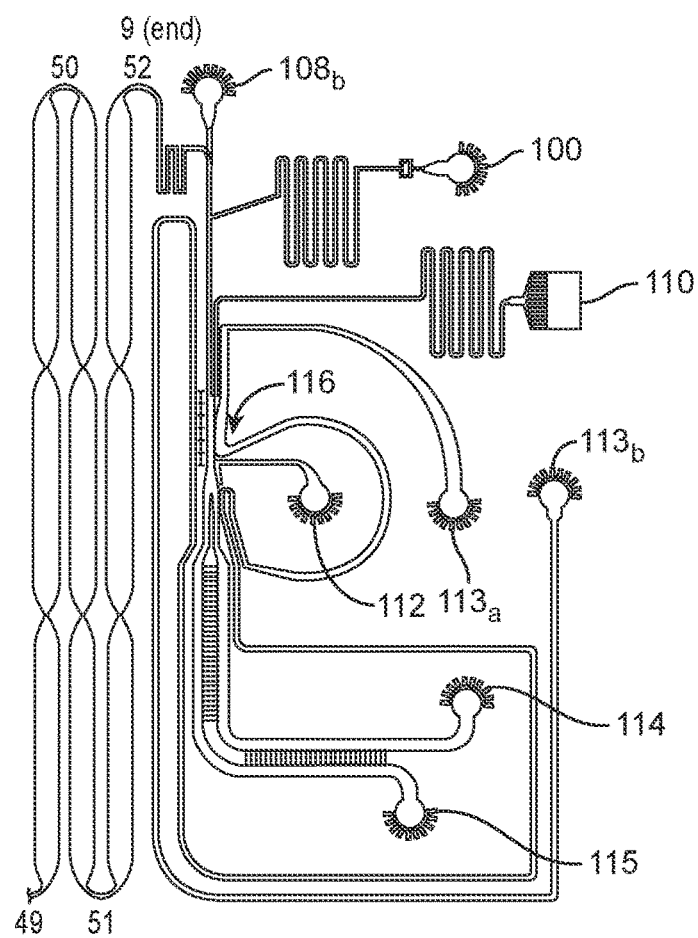
FIG. 9B provides a depiction of a specific section of an exemplary microfluidic device provided herein.
Figure 9C:
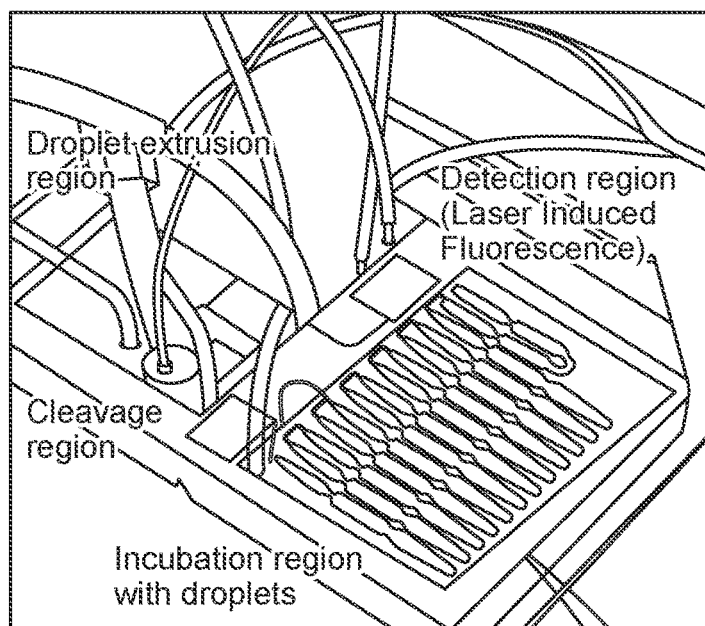
FIG. 9C shows a picture of an exemplary microfluidic device provided herein

A non-limiting, exemplary microfluidic device is shown in FIG. 9A. The exemplary microfluidic device contains a first inlet 101. The first inlet 101 is configured to accept an aqueous fluid, such as an aqueous assay reagent. The exemplary microfluidic device also contains a second inlet 102. In this example, the second inlet 102 is configured to accept another aqueous fluid. This may be the same or different as the aqueous fluid added to the first inlet 101. The second inlet 102 may be configured to accept beads as provided herein, or the first inlet 101 may be so configured. In other examples of a microfluidic device, there may only be a single inlet stream. The exemplary microfluidic device shown in FIG. 9A further comprises an inlet 103 for carrier fluid (e.g. an oil immiscible with an aqueous fluid) in fluid connection with a droplet formation junction or extrusion junction 104. The inlet 103 in this example is connected to the droplet formation junction 104 by two channels, each reaching an aqueous stream channel at the same point on opposite sides of the aqueous stream channel. The droplet formation junction 104 comprises a microfluidic channel that continues down the flow path towards cleavage region 106. Near cleavage region 106 is a fiberoptic waveguide 105a configured to deliver light into the microfluidic channel of the cleavage region 106. The fiberoptic waveguide 5a is embedded in the plane of the device such that the light emitted enters the microfluidic channel of cleavage region 106 from the device plane. Also near cleavage region 106 is a pillar 105b configured to fix a fiberoptic manifold which can be configured to emit light from above the plane of the device into the microfluidic channel of cleavage region 106. The light sources of 105a and 105b can be used alternatively or in combination. The device also comprises an inlet for calibration fluid 107a in fluid connection with the cleavage region 106 and an outlet for calibration fluid 107b. The inlet for calibration fluid 107a is configured to receive and deliver to the cleavage region 106 a fluid configured to normalize photon exposure within the cleavage region. After passing through the cleavage region 106, the calibration fluid exits through the outlet for calibration fluid 107b. The cleavage region 106 is in fluid communication via a microfluidic channel to an incubation region 109. In the example of FIG. 9A, the incubation region 109 contains a series of widened chambers, each chamber connected to the next chamber in the series by a microfluidic channel. The configuration of these chambers affect the flow rate and residence time of the droplets formed at droplet formation region 104 through the device. In some embodiments, the chambers are configured to prevent trapping of droplets as they pass through incubation region 109. Such configuration of the chambers is particularly important when using a carrier fluid that is denser than the aqueous droplets (e.g. 3-ethoxyperfluoro(2-methylhexane)). In some embodiments, this desired configuration is achieved by configuring the chambers and connecting channels to have only small difference in channel height between the chambers and the connecting channels. In some embodiments, the height of the chamber is about 80 µm and the height of the connecting channel is about 50 µm. As an additional design feature to aid in prevention of trapping of bubbles within the device, the height of the flow path does not change between the width of the chamber has been narrowed as the droplet approaches the connecting channel, thus facilitating the smooth transition of droplets from chamber to chamber without trapping. Configured on either end of incubation region 109 are bypass shunts 108a and 108b. The bypass shunts 108a and 108b are configured to allow a fluid coupled to the shunt to flow in or out of the main microfluidic channel. If fluid is diverted out of the main microfluidic channel at bypass shunt 108a, the material will not pass through incubation region 109. Positioned downstream of incubation region 109 is inlet for carrier fluid 110. Inlet for carrier fluid 110 is in fluid communication with the main microfluidic channel of the device and is configured to deliver additional immiscible carrier fluid into the main microfluidic channel in order to space droplets as desired. Also in fluid communication with the main microfluidic channel is inlet for carrier fluid 111, which is configured to deliver droplet focusing oil into the main microfluidic channel. Downstream of inlets for carrier fluid 110 and 111 is detection position 116. The detection position 116 indicates the point on the device that the desired signal from the assay being run on the chip is detected. The detection position 116 may be based on an alignment of an objective or fiber that directs an excitation light at the sample passing detection position 116 and an additional objective or fiber coupled to a detector configured to detect an emission from detection position 116. Alternatively, the objective for the excitation light may be configured to also collect the emission. In some embodiments, the excitation source is reflected from detection position 116 through an inverted objective lens, where the emission is collected, columnated, and directed through optical fibers for quantification by a photomultiplier tube or other detector. In some embodiments, the objective or fiber aligned at detection position 116 is not coupled to the device. When not coupled to the device, the detector or emission objective or fiber can be moved to adjust the detection positions 116 on the device in order to adjust the time between detection and sorting. When not coupled to the device, the detector or emission objective may also be moved for use in calibration of the device or initiation of the device, thus allowing a single light source to be used for multiple functions. Downstream of inlets for carrier fluid 110 and 111 and detection position 116 is discrimination junction electrode 112. The discrimination junction electrode 112 may be a dielectrophoresis electrode configured to propel droplets down outlet 114 if the droplet is determined to display a desired signal or to outlet 115 if the droplet is determined to lack a desired signal. The discrimination junction electrode 112 is connected to a discrimination junction ground circuit, which is connected to the device at circuit connection points 113a and 113b. A zoomed in drawing of the sorting and detection region of the exemplary device is shown in FIG. 9B. FIG. 9C shows a picture of a microfluidic device substantially as described in this example. FIG. 10 provides another exemplary depiction of the microfluidic device from FIG. 9A, wherein an Optical Glue is displayed within the fiberoptic waveguide. In some embodiments, the Optical Glue helps to minimize scattering of the light from the fiberoptic wave guide.

Figure 11:
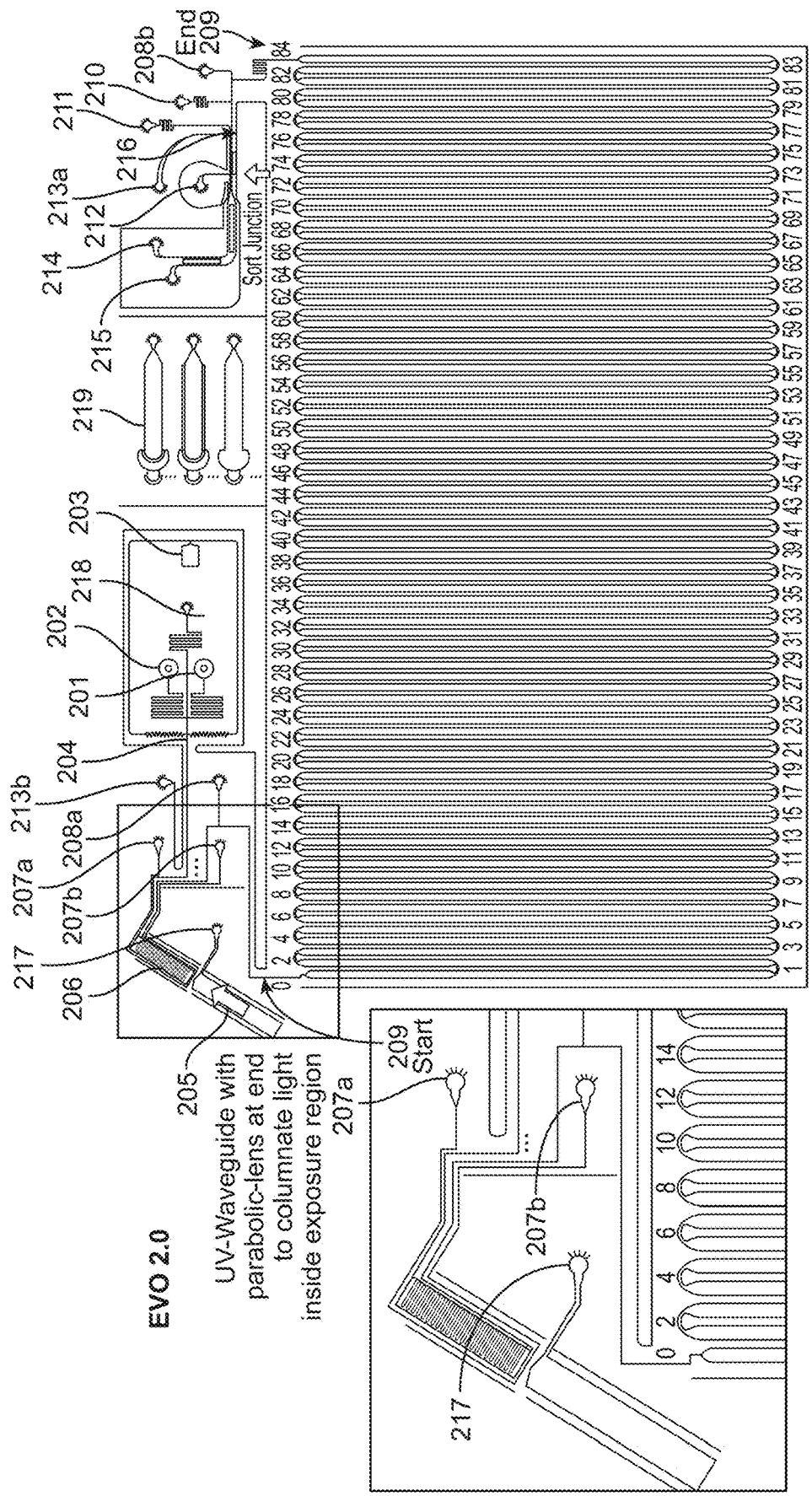
FIG. 11 provides a depiction of another exemplary microfluidic device used with the methods and systems described herein.

FIG. 11 provides another exemplary microfluidic device that can be used for the methods and systems described herein. The exemplary microfluidic device contains a first inlet 201. The first inlet 201 is configured to accept an aqueous fluid, such as an aqueous assay reagent. The exemplary microfluidic device also contains a second inlet 202. In this example, the second inlet 202 is configured to accept another aqueous fluid. This may be the same or different as the aqueous fluid added to the first inlet 201. The second inlet 202 may be configured to accept beads as provided herein, or the first inlet 201 may be so configured. In some embodiments, the exemplary microfluidic device also contains a third inlet 218. In this example, the third inlet 218 is configured to accept another aqueous fluid. This may be the same or different as the aqueous fluid added to the first inlet 201 and/or the second inlet 202. The third inlet 218 may be configured to accept beads as provided herein. In other examples of a microfluidic device, there may only be a single inlet stream. In some embodiments of a microfluidic device, there are four or more inlets. In some embodiments the four or more inlets may be aqueous inlets. The exemplary microfluidic device shown in FIG. 11 further comprises an inlet 203 for carrier fluid (e.g. an oil immiscible with an aqueous fluid) in fluid connection with a droplet formation junction or extrusion junction 204. The inlet 203 in this example is connected to the droplet formation junction 204 by two channels, each reaching an aqueous stream channel at the same point on opposite sides of the aqueous stream channel. The droplet formation junction 204 comprises a microfluidic channel that continues down the flow path towards cleavage region 206. Near cleavage region 206 is a UV waveguide 205 configured to deliver light into the microfluidic channel of the cleavage region 206. In some embodiments, the UV waveguide is a fiberoptic wave guide. The UV waveguide 205 is embedded in the plane of the device such that the light emitted enters the microfluidic channel of cleavage region 206 from the device plane. In some embodiments, the UV waveguide comprises a parabolic lens at an end closest to the cleavage region. In some embodiments, the parabolic lens is configured to columnate light inside the cleavage region. In some embodiments, the parabolic lens, or a curved lens, minimizes the tendency for the light from the UV waveguide to be scattered. In some embodiments, the cleavage region is exposed to UV light projected normal to the circuit plane, exposing a defined area to UV where the compound is cleaved. In some embodiments, an Optical Glue 217 is provided with the UV waveguide. In some embodiments, the Optical Glue 217 helps to minimize light being scattered by UV waveguide.

Also near cleavage region 206 may be a pillar (not shown) configured to fix a fiberoptic manifold which can be configured to emit light from above the plane of the device into the microfluidic channel of cleavage region 206. The device also comprises an inlet for calibration fluid 207a in fluid connection with the cleavage region 206 and an outlet for calibration fluid 207b. The inlet for calibration fluid 207a is configured to receive and deliver to the cleavage region 206 a fluid configured to normalize photon exposure within the cleavage region. In some embodiments, the cleavage region 206 comprises a serpentine flow path. After passing through the cleavage region 206, the calibration fluid exits through the outlet for calibration fluid 207b. The cleavage region 206 is in fluid communication via a microfluidic channel to an incubation region 209. In the example of FIG. 11, the incubation region 209 contains a series of widened chambers, each chamber connected to the next chamber in the series by a microfluidic channel. The configuration of these chambers affect the flow rate and residence time of the droplets formed at droplet formation region 204 through the device. In some embodiments, the chambers are configured to prevent trapping of droplets as they pass through incubation region 209. Such configuration of the chambers is particularly important when using a carrier fluid that is denser than the aqueous droplets (e.g. 3-ethoxyperfluoro(2-methylhexane)). In some embodiments, the height of the chamber is about 30 µm to about 1,000 µm. In some embodiments, the height of the chamber is about 50 µm to about 500 µm. In some embodiments, the depth of the chambers of this exemplary microfluidic device (FIG. 11) is larger than the depth of the chambers in the device from FIG. 9A. As such, in some embodiments, this exemplary device (FIG. 11) provides for a longer incubation region since a larger depth would result in faster moving droplets, and thereby a decreased residence time if the same length of incubation region as compared to the device in FIG. 9A was used. In some embodiments, collection chambers 219 are optionally provided with this exemplary microfluidic device. Configured on either end of incubation region 209 are bypass shunts 208a and 208b. The bypass shunts 208a and 208b are configured to allow a fluid coupled to the shunt to flow in or out of the main microfluidic channel. If fluid is diverted out of the main microfluidic channel at bypass shunt 208a, the material will not pass through incubation region 209. Positioned downstream of incubation region 209 is inlet for carrier fluid 210. Inlet for carrier fluid 210 is in fluid communication with the main microfluidic channel of the device and is configured to deliver additional immiscible carrier fluid into the main microfluidic channel in order to space droplets as desired. Also in fluid communication with the main microfluidic channel is inlet for carrier fluid 211, which is configured to deliver droplet focusing oil into the main microfluidic channel. In some embodiments, downstream of inlets for carrier fluid 210 and 211 is detection position 216. The detection position 216 indicates the point on the device that the desired signal from the assay being run on the chip is detected. The detection position 216 may be based on an alignment of an objective or fiber that directs an excitation light at the sample passing detection position 216 and an additional objective or fiber coupled to a detector configured to detect an emission from detection position 216. Alternatively, the objective for the excitation light may be configured to also collect the emission. In some embodiments, the excitation source is reflected from detection position 216 through an inverted objective lens, where the emission is collected, columnated, and directed through optical fibers for quantification by a photomultiplier tube or other detector. In some embodiments, the objective or fiber aligned at detection position 216 is not coupled to the device. When not coupled to the device, the detector or emission objective or fiber can be moved to adjust the detection positions 216 on the device in order to adjust the time between detection and sorting. When not coupled to the device, the detector or emission objective may also be moved for use in calibration of the device or initiation of the device, thus allowing a single light source to be used for multiple functions. Downstream of inlets for carrier fluid 210 and 211 and detection position 216 is discrimination junction electrode 212. The discrimination junction electrode 212 may be a dielectrophoresis electrode configured to propel droplets down outlet 214 if the droplet is determined to display a desired signal or to outlet 215 if the droplet is determined to lack a desired signal. The discrimination junction electrode 212 is connected to a discrimination junction ground circuit, which is connected to the device at circuit connection points 213a and 213b.

Figure 16:
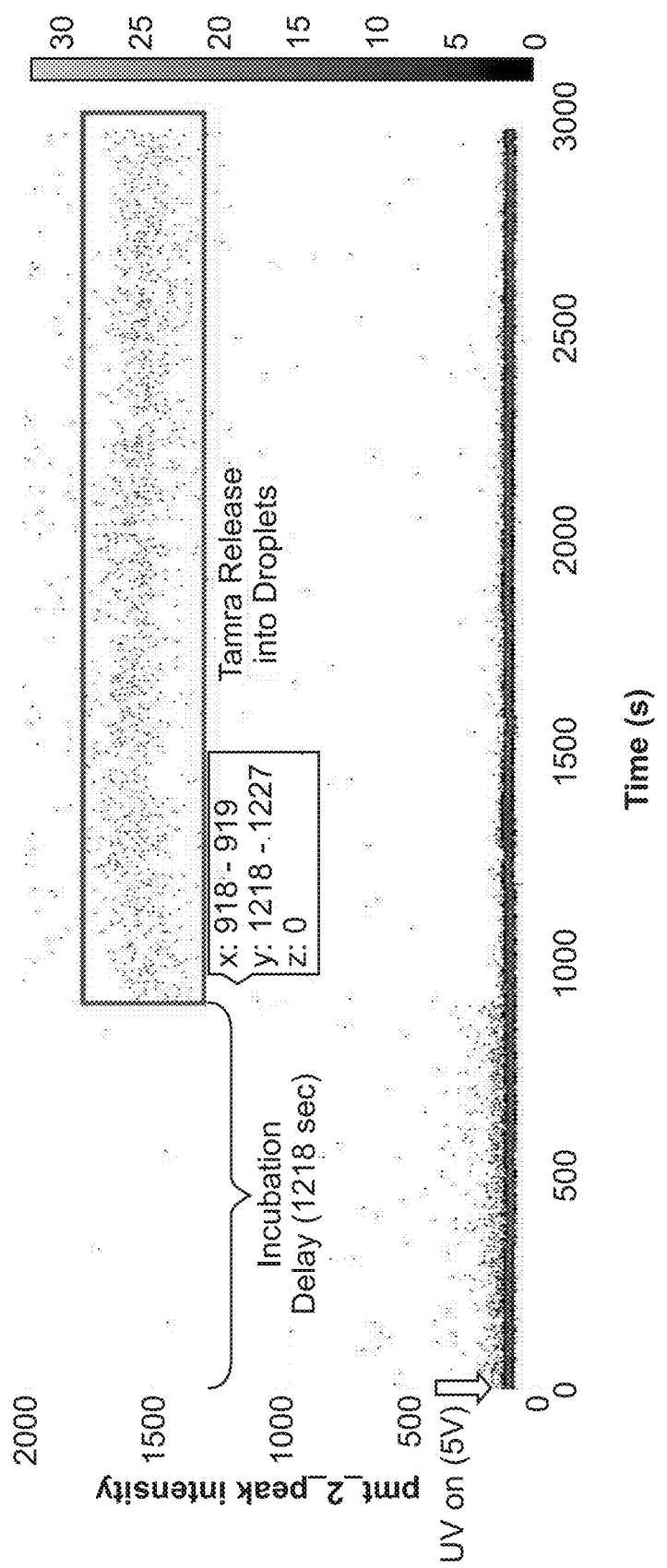
FIG. 16 provides exemplary data of UV confinement in a microfluidic device described herein.

FIG. 16 provides a data set indicating confinement of the UV light emitted to a cleavage region of a microfluidic device described herein. As such, UV light is not scattered throughout a microfluidic device that results in additional encoded effectors from being released while along an assay flow path. In some embodiments, targeting and confining the UV light onto a specific region of an assay flow path helps ensure a predetermined amount of encoded effector is released. As an exemplary method to confirm such confined UV emission, an assay flow path may be pre-filled with an assay comprising encapsulations having a fluorophore dye. Thus, a number of encapsulations are located downstream of a UV exposure region (e.g., cleavage region), and would not be expected to provide any detectable signals at a detection point of a microfluidic device. As depicted in FIG. 16, an incubation delay period of 1218 seconds is shown wherein there are minimal encapsulations exhibiting detectable signals, followed by a distinct number of encapsulations having detectable signals. As such, the UV light emitted was generally confined to the cleavage region of a microfluidic, such that the encapsulations passing through the cleavage region was exposed to the UV light, within minimal scattered light being exposed to encapsulations further along the assay flow path.

Figure 20:
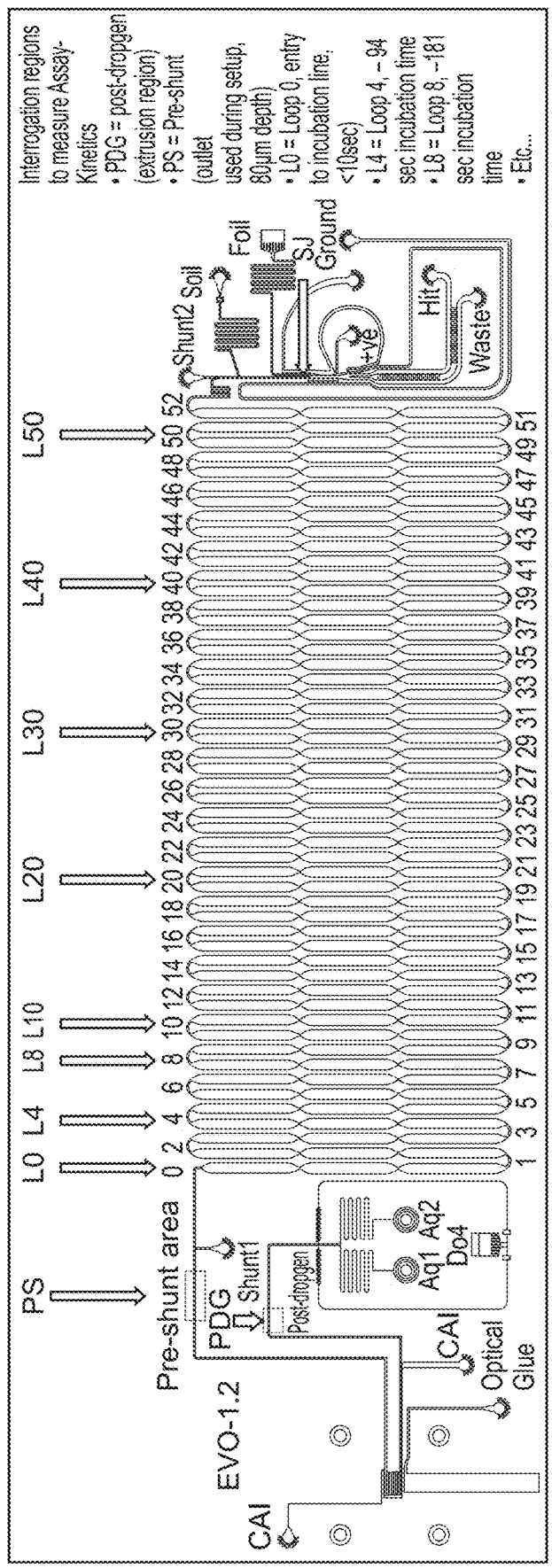
FIG. 20 shows the microfluidic device of FIG. 9A with various detector points along an assay flow path.
Figure 21:
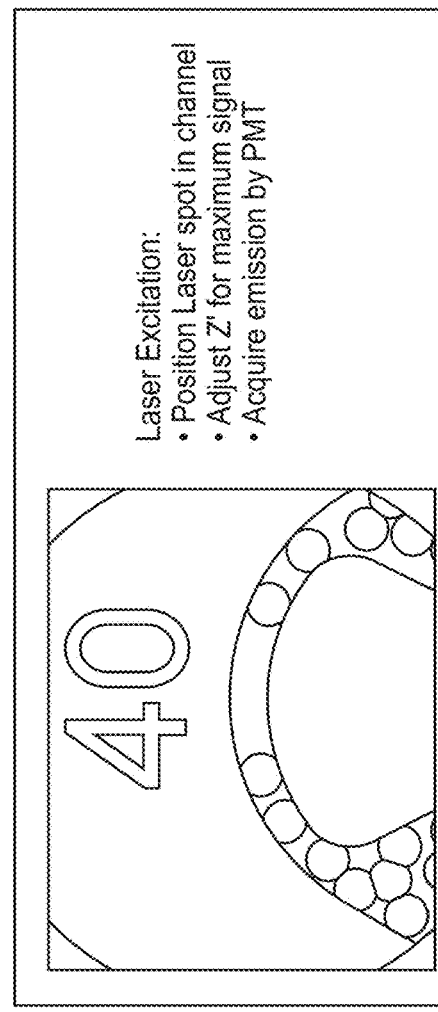
FIG. 21 shows an exemplary detection of a specific location along an assay flow path in a microfluidic device described herein.
Figure 23A:
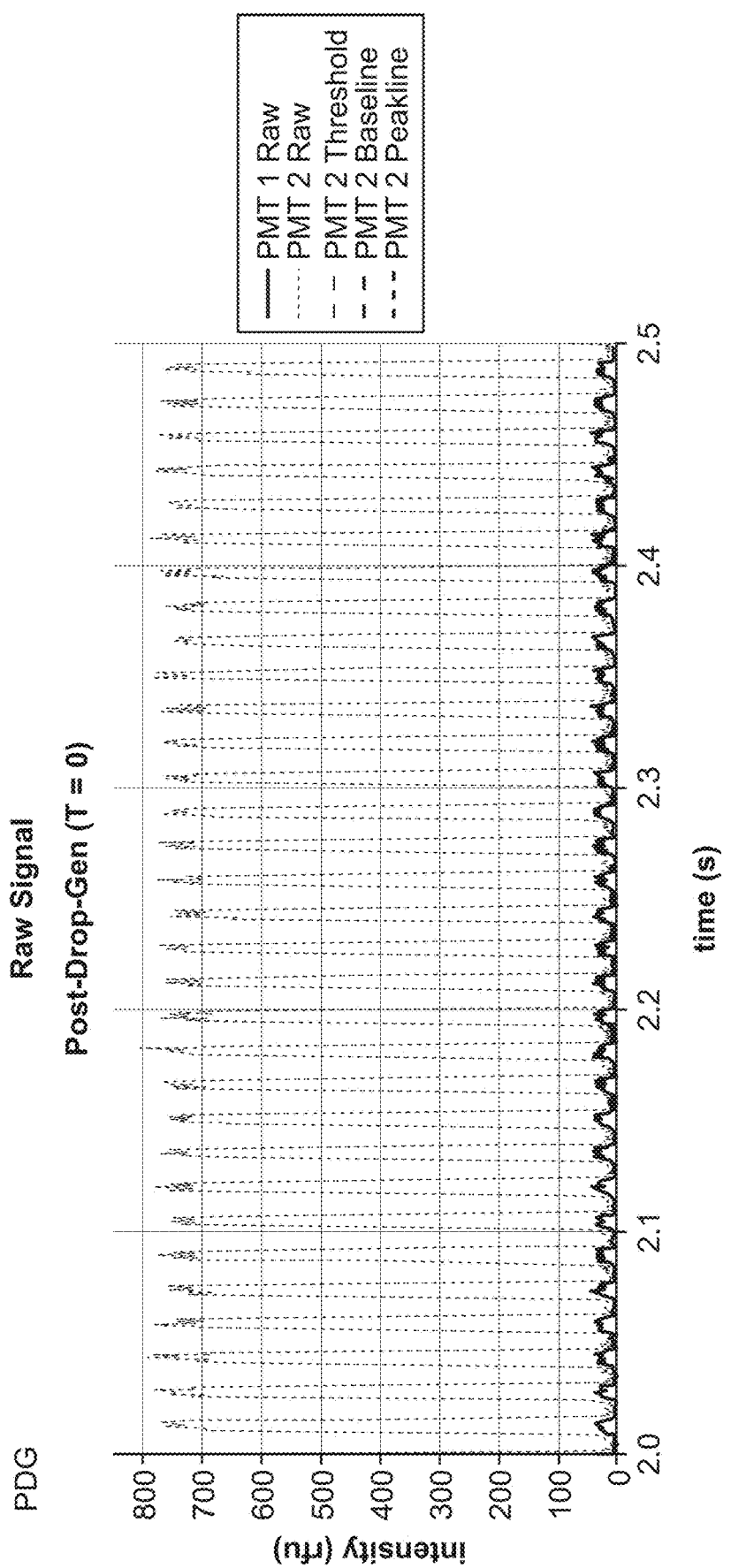
FIG. 23A provides the detection of raw intensity levels at an incubation time of 0 s for a fluorophore dye.
Figure 23B:
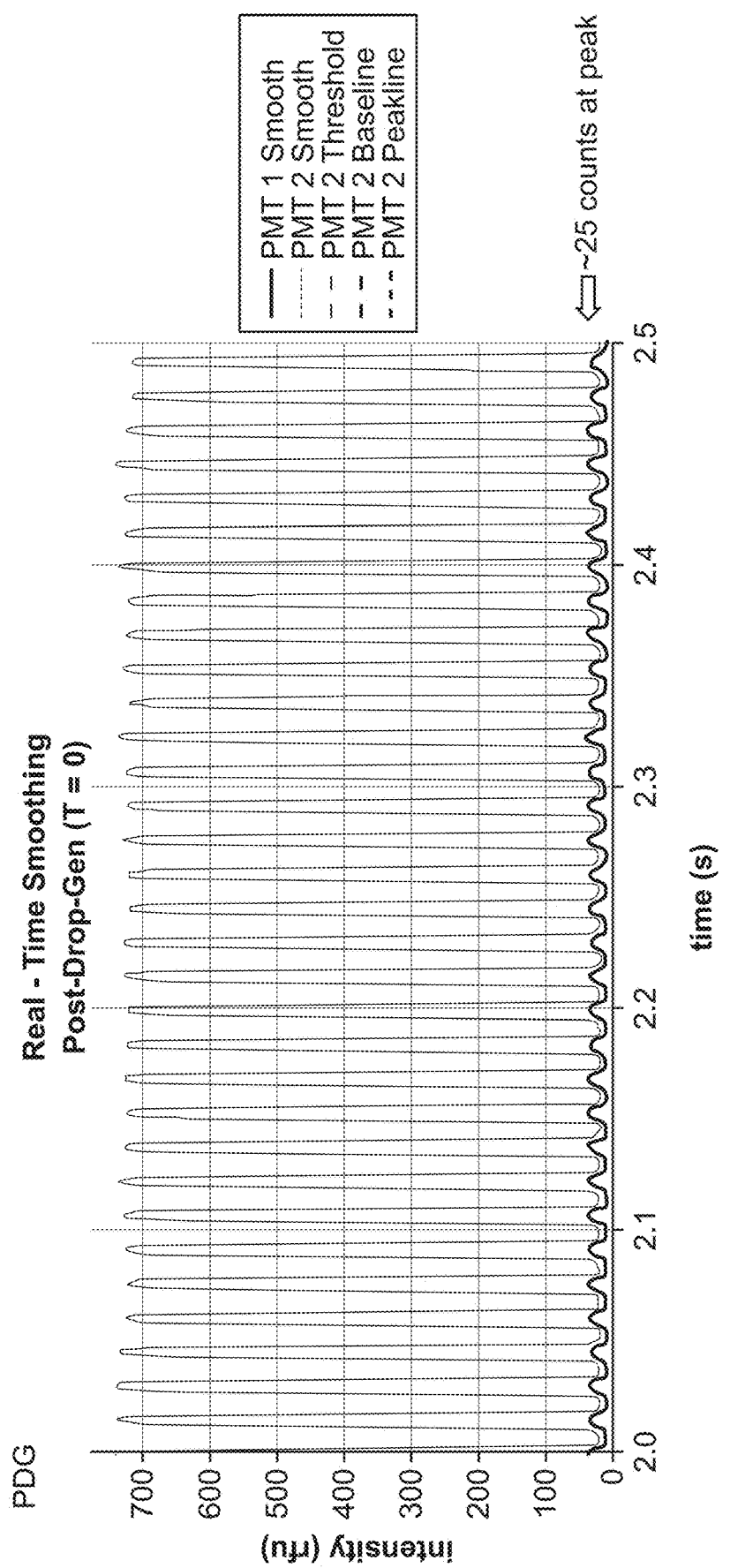
FIG. 23B provides the detection of real-time smoothing of the intensity levels from FIG. 23A.
Figure 24A:
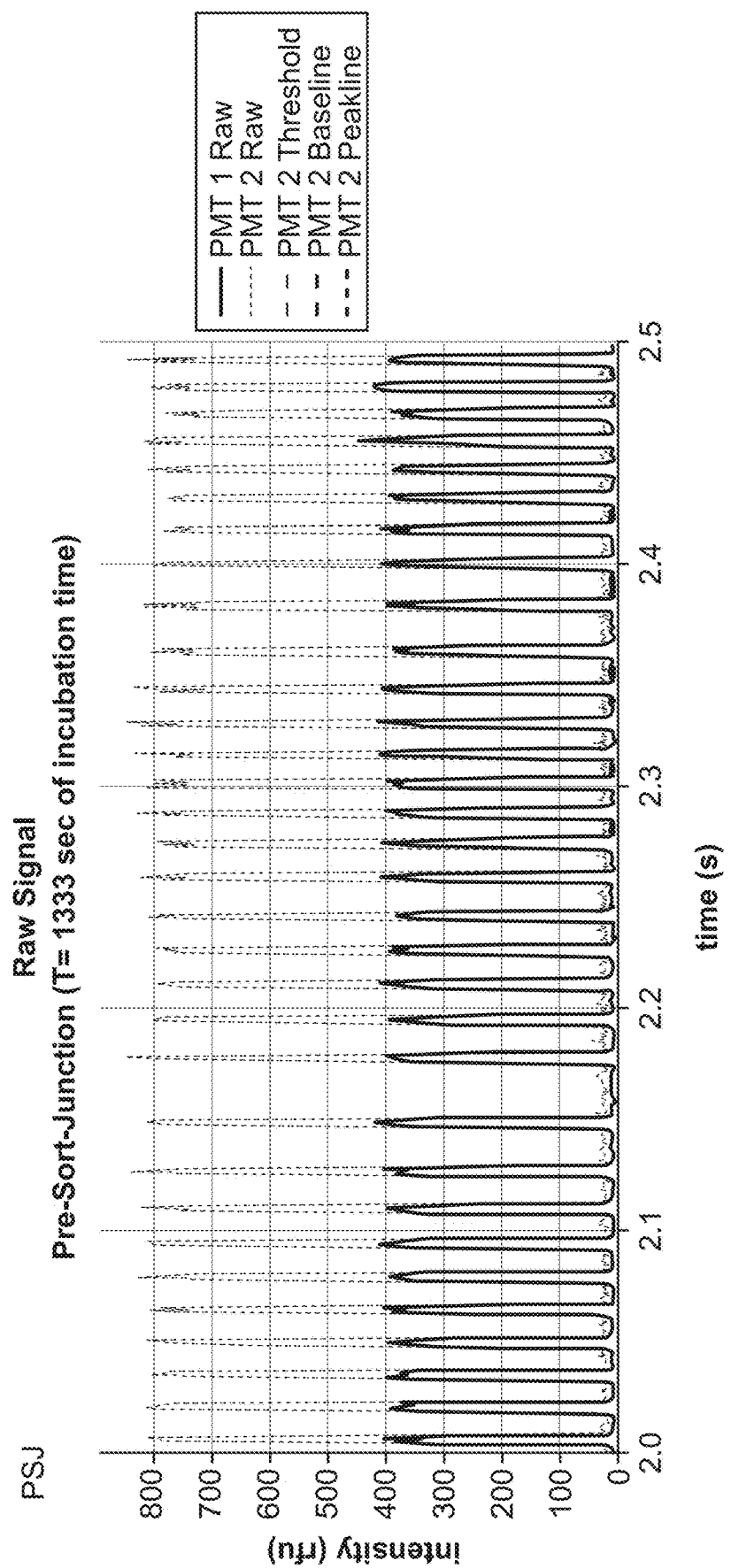
FIG. 24A provides the detection of raw intensity levels at an incubation time of 1333 s for a fluorophore dye.
Figure 24B:
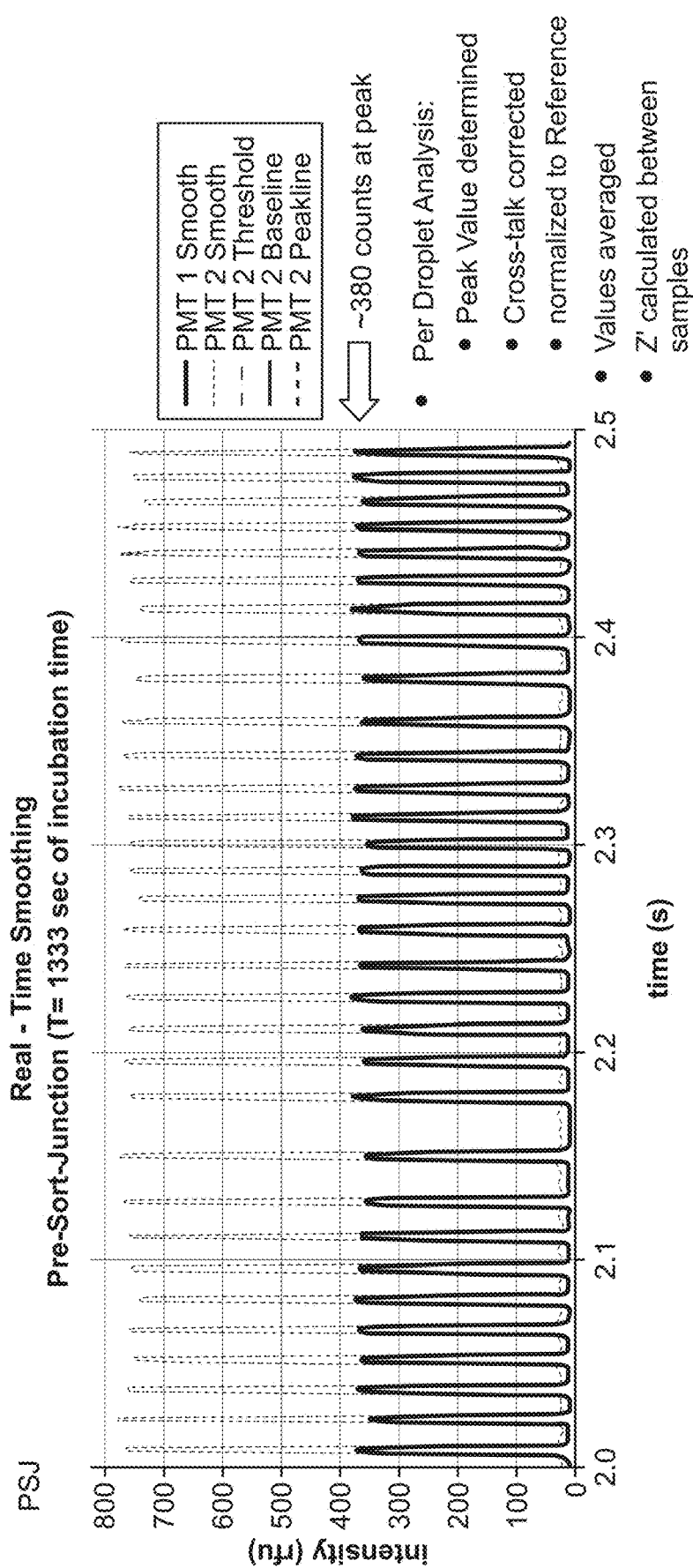
FIG. 24B provides the detection of real-time smoothing of the intensity levels from FIG. 24A.
Figure 25:
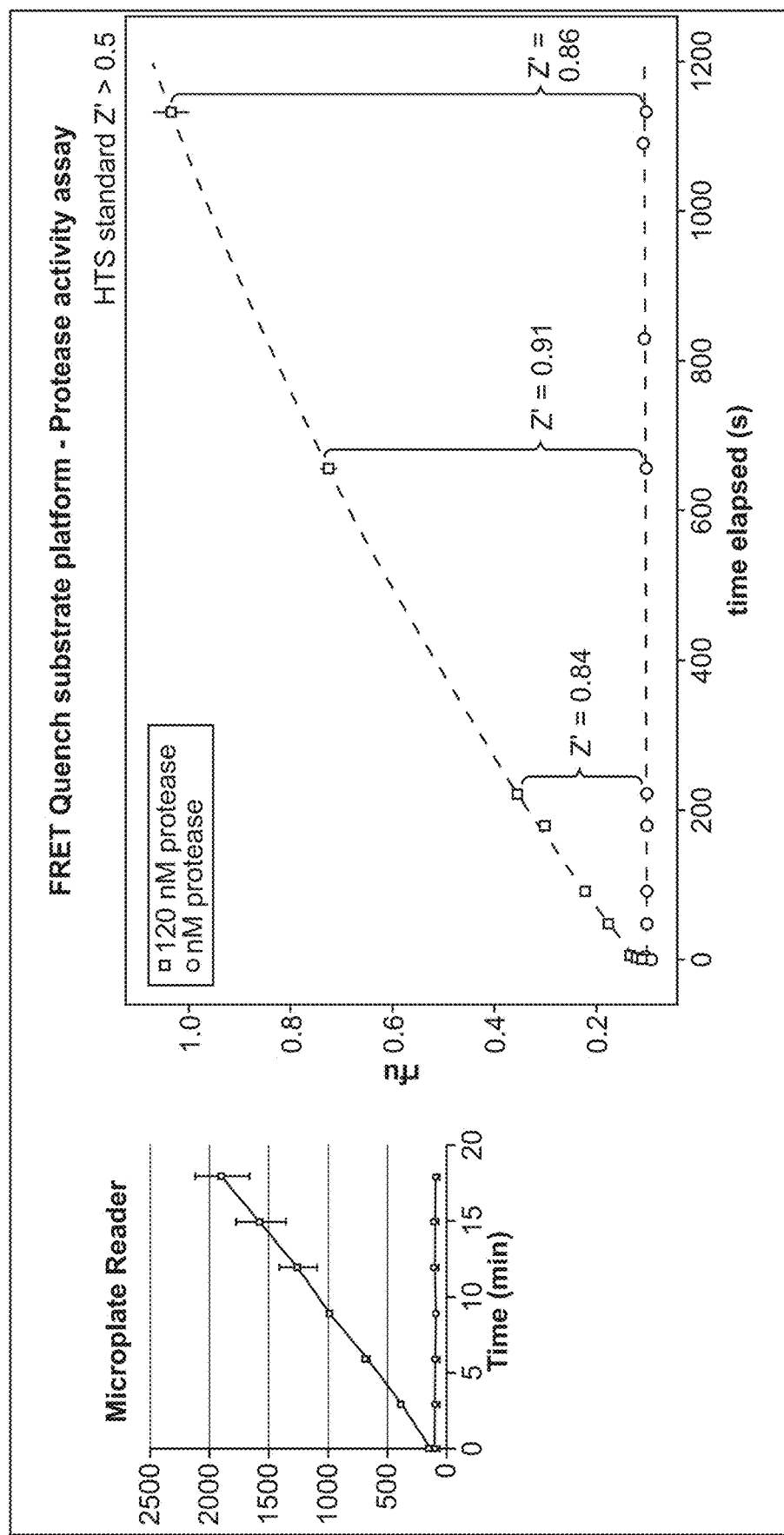
FIG. 25 shows increasing measured intensity peaks for a fluorophore dye across an incubation period of an assay.

FIG. 20 depicts an example of performing fluorescence assay kinetics using the microfluidic device from FIGS. 9A and 10 is provided. In some embodiments, the fluorescence is measured at various locations within the assay flow path, so as to measure the progression of interaction between an encoded effector and sample as it is incubated. FIG. 21 provides a depiction for positioning a laser spot in a given channel position so as to measure the PMT emission. FIGS. 23A-24B provide a graphical output of the intensity measured by an assay at different incubation times (PMT 1). For example, FIGS. 23A-B depicts a raw signal and real-time smoothing intensity measured at the outset of the incubation period (T=0 s), wherein a very low count is measured (e.g., 25 counts at peak). By contrast, FIGS. 24A-B depicts a raw signal and real-time smoothing intensity (PMT 1) measured at the pre-sort junction of the incubation period (T=1333 s), wherein a significantly higher count is measured (approximately 380 counts at the peak). FIG. 25 provides a comparison of data quality between standard microplate assay and a microfluidic device as described herein. The Figure traces show the kinetic activity of a protease within a microplate (left) and droplet compartment (right) on a microfluidic device. The uniform incubation time provides high reproducibility and uniformity at each time-point, Screen Normalization Methods Provided herein are methods for improving the output results of screens utilizing encoded effectors. Other methods suffer from high rates of false negatives or positives due to variable loading of effectors or encodings on scaffolds. The variations in amounts of effector or encoding loaded on a scaffold may be due to either low concentration of encoding/effector on scaffolds, or due to degradation of the encoding/effector during synthesis, the screening process, or storage. In some embodiments, the methods described herein overcome this limitation by amplifying the level of encodings on scaffolds to uniform levels. Thus, all the encodings are present at substantially the same level and none are drowned out by higher signals from more abundant encodings.

Additionally, in some embodiments, the methods provided herein provide a means for determining the concentration of effectors bound to scaffolds. In some embodiments, effector loading in an entire library can be determined. Having knowledge of the effector load on a scaffold can allow for determination if an effector that displays a positive result in a screen is due to high potency of the effector of interest, or if that particular effector was present at a high concentration within the encapsulation which was screened. Thus, the methods provided herein give the user a way to readily ascertain how potent a particular effector is and can help remove false positives from an effector screening set.

Further provided herein are methods for amplifying primers for linking nucleic acids from the samples to the encoding for optimal detection of nucleic acids. In methods without this amplification step, incomplete capture of nucleic acids released by the sample may occur due to low levels of encodings present on the scaffolds. Lower levels of nucleic acid capture could be interpreted as a lack of potency. By amplifying the primers within the encapsulation during or after the screen is completed, all of the sample nucleic acids can be captured. Thus, the method improves the readout of nucleic acid levels in a screen. In some instances, this results in improved yield and knowledge of the expression levels of various sample components or other knowledge ascertainable from capturing sample nucleic acids.

Barcode Normalization Method

Provided herein are methods for normalization of nucleic acid encoding levels across a library after performing a screen. During a library screen of nucleic acid encoded effectors, the levels of nucleic acid encodings bound to beads can vary substantially from bead to bead. This can be due to low synthesis yields during synthesis of the bead, or due to damage to the encoding itself during the screen or during storage. Some beads may have concentrations of encodings bound to beads far in excess of other beads. Consequently, when sequencing the resulting "hit" beads after performing a screen to determine which effectors were efficacious, effectors whose encodings are low in concentration are difficult to detect. This is due to the amplification reactions that occur during sequencing, which results in a much higher presence of encodings whose concentrations start higher. For example, amplifying the encodings from a pooled collection of encoded effectors can generate noise (e.g., background signal) during sequencing analysis, arising from template switching, or mis-hybridization, which generate chimeric sequences, which are misrepresentative of the true effector population. Therefore, it would take a prohibitively high number of reads to detect encodings which are present in substantially lower concentrations than others. For this reason, a method to normalize the levels of nucleic acid encodings after a screen is highly desirable and advantageous, as it allows detection of substantially all effectors that had a positive result in the screen. In an exemplary method, isolated amplification of each encoding from a collection of encoded effectors helps to prevent templates from different encodings being formed from the mechanisms leading to chimeric sequences.

In some embodiments, a plurality of screened encoded effectors and corresponding scaffolds are provided in a plurality of corresponding encapsulations, wherein each scaffold is bound to one or more nucleic acid encodings that encode a corresponding screened encoded effector. In some embodiments, the plurality of encapsulations are lysed. In some embodiments, contents within the plurality of encapsulations that were unbound to a scaffold are removed. In some embodiments, the plurality of scaffolds are then suspended in a liquid medium. In some embodiments, the plurality of scaffolds are then encapsulated in a plurality of new encapsulations, wherein each new encapsulation encapsulates one or more scaffolds. In some embodiments, the nucleic acid encodings of the beads. In some embodiments, the nucleic acids of each bead are amplified to form corresponding amplified nucleic acid encodings. In some embodiments, the amplified nucleic acid encodings within the plurality of new encapsulations are limited to the nucleic acid encodings and reagents within the respective new encapsulation, thereby improving uniformity of the number of amplicons representing each encoding. In some embodiments, the amplified nucleic acid encodings are amplified, such that the concentration of the amplified nucleic acid encodings for each scaffold are within a minimum level of uniformity to each other.

The nucleic acid encoded library can be subjected to a screen. Any type of screen can work with the methods and systems provided herein. In some embodiments, the screen previously performed is one of the screening methods provided herein. In some embodiments, the screened encoded effectors have been sorted in the previous screen. In some embodiments, only the "hit" effector beads from the library screen are included in the present method. In some embodiments, providing the screened encoded effectors and corresponding scaffolds comprises performing a screen of the nucleic acid encoded library. In some embodiments, the screen comprises a sorting step to separate nucleic acid encoded effectors that displayed a positive result in the screen.

In some embodiments, the screened encoded effectors and corresponding scaffolds are provided in an emulsion, within a plurality of encapsulations. The provided encapsulations containing the screened encoded effectors and scaffolds may be lysed by a variety of methods. In some embodiments, lysing the encapsulations comprises introducing a demulsifying reagent, filtration, or sonication to the emulsion. In some embodiments, lysing the encapsulations comprises introducing a demulsifying reagent to the emulsion. In some embodiments, lysing the encapsulations comprises filtering the emulsion. In some embodiments, lysing the encapsulations comprises introducing a demulsifying reagent to the emulsion.

Any demulsifying reagent can be used with the methods and systems provided herein. In some embodiments, the demulsifying reagent is an acid or a salt. In some embodiments, the demulsifying reagent is an acid. In some embodiments, the demulsifying reagent is sulfuric acid or hydrochloric acid. In some embodiments, the demulsifying reagent is an organic acid. In some embodiments, the demulsifying reagent is a salt. In some embodiments, the salt is sodium chloride, potassium pyrophosphate, or sodium sulfate. In some embodiments, the salt is sodium chloride. In some embodiments, the salt is potassium pyrophosphate. In some embodiments, the salt is sodium sulfate.

In some embodiments, the scaffolds with the encapsulations are washed to remove unbound contents. In some embodiments, washing the scaffolds comprises rinsing the scaffolds with a wash buffer. In some embodiments, the wash buffer is an aqueous buffer, an organic solution, or a mixture thereof. In some embodiments, the wash buffer is an aqueous buffer. In some embodiments, the buffer is from pH 4 to pH 10. In some embodiments, the buffer is from pH 5 to 9. In some embodiments, the buffer is from pH 6 to pH 8. In some embodiments, the pH is about pH 7. In some embodiments, the wash buffer is a phosphate buffer. In some embodiments, the wash buffer is an isotonic buffer. In some embodiments, the wash buffer is an organic solution. In some embodiments, the organic solution comprises methanol, ethanol, isopropyl alcohol, acetonitrile, benzene, toluene, dichloromethane, ethyl acetate, hexanes, any other organic solvent, or any combination thereof. In some embodiments, the wash buffer comprises a denaturing agent.

Washing the scaffolds may remove unbound content from the scaffolds and/or that were located within the corresponding encapsulation. In some embodiments, at least 50%, at least 60%, at least 70%, at least 80%, or at least 90% of unbound contents are removed from the scaffolds during one or more was steps. In some embodiments, at least 90%, at least 95%, at least 97%, at least 98%, or at least 99% of unbound contents are removed from the scaffolds during one or more wash steps.

Multiple washes may be performed. In some embodiments, the scaffolds are subject to multiple wash and collection steps. In some embodiments, the scaffolds are collected by centrifugation or filtration after each wash step. In some embodiments, the scaffolds are collected by centrifugation after each wash step. In some embodiments, the scaffolds are collected by filtration after each wash step. In some embodiments, there is a single wash step. In some embodiments, there are 2 wash steps. In some embodiments, the was step is repeated 3, 4, 5, 6, 7, 8, 9, 10 or more times.

After the wash step, in some embodiments, the scaffolds are suspended in a liquid medium. In some embodiments, the liquid medium is an aqueous solution. In some embodiments, the liquid medium comprises an organic solvent. In some embodiments, the liquid medium is compatible with nucleic acid amplification. In some embodiments, the liquid medium comprises the amplification mix.

In some embodiments, the scaffolds are then encapsulated in a plurality of encapsulations ("new encapsulations"). In some embodiments, the scaffolds are encapsulated into a plurality of droplets. In some embodiments, the scaffolds are reintroduced into an emulsion. In some embodiments, each new encapsulation comprises one or more scaffolds. In some embodiments, the scaffolds are encapsulated such that a majority of the new encapsulations comprise one or more single scaffolds. In embodiments, each droplet comprises an amplification mix.

In some embodiments, encapsulating the scaffolds or re-introducing the scaffold into an emulsion comprises placing the scaffolds through a microfluidic device. In some embodiments, the microfluidic device is a microfluidic chip. In some embodiments, the scaffolds are reintroduced into an emulsion by placing the scaffolds into a one-pot emulsifier.

As described herein, in some embodiments, the scaffold is a solid support. In some embodiments, the scaffold is a bead, a fiber, nanofibrous scaffold, a molecular cage, a dendrimer, or a multi-valent molecular assembly. In some embodiments, the scaffold is a bead. In some embodiments, the bead is a polymer bead, a glass bead, a metal bead, or a magnetic bead. In some embodiments, the bead is a polymer bead. In some embodiments, the bead is a glass bead. In some embodiments, the bead is a metal bead. In some embodiments, the bead is a magnetic bead. Beads for use in the systems and methods as described herein can be any size. In some embodiments, the beads are at most 10 nm, at most 100 nm, at most 1 µm, at most 10 µm, or at most 100 µm in diameter. In some embodiments, the beads are at least 10 nm, at least 100 nm, at least 1 µm, at least 10 µm, or at least 100 µm in diameter. In some embodiments, the beads are about 10 µm to about 100 µm in diameter.

In some embodiments, the amplification mix can be added to the new encapsulations in a separate step. In some embodiments, the amplification mix is added after the plurality of encapsulations are formed. In some embodiments, the amplification mix is encapsulated at the same time the scaffolds are being encapsulated. In some embodiments, the amplification mix is added after reintroducing the scaffolds into an emulsion. In some embodiments, the amplification mix is added by pico-injection. In some embodiments, the amplification mix is added by droplet merging. In some embodiments, the amplification mix is added at the encapsulation step.

The amplification mix is capable of amplifying the nucleic acids in the new encapsulations. In some embodiments, the amplification mix comprises PCR reagents. In some embodiments, the amplification mix comprises reagents for room temperature amplification.

In some embodiments, the nucleic acid encodings of each scaffold are amplified to form amplified nucleic acid encodings, such that the concentration of the amplified nucleic acid encodings for each scaffold are within a minimum level of uniformity to each other. In some embodiments, the minimum level of uniformity comprises a concentration of nucleic acid encodings in each new encapsulation, wherein about 90% of the new encapsulations have a concentration of amplified nucleic acid encodings within about 10% of an average concentration of amplified nucleic acid encodings in the plurality of new encapsulations. In some embodiments, the minimum level of uniformity comprises a concentration of nucleic acid encodings in each new encapsulation, wherein about 80% of the new encapsulations have a concentration of amplified nucleic acid encodings within about 20% of an average concentration of amplified nucleic acid encodings in the plurality of new encapsulations. In some embodiments, the minimum level of uniformity comprises a concentration of nucleic acid encodings in each new encapsulation, wherein about 75% of the new encapsulations have a concentration of amplified nucleic acid encodings within 25% of an average concentration of amplified nucleic acid encodings in the plurality of new encapsulations. In some embodiments, the minimum level of uniformity comprises a concentration of nucleic acid encodings in each new encapsulation, wherein about 70% to about 90% of the new encapsulations have a concentration of amplified nucleic acid encodings within about 10% to about 30% of an average concentration of amplified nucleic acid encodings in the plurality of new encapsulations. In some embodiments, the minimum level of uniformity comprises a concentration of nucleic acid encodings in each new encapsulation, wherein about 70% to about 90% of the new encapsulations containing scaffolds have a concentration of amplified nucleic acid encodings within 10-fold, 15-fold, 20-fold, 50-fold, or 100-fold of each other.

In some embodiments, sequencing the amplified nucleic acid encodings results in lower background signal than a nucleic acid encoded library that has not been subjected to the method. In some embodiments, the background signal is reduced by at least 10%, at least 20%, at least 30%, at least 40%, or at least 50%. In some embodiments, the background signal is reduced by at least 75%. In some embodiments, the background signal is reduced by at least 90%. In some embodiments, the background signal is reduced by at least 95%.

In some embodiments, the lower background signal allows for detection of nucleic acid encoded effectors whose encoding concentrations before the screen are 100×, 1000×, 10000×, 100000×, or 1000000× lower in concentration than the average encoding concentration in the library. In some embodiments, the lower background signal allows for detection of nucleic acid encoded effectors whose encoding concentrations before the screen are 10× lower in concentration than the average encoding concentration in the library. In some embodiments, the lower background signal allows for detection of nucleic acid encoded effectors whose encoding concentrations before the screen are 1000× lower in concentration than the average encoding concentration in the library. In some embodiments, the lower background signal allows for detection of nucleic acid encoded effectors whose encoding concentrations before the screen are 10000× lower in concentration than the average encoding concentration in the library. In some embodiments, the lower background signal allows for detection of nucleic acid encoded effectors whose encoding concentrations before the screen are 100000× lower in concentration than the average encoding concentration in the library. In some embodiments, the lower background signal allows for detection of nucleic acid encoded effectors whose encoding concentrations before the screen are 1000000× lower in concentration than the average encoding concentration in the library.

Primer Amplification Method

Provided herein is a method for amplifying a primer to maximize cellular nucleic acid capture. In some screening methods provided herein, nucleic acid contents of cells are transferred to the nucleic acid encodings of various effectors. The nucleic acid encodings are sometimes linked to scaffolds, such as beads. However, a library of beads may comprise individual beads that may have dramatically different levels of nucleic acids encodings on the beads. Consequently, such beads are unable to attach significant levels of cellular nucleic acids, or other beads are able to attach substantially more levels of cellular nucleic acids. Such discrepancies make it difficult to determine if the cellular nucleic acid level differences are due to the differential effects of various effectors, or if there were simply less capture sites available to gather the cellular nucleic acids. Therefore, a method of producing additional primers to label the cellular nucleic acids with the nucleic acid encoding would have substantial benefits.

In one aspect, provided herein, is a method for amplifying a primer to maximize cellular nucleic acid capture. In some embodiments, the primer is a copy of a nucleic acid encoding (encoded nucleic acid primer). In some embodiments, the method comprises encapsulating a nucleic acid encoded scaffold with one or more cells, an amplification mix, and a nicking enzyme. In some embodiments, the nicking enzyme targets a specific nucleotide sequence. As described herein, a nucleic acid encoded scaffold is bound to one or more nucleic acid encodings. In some embodiments, the one or more nucleic acid encodings comprise a specific nucleotide sequence. In some embodiments, the cell is lysed to release one or more cellular nucleic acids. In some embodiments, the nucleic acid encoding is nicked with the nicking enzyme, thereby creating an encoded nucleic acid primer. In some embodiments, nicking refers to a single strand of a an encoding being displaced. In some embodiments, the nicking enzyme targets a specific site in the nucleic acid encoding. In some embodiments, the specific site comprises the specific nucleotide sequence. In some embodiments, nicking the nucleic acid encoding creates an encoded nucleic acid primer. In some embodiments, the encoded nucleic acid primer is amplified. In some embodiments, the encoded nucleic acid primer is amplified via interaction between the nicking site and the amplification mix. In some embodiments, a released cellular nucleic acid is labeled with an encoded nucleic acid primer.

In some embodiments, amplifying the encoded nucleic acid primer comprises first creating a copy of the nucleic acid encoding, which is extended from the nicking site, followed by nicking the nucleic acid encoding copy. In some embodiments, amplifying the encoded nucleic acid primer comprises simultaneously 1) creating a copy of the nucleic acid encoding, which extends from the nicking site, and 2) displacing the nucleic acid encoding copy.

In some embodiments, the amplification mix comprises an amplification enzyme. In some embodiments, the amplification enzyme enables for the creation of a nucleic acid encoding copy, and then the subsequent nicking. In some embodiments, the nicking enzyme enables the nicking of the copy of the nucleic acid encoding copy. In some embodiments, the amplification enzyme enables for a copy of the nucleic acid encoding to be simultaneously created and displaced. In some embodiments, the amplification enzyme is a polymerase. In some embodiments, the creation of nucleic acid encoding copies and nicking, or the simultaneous creation and displacement of the nucleic acid encoding copies, repeats to generate a population of single stranded nucleic acid encodings that serve as a primer (encoded nucleic acid primer) for labeling cellular nucleic acids. In some embodiments, the encoded nucleic acid primers are generated isothermally.

In some embodiments, each encoded nucleic acid primer comprises a capture site that prescribes a target cellular nucleic acid to label a specific released cellular nucleic acid. In some embodiments, the target nucleic acid is a target mRNA. In some embodiments, the target mRNA encodes a protein of interest. In some embodiments, the nicking enzyme enables an increase in target mRNA capture and labeling with the nucleic acid encoding. In some embodiments, the target mRNA capture is increased by at least 10%, 25%, 50%, 100%, or 200%.

In some embodiments, a plurality of cellular nucleic acids are labeled with an respective encoded nucleic acid primer. In some embodiments, the nucleic acid encoded scaffold comprises a bead, and the encoded nucleic acid primer comprises a unique bead barcode and an effector encoding.

Figure 3:
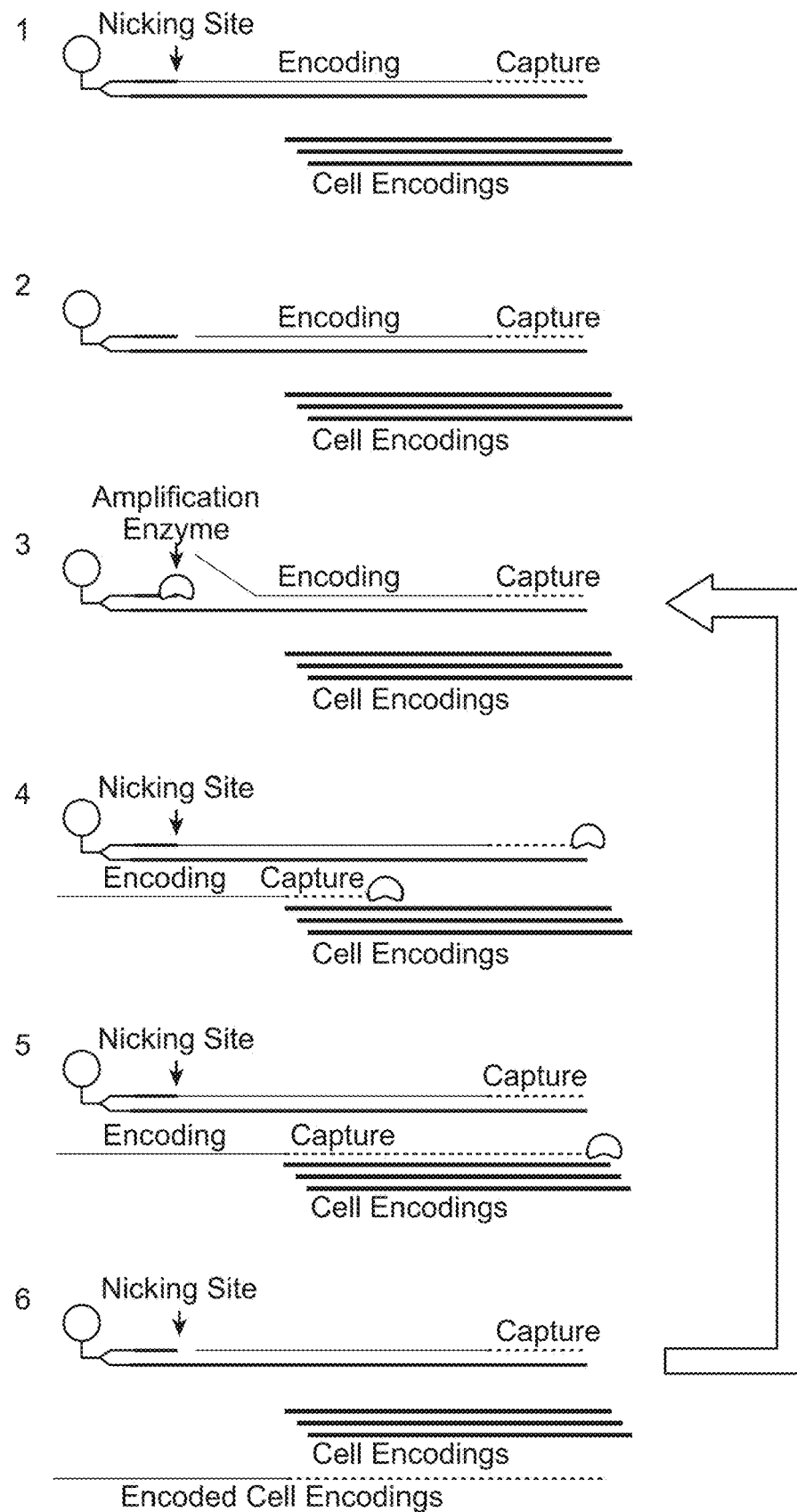
FIG. 3 illustrates an exemplary method for amplifying a primer to maximize cellular nucleic acid capture.

FIG. 3 illustrates an exemplary method for amplifying a primer to maximize cellular nucleic acid capture, as described herein. As shown in FIG. 3, in step 1, a nucleic acid encoded scaffold is shown with the nucleic acid encoding bound thereto, wherein a plurality of cellular encodings (e.g., nucleic acid) are also shown to have been released from a lysed cell. In some embodiments, the nucleic acid encoded scaffold and cellular encodings are provided within an encapsulation. The nicking site is identified on the nucleic acid encoding, along with a capture site. In some embodiments, the nicking site corresponds to a specific nucleotide sequence in the nucleic acid encoding. As shown in step 2, the nucleic acid encoding is nicked at the nicking site. As shown, in some embodiments, nicking herein refers to a single strand of the encoding being displaced from the nucleic acid encoded scaffold. As shown in steps 3-4 of FIG. 3, an amplification enzyme may interact with the nicking site, thereby creating a new copy of the nucleic acid encoding (step 4), while the previously nicked nucleic acid encoding copy (encoded nucleic acid primer) is unbound and moves within the encapsulation, such that the encoded nucleic acid primer may interact with a released cellular encoding (e.g., cellular nucleic acid), as shown in step 5. In some embodiments, the encoded nucleic acid primer labels the cellular encoding. In some embodiments, the capture site of the encoded nucleic acid primer prescribes a targeted cellular nucleic acid. In some embodiments, an enzyme enables such labeling. As shown in step 6, the encoded cell encoding is labeled with the encoded nucleic acid primer, while a created copy of the nucleic acid encoding is displaced from the scaffold, wherein the process returns to step 3.

The cell may be lysed in order to release the desired nucleic acids and to make the desired nucleic acids available for amplification. In some embodiments, the encapsulation further comprises a cell lysis buffer. In some embodiments, the lysis buffer is added by pico-injection. In some embodiments, the lysis buffer comprises a salt. In some embodiments, the lysis buffer comprises a detergent. In some embodiments, the detergent is SDS, Triton, or Tween. In some embodiments, the lysis buffer comprises a chemical which causes cell lysis. In some embodiments, cell lysis buffer is added to the encapsulation. In some embodiments, the cell lysis buffer is added to the encapsulation by pico-injection.

In some embodiments, the encapsulation is a droplet, an emulsion, a macrowell, a microwell, a bubble, or a microfluidic confinement. Once an encapsulation is formed, any component inside the encapsulation may remain in the encapsulation until the encapsulation is destroyed or broken down. In some embodiments, the encapsulations used in herein remain stable for at least 4 hours, at least 12 hours, at least 1 day, at least 2 days, at least 3 days, or at least 1 week. In some embodiments, the encapsulations are stable for the duration of the screen to be performed so that no intermingling of reagents between encapsulations occurs.

In some embodiments, the encapsulation is a droplet. In some embodiments, the droplet is at most 1 picoliter, at most 10 picoliters, at most 100 picoliters, at most 1 nanoliter, at most 10 nanoliters, at most 100 nanoliters, or at most 1 microliter in volume. In some embodiments, the droplet is at least 1 picoliter, at least 10 picoliters, at least 100 picoliters, at least 1 nanoliter, at least 10 nanoliters, at least 100 nanoliters, or at least 1 microliter in volume. In some embodiments, the droplet is between about 200 picoliters and about 10 nanoliters.

In some embodiments, the droplet is an aqueous droplet in a larger body of oil. In some embodiments, the oil acts as an immiscible carrier fluid. In some embodiments, the droplets are placed in an oil emulsion. In some embodiments, the oil comprises a silicone oil, a fluorosilicone oil, a hydrocarbon oil, a mineral oil, a paraffin oil, a halogenated oil, a fluorocarbon oil or any combination thereof. In some embodiments, the oil comprises a silicone oil. In some embodiments, the oil comprises a fluorosilicone oil. In some embodiments, the oil comprises a hydrocarbon oil. In some embodiments, the oil comprises a mineral oil. In some embodiments, the oil comprises a paraffin oil. In some embodiments, the oil comprises a halogenated oil. In some embodiments, the oil is a fluorocarbon oil.

In some embodiments, an amplification mix is used to amplify nucleic acid encodings to create additional primers for labeling cellular nucleic acids of interest in a screen. In some embodiments, the amplification mix is an isothermal amplification mix. In some embodiments, the isothermal amplification mix comprises reagents for loop-mediated isothermal amplification (LAMP), strand displacement amplification (SDA), helicase-dependent amplification (HAD), recombinase polymerase amplification (RPA), rolling circle replication (RCA), or nicking enzyme amplification reaction (NEAR). In some embodiments, the encapsulation further comprises reagents for isothermal amplification of the target nucleic acid. In some embodiments, the method comprises adding reagents for isothermal amplification to the encapsulation. In some embodiments, the reagents for isothermal amplification are targeted to the specific nucleic acid sequence. In some embodiments, the amplification mix comprises a nicking enzyme. In some embodiments, the amplification mix comprises a nicking-enzyme amplification mixture. In some embodiments, the nicking enzyme is an endonuclease. In some embodiments, the nicking enzyme is a restriction enzyme. In some embodiments, the amplification mix comprises a reverse transcriptase. In some embodiments, the amplification mix comprises an amplification enzyme. In some embodiments, the amplification enzyme comprises a polymerase.

In some embodiments, the specific nucleotide sequence of interest can be amplified within the encapsulation. In some embodiments, the method comprises amplifying the cellular nucleic acid comprising the specific nucleotide sequence to produce amplified cellular nucleic acids. In some embodiments, amplifying the cellular nucleic acids is accomplished by PCR. In some embodiments, amplifying the cellular nucleic acids is accomplished by isothermal amplification. In some embodiments, cellular nucleic acids comprising the specific nucleotide sequence are amplified. In some embodiments, the amplified cellular nucleic acid is barcoded with the nucleic acid encoding the scaffold.

Any type of scaffold may be utilized in this method. In some embodiments, the scaffold acts as a solid support and keeps the nucleic acid encoding the scaffold linked in space to the scaffold. In some embodiments, the scaffold is a structure with a plurality of attachment points that allow linkage of one or more molecules. In some embodiments, the nucleic acid encoding the scaffold is bound to the scaffold. In some embodiments, the scaffold is a solid support. In some embodiments, the scaffold is a bead, a fiber, nanofibrous scaffold, a molecular cage, a dendrimer, or a multi-valent molecular assembly.

In some embodiments, the scaffold is a bead. In some embodiments, the bead is a polymer bead, a glass bead, a metal bead, or a magnetic bead. In some embodiments, the bead is a polymer bead. In some embodiments, the bead is a glass bead. In some embodiments, the bead is a metal bead. In some embodiments, the bead is a magnetic bead.

Beads for use in the systems and methods as described herein can be any size. In some embodiments, the beads are at most 10 nm, at most 100 nm, at most 1 μm, at most 10 μm, or at most 100 μm in diameter. In some embodiments, the beads are at least 10 nm, at least 100 nm, at least 1 μm, at least 10 μm, or at least 100 μm in diameter. In some embodiments, the beads are about 10 μm to about 100 μm in diameter.

The scaffolds may comprise effectors attached to the scaffold. In some embodiments, the effectors are attached to the scaffold by the cleavable linkers described herein. In some embodiments, the cleavable linker is cleaved by electromagnetic radiation, an enzyme, chemical reagent, heat, pH adjustment, sound or electrochemical reactivity. In some embodiments, the cleavable linker is cleaved from the scaffold using electromagnetic radiation. In some embodiments, the amount of effector cleaved is controlled by the intensity or duration of exposure to electromagnetic radiation. In some embodiments, the cleavable linker is cleaved using a cleavage reagent. In some embodiments, the amount of effector cleaved is controlled by the concentration of the cleavage reagent in the encapsulation. In some embodiments, the effector is cleaved from the scaffold using an enzyme. In some embodiments, the enzyme is a protease, a nuclease, or a hydrolase. In some embodiments, the rate of effector cleavage is controlled by the amount of enzyme in the encapsulation.

In some embodiments, the encoded nucleic acid primers amplified in the present methods are utilized to detect and quantify the amount of a target nucleic acid in the one or more cells being screened with an effector utilizing the nucleic acid encoded scaffold. In some embodiments, the encoded nucleic acid primer hybridizes with a target nucleic acid.

In some embodiments, the specific nucleotide sequence acts as an amplification primer with the target nucleic acid. In some embodiments, the target nucleic acid is barcoded with the nucleic acid encoding the scaffold using the specific nucleotide sequence. In some embodiments, the target nucleic acid is barcoded with the nucleic acid encoding the scaffold using the specific nucleotide sequence which has been extended with the nucleic acid encoding the scaffold.

The target nucleic acid can by any type of nucleic acid from a cell. In some embodiments, the target nucleic acid is a target mRNA. In some embodiments, the target mRNA encodes a protein of interest. In some embodiments, the target nucleic acid comprises a plurality of target mRNAs. In some embodiments, barcoding the plurality of target mRNAs creates an expression fingerprint of the cell treated with an effector. In some embodiments, the target nucleic acid is genomic DNA. In some embodiments, the target nucleic acid is mitochondrial DNA.

The methods provided herein increase target nucleic acid capture and labeling with the nucleic acid encoding the scaffold. In some embodiments, target nucleic acid capture is increased by at least 10%, 25%, 50%, 100%, or 200% compared to a method without the nicking enzyme that targets the specific nucleotide sequence. In some embodiments, target nucleic acid labeling is increased by at least 10%, 25%, 50%, 100%, or 200% compared to a method without the nicking enzyme that targets the specific nucleotide sequence. In some embodiments, target nucleic acid capture is increased by at least 5-fold, at least 10-fold, at least 50-fold, or at least 100-fold compared to a method without the nicking enzyme that targets the specific nucleotide sequence. In some embodiments, target nucleic acid barcoding is increased by at least 5-fold, at least 10-fold, at least 50-fold, or at least 100-fold compared to a method without the nicking enzyme that targets the specific nucleotide sequence.

In some embodiments, labeling the cellular nucleic acids with encoded nucleic acid primers, as described herein, comprises barcoding the cellular nucleic acids. The encapsulation can further comprise barcoding reagents. In some embodiments, the encapsulation further comprises barcoding reagents. In some embodiments, the encapsulation further comprises barcoding reagents to effectuate the barcoding of the cellular nucleic acids with the encoded nucleic acid primers. In some embodiments, the encapsulation further comprises barcoding reagents to effectuate the barcoding of the nucleic acid encoding the scaffold with amplified nucleic acids.

The barcoding reagents can be any set of reagents that allow the joining of different nucleic acids. In some embodiments, the barcoding reagents comprise an enzyme or chemical cross-linking reagent. In some embodiments, the enzyme is a polymerase, a ligase, a restriction enzyme, or a recombinase. In some embodiments, the enzyme is a polymerase. In some embodiments, the additional reagents comprise a chemical cross-linking reagent. In some embodiments, the chemical cross-linking reagent is psoralen.

The amplification of primers described herein can be performed at any time. In some embodiments, the above methods can be performed at the same time as an effector screen. In some embodiments, the cell is being screened against the effector. In some embodiments, an effector screen occurs concomitantly with the primer amplification method. In some embodiments, the primer amplification method described herein occurs prior to an effector screen. In some embodiments, the method is used to prepare the nucleic acid encoded scaffold for a screen. In some embodiments, the cell is used to prepare the nucleic acid encoded scaffold for a screen.

Effector Load Normalization Method

Provided herein are methods of measuring effector loading onto scaffolds and libraries of scaffolds. Generally, when a library of encoded effectors bound to scaffolds is prepared, the final concentration of effectors bound to the scaffolds varies considerably among individual scaffolds. This is due to differences in yield of each synthesis step of the effector built onto the scaffold. Consequently, when ultimately used in a screen, different samples may receive different dosages of effectors. This can skew the results of the screen, as low potency, high abundance effectors may drown out the signal of higher potency, low abundance effectors. Thus, a method of determining effector loading onto scaffolds in a library can help avoid this skewing of results.

Provided herein are methods of measuring effector loading on scaffolds. In some embodiments, the method comprises (a) attaching an effector subunit to effector attachment sites on a plurality of scaffolds. In some embodiments, the method comprises (b) attaching a detectable label to any remaining free effector attachment sites on the plurality of scaffolds after the step of attaching an effector subunit. In some embodiments, the method comprises (c) removing a subset of scaffolds from the plurality. In some embodiments, the method comprises (d) measuring the amount of detectable label attached to the subset of scaffolds to determine the amount of effector subunits successfully attached to the effector attachment sites. In some embodiments, the method comprises (e) optionally activating the attached effector subunits to create new effector attachment sites. In some embodiments, the listed steps are repeated until a desired effector is assembled. In some embodiments, the scaffold further comprises a nucleic acid encoding the effector. In some embodiments, the method further comprises attaching nucleic acid encoding subunits to the scaffold corresponding to the effector subunits as the effector subunits are added to the scaffold. In some embodiments, there is no activating step after the last effector subunit is attached.

In some embodiments, each effector subunit attached to the scaffold is independently an amino acid, a small molecule fragment, a nucleotide, or a compound. In some embodiments, each effector subunit attached to the scaffold is an amino acid. In some embodiments, each effector subunit attached to the scaffold is a compound. In some embodiments, each effector subunit attached to the scaffold is a small molecule fragment. In some embodiments, each effector subunit attached to the scaffold is a nucleotide.

The effector attachment sites may have any group capable of performing a chemical reaction. In some embodiments, the effector attachment sites comprise reactive functionalities. In some embodiments, the effector attachment sites comprise amino groups, carboxylate groups, alcohol groups, phenol groups, alkyne groups, aldehyde groups, or ketone groups. In some embodiments, the effector attachment sites comprise amino or carboxylate groups. IN some embodiments, the effector attachment sites comprise biorthogonal or CLICK chemistry reactive groups.

The encoding subunits can comprise functional groups that may react with the reactive functionalities on the effector attachment site. In some embodiments, the encoding subunits form a covalent bond with the reactive functionalities. In some embodiments, the effector subunits comprise reactive groups complementary to the effector attachment sites.

The detectable labels, in some embodiments, comprise functional groups that may react with the reactive functionalities on the effector attachment site. In some embodiments, the detectable labels form a covalent bond with the reactive functionalities. In some embodiments, the detectable labels comprise reactive groups complementary to the effector attachment sites.

The detectable label may any label that can produce a signal that can be detected and quantified. In some embodiments, the detectable label is a fluorophore.

In some embodiments, there is a yield associated with each effector attachment step. In some embodiments, the yield is measured a percentage of free effector attachment sites after the step of attaching an effector subunit. In some embodiments, at most 10%, at most 20%, at most 30%, at most 40%, or at most 50% of the effector attachment sites are free after the step of attaching the effector subunit.

A subset of beads may be removed in order to quantify the loading at each step of the synthesis of the desired effector. In some embodiments, removing a subset of the plurality of scaffolds comprises removing no more than 1%, no more than 2%, no more than 3%, no more than 5%, or no more than 10% of the remaining scaffolds. In some embodiments, removing a subset of the plurality of scaffolds comprises removing no more than 1% of the remaining scaffolds. In some embodiments, removing a subset of the plurality of scaffolds comprises removing no more than 2% of the remaining scaffolds. In some embodiments, removing a subset of the plurality of scaffolds comprises removing no more than 3% of the remaining scaffolds. In some embodiments, removing a subset of the plurality of scaffolds comprises removing no more than 5% of the remaining scaffolds. In some embodiments, removing a subset of the plurality of scaffolds comprises removing no more than 10% of the remaining scaffolds.

In some embodiments, wherein measuring the amount of detectable label attached to the subset of scaffolds to determine the amount of effector subunits successfully attached to the effector attachment sites comprises comparing the measurement of the detectable label to the measurement of detectable label on a scaffold without any effector subunits attached. In some embodiments, the amount of effector subunits successfully attached to the subset of scaffolds is expressed as a percentage of total attachment sites occupied by the effector subunits.

To begin a new step of attaching effector subunits, a previously attached effector subunit may need to be activated. In some embodiments, activation reveals the presence of a new effector attachment site. In some embodiments, optionally activating the attached effector subunits to create a new effector attachment site comprises removing a protecting group from the attached effector subunit. In some embodiments, the protecting group is an amino protecting group, a carboxylate protecting group, an alcohol protecting group, a phenol protecting group, an alkyne protecting group, an aldehyde protecting group, or a ketone protecting group. In some embodiments, the protecting group is an amino protecting group. In some embodiments, the amino protecting group is 9-fluorenylmethyloxcarbonyl (Fmoc), tert-butyloxycarbonyl (BOC), carbobenzyloxy (Cbz), benzyl (Bz), tosyl (Ts) or trichloroethyl chloroformate (Troc). In some embodiments, the protecting group is a carboxylate protecting group. In some embodiments, the carboxylate protecting group is a methyl ester, a benzyl ester, a tert-butyl ester, a 2,6-disubstituted phenolic ester, a silyl ester, or an orthoester. In some embodiments, the protecting group is an alcohol protecting group. In some embodiments, the protecting group is a phenol protecting group. In some embodiments, the protecting group is an alkyne protecting group. In some embodiments, the protecting group is an aldehyde protecting group. In some embodiments, the protecting group is a ketone protecting group.

The new effector attachment site can be any suitable reactive functionality. In some embodiments, the new effector attachment site is the same functionality as the previous effector attachment site. In some embodiments, the new effector attachment site is a different functionality from the previous effector attachment site.

The desired effectors can be synthesized using any number of steps and use any number of effector subunits. In some embodiments, steps (a)-(e) are repeated at least 2, at least 3, at least 4, at least 5, at least 6, at least 7, at least 10, or at least 20 times. In some embodiments, the desired effector is comprised of at least 2, at least 3, at least 4, at least 5, at least 6, at least 7, at least 10, or at least 20 subunits.

Any type of scaffold may be used with the methods and systems provided herein. In some embodiments, the scaffold is a bead, a fiber, a nanofibrous scaffold, a molecular cage, a dendrimer, or a multi-valent molecular assembly. In some embodiments, the scaffold is a bead. In some embodiments, the bead is a polymer bead, a glass bead, a metal bead, or a magnetic bead. In some embodiments, the bead is a polymer bead. In some embodiments, the bead is a glass bead. In some embodiments, the bead is a metal bead. In some embodiments, the bead is a magnetic bead.

The beads utilized in the methods provided herein may be made of any material. In some embodiments, the bead is a polymer bead. In some embodiments, the bead comprises a polystyrene core. In some embodiments, the beads are derivatized with polyethylene glycol. In some embodiments, the beads are grafted with polyethylene glycol. In some embodiments, the polyethylene glycol contains reactive groups for the attachment of other functionalities, such as effectors or encodings. In some embodiments, the reactive group is an amino or carboxylate group. In some embodiments, the reactive group is at the terminal end of the polyethylene glycol chain. In some embodiments, the bead is a TentaGel® bead.

The polyethylene glycol (PEG) attached to the beads may be any size. In some embodiments, the PEG is up to 20 kDa. In some embodiments, the PEG is up to 5 kDa. In some embodiments, the PEG is about 3 kDa. In some embodiments, the PEG is about 2 to 3 kDa.

In some embodiments, the PEG group is attached to the bead by an alkyl linkage. In some embodiments, the PEG group is attached to a polystyrene bead by an alkyl linkage. In some embodiments, the bead is a TentaGel® M resin.

In some embodiments, the bead comprises a PEG attached to a bead through an alkyl linkage and the bead comprises two bifunction species. In some embodiments, the beads comprise surface modification on the outer surface of the beads that are orthogonally protected to reactive sites in the internal section of the beads. In some embodiments the beads comprise both cleavable and non-cleavable ligands. In some embodiments, the bead is a TentaGel® B resin.

Beads for use in the systems and methods as described herein can be any size. In some embodiments, the beads are at most 10 nm, at most 100 nm, at most 1 µm, at most 10 µm, or at most 100 µm in diameter. In some embodiments, the beads are at least 10 nm, at least 100 nm, at least 1 µm, at least 10 µm, or at least 100 µm in diameter. In some embodiments, the beads are about 10 µm to about 100 µm in diameter.

Nucleic acids encoding the effector are utilized in the described method. The nucleic acids encoding the effector may be bound to the scaffold as a pre-synthesized nucleic acid, synthesized concomitantly with the effector, or synthesized on the scaffold prior to synthesis of the effector. In some embodiments, a nucleic acid encoding the effector is attached to the scaffold. In some embodiments, the method further comprises attaching nucleic acid encoding subunits to the scaffold corresponding to the effector subunits as the effector subunits are added to the scaffold.

The methods described herein are especially useful when applied to libraries of effectors on scaffolds. In some embodiments, libraries of effectors are synthesized in parallel. In some embodiments, libraries of effectors are synthesized in individual wells. In some embodiments, libraries of effectors are synthesized using high-throughput synthesis techniques. In some embodiments, a library of effector loaded scaffolds are synthesized concurrently. The library of effector loaded scaffolds can be any size. In some embodiments, the library comprises at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, or $10^{16}$ effector loaded scaffolds. In some embodiments, each effector loaded scaffold comprises a unique effector. In some embodiments, some effector loaded scaffolds are repeated in the library.

In some embodiments, subsets of beads from an effector attachment step from the library are pooled prior to detection of the detectable label. In some embodiments, subsets of beads from all scaffolds in the library are pooled together. In some embodiments, a portion of the subset of beads from the scaffolds in the library are pooled together.

The pooled subsets of beads are placed into encapsulations for further analysis. An encapsulation refers to the formation of a compartment within a larger system. In some embodiments, the encapsulation is a droplet, an emulsion, a macrowell, a microwell, a bubble, or a microfluidic confinement. In some embodiments, a majority of the encapsulations comprise a single scaffold.

In some embodiments, the encapsulation is a droplet. In some embodiments, the droplet is at most 1 picoliter, at most 10 picoliters, at most 100 picoliters, at most 1 nanoliter, at most 10 nanoliters, at most 100 nanoliters, or at most 1 microliter in volume. In some embodiments, the droplet is at least 1 picoliter, at least 10 picoliters, at least 100 picoliters, at least 1 nanoliter, at least 10 nanoliters, at least 100 nanoliters, or at least 1 microliter in volume. In some embodiments, the droplet is between about 200 picoliters and about 10 nanoliters.

In some embodiments, the droplet is an aqueous droplet in a larger body of oil. In some embodiments, the droplets are placed in an oil emulsion. In some embodiments, the oil comprises a silicone oil, a fluorosilicone oil, a hydrocarbon oil, a mineral oil, a paraffin oil, a halogenated oil, or any combination thereof. In some embodiments, the oil comprises a silicone oil. In some embodiments, the oil comprises a fluorosilicone oil. In some embodiments, the oil comprises a hydrocarbon oil. In some embodiments, the oil comprises a mineral oil. In some embodiments, the oil comprises a paraffin oil. In some embodiments, the oil comprises a halogenated oil.

After the scaffolds are placed into encapsulations, the level of fluorophore bound to the scaffolds may be assessed. In some embodiments, scaffolds from the subset of scaffolds are binned according to the amount of detectable label detected. In some embodiments, each bin comprises a unique range of detectable label detected. In some embodiments, the bins correspond to 0-25%, 25-50%, 50-75%, and 75-100% loading of detectable label detected compared to scaffolds where no effector subunit was loaded. In some embodiments, the bins correspond to 0-20%, 20-40%, 40-60%, 60-80%, and 80-100% loading of detectable label detected compared to scaffolds where no effector subunit was loaded. In some embodiments, the bins correspond to 0-10%, 10-20%, 20-30%, 30-40%, 40-50%, 50-60%, 60-70%, 70-80%, 80-90%, and 90-100% loading of detectable label detected compared to scaffolds where no effector subunit was loaded. Any combination of bins is acceptable to use with the methods and systems provided herein.

The bins may then be sequenced to reveal which effectors had particular yields in the attachment step. In some embodiments, the method further comprises the step of sequencing encoding nucleic acids or encoding nucleic acid subunits of the pools to reveal which effector subunits correspond to a particular yield in a step of attaching effector subunits to effector attachment sites. In some embodiments, the sequencing step is performed each time steps (a)-(e) are repeated. In some embodiments, yields of each step (a)-(e) for each unique scaffold are collected to create a dataset which reveals the loading of the complete desired effector on each scaffold. In some embodiments, yields of attachment of each encoder subunit for each unique scaffold are collected to create a dataset which reveals the loading of the complete desired effector on each scaffold. In some embodiments, the loading of desired effector on each unique scaffold is calculated.

Screening Devices and Methods of Use

Further provided herein are devices for use in screening encoded effectors and methods of use. In some embodiments, the devices provided herein lock an encoded effector into a location. In some embodiments, the sample being screened is similarly fixed in a position. By locking the two in place, the risk of encapsulations breaking down or merging with other encapsulations may be minimized. In some embodiments, the need for encapsulation is eliminated entirely. Additionally, knowledge of the structure of the effector at particular locations of the device may allow a user to easily determine which effectors had a desired effect on a sample. The devices described below are compatible with any of the methods described elsewhere herein.

Nucleic Acid Patch Array

Provided herein is an array for screening encoded beads. The array can comprise nucleic acid patches interspersed on a hydrophobic surface. The positioning of the nucleic acid patches on the hydrophobic patch can be such that when a liquid media is added to the device, droplets form encapsulating the nucleic acid patches, but the hydrophobic surfaces remain free of media. In some embodiments, each nucleic acid patch is encapsulated in its own droplet. In some embodiments, there is no liquid or fluid connection between the different nucleic acid patches after the media is added. The nucleic acid patches may be able to bind beads, cells, or both. Additionally, the array may further comprise channels beneath the surface. The channels can have terminal ends that allow for fluids to flow through the channels to the nucleic acid patches. Such channels can allow for the addition of reagents to the nucleic acid patches.

In one aspect, provided herein, is an array device for screening encoded beads. In some embodiments, the device comprises a hydrophobic surface. In some embodiments, the device comprises nucleic acid patches. In some embodiments, the nucleic acid patches are interspersed on the hydrophobic surface. In some embodiments, the hydrophobic surface and nucleic acid patches are configured such that when a proscribed amount of media is deployed across the surface each nucleic acid patch is covered with media. In some embodiments, the hydrophobic surface between the nucleic acid patches does not contain media.

The array device may comprise channels. In some embodiments, the device comprises one or more channels beneath the hydrophobic surface. In some embodiments, the channels from a network. In some embodiments, the channels are microfluidic channels. In some embodiments, the channels are branched. In some embodiments, the channels comprise terminal ends within nucleic acid patches. In some embodiments, the channels comprise terminal ends within each nucleic acid patch of the array.

The channels may be configured to deliver liquid solutions to the nucleic acid patches. In some embodiments, the channels are configured to deliver reagents to the nucleic acid patches. In some embodiments, the reagents are delivered as a liquid solution. In some embodiments, the liquid solution is an aqueous solution.

The channels may be any size. In some embodiments, the channels have a diameter of about 0.1 µm, about 0.5 µm, about 1 µm, about 5 µm, about 10 µm, or about 20 µm. In some embodiments, the channels have a diameter of up to about 0.1 µm, up to about 0.5 µm, up to about 1 µm, up to about 5 µm, up to about 10 µm, or up to about 20 µm. In some embodiments, the channels have a diameter of at least about 0.1 µm, at least about 0.5 µm, at least about 1 µm, at least about 5 µm, at least about 10 µm, or at least about 20 µm.

The hydrophobic surface may be made of any suitable hydrophobic material. In some embodiments, the hydrophobic surface is comprised of a hydrophobic polymer. In some embodiments, the hydrophobic surface comprises a hydrophobic polymer. In some embodiments, the hydrophobic polymer comprises a polyacrylic, a polyamide, a polycarbonate, a polydiene, a polyester, a polyether, a polyfluorocarbon, a polyolefin, a polystyrene, a polyvinyl acetal, a polyvinyl chloride, a polyvinyl ester, a polyvinyl ether, a polyvinyl ketone, a polyvinyl pyridine, a polyvinylpyrrolidone, a polysilane, a polyfluorosilane, a poly perfluorosilane or a combination thereof. In some embodiments, the hydrophobic polymer comprises a polyfluorocarbon. In some embodiments, the hydrophobic polymer comprises a polyperfluorocarbon. In some embodiments, the hydrophobic polymer is fluorinated.

The hydrophobic surface may be a surface functionalized with groups having hydrophobic properties. In some embodiments, the hydrophobic surface is a surface functionalized with hydrophobic groups. In some embodiments, the hydrophobic groups are fatty acids, alkyl groups, alkoxy groups, aromatic groups, alkyl silanes, fluorosilanes, perfluorosilanes, or combinations thereof. In some embodiments, the hydrophobic groups are perfluorosilanes. In some embodiments, the hydrophobic groups are fatty acids. In some embodiments, the hydrophobic groups are fluorinated fatty acids. In some embodiments, the hydrophobic groups are perfluorinated fatty acids. In some embodiments, the hydrophobic groups are fluorinated.

The hydrophobic surface may exhibit desired binding properties. In some embodiments, cells do not bind to the hydrophobic surface. In some embodiments, cells do not grow on the hydrophobic surface.

The nucleic acid patches may exhibit desired binding properties. In some embodiments, the nucleic acid patches bind cells. In some embodiments, the nucleic acid patches bind cells through non-specific interaction. In some embodiments, the nucleic acid patches bind cells through specific interaction. In some embodiments, the nucleic acid patches are configured to attract media. In some embodiments, single nucleic acid patches encapsulated within single droplets of the media. In some embodiments, the nucleic acid patches are capable of binding beads. In some embodiments, the beads are nucleic acid encoded beads. In some embodiments, the nucleic acid patches bind beads. In some embodiments, the nucleic acid patches comprise nucleic acids capable of binding nucleic acid encoded beads. In some embodiments, the nucleic acids bind beads non-specifically, by binding a complementary nucleic acid on the bead, or by binding another group on the bead. In some embodiments, the nucleic acids bind nucleic acid encoded beads non-specifically, by binding a complementary nucleic acid on the bead, or by binding another group on the bead.

The nucleic acid patches may comprise any type of nucleic acid. In some embodiments, the nucleic acid patches comprise DNA, RNA, combinations thereof. In some embodiments, the nucleic acid patches comprise DNA. In some embodiments, the nucleic acid patches comprise double-stranded DNA. In some embodiments, the nucleic acid patches comprise single-stranded DNA. In some embodiments, the nucleic acid patches comprise RNA. In some embodiments, the nucleic acid patches comprise single-stranded RNA. In some embodiments, the nucleic acid patches comprise double-stranded RNA.

The nucleic acid patches may be any size. In some embodiments, the nucleic acid patches are up to about 1 $\mu m^2$ in size, up to about 10 $\mu m^2$ in size, up to about 100 $\mu m^2$ in size, up to about 1000 $\mu m^2$ in size, or up to about 10000 $\mu m^2$ in size. In some embodiments, the nucleic acid patches are at least about 1 $\mu m^2$ in size, at least about 10 $\mu m^2$ in size, at least about 100 $\mu m^2$ in size, at least about 1000 $\mu m^2$ in size, or at least about 10000 $\mu m^2$ in size. In some embodiments, the nucleic acid patches are about 1 $\mu m^2$ in size, about 10 $\mu m^2$ in size, about 100 $\mu m^2$ in size, about 1000 $\mu m^2$ in size, or about 10000 $\mu m^2$ in size.

The nucleic acid patches may be separated by a defined distance. In some embodiments, the nucleic acid patches are separated by up to about 1 µm, up to about 10 µm, up to about 100 µm, up to about 1000 µm, or up to about 10000 µm. In some embodiments, the nucleic acid patches are separated by at least about 1 µm, at least about 10 µm, at least about 100 µm, at least about 1000 µm, or at least about 10000 µm. In some embodiments, the nucleic acid patches are separated by about 1 µm, about 10 µm, about 100 µm, about 1000 µm, or about 10000 µm.

The nucleic acid patches may be arranged on the surface in any configuration. In some embodiments, the nucleic acid patches are arranged in a grid pattern. In some embodiments, the nucleic acid patches are distributed randomly. In some embodiments, the nucleic acid patches are arranged in a circular configuration.

The nucleic acid patches may be of any density on the surface. In some embodiments, the density of nucleic acid patches is at least 100 patches/cm$^2$, at least 1000 patches/cm$^2$, at least 10000 patches/cm$^2$, at least 100000 patches/cm$^2$, at least 1000000 patches/cm$^2$, or at least 10000000 patches/cm$^2$. In some embodiments, the density of nucleic acid patches is about 100 patches/cm$^2$, about 1000 patches/cm$^2$, about 10000 patches/cm$^2$, about 100000 patches/cm$^2$, about 1000000 patches/cm$^2$, or about 10000000 patches/cm$^2$.

The array device may be any size. In some embodiments, the surface area of the device is at least 1 cm$^2$, at least 5 cm$^2$, at least 10 cm$^2$, at least 25 cm$^2$, at least 50 cm$^2$, at least 100 cm$^2$, at least 500 cm$^2$, or at least 1000 cm$^2$. In some embodiments, the surface area of the device is about 1 cm$^2$, about 5 cm$^2$, about 10 cm$^2$, about 25 cm$^2$, about 50 cm$^2$, about 100 cm$^2$, about 500 cm$^2$, or about 1000 cm$^2$. In some embodiments, the surface area of the device is at most 1 cm$^2$, at most 5 cm$^2$, at most 10 cm$^2$, at most 25 cm$^2$, at most 50 cm$^2$, at most 100 cm$^2$, at most 500 cm$^2$, or at most 1000 cm$^2$.

In one aspect, provided herein, is a method of performing a screen using the arrays described herein. In some embodiments, the method comprises binding nucleic acid encoded beads to the nucleic acid patches of the array. In some embodiments, the method comprises sequencing the nucleic acid encoded beads. In some embodiments, cells are bound to the nucleic acid patches. In some embodiments, an assay is performed on the array.

The beads may contain an effector. In some embodiments the beads comprise encoded effectors. In some embodiments, the beads comprise nucleic acid encoded effectors. In some embodiments, the effectors are released from the beads. In some embodiments, the effectors are released by cleaving a cleavable linker. In some embodiments, the cleavable linker is cleaved by electromagnetic radiation. In some embodiments, the cleavable linker is cleaved by a cleaving reagent. In some embodiments, the method comprises adding a cleaving reagent to the nucleic acid patches.

In some embodiments, reagents are added through the channels beneath the surface. In some embodiments, the cleaving reagent is added through the channels. In some embodiments, detection reagents are added through the channels.

Sequencing the beads allows the locations of encoded beads in space to be determined. In some embodiments, sequencing the beads allows determination of the physical location of specific nucleic acid encoded beads.

Any assay may be performed on the array. In some embodiments, the assay produces a detectable signal. In some embodiments, the detectable signal is electromagnetic radiation. In some embodiments, the signal is fluorescence or luminescence.

The nucleic acid patches can bind any amount of cells or beads. In some embodiments, each nucleic acid patch binds a single bead. In some embodiments, each nucleic acid patch binds a single cell. In some embodiments, each nucleic acid patch binds a single bead and a single cell. In some embodiments, each nucleic acid patch binds a plurality of beads. In some embodiments, each nucleic acid patch binds a plurality of cells.

NUMBERED EMBODIMENTS

The following embodiments recite nonlimiting permutations of combinations of features disclosed herein. Other permutations of combinations of features are also contemplated. In particular, each of these numbered embodiments is contemplated as depending from or relating to every previous or subsequent numbered embodiment, independent of their order as listed. Embodiment 1: A method for screening an encoded effector, the method comprising: a) providing a sample, an encoded effector, and an encoding in an encapsulation; wherein the encoded effector is bound to a scaffold by a cleavable linker; b) activating the cleavable linker using an activating reagent; c) cleaving the cleavable linker so as to release a predetermined amount of the encoded effector; d) detecting a signal from the encapsulation, wherein the signal results from an interaction of the encoded effector and the sample; and e) sorting the encapsulation based on the detection of the signal. Embodiment 2: The method of Embodiment 1, wherein the activating reagent is provided with the encapsulation in step (a). Embodiment 3: The method of Embodiment 1, wherein the activating reagent is added into the encapsulation. Embodiment 4: The method of Embodiment 3, wherein the activating reagent is added into the encapsulation by pico-injection. Embodiment 5: The method of Embodiment 1, wherein the activating reagent is added to the encapsulation by droplet merging, wherein the encapsulation is a droplet. Embodiment 6: The method of Embodiment 1, wherein the activating reagent is a disulfide reducing reagent. Embodiment 7: The method of Embodiment 1, wherein the activating reagent is a tetrazine. Embodiment 8: The method of Embodiment 1, wherein the concentration of the activating reagent used to activate the cleavable linker is at most 100 picomolar (pM), at most 500 pM, at most 1 nanomolar (nM), at most 10 nM, at most 100 nM, at most 1 micromolar (pM), at most 10 pM, at most 100 pM, at most 1 millimolar (mM), at most 10 mM, at most 100 mM, or at most 500 mM. Embodiment 9: The method of Embodiment 1, wherein the activate reagent is added from a stock solution at least 2×, 5×, 10×, 20×, 30×, 50×, 100×, 500×, or 1000× more concentrated than the desired final concentration in the encapsulation. Embodiment 10: The method of Embodiment 1, wherein the predetermined amount of effector released from the scaffold is to a concentration of at least 100 pM, at least 500 pM, at least 1 nM, at least 10 nM, at least 100 nM, at least 1 µM, at least 10 µM, at least 100 µM, at least 1 mM. at least 10 mM, at least 50 mM, at least 100 mM, or at least 250 mM. Embodiment 11: The method of Embodiment 1, wherein the cleavable linker is a disulfide or substituted trans-cyclooctene. Embodiment 12: The method of Embodiment 1, wherein the sample comprises at least one cell, a protein, an enzyme, a nucleic acid, a cellular lysate, a tissue extract, or combinations thereof. Embodiment 13: The method of Embodiment 12, wherein the sample is one or more cells, a protein, or an enzyme. Embodiment 14: The method of Embodiment 1, wherein the scaffold is a bead, a fiber, a nanofibrous scaffold, a molecular cage, a dendrimer, or a multi-valent molecular assembly. Embodiment 15: The method of Embodiment 14, wherein the scaffold is polymer-bead, a glass bead, a metal bead, or a magnetic bead. Embodiment 16: The method of Embodiment 15, wherein the bead is about 1 μm to about 100 μm in diameter. Embodiment 17: The method of Embodiment 15, wherein the bead is about 1 μm to about 20 μm in diameter. Embodiment 18: The method of Embodiment 1, wherein the encoded effector is a peptide, a compound, protein, an enzyme, a macrocycle compound, or a nucleic acid. Embodiment 19: The method of Embodiment 18, wherein the encoded effector is a non-natural peptide. Embodiment 20: The method of Embodiment 18, wherein the encoded effector is a polymer. Embodiment 21: The method of Embodiment 18, wherein the compound is a drug-like small molecule. Embodiment 22: The method of Embodiment 1, wherein the encapsulation is a droplet. Embodiment 23: The method of Embodiment 22, wherein the droplet is at most 1 picoliter, at most 10 picoliters, at most 100 picoliters, at most 1 nanoliter, at most 10 nanoliters, at most 100 nanoliters, or at most 1 microliter in volume. Embodiment 24: The method of Embodiment 1, wherein the signal comprises electromagnetic radiation, thermal radiation, a visual change in the sample, or combinations thereof. Embodiment 25: The method of Embodiment 24, wherein the electromagnetic radiation is in the visible spectrum. Embodiment 26: The method of Embodiment 24, wherein the electromagnetic radiation is fluorescence or luminescence. Embodiment 27: The method of Embodiment 26, wherein the signal is fluorescence emitted by a TaqMan probe or a molecular beacon. Embodiment 28: The method of Embodiment 24, wherein the signal comprises thermal radiation detected with an infrared camera. Embodiment 29: The method of Embodiment 24, wherein the signal comprises a morphological or visual change in the sample measured by recording a series of images of the encapsulation. Embodiment 30: The method of Embodiment 1, further comprising incubating the encapsulation for a period of time to allow the effector and the sample to interact. Embodiment 31: The method of Embodiment 30, wherein the period of time is controlled by a residence time as the encapsulation travels through a microfluidic channel, wherein the residence time of each encapsulation is within a maximum dispersion ratio of the incubation period of time for the plurality of encapsulations, wherein the dispersion ratio is based on a deviation about an average residence time of the plurality of encapsulations passing through a region of the microfluidic device. Embodiment 32: The method of Embodiment 31, wherein the maximum dispersion is at most from about 3% to about 10%. Embodiment 33: The method of Embodiment 1, wherein sorting the encapsulation comprises placing the droplet into a first collection tube if the signal is at or above a predetermined threshold or placing the droplet into a second collection tube if the signal is below a predetermined threshold. Embodiment 34: The method of Embodiment 1, wherein sorting the encapsulation comprises using a waveform pulse generator to move the encapsulation to a collection tube by an electrical field gradient, by sound, by a diaphragm, by modifying geometry of the microfluidic channel, or by changing the pressure of the microfluidic channel. Embodiment 35: The method of Embodiment 1, wherein the encapsulation is an emulsion in an oil. Embodiment 36: The method of Embodiment 1, wherein the encoding is a nucleic acid and the method further comprises the step of sequencing the encoding nucleic acid. Embodiment 37: The method of Embodiment 36, wherein the encoding is cleaved from the scaffold prior to sequencing. Embodiment 38: The method of Embodiment 37, wherein cleaving the nucleic acid encoding from the scaffold comprises cleaving a cleavable linker with a cleaving reagent or through electromagnetic radiation.

Embodiment 39: A method for screening an encoded effector, the method comprising: a) providing a sample, an encoded effector, and an encoding in an encapsulation; wherein the encoded effector is bound to a scaffold by a cleavable linker; b) cleaving the cleavable linker with a cleaving reagent, wherein the cleaving reagent is added at a concentration configured to release a predetermined amount of the encoded effector; c) detecting a signal from the encapsulation, wherein the signal results from an interaction of the encoded effector and the sample; and d) sorting the encapsulation based on the detection of the signal. Embodiment 40: The method of Embodiment 39, wherein the cleaving reagent is added to the encapsulation by pico-injection. Embodiment 41: The method of Embodiment 39, wherein the cleaving reagent is added to the encapsulation at a step separate from forming the encapsulation. Embodiment 42: The method of Embodiment 39, wherein the cleaving reagent is added to the encapsulation using a solution comprising the cleaving reagent and the sample prior to formation of the encapsulation. Embodiment 43: The method of Embodiment 39, wherein the concentration of cleaving reagent used to cleave the cleavable linker is at most 100 picomolar (pM), at most 500 pM, at most 1 nanomolar (nM), at most 10 nM, at most 100 nM, at most 1 micromolar (pM), at most 10 pM, at most 100 pM, at most 1 millimolar (mM), at most 10 mM, at most 100 mM, or at most 500 mM. Embodiment 44: The method of Embodiment 39, wherein the cleaving reagent is added from a stock solution at least 2×, 5×, 10×, 20×, 30×, 50×, 100×, 500×, or 1000× more concentrated than the desired final concentration in the encapsulation. Embodiment 45: The method of Embodiment 39, wherein the predetermined amount of effector released from the scaffold is to a concentration of at least 100 pM, at least 500 pM, at least 1 nM, at least 10 nM, at least 100 nM, at least 1 μM, at least 10 μM, at least 100 μM, at least 1 mM. at least 10 mM, at least 50 mM, at least 100 mM, or at least 250 mM. Embodiment 46: The method of Embodiment 39, wherein the cleavable linker is a disulfide or substituted trans-cyclooctene. Embodiment 47: The method of Embodiment 39, wherein the cleaving reagent is a disulfide reducing reagent. Embodiment 48: The method of Embodiment 39, wherein the cleaving reagent is a tetrazine. Embodiment 49: The method of Embodiment 39, wherein the sample comprises at least one cell, a protein, an enzyme, a nucleic acid, a cellular lysate, a tissue extract, or combinations thereof. Embodiment 50: The method of Embodiment 49, wherein the sample is one or more cells, a protein, or an enzyme. Embodiment 51: The method of Embodiment 49, wherein the scaffold is a bead, a fiber, a nanofibrous scaffold, a molecular cage, a dendrimer, or a multi-valent molecular assembly. Embodiment 52: The method of Embodiment 51, wherein the scaffold is polymer-bead, a glass bead, a metal bead, or a magnetic bead. Embodiment 53: The method of Embodiment 52, wherein the bead is about 1 μm to about 100 μm in diameter. Embodiment 54: The method of Embodiment 52, wherein the bead is about 1 μm to about 20 μm in diameter. Embodiment 55: The method of Embodiment 39, wherein the encoded effector is a peptide, a compound, protein, an enzyme, a macrocycle compound, or a nucleic acid. Embodiment 56: The method of Embodiment 55, wherein the encoded effector is a non-natural peptide. Embodiment 57: The method of Embodiment 55, wherein the encoded effector is a polymer. Embodiment 58: The method of Embodiment 55, wherein the compound is a drug-like small molecule. Embodiment 59: The method of Embodiment 39, wherein the encapsulation is a droplet. Embodiment 60: The method of Embodiment 59, wherein the droplet is at most 1 picoliter, at most 10 picoliters, at most 100 picoliters, at most 1 nanoliter, at most 10 nanoliters, at most 100 nanoliters, or at most 1 microliter in volume. Embodiment 61: The method of Embodiment 39, wherein the signal comprises electromagnetic radiation, thermal radiation, a visual change in the sample, or combinations thereof. Embodiment 62: The method of Embodiment 61, wherein the electromagnetic radiation is in the visible spectrum. Embodiment 63: The method of Embodiment 61, wherein the electromagnetic radiation is fluorescence or luminescence. Embodiment 64: The method of Embodiment 63, wherein the signal is fluorescence emitted by a TaqMan probe or a molecular beacon. Embodiment 65: The method of Embodiment 61, wherein the signal comprises thermal radiation detected with an infrared camera. Embodiment 66: The method of Embodiment 61, wherein the signal comprises a morphological or visual change in the sample measured by recording a series of images of the encapsulation. Embodiment 67: The method of Embodiment 39, further comprising incubating the encapsulation for a period of time to allow the effector and the sample to interact. Embodiment 68: The method of Embodiment 67, wherein the period of time is controlled by a residence time as the encapsulation travels through a microfluidic channel, wherein the residence time of each encapsulation is within a maximum dispersion ratio of the incubation period of time for the plurality of encapsulations, wherein the dispersion ratio is based on a deviation about an average residence time of the plurality of encapsulations passing through a region of the microfluidic device. Embodiment 69: The method of Embodiment 68, wherein the maximum dispersion is at most from about 3% to about 10%. Embodiment 70: The method of Embodiment 39, wherein sorting the encapsulation comprises placing the droplet into a first collection tube if the signal is at or above a predetermined threshold or placing the droplet into a second collection tube if the signal is below a predetermined threshold. Embodiment 71: The method of Embodiment 39, wherein sorting the encapsulation comprises using a waveform pulse generator to move the encapsulation to a collection tube by an electrical field gradient, by sound, by a diaphragm, by modifying geometry of the microfluidic channel, or by changing the pressure of the microfluidic channel. Embodiment 72: The method of Embodiment 39, wherein the encapsulation is an emulsion in an oil. Embodiment 73: The method of Embodiment 39, wherein the encoding is a nucleic acid and the method further comprises the step of sequencing the encoding nucleic acid. Embodiment 74: The method of Embodiment 73, wherein the encoding is cleaved from the scaffold prior to sequencing. Embodiment 75: The method of Embodiment 74, wherein cleaving the nucleic acid encoding from the scaffold comprises cleaving a cleavable linker with a cleaving reagent or through electromagnetic radiation.

Embodiment 76: A method for screening an encoded effector, the method comprising: a) providing at least one cell and a scaffold in an encapsulation, wherein the scaffold comprises an encoded effector bound to the scaffold by a photocleavable linker and a nucleic acid encoding the effector; b) cleaving the photocleavable linker to release the encoded effector from the scaffold; and c) detecting a signal from the droplet, wherein the signal results from an interaction between the encoded effector and the at least one cell. Embodiment 77: The method of Embodiment 76, further comprising sorting the encapsulation based on the detection of the signal. Embodiment 78: The method of Embodiment 77, wherein sorting the droplet comprises using a waveform pulse generator to move the droplet to a collection tube by an electrical field gradient, by sound, by a diaphragm, by modifying geometry of the microfluidic channel, or by changing the pressure of the microfluidic channel. Embodiment 79: The method of Embodiment 77, further comprising identifying the encoded effector by sequencing the nucleic acid encoding the effector. Embodiment 80: The method of Embodiment 76, further comprising barcoding the nucleic acid encoding the effector. Embodiment 81: The method of Embodiment 80, wherein the barcoding is via the addition of a reagent into the droplet. Embodiment 82: The method of Embodiment 76, wherein cleaving the photocleavable linker releases a pre-determined amount of the encoded effector into the droplet. Embodiment 83: The method of Embodiment 76, wherein the photocleavable linker is cleaved using electromagnetic radiation. Embodiment 84: The method of Embodiment 76, wherein cleaving the photocleavable linker comprises exposing the encapsulation to a light from a light source. Embodiment 85: The method of Embodiment 84, wherein the light is a calibrated amount of light. Embodiment 86: The method of Embodiment 84, wherein the light is UV light. Embodiment 87: The method of Embodiment 84, wherein the light intensity of a light is from about 0.01 $J/cm^2$ to about 200 $J/cm^2$. Embodiment 88: The method of Embodiment 76, wherein detecting the signal comprises detecting morphological changes in the sample measured by recording a series of images of the droplet or detecting fluorescence emitted by a molecular beacon or probe. Embodiment 89: The method of Embodiment 76, wherein the interaction between the encoded effector and the cell comprises inhibition of one or more cellular components. Embodiment 90: The method of Embodiment 76, further comprising identifying the encoded effector by sequencing the nucleic acid encoding the effector. Embodiment 91: The method of Embodiment 76, wherein two or more cells are provided with the scaffold. Embodiment 92: The method of Embodiment 76, further comprising providing an activating reagent to activate the photocleavable linker, so as to enable the photocleavable linker to be cleaved from the encoded effector. Embodiment 93: The method of Embodiment 92, wherein the activating reagent is provided with the encapsulation. Embodiment 94: The method of Embodiment 92, wherein the activating reagent is added into the encapsulation through pico injection or droplet merging. Embodiment 95: The method Embodiment 76, further comprising the step of lysing the one or more cells. Embodiment 96: The method of Embodiment 95, wherein lysing the one or more cells comprises adding lysis buffer to the encapsulation. Embodiment 97: The method of Embodiment 96, wherein the lysis buffer is added to the encapsulation by pico-injection. Embodiment 98: The method of Embodiment 76, wherein the scaffold is a bead, a fiber, a nanofibrous scaffold, a molecular cage, a dendrimer, or a multi-valent molecular assembly. Embodiment 99: The method of Embodiment 98, wherein the scaffold is polymer-bead, a glass bead, a metal bead, or a magnetic bead. Embodiment 100: The method of Embodiment 98, wherein the bead is about 1 µm to about 100 µm in diameter. Embodiment 101: The method of Embodiment 98, wherein the bead is about 1 µm to about 20 µm in diameter. Embodiment 102: The method of Embodiment 76, wherein the encoded effector is a peptide, a compound, protein, an enzyme, a macrocycle compound, or a nucleic acid. Embodiment 103: The method of Embodiment 102, wherein the encoded effector is a non-natural peptide. Embodiment 104: The method of Embodiment 102, wherein the encoded effector is a polymer. Embodiment 105: The method of Embodiment 102, wherein the compound is a drug-like small molecule. Embodiment 106: The method of Embodiment 76, wherein the encapsulation is a droplet. Embodiment 107: The method of Embodiment 106, wherein the droplet is at most 1 picoliter, at most 10 picoliters, at most 100 picoliters, at most 1 nanoliter, at most 10 nanoliters, at most 100 nanoliters, or at most 1 microliter in volume. Embodiment 108: The method of Embodiment 76, further comprising incubating the droplet for a period of time to allow the effector and the at least one cell to interact. Embodiment 109: The method of Embodiment 108, wherein the period of time is controlled by a residence time as the encapsulation travels through a microfluidic channel, wherein the residence time of each encapsulation is within a maximum dispersion ratio of the incubation period of time for the plurality of encapsulations, wherein the dispersion ratio is based on a deviation about an average residence time of the plurality of encapsulations passing through a region of the microfluidic device. Embodiment 110: The method of Embodiment 109, wherein the maximum dispersion is at most from about 3% to about 10%. The method of Embodiment 33, wherein sorting the droplet comprises placing the droplet into a first collection tube if the signal is at or above a predetermined threshold or placing the droplet into a second collection tube if the signal is below a predetermined threshold. Embodiment 111: The method of Embodiment 76, wherein the signal comprises electromagnetic radiation, thermal radiation, a visual change in the sample, or combinations thereof. Embodiment 112: The method of Embodiment 111, wherein the electromagnetic radiation is in the visible spectrum. Embodiment 113: The method of Embodiment 111, wherein the electromagnetic radiation is fluorescence or luminescence. Embodiment 114: The method of Embodiment 113, wherein the signal is fluorescence emitted by a TaqMan probe or a molecular beacon. Embodiment 115: The method of Embodiment 111, wherein the signal comprises thermal radiation detected with an infrared camera. Embodiment 116: The method of Embodiment 111, wherein the signal comprises a morphological or visual change in the sample measured by recording a series of images of the encapsulation.

Embodiment 117: A method for screening an encoded effector, the method comprising: a) providing a sample, an encoded effector, and an encoding in an encapsulation; b) detecting a signal resulting from an interaction between the effector and sample, wherein detecting the signal comprises 1) detecting morphological changes in the sample measured by recording a series of images of the encapsulation, 2) detecting fluorescence emitted by a molecular beacon or probe, or 3) combinations thereof, and c) sorting the encapsulation based on the detection of the signal. Embodiment 118: The method of Embodiment 117, wherein the signal comprises detecting a morphological or visual change in the sample measured by recording a series of images of the encapsulation. Embodiment 119: The method of Embodiment 118, wherein the encapsulation further comprises a detection reagent. Embodiment 120: The method of Embodiment 119, wherein the detection reagent comprises an intercalation dye. Embodiment 121: The method of Embodiment 120, wherein the intercalation dye comprises ethidium bromide, propidium iodide, crystal violet, a dUTP-conjugated probe, DAPI (4',6-diamidino-2-phenylindole), 7-AAD (7-aminoactinomycin D), Hoechst 33258, Hoechst 33342, Hoechst 34580, combinations thereof, or derivatives thereof. Embodiment 122: The method of Embodiment 118, further comprising superimposing the series of images of the sample in the encapsulation. Embodiment 123: The method of Embodiment 117, wherein the signal comprises detecting fluorescence emitted by a molecular beacon or TaqMan probe. Embodiment 124: The method of Embodiment 123, wherein the signal comprises detecting fluorescence emitted by a molecular beacon, wherein molecular beacon is complementary to a portion of a target nucleic acid sequence of the sample. Embodiment 125: The method of Embodiment 123, wherein the signal comprises detecting fluorescence emitted by a TaqMan probe, wherein the TaqMan probe is complementary to a portion of a target nucleic acid sequence. Embodiment 126: The method of Embodiment 123, wherein the encapsulation further comprises a Taq polymerase. Embodiment 127: The method of Embodiment 123, wherein the TaqMan probe or molecular beacon is added to the encapsulation by pico-injection. Embodiment 128: The method of Embodiment 117, wherein the encoded effector is attached to a scaffold. Embodiment 129: The method of Embodiment 128, wherein the scaffold is a bead, a fiber, a nanofibrous scaffold, a molecular cage, a dendrimer, or a multi-valent molecular assembly. Embodiment 130: The method of Embodiment 129, wherein the scaffold is polymer-bead, a glass bead, a metal bead, or a magnetic bead. Embodiment 131: The method of Embodiment 128, wherein the encoded effector is covalently bound to the scaffold. Embodiment 132: The method of Embodiment 128, wherein the encoded effector is bound to the scaffold by a cleavable linker. Embodiment 133: The method of Embodiment 132, wherein the cleavable linker is a disulfide or substituted trans-cyclooctene. Embodiment 134: The method of Embodiment 132, further comprising cleaving the cleavable linker. Embodiment 135: The method of Embodiment 134, wherein the number of encoded effectors cleaved from the scaffold is controlled by the intensity or duration of exposure to electromagnetic radiation. Embodiment 136: The method of Embodiment 134, wherein the number of encoded effectors cleaved from the scaffold is controlled by controlling the concentration of a cleaving reagent in the encapsulation. Embodiment 137: The method of Embodiment 136, wherein the cleaving reagent is added by pico-injection. Embodiment 138: The method of Embodiment 134, wherein the cleavable linker is activated through interaction with an activating reagent, thereby enabling the cleavable linker to be cleaved. Embodiment 139: The method of Embodiment 134, wherein the encoded effectors are released to a desired concentration within the encapsulation. Embodiment 140: The method of Embodiment 117, further comprising incubating the encapsulation for a period of time to allow the encoded effector and the sample to interact. Embodiment 141: The method of Embodiment 140, wherein the period of time is at least 1 minute, at least 10 minutes, at least 1 hour, at least 4 hours, or at least 1 day. Embodiment 142: The method of Embodiment 140, wherein the period of time is controlled by a residence time as the encapsulation travels through a microfluidic channel, wherein the residence time of each encapsulation is within a maximum dispersion ratio of the incubation period of time for the plurality of encapsulations, wherein the dispersion ratio is based on a deviation about an average residence time of the plurality of encapsulations passing through a region of the microfluidic device. Embodiment 143: The method of Embodiment 142, wherein the maximum dispersion is at most from about 3% to about 10%. Embodiment 144: The method of Embodiment 142, wherein the residence time is controlled by a flow rate through the microfluidic channel, a geometry of the microfluidic channel, a valve in the microfluidic channel, or by removing the one or more droplets from the microfluidic channel and transferring the one or more droplets to a separate vessel. Embodiment 145: The method of Embodiment 117, wherein the encoded effector comprises a compound, a peptide, a protein, an enzyme, a macrocycle compound, or a nucleic acid. Embodiment 146: The method of Embodiment 145, wherein the encoded effector is a non-natural peptide. Embodiment 147: The method of Embodiment 145, wherein the encoded effector is a polymer. Embodiment 148: The method of Embodiment 145, wherein the compound is a drug-like small molecule. Embodiment 149: The method of Embodiment 117, wherein the sample comprises one or more cells. Embodiment 150: The method of Embodiment 149, further comprising the step of lysing the one or more cells. Embodiment 151: The method of Embodiment 117, wherein detecting the signal comprises providing one or more droplets through a microfluidic channel comprising a detector. Embodiment 152: The method of Embodiment 117, wherein sorting the encapsulation comprises placing the encapsulation into a first collection tube if the signal is at or above a predetermined threshold or placing the encapsulation into a second collection tube if the signal is below a predetermined threshold. Embodiment 153: The method of Embodiment 117, wherein sorting the encapsulation comprises using a waveform pulse generator to move encapsulation to a collection tube by an electrical field gradient, by sound, by a diaphragm, by modifying geometry of a microfluidic channel, or by changing the pressure of the microfluidic channel. Embodiment 154: The method of Embodiment 117, wherein the encoding comprises a nucleic acid. Embodiment 155: The method of Embodiment 154, further comprising sequencing the encoding nucleic acid. Embodiment 156: The method of Embodiment 155, wherein the encoding is cleaved from the scaffold prior to sequencing. Embodiment 157: The method of Embodiment 156, wherein cleaving the nucleic acid encoding from the scaffold comprises cleaving a cleavable linker with a cleaving reagent or through electromagnetic radiation. Embodiment 158: The method of Embodiment 117, wherein the encapsulation is a droplet. Embodiment 159: The method of Embodiment 158, wherein the droplet the is at most 1 picoliter, at most 10 picoliters, at most 100 picoliters, at most 1 nanoliter, at most 10 nanoliters, at most 100 nanoliters, or at most 1 microliter in volume. Embodiment 160: The method of Embodiment 117, wherein the encapsulation is an emulsion in an oil. Embodiment 161: The method of Embodiment 160, wherein the oil is a silicone oil, fluorosilicone oil, hydrocarbon oil, mineral oil, paraffin oil, halogenated oil, or any combination thereof. Embodiment 162: The method of Embodiment 117, further comprising injecting one or more reagents into one or more encapsulations. Embodiment 163: The method of Embodiment 162, wherein the one or more reagents are injected by pico-injection or droplet merging. Embodiment 164: The method of Embodiment 162, wherein injecting the one or more reagents further comprises monitoring the one or more encapsulations in flow, wherein the one or more reagents are injected at the same frequency at which the one or more encapsulations are passing an injection site. Embodiment 165: The method of Embodiment 140, wherein a rate of injection of the one or more reagents is determined by a flow rate of the one or more encapsulations.

Embodiment 166: A method for detecting one or more cellular nucleic acid using a nucleic acid encoded effector screen, the method comprising: a) providing an encoded effector, a nucleic acid encoding the encoded effector, and one or more cells comprising the one or more cellular nucleic acids, wherein the encoded effector, nucleic acid encoding and the one or more cells are provided in an encapsulation; b) incubating the encapsulation for a period of time to allow for the encoded effector and the one or more cells to interact, thereby producing a signal; c) transferring at least one cellular nucleic acid of the one or more cellular nucleic acids to the nucleic acid encoding; d) detecting the signal; and e) sorting the encapsulation based on the detection of the signal.

Embodiment 167: The method Embodiment 166, further comprising the step of lysing the one or more cells. Embodiment 168: The method of Embodiment 167, wherein lysing the one or more cells comprises adding lysis buffer to the encapsulation. Embodiment 169: The method of Embodiment 168, wherein the lysis buffer is added to the encapsulation by pico-injection. Embodiment 170: The method of Embodiment 166, wherein the one or more cellular nucleic acids comprise DNA, RNA, or combinations thereof. Embodiment 171: The method of Embodiment 166, wherein the one or more cellular nucleic acids comprise mRNA. Embodiment 172: The method of Embodiment 664, wherein the one or more cellular nucleic acids are added to the nucleic acid encoding as antibody-DNA constructs, proximity ligation products, or proximity extension products. Embodiment 173: The method of Embodiment 166, wherein transferring the at least one cellular nucleic acid to the nucleic acid encoding comprises annealing, ligating, amplifying, or chemically crosslinking the at least one cellular nucleic acid to the nucleic acid encoding. Embodiment 174: The method Embodiment 166, wherein transferring the at least one cellular nucleic acid to the nucleic acid encoding allows for quantification of the amount of the one or more cellular nucleic acids encapsulated with the nucleic acid encoded effector. Embodiment 175: The method of Embodiment 166, wherein a plurality of different cellular nucleic acids are transferred to the nucleic acid encoding. Embodiment 176: The method of Embodiment 166, further comprising adding one or more reagents for transferring the at least one cellular nucleic acid to the nucleic acid encoding. Embodiment 177: The method of Embodiment 176, wherein the one or more reagents are provided in the encapsulation in step (a). Embodiment 178: The method of Embodiment 176, wherein the one or more reagents are added during the incubation step or after the incubation step. Embodiment 179: The method of Embodiment 176, wherein the one or more reagents are added by droplet merging, pico-injection, or interaction with solid-phase particles comprising the one or more reagents. Embodiment 180: The method of Embodiment 176, wherein the one or more reagents comprises an enzyme. Embodiment 181: The method of Embodiment 180, wherein the enzyme is a ligase, a polymerase, a restriction enzyme, or a recombinase. Embodiment 182: The method of Embodiment 176, wherein the one or more reagents comprises assay detection reagents, labelling reagents, antibodies, target effectors, cell lysis reagents, nucleic acid ligation reagents, amplification reagents, or combinations thereof. Embodiment 183: The method of Embodiment 176, wherein the one or more reagents are only added if a signal is detected. Embodiment 184: The method of Embodiment 166, wherein the signal is electromagnetic radiation, thermal radiation, or a visual change in the sample. Embodiment 185: The method of Embodiment 166, wherein detecting the signal comprises providing the encapsulation through a microfluidic channel equipped with a detector. Embodiment 186: The method of Embodiment 166, wherein sorting the encapsulation is based on the level, presence, or absence of the signal. Embodiment 187: The method of Embodiment 166, wherein the period of time is controlled by a residence time as the encapsulation travels through a microfluidic channel, wherein the residence time of each encapsulation is within a maximum dispersion ratio of the incubation period of time for the plurality of encapsulations, wherein the dispersion ratio is based on a deviation about an average residence time of the plurality of encapsulations passing through a region of the microfluidic device. Embodiment 188: The method of Embodiment 187, wherein the maximum dispersion is at most from about 3% to about 10%. Embodiment 189: The method of Embodiment 166, wherein the period of time is at least 1 minute, at least 10 minutes, at least 1 hour, at least 4 hours, or at least 1 day. Embodiment 190: The method of Embodiment 166, wherein the encapsulation is a droplet, an emulsion, a picowell, a microwell, a bubble, or a microfluidic confinement. Embodiment 191: The method of Embodiment 166, wherein the encapsulation is a droplet. Embodiment 192: The method of Embodiment 191, wherein the droplet is at most 1 picoliter, at most 10 picoliters, at most 100 picoliters, at most 1 nanoliter, at most 10 nanoliters, at most 100 nanoliters, or at most 1 microliter in volume. Embodiment 193: The method of Embodiment 191, wherein the droplet is suspended in an emulsion. Embodiment 194: The method of Embodiment 1166, wherein the effector comprises a compound, a peptide, a protein, an enzyme, a macrocycle compound, or a nucleic acid. Embodiment 195: The method of Embodiment 166, further comprising 1) amplifying the nucleic acid encoding the encoded effector with the transferred at least one cellular nucleic acid, 2) sequencing the nucleic acid encoding with the transferred at least one cellular nucleic acid, 3) quantifying the at least one cellular nucleic acid, or any combination thereof. Embodiment 196: The method of Embodiment 166, wherein the encoded effector is attached to a scaffold. Embodiment 197: The method of Embodiment 196, wherein the scaffold is a bead. Embodiment 198: The method of Embodiment 196, wherein the scaffold is a polymer-bead, a glass bead, a metal bead, a molecular cage, or a multi-valent molecular assembly. Embodiment 199: The method of Embodiment 196, wherein the encoded effector is attached to the scaffold by a cleavable linker. Embodiment 200: The method of Embodiment 199, wherein the cleavable linker is a photocleavable linker. Embodiment 201: The method of Embodiment 199, wherein the encoded effector is covalently attached to the cleavable linker. Embodiment 201: The method of Embodiment 199, further comprising cleaving the cleavable linker. Embodiment 202: The method of Embodiment 199, wherein the nucleic acid encoding is attached to the scaffold by a second cleavable linker. Embodiment 203: The method of Embodiment 203, further comprising cleaving the second cleavable linker.

Embodiment 205: A method for screening a nucleic acid encoded protein, the method comprising: a) providing an encapsulation comprising: i) a nucleic acid encoding attached to a scaffold, the nucleic acid encoding comprises an encoding barcode and a coding section for the expression of an encoded effector protein, and ii) an expression system for the production of the encoded effector protein; b) expressing the encoded effector protein within the encapsulation; c) detecting the signal produced from an interaction with the encoded effector protein and one or more detection reagents disposed within the encapsulation; and d) sorting the encapsulation based on the signal. Embodiment 206: The method of Embodiment 205, further comprising the step of sequencing the nucleic acid encoding based on the sorted encapsulation. Embodiment 207: The method of Embodiment 205, wherein the encoded effector protein is a signaling protein, an enzyme, a binding protein, an antibody or antibody fragment, a structural protein, a storage protein, or a transport protein, or any mutant thereof. Embodiment 208: The method of Embodiment 205, wherein the encoded effector protein is an enzyme or enzyme mutant being screened for an enzymatic activity. Embodiment 209: The method of Embodiment 208, wherein the enzymatic activity comprises oxidation, reduction, ligation, polymerization, bond cleavage, bond formation, or isomerization. Embodiment 210: The method of Embodiment 205, wherein the encoded effector protein is an amino acid dehydrogenase, a natural amine dehydrogenase, an opine dehydrogenase, or an imine reductase. Embodiment 211: The method of Embodiment 205, wherein the interaction between the encoded effector protein and the one or more detection reagents comprises forming a bond between 1) a first molecular probe from a first detection reagent and second molecular probe from a second detection reagent of the one or more reagents, or 2) one or more chemical compounds for a first detection reagent and one or more chemical compounds from a second detection reagent. Embodiment 212: The method of Embodiment 211, wherein the bond is a covalent bond. Embodiment 213: The method of Embodiment 211, wherein the bond is an irreversible covalent bond. Embodiment 214: The method of Embodiment 211, wherein the first reagent and the second reagent exhibit a fluorescent signal when the first and second molecular probes are bound together. Embodiment 215: The method of Embodiment 214, wherein the fluorescent signal is due to fluorescence resonance energy transfer (FRET), bioluminescence resonance energy transfer (BRET), lanthanide chelate excite time resolved fluorescence resonance energy transfer (LANCE TR-FRET), or an amplified luminescent proximity homogeneous assay. Embodiment 216: The method of Embodiment 211, wherein the first and second detection reagents comprise chemical compounds. Embodiment 217: The method of Embodiment 211, wherein the first and second reagents comprise a FRET pair or a fluorophore/quencher pair. Embodiment 218: The method of Embodiment 217, wherein the first and second detection reagents comprise fluorophores or quenchers independently selected from 4-(4-dimethylaminophenyl azo), 5-((3-aminoethyl) amino)-1-napthalene sulfonic acid, 5-((2-aminoethyl) amino)-1-napthalene sulfonic acid (EDANS), 4-(dimethylaminoazo)benzene-4-carboxylic acid (DABCYL), and fluorescein-isothiocyanate (FITC), or derivatives thereof. Embodiment 219: The method of Embodiment 217, wherein the FRET pair or fluorophore/quencher pair comprise different fluorophores. Embodiment 220: The method of Embodiment 217, wherein the FRET pairing is duplicate copies of the same fluorophore. Embodiment 221: The method of Embodiment 211, wherein forming of the bond comprising an imine reduction. Embodiment 222: The method of Embodiment 221, wherein the imine reduction is enantiospecific. Embodiment 223: The method of Embodiment 211, wherein the encapsulation further comprises a reporter enzyme. Embodiment 224: The method of Embodiment 223, wherein the reporter enzyme reacts with another reagent to produce a functional readout. Embodiment 225: The method of Embodiment 223, wherein the bond between the first and second molecular probes creates a new molecule that inhibits the reporter enzyme. Embodiment 226: The method of Embodiment 205, wherein the scaffold is a bead, a fiber, a nanofibrous scaffold, a molecular cage, a dendrimer, or a multi-valent molecular assembly. Embodiment 227: The method of Embodiment 226, wherein the scaffold is a bead. Embodiment 228: The method of Embodiment 226, wherein the scaffold is polymer-bead, a glass bead, a metal bead, or a magnetic bead. Embodiment 229: The method of Embodiment 205, wherein the encapsulation is a droplet, an emulsion, a picowell, a macrowell, a microwell, a bubble, or a microfluidic confinement. Embodiment 230: The method of any Embodiment 229, wherein the encapsulation is a droplet. Embodiment 231: The method of Embodiment 230, wherein the droplet is at most 1 picoliter, at most 10 picoliters, at most 100 picoliters, at most 1 nanoliter, at most 10 nanoliters, at most 100 nanoliters, or at most 1 microliter in volume. Embodiment 232: The method of Embodiment 205, wherein the expression system comprises an in vitro transcription/translation system. Embodiment 233: The method of Embodiment 205, wherein the one or more detection reagents are added through pico-injection or droplet merging. Embodiment 234: The method of Embodiment 205, further comprising incubating the encapsulation for a period of time after the one or more detection reagents have been added. Embodiment 235: The method of Embodiment 205, wherein detecting the signal comprises providing the encapsulation through a microfluidic channel equipped with a detector. Embodiment 236: A method of screening a library of nucleic acid encoded proteins, the method comprising performing the screen of any of Embodiments 205-235 against a library of nucleic acid encoded proteins, wherein the library of nucleic acid encoded proteins comprises a plurality of different mutant versions of the nucleic acid encoded protein. Embodiment 237: The method of Embodiment 236, wherein each mutant version of the nucleic acid encoded protein is encoded by a unique barcode.

Embodiment 238: A method for normalizing the results of a nucleic acid encoded library screen comprising: a) providing a plurality of screened encoded effectors and corresponding scaffolds in a plurality of encapsulations, wherein each scaffold is bound to one or more nucleic acid encodings that encode a corresponding screened encoded effector; b) lysing the plurality of encapsulations; c) removing contents unbound to the plurality of scaffolds; d) suspending the plurality of scaffolds in a liquid medium; e) encapsulating the plurality of scaffolds in a plurality of new encapsulations, wherein each new encapsulation encapsulates one or more scaffolds of the plurality of scaffolds; and f) amplifying the one or more nucleic acid encodings of each scaffold to form corresponding amplified nucleic acid encodings, such that the amplified nucleic encodings within the plurality of new encapsulations are limited to the contained encoding scaffold(s) and the reagent(s) within the plurality of new encapsulations. Embodiment 239: The method of Embodiment 238, wherein 90% of the plurality of new encapsulations have a concentration of amplified nucleic acid encodings within 10% of an average concentration of the amplified nucleic acid encodings in the plurality of new encapsulations. Embodiment 240: The method of Embodiment 238, wherein providing a plurality of screened encoded effectors comprises performing a screen of a pre-screened nucleic acid encoded library. Embodiment 241: The method of Embodiment 240, wherein performing the screen comprises a sorting step to separate nucleic acid encoded effectors from the pre-screened nucleic acid encoded library that displayed a positive result in the screen. Embodiment 242: The method of Embodiment 240, wherein the plurality of screened encoded effectors comprises the nucleic acid encoded effectors that displayed a positive result in the screen of the pre-screened nucleic acid encoded library. Embodiment 243: The method of Embodiment 238, wherein lysing the plurality of encapsulations comprises introducing a demulsifying reagent, filtration, centrifugation, or sonication to an emulsion containing the plurality of encapsulations. Embodiment 244: The method of Embodiment 243, wherein the demulsifying reagent is an acid or a salt. Embodiment 245: The method of Embodiment 243, wherein the demulsifying reagent is sulfuric acid or hydrochloric acid. Embodiment 246: The method of Embodiment 243, wherein the demulsifying reagent is sodium chloride, potassium pyrophosphate, or sodium sulfate. Embodiment 247: The method of Embodiment 238, wherein the removing of unbound contents from the plurality of scaffolds comprises washing the plurality of scaffolds. Embodiment 248: The method of Embodiment 247, wherein washing the plurality of scaffolds comprises rinsing the plurality of scaffolds with a wash buffer. Embodiment 249: The method of Embodiment 248, wherein the wash buffer is an aqueous buffer, an organic solution, or a mixture thereof. Embodiment 250: The method of Embodiment 247, wherein the plurality of scaffolds are subject to multiple wash and collection steps, wherein each wash step comprises rinsing the plurality of scaffolds with a wash buffer, and each collection step comprises centrifugation or filtration of the plurality of scaffolds. Embodiment 251: The method of Embodiment 238, wherein the liquid medium is an aqueous solution. Embodiment 252: The method of Embodiment 238, wherein the liquid medium comprises an organic solvent. Embodiment 253: The method of Embodiment 238, wherein each scaffold of the plurality of scaffolds is a bead, a fiber, a nanofibrous scaffold, a molecular cage, a dendrimer, or a multi-valent molecular assembly. Embodiment 254: The method of Embodiment 238, wherein each scaffold of the plurality of scaffolds is polymer-bead, a glass bead, a metal bead, or a magnetic bead. Embodiment 255: The method of Embodiment 238, wherein the liquid medium comprises an amplification mix. Embodiment 256: The method of Embodiment 238, wherein each new encapsulation is a droplet. Embodiment 257: The method of Embodiment 238, wherein encapsulating the plurality of scaffolds in new encapsulations comprises introducing the plurality of scaffolds into an emulsion. Embodiment 258: The method of Embodiment 257, wherein introducing the plurality of scaffolds into an emulsion comprises placing the plurality of scaffolds through a microfluidic device. Embodiment 259: The method of Embodiment 258, wherein the microfluidic device is a microfluidic chip. Embodiment 260: The method of Embodiment 257, wherein introducing the plurality of scaffolds into an emulsion comprises placing the plurality of scaffolds into a one-pot emulsifier. Embodiment 261: The method of Embodiments 238, wherein an amplification mix is encapsulated with the plurality of scaffolds in the plurality of new encapsulations. Embodiment 262: The method of Embodiment 238, wherein an amplification mix is added to the plurality of new encapsulations. Embodiment 263: The method of Embodiment 262, wherein the amplification mix is added by pico-injection. Embodiment 264: The method of embodiment 262, wherein the amplification mix is added by droplet merging, wherein each encapsulation is a droplet. Embodiment 265: The method of Embodiment 261 or 262, wherein the amplification mix comprises PCR reagents. Embodiment 266: The method of Embodiment 238, further comprising sequencing the amplified nucleic acid encodings of each scaffold. Embodiment 267: The method of Embodiment 238, wherein the method results in a lower background signal than a nucleic acid encoded library that has not been subjected to the method. Embodiment 268: The method of Embodiment 267, wherein the background signal is reduced by at least 10%, at least 20%, at least 30%, at least 40%, or at least 50%. Embodiment 269: The method of Embodiment 267, wherein the lower background signal allows for detection of nucleic acid encoded effectors whose encoding concentrations before the screen are 100×, 1000×, 10000×, 100000×, or 1000000× lower in concentration than the average encoding concentration of the provided screened encoded effectors and corresponding scaffolds.

Embodiment 270: A system for screening an encoded effector, the system comprising: a) a sample; b) a scaffold, wherein an encoded effector is bound to the scaffold by a cleavable linker, wherein a nucleic acid encoding the effector is bound to the scaffold; and c) a microfluidic device configured to: i) receive the sample and scaffold; ii) encapsulate the sample and scaffold within an encapsulation; iii) cleave the cleavable linker from the encoded effector to release a predetermined amount of the encoded effector within the encapsulation; iv) incubate the encoded effector with the sample for an incubation period of time; v) detect a signal from the encapsulation, wherein the signal results from an interaction between the encoded effector and the sample; and vi) sort the encapsulation based on the detection of the signal. Embodiment 271: The system of Embodiment 270, wherein the cleavable linker is a photocleavable linker. Embodiment 272: The system of Embodiment 271, wherein cleaving the photocleavable linker comprises exposing the droplet to a light from a light source. Embodiment 273: The system of Embodiment 272, wherein the light is UV light. Embodiment 274: The system of Embodiment 272, wherein the light intensity of the light is from about 0.01 J/cm$^2$ to about 200 J/cm$^2$. Embodiment 275: The system of Embodiment 271, wherein the encapsulation further encapsulates a reagent configured to activate the photocleavable linker so as to enable the photocleavable linker to be cleaved from the encoded effector. Embodiment 276: The system of Embodiment 275, wherein the microfluidic device is configured to introduce the reagent within the encapsulation. Embodiment 277: The system of Embodiment 270, wherein the signal is detected based on detecting morphological changes in the sample measured by recording a series of images of the droplet or detecting fluorescence emitted by a molecular beacon or probe. Embodiment 278: The system of Embodiment 270, wherein the interaction between the encoded effector and the cell comprises inhibition of one or more cellular components. Embodiment 279: The system of Embodiment 270, further comprising a sequencing apparatus configured to identify the encoded effector by sequencing the nucleic acid encoding the effector. Embodiment 280: The system of Embodiment 270, wherein the scaffold is a bead, a fiber, a nanofibrous scaffold, a molecular cage, a dendrimer, or a multi-valent molecular assembly. Embodiment 281: The system of Embodiment 280, wherein the scaffold is polymer-bead, a glass bead, a metal bead, or a magnetic bead. Embodiment 282: The system of Embodiment 280, wherein the bead is about 1 µm to about 100 µm in diameter. Embodiment 283: The system of Embodiment 280, wherein the bead is about 1 µm to about 20 µm in diameter. Embodiment 284: The system of Embodiment 270, wherein the encoded effector is a peptide, a compound, protein, an enzyme, a macrocycle compound, or a nucleic acid. Embodiment 285: The system of Embodiment 284, wherein the encoded effector is a non-natural peptide or a polymer. Embodiment 286: The system of Embodiment 284, wherein the encoded effector is a small molecule or macromolecule. Embodiment 287: The system of Embodiment 284, wherein the compound is a drug-like small molecule. Embodiment 288: The system of Embodiment 270, wherein the encapsulation is a droplet. Embodiment 289: The system of Embodiment 288, wherein the droplet is at most 1 picoliter, at most 10 picoliters, at most 100 picoliters, at most 1 nanoliter, at most 10 nanoliters, at most 100 nanoliters, or at most 1 microliter in volume. Embodiment 290: The system of Embodiment 270, wherein the sample comprises at least one cell, a protein, or an enzyme. Embodiment 291: The system of Embodiment 270, wherein the period of time is controlled by residence time as the encapsulation travels through a microfluidic channel of the microfluidic device. Embodiment 292: The system of Embodiment 270, wherein the microfluidic device further comprises a first collection tube and second collection tube for sorting the encapsulation, wherein the encapsulation is placed in 1) the first collection tube if the signal is at or above a predetermined threshold or 2) the second collection tube if the signal is below a predetermined threshold. Embodiment 293: The system of Embodiment 292, further comprising a waveform pulse generator to move the encapsulation to the first or second collection tube by an electrical field gradient, by sound, by a diaphragm, by modifying geometry of the microfluidic channel, or by changing the pressure of a microfluidic channel of the microfluidic device. Embodiment 294: The system of Embodiment 270, wherein the microfluidic device further comprises: a) a first microfluidic channel comprising an aqueous fluid comprising the sample and scaffold; b) a second microfluidic channel comprising a fluid immiscible with the aqueous fluid; c) a junction at which the first microfluidic channel is in fluid communication with the second microfluidic channel, wherein the junction of the first and second microfluidic channels defines a device plane, wherein the junction is configured to form the encapsulations of the aqueous fluid within the fluid from the second microfluidic channel, wherein the fluid from the second microfluidic channel with the encapsulations therein moves past the junction in a third microfluidic channel that defines an assay flow path; d) a cleavage region to cleave the cleavable linker within the encapsulation disposed in the assay flow path; e) a detection region to detect the signal; and f) a sorting region to sort the encapsulation. Embodiment 295: The system of Embodiment 294, wherein the third microfluidic channel is a continuation of the second microfluidic channel. Embodiment 296: The system of Embodiment 294, wherein a plurality of encapsulations are disposed within the assay flow path. Embodiment 297: The system of Embodiment 294, wherein cleavage region is configured to expose each encapsulation to a light from a light source so as to cleave the encoded effector from the scaffold disposed within the assay flow path. Embodiment 298: The system of Embodiment 297, wherein the light intensity of the light is from about 0.01 J/cm$^2$ to about 200 J/cm$^2$. Embodiment 299: The system of Embodiment 297, wherein the plurality of encapsulations are exposed to a uniform intensity or duration of the light. Embodiment 300: The system of Embodiment 297, wherein the intensity or duration of the light that each encapsulation is exposed to within about 0.1% to about 10% of each other. Embodiment 301: The system of Embodiment 270, wherein the incubation period of time for each encapsulation is within a maximum dispersion ratio of the incubation period of time for the plurality of encapsulations, wherein the dispersion ratio is based on a deviation about an average residence time of the plurality of encapsulations passing through a region of the microfluidic device. Embodiment 302: The system of Embodiment 301, wherein the region of the microfluidic device is the assay flow path. Embodiment 303: The system of Embodiment 301, wherein the maximum dispersion ratio is at most about 10%. Embodiment 304: The system of Embodiment 301, wherein the maximum dispersion ratio is at most about 5%. Embodiment 305: The system of Embodiment 270, the incubation period of time for each encapsulation is within about 0.1% to about 10% of each other. Embodiment 306:

The system of Embodiment 294, wherein the detection region comprises a fluorometer. Embodiment 307: The system of Embodiment 294, wherein the detection region comprises a confocal detection, laser scanning, or fluorescence, or combinations thereof. Embodiment 308: The system of Embodiment 294, wherein the sorting region comprises a sorter configured to sort the encapsulations based on a signal detected in the detection region.

Embodiment 309: A system for screening an encoded effector, the system comprising: a) one or more cells; b) a scaffold, wherein an encoded effector is bound to the scaffold by a cleavable linker, wherein a nucleic acid encoding the effector is bound to the scaffold; and c) a microfluidic device configured to: i) receive the one or more cells and scaffold; ii) encapsulate the one or more cells and scaffold within an encapsulation; iii) cleave the cleavable linker from the encoded effector to release a predetermined amount of the encoded effector within the encapsulation; iv) incubate the encoded effector with the one or more cells for an incubation period of time; v) detect a signal from the encapsulation, wherein the signal results from an interaction between the encoded effector and one or more cells; and vi) sort the encapsulation based on the detection of the signal. Embodiment 310: The system of Embodiment 309, wherein the cleavable linker is a photocleavable linker. Embodiment 311: The system of Embodiment 310, wherein cleaving the photocleavable linker comprises exposing the droplet to a light from a light source. Embodiment 312: The system of Embodiment 311, wherein the light is UV light. Embodiment 313: The system of Embodiment 311, wherein the light intensity of the light is from about 0.01 J/cm$^2$ to about 200 J/cm$^2$. Embodiment 314: The system of Embodiment 310, wherein the encapsulation further encapsulates a reagent configured to activate the photocleavable linker so as to enable the photocleavable linker to be cleaved from the encoded effector. Embodiment 315: The system of Embodiment 314, wherein the microfluidic device is configured to introduce the reagent within the encapsulation. Embodiment 316: The system of Embodiment 309, wherein the signal is detected based on detecting morphological changes in the one or more cells measured by recording a series of images of the droplet or detecting fluorescence emitted by a molecular beacon or probe. Embodiment 317: The system of Embodiment 309, wherein the interaction between the encoded effector and the one or more cells comprises inhibition of one or more cellular components. Embodiment 318: The system of Embodiment 309, further comprising a sequencing apparatus configured to identify the encoded effector by sequencing the nucleic acid encoding the effector. Embodiment 319: The system of Embodiment 309, wherein the scaffold is a bead, a fiber, a nanofibrous scaffold, a molecular cage, a dendrimer, or a multi-valent molecular assembly. Embodiment 320: The system of Embodiment 319, wherein the scaffold is polymer-bead, a glass bead, a metal bead, or a magnetic bead. Embodiment 321: The system of Embodiment 320, wherein the bead is about 1 µm to about 100 µm in diameter. Embodiment 322: The system of Embodiment 320, wherein the bead is about 1 µm to about 20 µm in diameter. Embodiment 323: The system of Embodiment 309, wherein the encoded effector is a peptide, a compound, protein, an enzyme, a macrocycle compound, or a nucleic acid. Embodiment 324: The system of Embodiment 323, wherein the encoded effector is a non-natural peptide or a polymer. Embodiment 325: The system of Embodiment 323, wherein the encoded effector is a small molecule or macromolecule. Embodiment 326: The system of Embodiment 323, wherein the compound is a drug-like small molecule. Embodiment 327: The system of Embodiment 309, wherein the encapsulation is a droplet. Embodiment 328: The system of Embodiment 327, wherein the droplet is at most 1 picoliter, at most 10 picoliters, at most 100 picoliters, at most 1 nanoliter, at most 10 nanoliters, at most 100 nanoliters, or at most 1 microliter in volume. Embodiment 329: The system of Embodiment 309, wherein the period of time is controlled by residence time as the encapsulation travels through a microfluidic channel of the microfluidic device. Embodiment 330: The system of Embodiment 309, wherein the microfluidic device further comprises a first collection tube and second collection tube for sorting the encapsulation, wherein the encapsulation is placed in 1) the first collection tube if the signal is at or above a predetermined threshold or 2) the second collection tube if the signal is below a predetermined threshold. Embodiment 331: The system of Embodiment 330, further comprising a waveform pulse generator to move the encapsulation to the first or second collection tube by an electrical field gradient, by sound, by a diaphragm, by modifying geometry of the microfluidic channel, or by changing the pressure of a microfluidic channel of the microfluidic device. Embodiment 332: The system of Embodiment 309, wherein the microfluidic device further comprises: a) a first microfluidic channel comprising an aqueous fluid comprising the one or more cells and scaffold; b) a second microfluidic channel comprising a fluid immiscible with the aqueous fluid; c) a junction at which the first microfluidic channel is in fluid communication with the second microfluidic channel, wherein the junction of the first and second microfluidic channels defines a device plane, wherein the junction is configured to form the encapsulations of the aqueous fluid within the fluid from the second microfluidic channel, wherein the fluid from the second microfluidic channel with the encapsulations therein moves past the junction in a third microfluidic channel that defines an assay flow path; d) a cleavage region to cleave the cleavable linker within the encapsulation disposed in the assay flow path; e) a detection region to detect the signal; and f) a sorting region to sort the encapsulation. Embodiment 333: The system of Embodiment 332, wherein the third microfluidic channel is a continuation of the second microfluidic channel. Embodiment 334: The system of Embodiment 332, wherein a plurality of encapsulations are disposed within the assay flow path. Embodiment 335: The system of Embodiment 332, wherein cleavage region is configured to expose each encapsulation to a light from a light source so as to cleave the encoded effector from the scaffold disposed within the assay flow path. Embodiment 336: The system of Embodiment 335, wherein the light intensity of the light is from about 0.01 J/cm$^2$ to about 200 J/cm$^2$. Embodiment 337: The system of Embodiment 335, wherein the plurality of encapsulations are exposed to a uniform intensity or duration of the light. Embodiment 338: The system of Embodiment 335, wherein the intensity or duration of the light that each encapsulation is exposed to is within about 0.1% to about 10% of each other. Embodiment 339: The system of Embodiment 332, wherein the incubation period of time for each encapsulation is within a maximum dispersion ratio of the incubation period of time for the plurality of encapsulations, wherein the dispersion ratio is based on a deviation about an average residence time of the plurality of droplets passing through a region of the microfluidic device. Embodiment 340: The system of Embodiment 339, wherein the region of the microfluidic device is the assay flow path. Embodiment 341: The system of Embodiment 339, wherein the maximum dispersion ratio is at most about 10%.

Embodiment 342: The system of Embodiment 339, wherein the maximum dispersion ratio is at most about 5%. Embodiment 343: The system of Embodiment 309, the incubation period of time for each encapsulation is within about 0.1% to about 10% of each other. Embodiment 344: The system of Embodiment 332, wherein the detection region comprises a fluorometer. Embodiment 345: The system of Embodiment 332, wherein the detection region comprises a confocal detection, laser scanning, or fluorescence, or combinations thereof. Embodiment 346: The system of Embodiment 332, wherein the sorting region comprises a sorter configured to sort the encapsulations based on a signal detected in the detection region.

Embodiment 347: A microfluidic device for droplet based encoded library screening comprising: a) a first microfluidic channel comprising an aqueous fluid; b) a second microfluidic channel comprising a fluid immiscible with the aqueous fluid; c) a junction at which the first microfluidic channel is in fluid communication with the second microfluidic channel, wherein the junction of the first and second microfluidic channels defines a device plane, wherein the junction is configured to form encapsulations of the aqueous fluid within the fluid from the second microfluidic channel, wherein the fluid from the second microfluidic channel with the encapsulations therein moves past the junction in a third microfluidic channel that defines an assay flow path; d) a cleavage region for cleaving effectors bound to scaffolds disposed within the assay flow path; e) a detection region; and f) a sorting region; g) wherein the device is configured for a droplet generation frequency of at least about 80 Hz. Embodiment 348: The microfluidic device of Embodiment 347, wherein the third microfluidic channel is a continuation of the second microfluidic channel. Embodiment 349: The microfluidic device of Embodiment 347, wherein the cleavage region is upstream of the detection region and the sorting region. Embodiment 350: The microfluidic device of Embodiment 347, wherein the cleavage region is downstream of the junction. Embodiment 351: The microfluidic device of Embodiment 347, wherein the assay flow path comprises a serpentine flow path region. Embodiment 352: The microfluidic device of Embodiment 351, wherein the serpentine flow path region comprises at least 10, at least 20, at least 30, at least 40, at least 50, or at least 100 curves. Embodiment 353: The microfluidic device of Embodiment 347, wherein the detection region comprises a fluorometer. Embodiment 354: The microfluidic device of Embodiment 353, wherein the fluorometer is configured to have an optical axis substantially parallel to the device plane. Embodiment 355: The microfluidic device of Embodiment 353, wherein the fluorometer illuminates a passing droplet at a curve in the assay flow path. Embodiment 356: The microfluidic device of Embodiment 353, wherein the fluorometer is configured to detect two or more wavelengths of fluorescence. Embodiment 357: The microfluid device of Embodiment 347, wherein the detection region comprises a confocal detection, laser scanning, or fluorescence, or combinations thereof. Embodiment 358: The microfluidic device of Embodiment 347, wherein the device comprises two or more channels comprising an aqueous fluid. Embodiment 359: The microfluidic device of Embodiment 347, wherein the detection region is upstream of the sorting region. Embodiment 360: The microfluidic device of Embodiment 347, wherein the sorting region comprises a sorter configured to sort droplets based on a signal detected in the detection region. Embodiment 361: The microfluidic device of Embodiment 347, wherein the assay flow path comprises one or more chambers disposed within the assay flow path. Embodiment 362: The microfluidic device of Embodiment 347, wherein the assay flow path comprises a plurality of chambers disposed within the assay flow path, wherein the chambers are connected by connecting channels. Embodiment 363: The microfluidic device of Embodiment 362, wherein the height of a chamber of the plurality of chambers is at most about 2× greater than the height of a connecting channel of the plurality of connecting channels. Embodiment 364: The microfluidic device of Embodiment 362, wherein the height of the chamber does not decrease until the width of the channel has been narrowed to substantially match the width of the connecting channel. Embodiment 365: The microfluidic device of Embodiment 361, wherein the flow rate through the chambers is about 10% of the flow rate of the flow rate through the assay flow path upstream of the chambers. Embodiment 366: The microfluidic device of Embodiment 347, wherein the device has a dispersion ratio of at most about 10%. Embodiment 367: The microfluidic device of Embodiment 347, wherein the device is configured to incubate the encapsulations for an incubation period of time, wherein the incubation period of time for each encapsulation is within a maximum dispersion ratio of the incubation period of time for the plurality of encapsulations, wherein the dispersion ratio is based on a deviation about an average residence time of the plurality of droplets passing through a region of the microfluidic device. Embodiment 368: The system of Embodiment 367, wherein the region of the microfluidic device is the assay flow path. Embodiment 369: The system of Embodiment 368, wherein the maximum dispersion ratio is at most about 10%. Embodiment 370: The system of Embodiment 368, wherein the maximum dispersion ratio is at most about 5%. Embodiment 371: The system of Embodiment 367, the incubation period of time for each encapsulation is within about 0.1% to about 10% of each other.

Embodiment 372: A method for amplifying a primer to maximize cellular nucleic acid capture comprising: a) providing an encapsulation comprising a nucleic acid encoded scaffold with one or more cells, an amplification mix, and a nicking enzyme, wherein a nucleic acid encoding is bound to the nucleic acid encoded scaffold; b) lysing the one or more cells to release one or more cellular nucleic acids; c) nicking the nucleic acid encoding with the nicking enzyme, thereby creating an encoded nucleic acid primer; d) amplifying the encoded nucleic acid primer via the nicking site and amplification mix; and e) labeling a released cellular nucleic acid with the encoded nucleic acid primer. Embodiment 373: The method of Embodiment 372, wherein the nicking enzyme targets a specific site in the nucleic acid encoding. Embodiment 374: The method of Embodiment 373, wherein the specific site comprises a specific nucleotide sequence. Embodiment 375: The method of Embodiment of Embodiment 372, wherein amplifying the encoded nucleic acid primer comprises 1) creating a copy of the nucleic acid encoding that extends from the nicking site, and 2) nicking the nucleic acid encoding copy to create another encoded nucleic acid primer. Embodiment 376: The method of Embodiment of Embodiment 372, wherein amplifying the encoded nucleic acid primer comprises simultaneously 1) creating a copy of the nucleic acid encoding that extends from the nicking site, and 2) displacing the nucleic acid encoding copy to create another encoded nucleic acid primer. Embodiment 377: The method of Embodiment 376, wherein the amplification mix comprises an amplification enzyme, such that the amplification enzyme enables for a copy of the nucleic acid encoding to be simultaneously created and displaced. Embodiment 378: The method of Embodiment 377, wherein the amplification enzyme comprises a polymerase. Embodiment 379: The method of Embodiment 372, wherein each nucleic acid encoding comprises a capture site that prescribes a target cellular coding or a target cellular nucleic acid to label a released cellular nucleic acid. Embodiment 380: The method of Embodiment 379, wherein the target nucleic acid is a target mRNA. Embodiment 381: The method of Embodiment 380, wherein the target mRNA encodes a protein of interest. Embodiment 382: The method of Embodiment 380, wherein the nicking enzyme enables an increase in target mRNA capture and labeling with the nucleic acid encoding. Embodiment 383: The method of Embodiment 380, wherein target mRNA capture is increased by at least 10%, 25%, 50%, 100%, or 200%. Embodiment 384: The method of Embodiment 372, wherein a plurality of cellular nucleic acids are labeled with an respective encoded nucleic acid primer. Embodiment 385: The method of Embodiment 372, wherein the nucleic acid encoded scaffold comprises a bead, and the encoded nucleic acid primer comprises a unique bead barcode and an effector encoding. Embodiment 386: The method of Embodiment 372, wherein the encapsulation further comprises a cell lysis buffer. Embodiment 387: The method of Embodiment 372, wherein the encapsulation is a droplet, an emulsion, a picowell, a macrowell, a microwell, a bubble, or a microfluidic confinement. Embodiment 388: The method of Embodiment 372, wherein the encapsulation is a droplet. Embodiment 389: The method of Embodiment 388, wherein the droplet is at most 1 picoliter, at most 10 picoliters, at most 100 picoliters, at most 1 nanoliter, at most 10 nanoliters, at most 100 nanoliters, or at most 1 microliter in volume. Embodiment 390: The method of Embodiment 372, wherein the amplification mix is an isothermal amplification mix. Embodiment 391: The method of Embodiment 372, wherein the amplification mix comprises a nicking-enzyme-amplification mixture. Embodiment 392: The method of Embodiment 372, wherein the amplification mix comprises a reverse transcriptase. Embodiment 393: The method of Embodiment 372, wherein the nucleic acid encoded scaffold is a bead, a fiber, a nanofibrous scaffold, a molecular cage, a dendrimer, or a multi-valent molecular assembly. Embodiment 394: The method of Embodiment 393, wherein the scaffold is polymer-bead, a glass bead, a metal bead, or a magnetic bead. Embodiment 395: The method of Embodiment 372, wherein the nucleic acid encoded scaffold comprises an effector attached thereto. Embodiment 396: The method of Embodiment 395, wherein the effector comprises a compound, a peptide, a protein, an enzyme, or a nucleic acid. Embodiment 397: The method of Embodiment 395, wherein effector is attached to the scaffold by a cleavable linker. Embodiment 398: The method of Embodiment 397, wherein the cleavable linker is cleaved by electromagnetic radiation, an enzyme, chemical reagent, heat, pH adjustment, sound or electrochemical reactivity. Embodiment 399: The method of Embodiment 398, wherein the effector is cleaved from the scaffold using electromagnetic radiation. Embodiment 400: The method of Embodiment 398, wherein the amount of effector cleaved is controlled by the intensity or duration of exposure to electromagnetic radiation. Embodiment 401: The method of Embodiment 398, wherein the cleavable linker is cleaved using a cleavage reagent. Embodiment 402: The method of Embodiment 401, wherein the amount of effector cleaved is controlled by the concentration of the cleavage reagent in the encapsulation. Embodiment 403: The method of Embodiment 398, wherein the rate of effector cleavage is controlled by the concentration of the cleavage reagent in the encapsulation. Embodiment 404: The method of Embodiment 398, wherein the effector is cleaved from the scaffold using an enzyme. Embodiment 405: The method of Embodiment 404, wherein the enzyme is a protease, a nuclease, or a hydrolase. Embodiment 406: The method of Embodiment 404, wherein the rate of effector cleavage is controlled by the amount of enzyme in the encapsulation. Embodiment 407: The method of Embodiment 372, wherein labeling a released cellular nucleic acids with the encoded nucleic acid primer comprises barcoding the released cellular nucleic acid. Embodiment 408: The method of Embodiment 407, wherein the encapsulation further comprises barcoding reagents. Embodiment 409: The method of Embodiment 407, wherein barcoding the encoded nucleic acid primer comprises adding barcoding reagents to the encapsulation. Embodiment 410: The method of Embodiment 408 or 409, wherein the barcoding reagents comprise an enzyme or chemical cross-linking reagent. Embodiment 411: The method of Embodiment 410, wherein the barcoding reagents comprise an enzyme. Embodiment 412: The method of Embodiment 411, wherein the enzyme is polymerase, a ligase, a restriction enzyme, or a recombinase. Embodiment 413: The method of Embodiment 410, wherein the barcoding reagent is a chemical cross-linking reagent. Embodiment 414: The method of Embodiment 413, wherein the chemical cross-linking reagent is psoralen. Embodiment 415: The method of Embodiment 372, further comprising performing an effector screen, wherein the one or more cells are being screened against an encoded effector. Embodiment 416: The method of Embodiment 372, wherein the one or more cells are used to prepare the nucleic acid encoded scaffold for a screen.

Embodiment 417: A method for screening an encoded effector, the method comprising: a) providing an encapsulation comprising a sample and one or more scaffolds, wherein the scaffold comprises: i) an encoded effector bound to the scaffold by a cleavable linker and a nucleic acid encoding the effector; b) adding one or more reagents to the encapsulation through pico-injection or by droplet merging; c) cleaving the cleavable linker to release a pre-determined amount of the effector; d) detecting one or more signals from the encapsulation, wherein the signal results from an interaction between the encoded effector and the sample; and e) sorting the encapsulation based on the detection of the signal. Embodiment 418: The method of Embodiment 417, wherein the reagent is added after a pre-determined amount of the effector has been released. Embodiment 419: The method of Embodiment 417, wherein the one or more reagents are added to the encapsulation by pico-injection. Embodiment 420: The method of Embodiment 417, wherein the concentration a reagent of the one or more reagents is at most 100 picomolar (pM), at most 500 pM, at most 1 nanomolar (nM), at most 10 nM, at most 100 nM, at most 1 micromolar (pM), at most 10 pM, at most 100 pM, at most 1 millimolar (mM), at most 10 mM, at most 100 mM, or at most 500 mM. Embodiment 421: The method of Embodiment 417, wherein at least one reagent comprises antibodies. Embodiment 422: The method of Embodiment 417, wherein the predetermined amount of effector released from the scaffold is to a concentration of at least 100 pM, at least 500 pM, at least 1 nM, at least 10 nM, at least 100 nM, at least 1 pM, at least 10 pM, at least 100 pM, at least 1 mM. at least 10 mM, at least 50 mM, at least 100 mM, or at least 250 mM. Embodiment 423: The method of Embodiment 417, wherein the sample comprises at least one cell, a protein, an enzyme, a nucleic acid, a cellular lysate, a tissue extract, or combinations thereof. Embodiment 424: The method of Embodiment 417, at least one reagent comprises one or more fluorophores. Embodiment 425: The method of Embodiment 417, further comprising barcoding the nucleic acid encoding the effector. Embodiment 426: The method of Embodiment 425, wherein the barcoding is via the one or more reagents added to the encapsulation. Embodiment 427: The method of Embodiment 417, wherein the cleavable linker is a photocleavable linker. Embodiment 428: The method of Embodiment 427, wherein the photocleavable linker is cleaved using electromagnetic radiation. Embodiment 429: The method of Embodiment 427, wherein cleaving the photocleavable linker comprises exposing the encapsulation to a light from a light source. Embodiment 430: The method of Embodiment 429, wherein the light intensity of the light is from about 0.01 J/cm$^2$ to about 200 J/cm$^2$. Embodiment 431: The method of Embodiment 427, wherein the one or more reagents are configured to activate the photocleavable linker, so as to enable the photocleavable linker to be cleaved from the encoded effector. Embodiment 432: The method of Embodiment 431, wherein at least one reagent is a disulfide reducing reagent. Embodiment 433: The method of Embodiment 431, wherein at least one reagent is a tetrazine. Embodiment 434: The method of Embodiment 417, wherein detecting the signal comprises detecting morphological changes in the sample measured by recording a series of images of the droplet or detecting fluorescence emitted by a molecular beacon or probe. Embodiment 435: The method of Embodiment 417, wherein the scaffold is a bead, a fiber, a nanofibrous scaffold, a molecular cage, a dendrimer, or a multi-valent molecular assembly. Embodiment 436: The method of Embodiment 417, wherein the scaffold is polymer-bead, a glass bead, a metal bead, or a magnetic bead. Embodiment 437: The method of Embodiment 435, wherein the bead is about 1 µm to about 100 µm in diameter. Embodiment 438: The method of Embodiment 435, wherein the bead is about 1 µm to about 20 µm in diameter. Embodiment 439: The method of Embodiment 417, wherein the encoded effector is a peptide, a compound, protein, an enzyme, a macrocycle compound, or a nucleic acid. Embodiment 440: The method of Embodiment 417, wherein the encapsulation is a droplet. Embodiment 441: The method of Embodiment 440, wherein the droplet is at most 1 picoliter, at most 10 picoliters, at most 100 picoliters, at most 1 nanoliter, at most 10 nanoliters, at most 100 nanoliters, or at most 1 microliter in volume. Embodiment 442: The method of Embodiment 440, further comprising incubating the droplet for a period of time to allow the effector and the at least one cell to interact. Embodiment 443: The method of Embodiment 417, wherein the signal comprises electromagnetic radiation, thermal radiation, a visual change in the sample, or combinations thereof.

Embodiment 444: A method for screening a library of encoded effectors, the method comprising: (a) encapsulating a plurality of beads into a plurality of droplets in a microfluidic channel with a sample, wherein the plurality of beads are bound to a library of unique encoded effectors, wherein each bead of the plurality of beads is bound to one or more encoded effectors, wherein the library of unique encoded effectors comprise at least about 250,000 unique effectors, wherein each unique encoded effector is encoded with a unique nucleic acid encoding, wherein each droplet comprises one or more beads, (b) cleaving the photocleavable linker between at least one encoded effector and corresponding bead; (c) detecting a signal from one or more droplets of the plurality of droplets, wherein each signal results from an interaction between a respective encoded effector and sample within the corresponding droplet; and (d) sorting the plurality of droplets based on the detection of a corresponding signal. Embodiment 445: The method of Embodiment 444, wherein cleaving the photocleavable linker releases a predetermined amount of an encoded effector. Embodiment 446: The method of Embodiment 445, wherein the predetermined amount of an encoded effector released from the bead is to a concentration of at least 100 pM, at least 500 pM, at least 1 nM, at least 10 nM, at least 100 nM, at least 1 µM, at least 10 µM, at least 100 µM, at least 1 mM, at least 10 mM, at least 50 mM, at least 100 mM, or at least 250 mM. Embodiment 447: The method of Embodiment 444, wherein the sample comprises at least one cell, a protein, an enzyme, a nucleic acid, a cellular lysate, a tissue extract, or combinations thereof. Embodiment 448: The method of Embodiment 447, wherein the sample is one or more cells, a protein, or an enzyme. Embodiment 449: The method of Embodiment 447, further comprising barcoding a nucleic acid encoding a respective effector. Embodiment 450: The method of Embodiment 447, wherein the barcoding is via adding one or more reagents to a droplet. Embodiment 451: The method of Embodiment 447, wherein the photocleavable linker is cleaved using electromagnetic radiation. Embodiment 452: The method of Embodiment 451, wherein cleaving the photocleavable linker comprises exposing the encapsulation to a light from a light source. Embodiment 453: The method of Embodiment 452, wherein the light intensity of the light is from about 0.01 J/cm$^2$ to about 200 J/cm$^2$. Embodiment 454: The method of Embodiment 447, wherein one or more reagents are added to a droplet, wherein the one or more reagents are configured to activate the photocleavable linker of a respective encoded effector, so as to enable the photocleavable linker to be cleaved from said encoded effector. Embodiment 455: The method of Embodiment 454, wherein the activating reagent is a disulfide reducing reagent. Embodiment 456: The method of Embodiment 454, wherein the activating reagent is a tetrazine. Embodiment 457: The method of Embodiment 447, wherein detecting the signal comprises detecting morphological changes in the sample measured by recording a series of images of the droplet or detecting fluorescence emitted by a molecular beacon or probe. Embodiment 458: The method of Embodiment 447, wherein one or more beads is a polymer-bead, a glass bead, a metal bead, or a magnetic bead. Embodiment 459: The method of Embodiment 458, wherein one or more beads is about 1 µm to about 100 µm in diameter. Embodiment 460: The method of Embodiment 458, wherein one or more beads is about 1 µm to about 20 µm in diameter. Embodiment 461: The method of Embodiment 447, wherein an encoded effector is a peptide, a compound, protein, an enzyme, a macrocycle compound, or a nucleic acid. Embodiment 462: The method of Embodiment 447, wherein one or more droplets is at most 1 picoliter, at most 10 picoliters, at most 100 picoliters, at most 1 nanoliter, at most 10 nanoliters, at most 100 nanoliters, or at most 1 microliter in volume. Embodiment 463: The method of Embodiment 447, further comprising incubating a droplet for a period of time to allow the respective effector and the corresponding sample to interact. Embodiment 464: The method of Embodiment 447, wherein the signal comprises electromagnetic radiation, thermal radiation, a visual change in the sample, or combinations thereof.

Disclosed herein, in some embodiments, is a method for screening combinations of encoded effectors against a sample, the method comprising: (a) amplifying a target protein within an encapsulation, wherein the encapsulation comprises: (i) a nucleic acid coding the expression of the target protein, wherein the nucleic acid comprises a barcode region; and (ii) an in vitro transcription/translation system;

(b) introducing two or more nucleic acid encoded effectors into the encapsulation, wherein the two or more nucleic acid encoded effectors comprise nucleic acid encodings; (c) barcoding the nucleic acid encodings of the two or more encoded effectors using the barcode on the nucleic acid encoding the target protein; (d) incubating the encapsulation for a period of time to allow the two or more effectors to interact with the target protein; and (e) measuring a signal produced by the interaction between the two or more effectors and the target protein. In some embodiments, the method further comprising the step (f) sorting the encapsulation based on the measurement of the signal as compared to a predetermined threshold. In some embodiments, the method further comprising the step (g) sequencing the nucleic acid encoding the effector which now comprises the barcode from the nucleic acid coding for the target protein. In some embodiments, the method further comprising the step of (h) identifying combinations of effectors that conferred efficacy against the target protein. In some embodiments, wherein amplifying the target protein comprises activating expression of the target protein. In some embodiments, wherein amplifying the target protein comprises expressing the protein to a desired concentration. In some embodiments, the target protein is a signaling protein, an enzyme, a binding protein, an antibody or antibody fragment, a structural protein, a storage protein, or a transport protein In some embodiments, the target protein is an enzyme. 99. In some embodiments, the encapsulation is a droplet. In some embodiments, the droplet is at most 1 picoliter, at most 10 picoliters, at most 100 picoliters, at most 1 nanoliter, at most 10 nanoliters, at most 100 nanoliters, or at most 1 microliter in volume. In some embodiments, the barcoded nucleic acid encoding the target protein comprises a primer sequence complementary to a sequence on the one or more nucleic acids encoding the one or more effectors. In some embodiments, the barcoded nucleic acid coding the expression of the target protein comprises a promoter sequence. In some embodiments, wherein introducing two or more nucleic acid encoded effectors to the droplet comprises pico-injection or droplet merging. In some embodiments, wherein two or more nucleic acid encoded effectors are introduced into the encapsulation. In some embodiments, wherein at least two nucleic acid encoded effectors are introduced into the droplet. In some embodiments, wherein the nucleic acids encoding the two or more effectors are least 10, 15, 20, 25, 50, 75, or 100 nucleotides in length. In some embodiments, wherein each nucleic acid encoding the one or more effectors comprises a primer sequence complementary to a sequence encoded on the barcoded nucleic acid coding the expression of the target protein. In some embodiments, wherein each effector is a chemical compound. In some embodiments, wherein each effector is a chemical fragment. In some embodiments, wherein at least one of the nucleic acids encoded effectors is attached to a scaffold. In some embodiments, the scaffold is a bead, a fiber, a nanofibrous scaffold, a molecular cage, a dendrimer, or a multivalent molecular assembly. In some embodiments, the scaffold is polymer-bead, a glass bead, a metal bead, or a magnetic bead. In some embodiments, the nucleic acid encoding the effector is attached to the scaffold. In some embodiments, the attachment to the scaffold is through a cleavable linker. In some embodiments, the cleavable linker is cleavable by electromagnetic radiation, an enzyme, chemical reagent, heat, pH adjustment, sound or electrochemical reactivity. In some embodiments, the cleavable linker is cleavable by electromagnetic radiation. In some embodiments, the amount of effector, nucleic acid, or molecular weight barcode released can be controlled by the intensity or duration of exposure to electromagnetic radiation. In some embodiments, the cleavable linker is cleavable by a cleaving reagent. In some embodiments, the cleavable linker is a disulfide bond or a substituted trans-cyclooctene, and the cleaving reagent is a phosphine or a tetrazine. In some embodiments, the amount of effector, nucleic acid, or molecular weight barcode released is controlled by the concentration of the chemical reagent in the encapsulation. In some embodiments, the rate of effector, nucleic acid, or molecular weight barcode released is controlled by the concentration of the chemical reagent in the droplet. In some embodiments, the cleavable linker is cleavable by an enzyme. In some embodiments, the enzyme is a protease, a nuclease, or a hydrolase. In some embodiments, the rate of effector, nucleic acid, or molecular weight barcode released is controlled by the amount of enzyme in the droplet. In some embodiments, wherein barcoding the nucleic acids encoding the two or more effectors with the barcode on the nucleic acid coding the target protein comprises hybridizing the one or more nucleic acids encoding the effector with mRNA transcribed from the nucleic acid coding for the target protein and extending the transcribed mRNA or the nucleic acid encoding the effector with a polymerase enzyme. In some embodiments, the period of time is at least 1 minute, at least 10 minutes, at least 1 hour, at least 4 hours, or at least 1 day. In some embodiments, the period of time is controlled by residence time as the droplet travels through a microfluidic channel. In some embodiments, the residence time is controlled by a flow rate through the microfluidic channel, a geometry of the microfluidic channel, a valve in the microfluidic channel, or by removing the droplet from the microfluidic channel, or transferring the droplet to a separate vessel. In some embodiments, the signal is electromagnetic radiation, thermal radiation, or a visual change in the sample. In some embodiments, the signal is electromagnetic radiation. In some embodiments, the electromagnetic radiation is in the visible spectrum. In some embodiments, the electromagnetic radiation is fluorescence or luminescence. In some embodiments, the signal is fluorescence emitted by a TaqMan probe or a molecular beacon. In some embodiments, the signal is thermal radiation detected with an infrared camera. In some embodiments, the signal is a morphological of visual change in the sample measured by recording a series of images of the encapsulation.

Disclosed herein, in some embodiments, is a method for screening an encoded effector without a physical sorting step, the method comprising: (a) providing a sample, a nucleic acid encoded effector, and a nucleic acid encoding in an encapsulation; (b) detecting a signal in the encapsulation resulting from an interaction between the effector and the sample; and (c) adding a first capping mix to the droplet based on the detection, absence, or level of the signal, wherein the first capping mix adds a first nucleic acid cap to the nucleic acid encoding. In some embodiments, the first nucleic acid cap comprises a first nucleic acid barcode. In some embodiments, the first nucleic acid barcode indicates that the effector has a desired activity. In some embodiments, the first nucleic acid cap is added to the nucleic acid encoding by ligation, hybridization, or extension of the nucleic acid encoding. In some embodiments, the first capping mix further comprises additional reagents to effectuate the adding of the first nucleic acid cap. In some embodiments, the first nucleic acid cap is single-stranded DNA, double-stranded DNA, single-stranded RNA, or double-stranded RNA. In some embodiments, the method further comprising the step of adding a second capping mix to the encapsulation if the first capping mix is not added to the encapsulation, wherein the second capping mix ads a second nucleic acid cap to the nucleic acid encoding, wherein the first nucleic acid cap and the second nucleic acid cap have different sequences. In some embodiments, the second nucleic acid cap comprises a second nucleic acid barcode. In some embodiments, the second nucleic acid barcode indicates that the effector does not have a desired activity. In some embodiments, the second nucleic acid cap is added to the nucleic acid encoding by ligation, hybridization, or extension of the nucleic acid encoding. In some embodiments, the second capping mix further comprises additional reagents to effectuate the adding of the second nucleic acid cap. In some embodiments, the second nucleic acid cap is single-stranded DNA, double-stranded DNA, single-stranded RNA, or double-stranded RNA. In some embodiments, the second capping mix is added by pico-injection. In some embodiments, only the first capping mix or only the second capping mix is added to the encapsulation. In some embodiments, the first capping mix is added by pico-injection. In some embodiments, the method does not comprise a further physical sorting of the encapsulations. In some embodiments, the sample is a biological sample. In some embodiments, the sample is one or more cells, one or more proteins, one or more enzymes, one or more nucleic acids, one or more cellular lysates, or one or more tissue extracts. In some embodiments, the sample is a single cell. In some embodiments, the effector is a compound, a protein, a peptide, an enzyme, or a nucleic acid. In some embodiments, the effector is a compound. In some embodiments, the effector is a drug-like small molecule. In some embodiments, the nucleic acid encoding comprises a terminal capping site. In some embodiments, the terminal capping site comprises a sequence complementary to a sequence on the first nucleic acid cap. In some embodiments, the nucleic acid encoding comprises single-stranded DNA, double-stranded DNA, single-stranded RNA, or double-stranded RNA. In some embodiments, the encapsulation is a droplet. In some embodiments, the droplet is at most 1 picoliter, at most 10 picoliters, at most 100 picoliters, at most 1 nanoliter, at most 10 nanoliters, at most 100 nanoliters, or at most 1 microliter in volume. In some embodiments, the encapsulation is an emulsion in an oil. In some embodiments, the effector is attached to a scaffold. In some embodiments, the scaffold is a bead, a fiber, a nanofibrous scaffold, a molecular cage, a dendrimer, or a multi-valent molecular assembly. In some embodiments, the scaffold is polymer-bead, a glass bead, a metal bead, or a magnetic bead. In some embodiments, the effector is covalently attached to the scaffold by a first cleavable linker. In some embodiments, the method further comprising cleaving the first cleavable linker. In some embodiments, the nucleic acid encoding is attached to the scaffold. In some embodiments, the nucleic acid encoding is covalently attached to the scaffold by a second cleavable linker. In some embodiments, the first and second cleavable linkers are different. In some embodiments, the method further comprising cleaving the second cleavable linker. In some embodiments, the second cleavable linker is cleaved prior to adding the first or second capping mix. In some embodiments, the signal is electromagnetic radiation, thermal radiation, or a visual change in the sample. In some embodiments, detecting the signal comprises providing the encapsulation through a microfluidic channel equipped with a detector. In some embodiments, the method further comprising incubating the encapsulation for a period of time to allow the effector and sample to interact. In some embodiments, the period of time is controlled by a residence time as the encapsulation travels through a microfluidic channel. In some embodiments, the method of further comprising sequencing the nucleic acid encoding. In some embodiments, the sequencing is next-generation sequencing. In some embodiments, the method comprising performing the screen of any embodiment described herein against a library of encoded effectors, wherein the library of encoded effectors comprises a plurality of different effectors.

In some embodiments, disclosed herein is a method of measuring effector loading on scaffolds, the method comprising: (a) attaching an effector subunit to effector attachment sites on a plurality of scaffolds; (b) attaching a detectable label to any remaining free effector attachment sites on the plurality of scaffolds after the step of attaching an effector subunit; (c) removing a subset of scaffolds from the plurality; (d) measuring the amount of detectable label attached to the subset of scaffolds to determine the amount of effector subunits successfully attached to the effector attachment sites; (e) optionally activating the attached effector subunits to create new effector attachment sites; and (f) repeating steps (a)-(e) until a desired effector is assembled; wherein the scaffold further comprises a nucleic acid encoding the effector or wherein the method further comprises attaching nucleic acid encoding subunits to the scaffold corresponding to the effector subunits as the effector subunits are added to the scaffold. In some embodiments, In some embodiments, step (e) is omitted after the last effector subunit is attached. In some embodiments, each effector subunit attached to the scaffold is independently an amino acid, a small molecule fragment, a nucleotide, or a compound. In some embodiments, each effector subunit attached to the scaffold is an amino acid. In some embodiments, each effector subunit attached to the scaffold is a compound. In some embodiments, the effector attachment sites comprise reactive functionalities. In some embodiments, the effector attachment sites comprise amino or carboxylate groups. In some embodiments, the effector attachment sites comprise biorthogonal or CLICK chemistry reactive groups. In some embodiments, the effector subunits comprise a reactive group complementary to the effector attachment sites. In some embodiments, the detectable label comprises a reactive group complementary to the effector attachment sites. In some embodiments, the detectable label comprises a reactive group which is the same as a reactive group on the effector subunit whose attachment is being measured by the detectable label. In some embodiments, the detectable label is a fluorophore. In some embodiments, at most 10%, at most 20%, at most 30%, at most 40%, or at most 50% of the effector attachment sites are free after the step of attaching the effector subunit. In some embodiments, removing a subset of the plurality of scaffolds comprises removing no more than 1%, no more than 2%, no more than 3%, no more than 5%, or no more than 10% of the remaining scaffolds. In some embodiments, measuring the amount of detectable label attached to the subset of scaffolds to determine the amount of effector subunits successfully attached to the effector attachment sites comprises comparing the measurement of the detectable label to the measurement of detectable label on a scaffold without any effector subunits attached. In some embodiments, the amount of effector subunits successfully attached to the subset of scaffolds is expressed as a percentage of total attachment sites occupied by the effector subunits. In some embodiments, optionally activating the attached effector subunits to create a new effector attachment site comprises removing a protecting group from the attached effector subunit. In some embodiments, the protecting group is an amino protecting group, a carboxylate protecting group, an alcohol protecting group, a phenol protecting group, an alkyne protecting group, an aldehyde protecting group, or a ketone protecting group. In some embodiments, the protecting group is an amino protecting group. In some embodiments, the amino protecting group is 9-fluorenylmethyloxcarbonyl (Fmoc), tert-butyloxycarbonyl (BOC), carbobenzyloxy (Cbz), benzyl (Bz), tosyl (Ts) or trichloroethyl chloroformate (Troc). In some embodiments, the protecting group is a carboxylate protecting group. In some embodiments, the carboxylate protecting group is a methyl ester, a benzyl ester, a tert-butyl ester, a 2,6-disubstituted phenolic ester, a silyl ester, or an orthoester. In some embodiments, the new effector attachment site is the same functionality as the previous effector attachment site. In some embodiments, the new effector attachment site is a different functionality from the previous effector attachment site. In some embodiments, steps (a)-(e) are repeated at least 2, at least 3, at least 4, at least 5, at least 6, at least 7, at least 10, or at least 20 times. 343. In some embodiments, the scaffold is a bead, a fiber, a nanofibrous scaffold, a molecular cage, a dendrimer, or a multi-valent molecular assembly. In some embodiments, the scaffold is polymer-bead, a glass bead, a metal bead, or a magnetic bead. In some embodiments, the scaffold comprises a nucleic acid encoding the effector. In some embodiments, the method further comprises attaching nucleic acid encoding subunits to the scaffold corresponding to the effector subunits as the effector subunits are added to the scaffold. In some embodiments, a library of effector loaded scaffolds are synthesized concurrently. In some embodiments, subsets of scaffolds from an effector attachment step from the library are pooled prior to detection of the detectable label In some embodiments, the subsets of scaffolds are encapsulated in an encapsulation. In some embodiments, the encapsulations are droplets. In some embodiments, a majority of the encapsulations comprise a single scaffold. In some embodiments, scaffolds from the subset of scaffolds are binned according to the amount of detectable label detected. In some embodiments, each bin comprises a unique range of detectable label detected. In some embodiments, for any method described herein, further comprising the step of sequencing encoding nucleic acids or encoding nucleic acid subunits of the pools to reveal which effector subunits correspond to a particular yield in a step of attaching effector subunits to effector attachment sites. In some embodiments, the sequencing step is performed each time steps (a)-(e) are repeated. In some embodiments, yields of each step (a)-(e) for each unique scaffold are collected to create a dataset which reveals the loading of the complete desired effector on each scaffold.

Disclosed herein, in some embodiments, is an array device for screening encoded beads comprising: (a) a hydrophobic surface; and (b) nucleic acid patches interspersed on the hydrophobic surface; wherein the hydrophobic surface and nucleic acid patches are configured such that when a proscribed amount of media is deployed across the surface each nucleic acid patch is covered with media and the hydrophobic surface between the nucleic acid patches does not contain media. In some embodiments, an array device described herein further comprising one or more channels beneath the hydrophobic surface, wherein the channels comprise terminal ends within nucleic acid patches. In some embodiments, the channels are configured to deliver reagents to the nucleic acid patches. In some embodiments, the reagents are delivered as a liquid solution. In some embodiments, the hydrophobic surface comprises a hydrophobic polymer. 3 In some embodiments, the hydrophobic polymer comprises a polyacrylic, a polyamide, a polycarbonate, a polydiene, a polyester, a polyether, a polyfluorocarbon, a polyolefin, a polystyrene, a polyvinyl acetal, a polyvinyl chloride, a polyvinyl ester, a polyvinyl ether, a polyvinyl ketone, a polyvinyl pyridine, a polyvinylpyrrolidone, a polysilane, a polyfluorosilane, a poly perfluorosilane or a combination thereof. In some embodiments, the hydrophobic polymer comprises a polyfluorocarbon. In some embodiments, the hydrophobic polymer is fluorinated. In some embodiments, the hydrophobic surface is a surface functionalized with hydrophobic groups. In some embodiments, the hydrophobic groups are fatty acids, alkyl groups, alkoxy groups, aromatic groups, alkyl silanes, fluorosilanes, perfluorosilanes, or combinations thereof. In some embodiments, the hydrophobic groups are fluorinated. In some embodiments, cells do not bind to the hydrophobic surface. In some embodiments, the nucleic acid patches bind cells. In some embodiments, single nucleic acid patches are encapsulated within single droplets of the media. In some embodiments, the nucleic acid patches comprise DNA, RNA, combinations thereof. In some embodiments, the nucleic acid patches comprise nucleic acids capable of binding nucleic acid encoded beads. In some embodiments, the nucleic acids bind nucleic acid encoded beads non-specifically, by binding a complementary nucleic acid on the bead, or by binding another group on the bead. In some embodiments, the nucleic acid patches are up to about 1 $\mu m^2$ in size, up to about 10 $\mu m^2$ in size, up to about 100 $\mu m^2$ in size, up to about 1000 $\mu m^2$ in size, or up to about 10000 $\mu m^2$ in size. In some embodiments, the nucleic acid patches are separated by up to about 1 $\mu m$, up to about 10 $\mu m$, up to about 100 $\mu m$, up to about 1000 $\mu m$, or up to about 10000 $\mu m$. In some embodiments, the nucleic acid patches are arranged in a grid pattern. In some embodiments, the media is an aqueous media. In some embodiments, the density of nucleic acid patches is at least 100 patches/$cm^2$, at least 1000 patches/$cm^2$, at least 10000 patches/$cm^2$, at least 100000 patches/$cm^2$, at least 1000000 patches/$cm^2$, or at least 10000000 patches/$cm^2$. In some embodiments, the surface area of the device is at least 1 $cm^2$, at least 5 $cm^2$, at least 10 $cm^2$, at least 25 $cm^2$, at least 50 $cm^2$, at least 100 $cm^2$, at least 500 $cm^2$, or at least 1000 $cm^2$.

Disclosed herein, in some embodiments, is a method of performing a screen, the method comprising: (a) binding nucleic acid encoded beads to the nucleic acid patches of the array of any one of embodiments described herein; (b) sequencing the nucleic acid encoded beads (c) binding cells to the nucleic acid patches; and (d) performing an assay on the array. In some embodiments, the beads further comprise encoded effectors. In some embodiments, the method further comprising the step of releasing the effectors from the beads. In some embodiments, releasing the effectors from the beads comprises adding a cleaving reagent to the nucleic acid patches. In some embodiments, sequencing the beads allows determination of the physical location of specific nucleic acid encoded beads. In some embodiments, the assay produces a detectable signal. 412. In some embodiments, each nucleic acid patch binds a single bead and a single cell.

Disclosed herein, in some embodiments, is a method for stimulating an ion channel, the method comprising: (a) providing a cell in an encapsulation; (b) stimulating an ion channel of the cell by electrostimulation, optical stimulation, or chemical stimulation; and (c) detecting a signal from the cell by capturing images of the cell in the encapsulation. In some embodiments, the ion channel is stimulated by electrostimulation. In some embodiments, the electrostimulation is performed by an electrode. In some embodiments, the electrode is within a flow path of the encapsulation. In some embodiments, the electrode is outside of a flow path of the encapsulation. In some embodiments, the ion channel is stimulated by optical stimulation. In some embodiments, the ion channel of the cell comprises a mutation. In some embodiments, the mutation sensitizes the ion channel to optical stimulation. In some embodiments, the ion channel is stimulated by chemical stimulation. In some embodiments, the chemical stimulation comprises contacting the ion channel with a toxin. In some embodiments, the toxin is added to the encapsulation by pico-injection. In some embodiments, the pico-injection is conditional pico-injection. 4 In some embodiments, the toxin is an ion channel toxin. In some embodiments, the signal is a morphological or visual change in the cell. In some embodiments, capturing images of the cell comprises recording a series of images of the encapsulation. In some embodiments, the method further comprising superimposing the series of images of the sample in the encapsulation. In some embodiments, the encapsulation further comprises a detection reagent.

In one aspect, provided herein, is a method for stimulating an ion channel, the method comprising: (a) providing a cell in an encapsulation; (b) stimulating an ion channel of the cell by electrostimulation, optical stimulation, or chemical stimulation; and (c) detecting a signal from the cell by capturing images of the cell in the encapsulation.

In one aspect, provided herein, is a method for screening ion channel modulators, the method comprising: (a) providing an encapsulation comprising: (i) a cell expressing an ion channel protein; (ii) a set of voltage sensor probes; and (iii) an encoded effector and its corresponding encoding; (b) stimulating an ion channel of the cell; and (c) detecting a signal from at least one member of the set of voltage sensor probes. In some embodiments, the encapsulation is a droplet, an emulsion, a picowell, a macrowell, a microwell, a bubble, or a microfluidic confinement. In some embodiments, the encapsulation is a droplet. In some embodiments, the droplet is at most 1 picoliter, at most 10 picoliters, at most 100 picoliters, at most 1 nanoliter, at most 10 nanoliters, at most 100 nanoliters, or at most 1 microliter in volume. In some embodiments, the cell comprises a mammalian cell. In some embodiments, the cell comprises a human cell. In some embodiments, the cell comprises a HEK293 cell. In some embodiments, the ion channel protein comprises a sodium, calcium, chloride, proton, or potassium ion channel protein. In some embodiments, wherein the ion channel protein comprises a voltage gated ion channel protein. In some embodiments, the ion channel protein comprises an endogenous ion channel protein. In some embodiments, the ion channel protein comprises an exogenous ion channel protein. In some embodiments, the ion channel protein comprises a sodium, calcium, chloride, proton, or potassium voltage gated ion channel protein. In some embodiments, the ion channel protein comprises a voltage gated calcium channel protein (VGCC). In some embodiments, the ion channel protein comprises an L-type calcium channel, a P-type calcium channel, an N-type calcium channel, an R-type calcium channel, or a T-type calcium channel, or any mutant, fragment, or conjugate thereof. In some embodiments, the ion channel protein comprises a channelrhodopsin or any mutant, fragment, or conjugate thereof. In some embodiments, the channelrhodopsin is ChrimsonR or any mutant, fragment, or conjugate thereof. In some embodiments, the ion channel protein is overexpressed. In some embodiments, the set of voltage sensor probes comprise a FRET pair. In some embodiments, the set of voltage sensor probes comprises a voltage-sensitive oxonol, a fluorescent coumarin, or both. In some embodiments, the set of voltage sensor probes comprises a DiSBAC compound, a coumarin phospholipid, or any combination or derivative thereof. In some embodiments, the set of voltage sensors comprises a $DiSBAC_2$, $DiSBAC_4$, $DiSBAC_6$, CC1-DMPE, CC2-DMPE, or any combination or derivative thereof. In some embodiments, the set of voltage sensors comprises $DiSBAC_6$ and CC2-DMPE. In some embodiments, the encapsulation further comprises a voltage assay background suppression compound. In some embodiments, the voltage assay background suppression compound comprises VABSC-1. In some embodiments, the effector and its corresponding encoding are bound to a scaffold. In some embodiments, the scaffold is a bead, a fiber, a nanofibrous scaffold, a molecular cage, a dendrimer, or a multivalent molecular assembly. In some embodiments, the scaffold is polymer-bead, a glass bead, a metal bead, or a magnetic bead. In some embodiments, the scaffold is a bead from 10 µm to about 100 µm in diameter. In some embodiments, the effector is bound to the scaffold through a cleavable linker. In some embodiments, the cleavable linker is a photocleavable linker. In some embodiments, the method further comprises the step of cleaving the cleavable linker. In some embodiments, the effector is a compound or a peptide. In some embodiments, the effector is a small molecule. In some embodiments, the encoding is a nucleic acid. In some embodiments, stimulating the ion channel comprises electrostimulation, optical stimulation, chemical stimulation, or any combination thereof. In some embodiments, stimulating the ion channel comprises electrostimulation. In some embodiments, wherein stimulating the ion channel is performed by at least one electrode. In some embodiments, the at least one electrode is in the flow path of the encapsulation. In some embodiments, electrostimulation is performed by non-contact electrodes to generate electric fields, dielectrophoretic forces, or embedded metal-contact electrodes. In some embodiments, electrostimulation is dictated by geometry of a microfluidic device containing the encapsulation. In some embodiments, the frequency of electrostimulation is about 10 Hz. In some embodiments, stimulating the ion channel comprises optical stimulation. In some embodiments, the optical stimulation is UV, VIS, or near-infrared radiation. In some embodiments, the optical stimulation is performed using an embedded fiber-optic wave guide embedded in a microfluidic device containing the encapsulation. In some embodiments, wherein the frequency of optical stimulation is about 10 Hz. In some embodiments, the wavelength of light for optical stimulation is about 660 nm. In some embodiments, the intensity of light for optical stimulation is about 500 $mJ/s/cm^2$. In some embodiments, stimulating the ion channel comprises chemical stimulation. In some embodiments, chemical stimulation comprises contacting the ion channel with an ion channel toxin. In some embodiments, the ion channel toxin comprises veratridine, OD-1, or another ion channel toxin, or any combination thereof. In some embodiments, the ion channel toxin as added to the encapsulation by pico-injection, droplet fusion, or through a pre-arranged architecture of a microfluidic device which contains the encapsulation. In some embodiments, the signal is electromagnetic radiation. In some embodiments, the electromagnetic radiation is luminescence or fluorescence. In some embodiments, the electromagnetic radiation is fluorescence. In some embodiments, the electromagnetic radiation is emitted due to a FRET interaction. In some embodiments, the signal is an increase, decrease, or change in electromagnetic radiation as compared to an identical encapsulation without the encoded effector. In some embodiments, the signal is an increase, decrease, or change in electromagnetic radiation as compared to the encapsulation before the stimulation of the ion channel. In some embodiments, the method further comprises the step of sorting the encapsulation based on the presence, absence, level, or change of the signal. In some embodiments, the method further comprises measuring a property of the encoding to ascertain the identity of the effector.

In one aspect, provided herein, is a microfluidic device for droplet based encoded library screening comprising: (a) a first microfluidic channel comprising an aqueous fluid; (b) a second microfluidic channel comprising a fluid immiscible with the aqueous fluid; (c) a junction at which the first microfluidic channel is in fluid communication with the second microfluidic channel, wherein the junction of the first and second microfluidic channels defines a device plane, wherein the junction is configured to form droplets of the aqueous fluid within the fluid from the second microfluidic channel, wherein the second microfluidic channel is configured to continue past the junction thereby defining an assay flow path; (d) a cleavage region for cleaving effectors from scaffolds disposed within the assay flow path; (e) a detection region; and (f) a sorting region. In some embodiments, the device further comprises a stimulation region. In some embodiments, the stimulation region comprises one or more actuators for stimulating an ion channel. In some embodiments, the one or more actuators for stimulating the ion channel comprises at least one light source, at least one electrode, or at least one pico-injection site equipped with an ion channel toxin. In some embodiments, the one or more actuators comprises at least one electrode. In some embodiments, the one or more actuators comprises a pair of electrodes on opposite walls of the assay flow path such that when a droplet passes the pair of electrodes the droplet contacts the electrodes, thereby allowing a current to flow through the droplet. In some embodiments, the stimulation region comprises at least 1, at least 2, at least 3, at least 5, at least 7, at least 10, or at least 20 actuators. In some embodiments, at least one of the actuators for stimulating the ion channel is substantially parallel with the device plane. In some embodiments, at least one of the actuators for stimulating the ion channel lies at a curve in the assay flow path. In some embodiments, the stimulation region is upstream of the detection region and downstream of the cleavage region. In some embodiments, the cleavage region comprises a light source configured to cleave effectors from scaffolds disposed within the assay flow path. In some embodiments, the light source is a source of UV light. In some embodiments, the light source is configured to have an optical axis substantially parallel with the device plane. In some embodiments, the light source illuminates a passing droplet at a curve in the assay flow path. In some embodiments, the cleavage region is upstream of the detection region and the sorting region. In some embodiments, the cleavage region is downstream of the junction. In some embodiments, the assay flow path comprises a serpentine flow path region. In some embodiments, the serpentine flow path region comprises at least 10, at least 20, at least 30, at least 40, at least 50, or at least 100 curves. In some embodiments, the detection region comprises a fluorometer. In some embodiments, the fluorometer is configured to have an optical axis substantially parallel to the device plane. In some embodiments, the fluorometer illuminates a passing droplet at a curve in the assay flow path. In some embodiments, the fluorometer is configured to detect two or more wavelengths of fluorescence. In some embodiments, the detection region is downstream of the cleavage region. In some embodiments, the detection region is upstream of the sorting region. In some embodiments, the sorting region comprises a sorter configured to sort droplets based on a signal detected in the detection region.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "detecting," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The term "in vivo" is used to describe an event that takes place in a subject's body.

The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay.

The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

The term "hit" refers to an effector that has been screened against a sample and returned a positive result. The positive result may depend upon the nature of the screen being employed, but may include, without limitation, an indication of efficacy against a target being interrogated.

The term "screen" as used herein refers to performing an assay using a plurality of effectors in order to determine the effect various effectors have on a particular sample.

The term "sequencing" refers to determining the nucleotide sequence of a nucleic acid. Any suitable method for sequencing may be employed with the methods and systems provided herein. The sequencing may be accomplished by next generation sequencing. Next generation sequencing encompasses many kinds of sequencing such as pyrosequencing, sequencing-by-synthesis, single-molecule sequencing, second-generation sequencing, nanopore sequencing, sequencing by ligation, or sequencing by hybridization. Next-generation sequencing platforms are those commercially available from Illumina (RNA-Seq) and Helicos (Digital Gene Expression or "DGE"). Next generation sequencing methods include, but are not limited to those commercialized by: 1) 454/Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305; 2) Helicos Biosciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; 3) Applied Biosystems (e.g. SOLiD sequencing); 4) Dover Systems (e.g., Polonator G.007 sequencing); 5) Illumina, Inc. as described in U.S. Pat. Nos. 5,750,341; 6,306,597; and 5,969,119; and 6) Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764. Such methods and apparatuses are provided here by way of example and are not intended to be limiting.

The term "barcode" refers to a nucleic acid sequence that is unique to a particular system. The barcode may be unique to a particular method or to a particular effector. The nucleic acid encodings of the methods and systems provided herein are analogous to barcodes in that they are unique nucleic acid sequences that can be used to identify the structure of a given effector. The length of a barcode or nucleic acid encoding should be sufficient to differentiate between all the effectors in a given library.

The term "flow" means any movement of liquid or solid through a device or in a method of the disclosure, and encompasses without limitation any fluid stream, and any material moving with, within or against the stream, whether or not the material is carried by the stream. For example, the movement of molecules, cells or virions through a device or in a method of the disclosure, e.g. through channels of a microfluidic chip of the disclosure, comprises a flow. This is so, according to the disclosure, whether or not the molecules, cells or virions are carried by a stream of fluid also comprising a flow, or whether the molecules, cells or virions are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as molecules, cells or virions are directed for detection, measurement or sorting according to the disclosure.

An "inlet region" is an area of a microfabricated chip that receives molecules, cells or virions for detection measurement or sorting. The inlet region may contain an inlet channel, a well or reservoir, an opening, and other features which facilitate the entry of molecules, cells or virions into the device. A chip may contain more than one inlet region if desired. The inlet region is in fluid communication with the main channel and is upstream therefrom.

An "outlet region" is an area of a microfabricated chip that collects or dispenses molecules, cells or virions after detection, measurement or sorting. An outlet region is downstream from a discrimination region, and may contain branch channels or outlet channels. A chip may contain more than one outlet region if desired.

An "analysis unit" is a microfabricated substrate, e.g., a microfabricated chip, having at least one inlet region, at least one main channel, at least one detection region and at least one outlet region. Sorting embodiments of the analysis unit include a discrimination region and/or a branch point, e.g. downstream of the detection region, that forms at least two branch channels and two outlet regions. A device according to the disclosure may comprise a plurality of analysis units.

A "main channel" is a channel of the chip of the disclosure which permits the flow of molecules, cells or virions past a detection region for detection (identification), measurement, or sorting. In a chip designed for sorting, the main channel also comprises a discrimination region. The detection and discrimination regions can be placed or fabricated into the main channel. The main channel is typically in fluid communication with an inlet channel or inlet region, which permits the flow of molecules, cells or virions into the main channel. The main channel is also typically in fluid communication with an outlet region and optionally with branch channels, each of which may have an outlet channel or waste channel. These channels permit the flow of cells out of the main channel.

A "detection region" is a location within the chip, typically within the main channel where molecules, cells or virions to be identified, measured or sorted on the basis of a predetermined characteristic. In an embodiment, molecules, cells or virions are examined one at a time, and the characteristic is detected or measured optically, for example, by testing for the presence or amount of a reporter. For example, the detection region is in communication with one or more microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at the discrimination region. In sorting embodiments, the detection region is in fluid communication with a discrimination region and is at, proximate to, or upstream of the discrimination region.

A "carrier fluid," "immiscible fluid," or "immiscible carrier fluid" or similar term as used herein refers to a liquid in which a sample or assay liquid is incapable of mixing and allows formation of droplets of the sample or assay liquid within the carrier fluid. These terms are used interchangeable herein and are meant to encompass the same materials. Non-limiting examples of such carrier fluids include silicon based oils, silicone oils, hydrophobic oils (e.g. squalene, fluorinated oils, perfluorinated oils), or any fluid capable of encapsulating another desired liquid containing a sample to be analyzed.

An "extrusion region," "droplet extrusion region," or "droplet formation region" is a junction between an inlet region and the main channel of a chip of the disclosure, which permits the introduction of a pressurized fluid to the main channel at an angle perpendicular to the flow of fluid in the main channel. In some embodiments, the fluid introduced to the main channel through the extrusion region is "incompatible" (i.e., immiscible) with the fluid in the main channel so that droplets of the fluid introduced through the extrusion region are sheared off into the stream of fluid in the main channel.

A "discrimination region" or "branch point" is a junction of a channel where the flow of molecules, cells or virions can change direction to enter one or more other channels, e.g., a branch channel, depending on a signal received in connection with an examination in the detection region. Typically, a discrimination region is monitored and/or under the control of a detection region, and therefore a discrimination region may "correspond" to such detection region. The discrimination region is in communication with and is influenced by one or more sorting techniques or flow control systems, e.g., electric, electro-osmotic, (micro-) valve, etc. A flow control system can employ a variety of sorting techniques to change or direct the flow of molecules, cells or virions into a predetermined branch channel.

A "branch channel" is a channel which is in communication with a discrimination region and a main channel. Typically, a branch channel receives molecules, cells or virions depending on the molecule, cell or virion characteristic of interest as detected by the detection region and sorted at the discrimination region. A branch channel may be in communication with other channels to permit additional sorting. Alternatively, a branch channel may also have an outlet region and/or terminate with a well or reservoir to allow collection or disposal of the molecules, cells or virions.

The term "forward sorting" or flow describes a one-direction flow of molecules, cells or virions, typically from an inlet region (upstream) to an outlet region (downstream), and in some instances without a change in direction, e.g., opposing the "forward" flow. In some embodiments, molecules, cells or virions travel forward in a linear fashion, i.e., in single file. A "forward" sorting algorithm consists of running molecules, cells or virions from the input channel to the waste channel, until a molecule, cell or virion is identified to have an optically detectable signal (e.g. fluorescence) that is above a pre-set threshold, at which point voltages are temporarily changed to electro-osmotically divert the molecule or to the collection channel.

The term "reversible sorting" or flow describes a movement or flow that can change, i.e., reverse direction, for example, from a forward direction to an opposing backwards direction. Stated another way, reversible sorting permits a change in the direction of flow from a downstream to an upstream direction. This may be useful for more accurate sorting, for example, by allowing for confirmation of a sorting decision, selection of particular branch channel, or to correct an improperly selected channel.

Different "sorting algorithms" for sorting in the microfluidic device can be implemented by different programs, for example under the control of a personal computer. As an example, consider a pressure-switched scheme instead of electro-osmotic flow. Electro-osmotic switching is virtually instantaneous and throughput is limited by the highest voltage that can be applied to the sorter (which also affects the run time through ion depletion effects). A pressure switched-scheme does not require high voltages and is more robust for longer runs. However, mechanical compliance in the system is likely to cause the fluid switching speed to become rate-limiting with the "forward" sorting program.

Since the fluid is at low Reynolds number and is completely reversible, when trying to separate rare molecules, cells or virions, one can implement a sorting algorithm that is not limited by the intrinsic switching speed of the device. The molecules, cells or virions flow at the highest possible static (non-switching) speed from the input to the waste. When an interesting molecule, cell or virion is detected, the flow is stopped. By the time the flow stops, the molecule, cell or virion may be past the junction and part way down the waste channel. The system is then run backwards at a slow (switchable) speed from waste to input, and the molecule, cell or virion is switched to the collection channel when it passes through the detection region. At that point, the molecule, cell or virion is "saved" and the device can be run at high speed in the forward direction again. Similarly, a device of the disclosure that is used for analysis, without sorting, can be run in reverse to re-read or verify the detection or analysis made for one or more molecules, cells or virions in the detection region. This "reversible" analysis or sorting method is not possible with standard gel electrophoresis technologies (for molecules) nor with conventional FACS machines (for cells). Reversible algorithms are particularly useful for collecting rare molecules, cells or virions or making multiple time course measurements of a molecule or single cell.

The term "emulsion" refers to a preparation of one liquid distributed in small globules (also referred to herein as drops or droplets) in the body of a second liquid. The first liquid, which is dispersed in globules, is referred to as the discontinuous phase, whereas the second liquid is referred to as the continuous phase or the dispersion medium. In one embodiment, the continuous phase is an aqueous solution and the discontinuous phase is a hydrophobic fluid, such as an oil (e.g., decane, tetradecane, or hexadecane). Such an emulsion is referred to here as an oil in water emulsion. In another embodiment, an emulsion may be a water in oil emulsion. In such an embodiment, the discontinuous phase is an aqueous solution and the continuous phase is a hydrophobic fluid such as an oil. The droplets or globules of oil in an oil in water emulsion are also referred to herein as "micelles", whereas globules of water in a water in oil emulsion may be referred to as "reverse micelles".

As used herein, the term "about" a number refers to that number plus or minus 10% of that number. The term "about" a range refers to that range minus 10% of its lowest value and plus 10% of its greatest value.

The section headings used herein are for organizational purposes only and are not to be construed as limiting the subject matter described.

EXAMPLES

The following examples are included for illustrative purposes only and are not intended to limit the scope of the disclosure.

Figure 4:
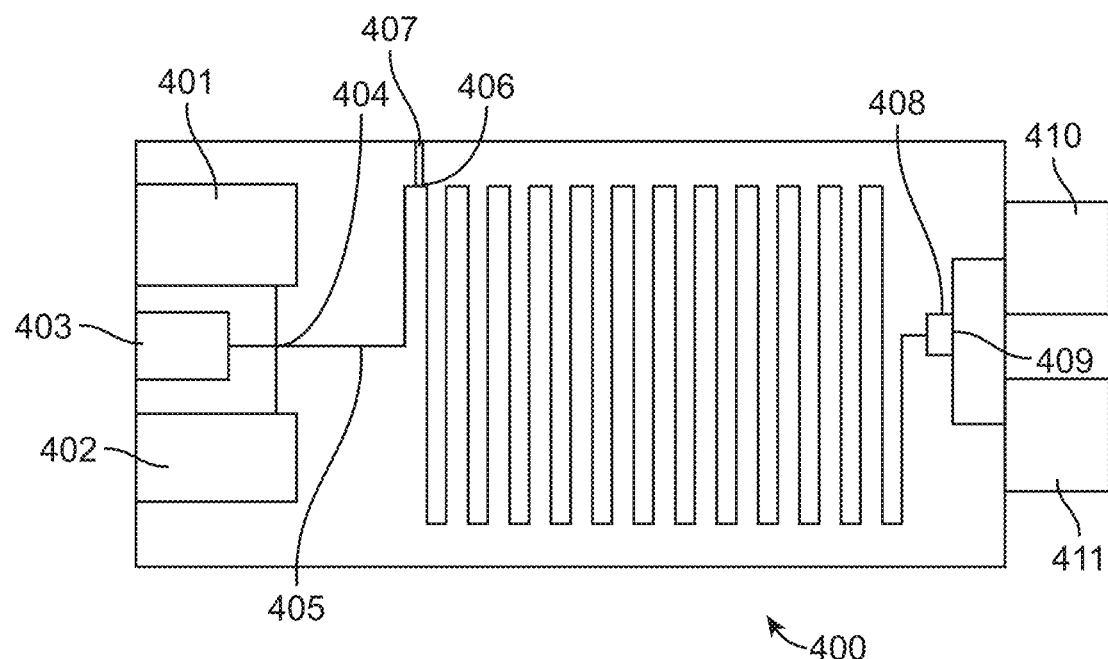
FIG. 4 shows an exemplary microfluidic device for performing a screen according to the methods provided herein.

Example 1: Stoichiometric Cleavage of Encoded Effectors to Probe Protease Inhibition A library of beads containing nucleic acid encoded small molecules is prepared, wherein the small molecules are linked to the beads by a substituted trans-cyclooctene. In this example, the library is being screened to detect small molecule inhibitors of trypsin. A solution comprising the library of beads is placed in a first reagent well 401 of a microfluidic device 400, as shown in FIG. 4. A solution comprising trypsin is added to a reagent well 402, and an oil medium is added to reagent well 403. The contents of reagent wells 401, 402, and 403 flow until they meet at a junction 404, where the trypsin solution and bead solution form droplets in an oil emulsion. The droplets then flow along flow path 405 until they reach pico-injection site 406. At pico-injection site 406, pico-injector 407 adds a solution containing dimethyl tetrazine and fluorescein isothiocyanate (FITC) labelled casein. The pico-injection is configured such that each drop passing by receives a uniform dose of the solution. The concentration of dimethyl tetrazine in the solution is configured such that each droplet comprising a bead releases substantially the same amount of effector upon receiving the pico-injection. The droplet then continues along flow path 405 until it reaches detector 408. Detector 408 is a fluorimeter configured to measure the FITC FRET emission (excitation 485 nm/emission 538 nm). Based on the resulting fluorescence detected by detector 408, the sample is sorted at junction 409 onto a path toward bin 410 if the FRET emission is detected above a certain threshold and onto a path toward bin 411 if the FRET emission is not detected above the threshold. After the screen is completed, the nucleic acid encodings in bin 410 are sequenced by next generation sequencing to determine which small molecules had an inhibitory effect on trypsin.

Example 2: Nucleic Acid Detection with Molecular Beacons

A library of beads containing nucleic acid encoded small molecules is prepared, wherein the small molecules are linked to the beads by a disulfide bond. In this example, the library is being screened to detect an increase in cellular expression of a protein of interest by measuring cellular mRNA using molecular beacons. The molecular beacons used in this example contains a sequence complementary to the mRNA which codes for the protein of interest. The molecular beacons further comprises a Cyanine 5 dye at one loop end and a DABCYL quencher at the other end. In this example, the protein of interest is expressed by a sample cell, and the desired outcome of the screen is an increase in the expression of the protein of interest.

Figure 5:
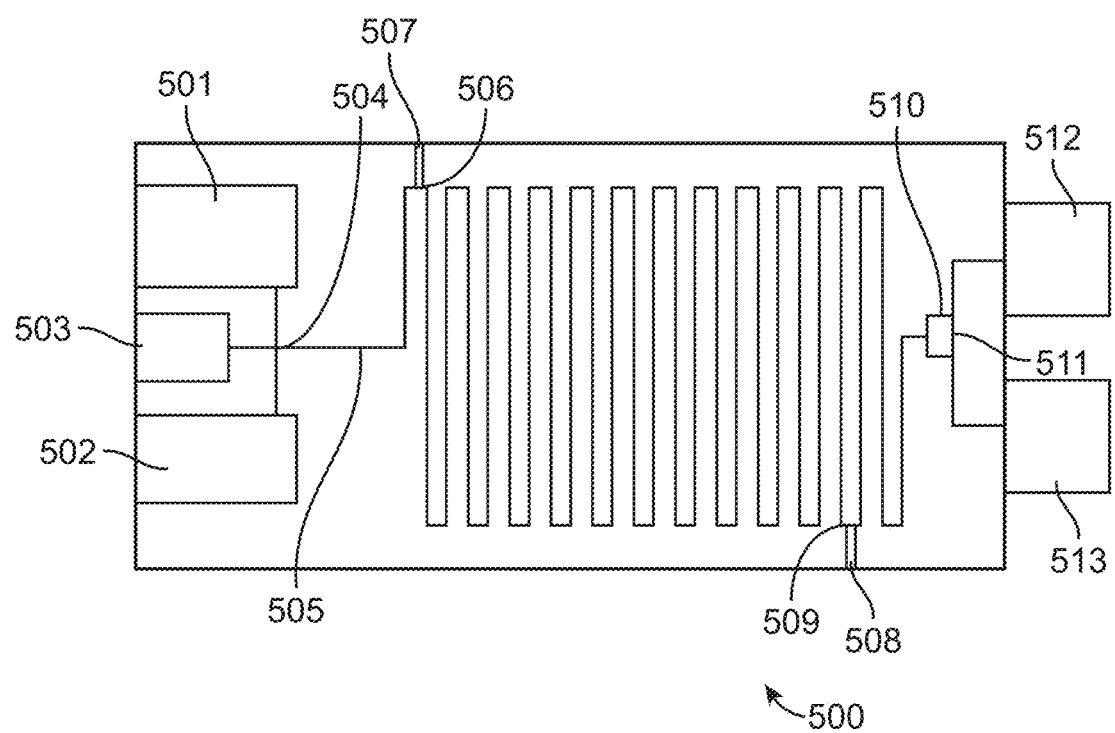
FIG. 5 shows an exemplary microfluidic device for performing a screen according to the methods provided herein.

A solution comprising the library of beads is placed in a first reagent well 501 of a microfluidic device 500, as shown in FIG. 5. A solution comprising the cells that express the protein of interest is added to a reagent well 502, and an oil medium is added to reagent well 503. The contents of reagent wells 501, 502, and 503 flow until they meet at a junction 504, where the solution containing the cells and the bead solution form droplets in an oil emulsion. The device is configured such that a majority of the encapsulations receive a single cell and a single bead. The droplets then flow along flow path 505 until they reach pico-injection site 506. At pico-injection site 506, pico-injector 507 adds a solution containing tris(2-carboxyethyl)phosphine (TCEP). The pico-injection is configured such that each drop passing by receives a uniform dose of the solution. The concentration of TCEP in the solution is configured such that each droplet comprising a bead releases substantially the same amount of effector upon receiving the pico-injection. The droplet then continues along flow path 505 until it reaches the second pico-injection site 508, at which point the molecular beacon is added to the encapsulation, along with lysis buffer to lyse the cell, by pico-injector 509. The molecular beacons then hybridize with any mRNA encoding the protein of interest, thereby allowing a fluorescent emission from the Cyanine 5 moiety. The droplet continues along flow path 505 until it reaches the detector 510. Detector 510 is a fluorimeter configured to measure the Cyanine 5 fluorescent signal (excitation 646 nm/emission 669 nm). Based on the resulting fluorescence detected by detector 510, the sample is sorted at junction 511 onto a path toward bin 512 if the fluorescence emission is detected above a certain threshold and onto a path toward bin 513 if the fluorescence emission is not detected above the threshold. After the screen is completed, the nucleic acid encodings in bin 512 are sequenced by next generation sequencing to determine which small molecules had the desired effect of increasing production of the protein of interest.

Example 3: Screening of Mutant Imine Reductases

A library of beads containing nucleic acids coding for different mutants of an imine reductase enzyme and a corresponding barcode is provided. In this example, the library is being screened to detect an enzyme that can effectuate an imine reduction between Reagent 1

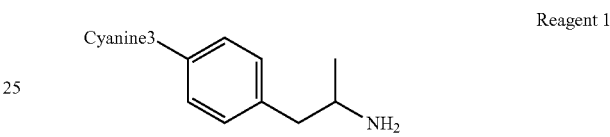

Reagent 1 and Reagent 2

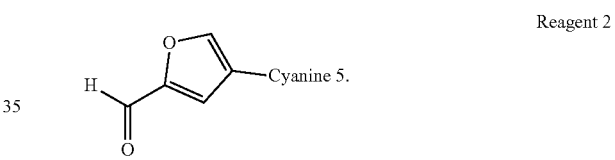

Reagent 2

If the enzyme screened is capable of performing the imine reduction, the Cyanine 3 and Cyanine 5 dyes will undergo a FRET interaction and an emission at 680 nm will be observed after an excitation at 540 nm.

Figure 6:
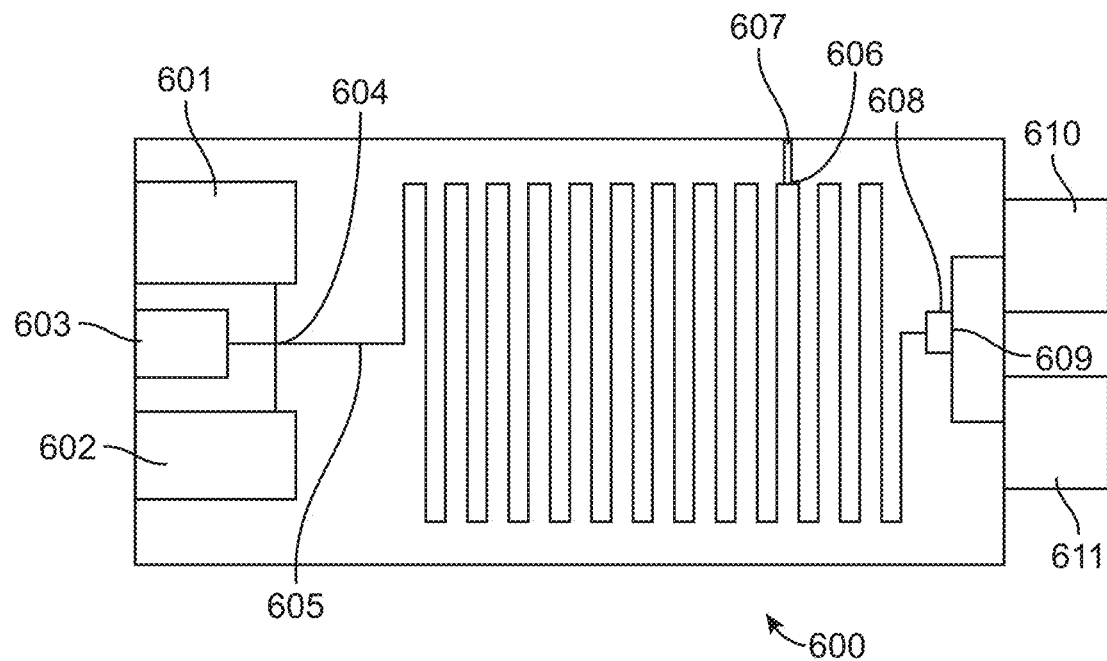
FIG. 6 shows an exemplary microfluidic device for performing a screen according to the methods provided herein.

A solution comprising the library of beads is placed in a first reagent well 601 of a microfluidic device 600, as shown in FIG. 6. A solution comprising an in vitro transcription/translation system (IVTT) is then added to a reagent well 602, and an oil medium is added to reagent well 603. The contents of reagent wells 601, 602, and 603 flow until they meet at a junction 604, where the solution containing the IVTT and the bead solution form droplets in an oil emulsion. The device is configured such that a majority of the encapsulations receive a single bead. The IVTT then allows expression of the mutant imine reductases within the droplets. The droplets then flow along flow path 605 until they reach pico-injection site 606. At pico-injection site 606, pico-injector 607 adds a solution containing Reagent 1 and Reagent 2. The pico-injection is configured such that each drop passing by receives a uniform dose of the solution. The droplet continues along flow path 605 until it reaches the detector 508. Detector 510 is a fluorimeter configured to measure the Cyanine 5/Cyanine 3 FRET emission (excitation 540 nm/emission 680 nm). Based on the resulting fluorescence detected by detector 608, the sample is sorted at junction 609 onto a path toward bin 610 if the fluorescence emission is detected above a certain threshold and onto a path toward bin 611 if the fluorescence emission is not detected above the threshold. After the screen is completed, the nucleic acid on the beads in bin 610 are sequenced by next generation sequencing to determine which imine reductase mutants had the desired effect of forming the amine bond between Reagent 1 and Reagent 2 during the screening

Example 4: Ion Channel Screening Using a Chip-Based Spatio-Temporally Controlled Electrical Stimulation Assay A library of nucleic acid encoded beads containing candidate ion channel inhibitor molecules is prepared, wherein the inhibitor molecules are linked to the beads by nitrobenzyl photocleavable linker. The cell line used is the Human Embryonic Kidney (HEK) cell line that expresses a sodium ion channel of interest. The cells are treated with a FRET probe system, containing the dyes $DiSBAC_6$ and CC2-DMPE which report a rapid change in fluorescence upon the stimulation of an ion channel. Stimulation can occur by chemical, optical and electrical means.

Figure 7:
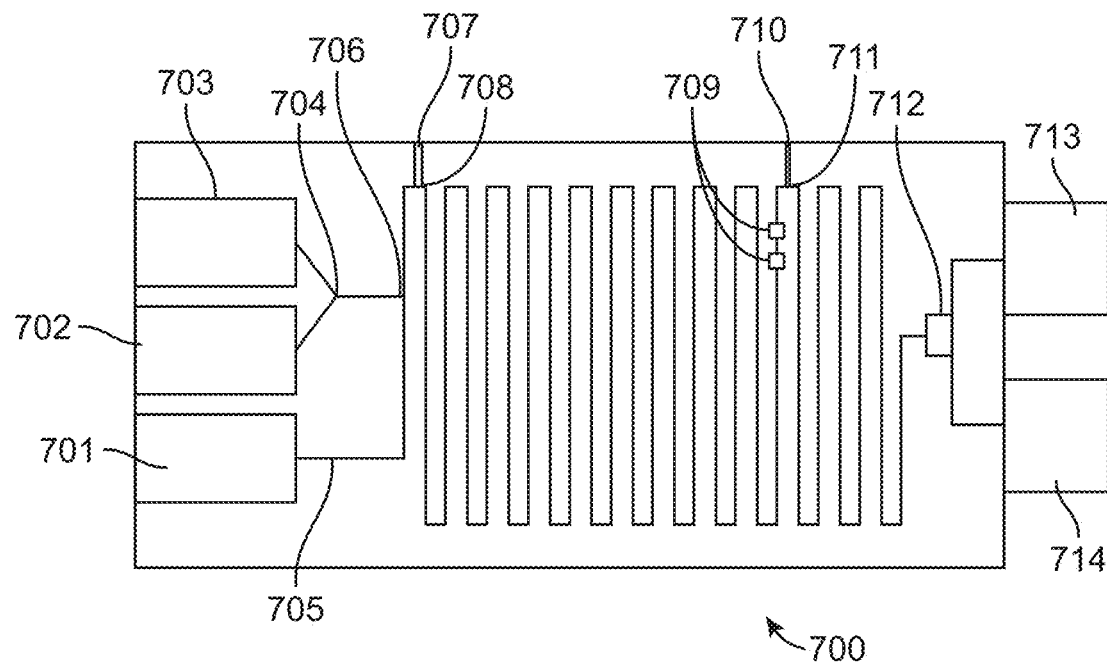
FIG. 7 shows an exemplary microfluidic device for performing a screen according to the methods provided herein.

In this example, electrical stimulation is used. The bead encoded library is placed in reagent well 702 of microfluidic device 700, as shown in FIG. 7. The cell solution containing the FRET probe system is added to reagent well 703, and an oil medium is added to reagent well 701. From the reagent well 701, the oil travels along flow path 705. The contents of reagent wells 702 and 703 flow along separate flow paths until they meet at junction 704. The aqueous sample solution flows down the flow path channel until it meets the oil at junction 706, where the solution containing the cells and the bead solution form an emulsion stream of aqueous droplets separated by the oil. The device can be configured such that a majority of the droplets form containing a single cell and a single bead, but this is not necessary. The droplets then flow along the flow path 705 until they reach UV light exposure site 708, coupled to a UV source 707 by optical fiber, where the inhibitor molecule is released into the droplet from the nucleic acid encoded bead. As the droplet flows down the flow path 705, the candidate inhibitor contacts the cell. The droplet continues along the flow path 705, where multiple electrodes 709 are placed along the flow path. The droplets are individually exposed to electrical stimulation at each set of electrodes 709. The electrode spacing and flow velocity defines the desired stimulation frequency, which in this case is case 10 Hz. After stimulation, the droplets are passed through a fluorescence detection region 711, coupled to a light source and detector 710 by optical fiber. Droplets which contain effective inhibitors will exhibit a distinctly different fluorescence intensity, after electrical stimulation, relative to droplets that contain ineffective inhibitors. Droplets are then sorted at the sorting site 712 according to their distinctive fluorescence signal and are directed to collection bin 713 if designated as a hit. Misses are directed to collection bin 714.

Figure 8:
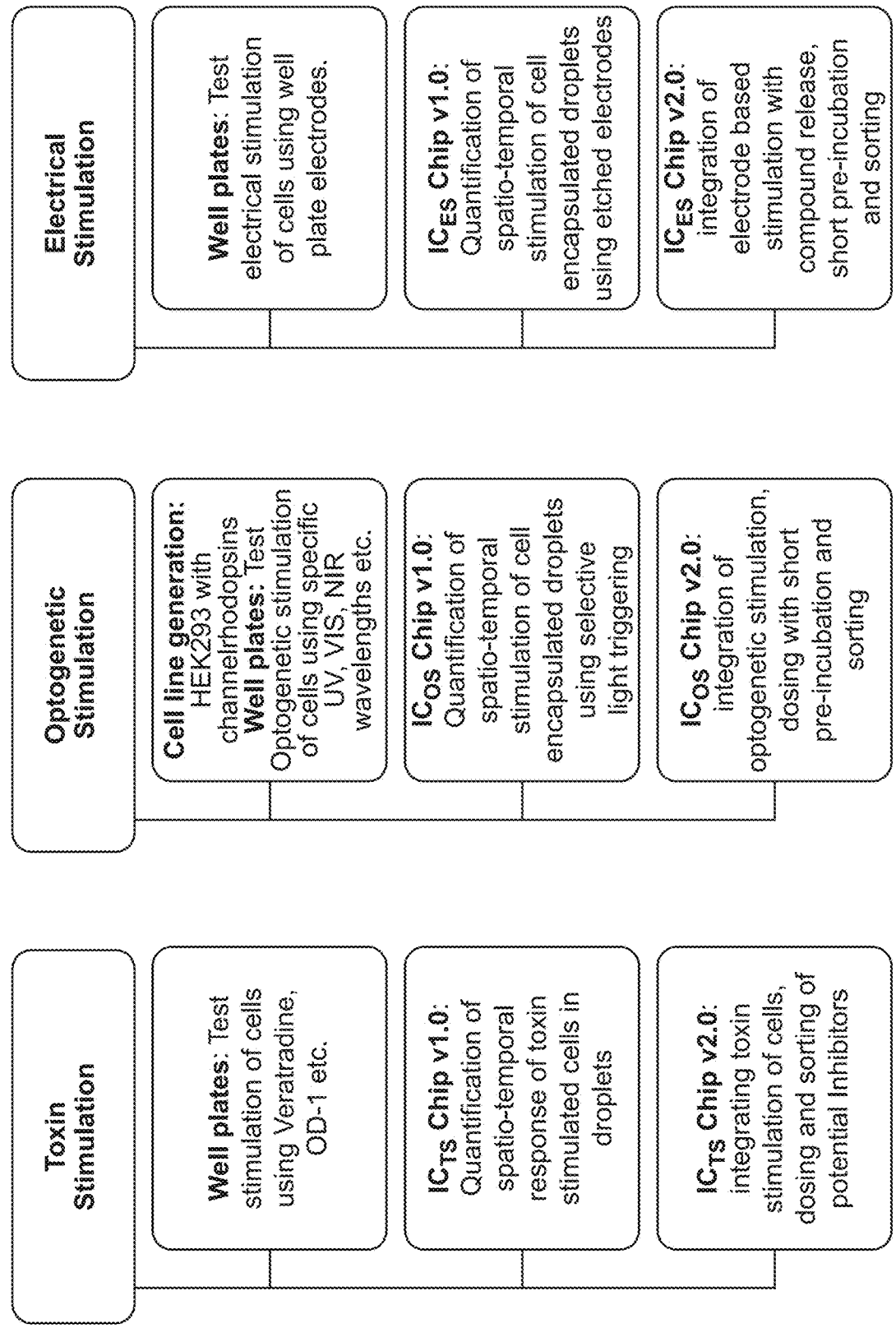
FIG. 8 shows an overview of specifically designed IC chips and their related development workflow.

Example 5: Development of a Chip Device for Screening Ion Channel Modulators Phase 1
Goals:
Phase 1: To determine the feasibility of deploying an ultra-high-throughput microfluidic system, Ion Channel Chip (IC Chip), to accommodate cell-based sodium ion channel activity assays. Propose three different droplet microfluidic approaches to trigger cell surface ion channel activities in a microfluidic chip by spatio-temporally controlled electrical-stimulation (ES); controlled optical-stimulation (OS), or by toxin-induced stimulation (TS) subsequent to compound liberation and brief incubation. These methods will be tested to demonstrate sodium ion channel assay compatibility and screening feasibility in droplets. The aforementioned three methods of triggering live cell sodium ion channels may be executed. FIG. 8 shows an overview of the development workflow for the design and evaluation of the devices to accomplish the aforementioned methods.

The goal of Phase 1 is to demonstrate a proof-of-concept system using known inhibitor control compounds photolytically released from carrier beads in droplets. The released compound will inhibit Na+ ion channel activity in cells with sufficient discretion when compared to uninhibited cells from a model cell line.

Objectives:
Stage 1: Detection of Droplet-Cell-Assay for Ion Channel Inhibition
Summary: Demonstrate cell line compatibility, and cell assay monitoring in microdroplets via $DiSBAC_6$+CC2-DMPE FRET probe emission. This early proof-of-concept will rely on merging cell suspension with stimulatory toxin (Veratridine, etc.) just prior to droplet-formation, followed by emission detection. The goal of this stage is to optimize the optical interrogation techniques and quantitate the confidence of discerning an inhibited ion channel cell population from a control population, within droplets in flow. Measuring fluorogenic probe emission in system is a basic requirement for further development of in-droplet stimulation methods within Stage 2. In addition, will initiate cloning and selection of a channel rhodopsin expressing cell line, unless is able to provide a cell line capable of optogenetic stimulation that is compatible with the capabilities of for detection, to evaluate optical stimulation methods in electrophysiology well-plates and control assays.

Milestone: Satisfy a benchmark of ≥10% ratio amplitude (+/− inhibitor) after toxin stimulation at peak or during the tail-current, whichever is more sensitive. A Z'-score calculation can also be applied to determine statistical confidence in separating inhibited from control populations if ratio amplitude is not relevant for toxin stimulation.

Stage 2: Stimulation of Droplet-Cell-Assay with Spatio-Temporal Control and Design and Construction of a 10K Member "Targeted Library" Against Desired Ion Channel
Summary: Demonstrate the ability to stimulate cells in droplets, in flow, by one or more of three methods (ES, OS, or TS) using appropriately designed IC chips (see FIG. 1). Subsequent to stimulation, demonstrate detection of $DiSBAC_6$+CC2-DMPE FRET emission at an optimal time-point to segregate inhibited cell population from a positive control. In addition, the design of a 10K member "targeted library" around chemotypes present in the control molecules used in Stage 3 will be demonstrated using chemoinformatic tools to maximize the structural and chemical diversity of the 10K member targeted library. The initial synthetic methodologies used to construct the library will be tested and the chemical products of the methodologies will be validated with LC/MS analysis. Lastly, the "targeted library" will be subjected to UV-cleavage to demonstrate the release of library members from BELs and the degree of cleavage will be quantified with LC/MS analysis.

Milestone: Stimulation method and timing must satisfy a qualifying Z'≥0.4 beten+/− inhibitor cell populations. This is a basic requirement for further microfluidic development to include compound delivery, dosing, and sorting of inhibited cells within Stage 3. The "targeted library" will be constructed with yields >30% for each individual library member using the desired synthetic methodologies and the library should demonstrate the ability to be cleaved from beads using UV-cleavage methods Stage 3: Complete Integrated Chip Design for POC Screen Using Controls and a Subsequent Screen of a 10K Member Targeted Library Summary: Integrate the cell-in-droplet stimulation architectures into a complete integrated device, including in-situ release of control inhibitors, pre-stimulation mixing and incubation, and post-stimulation sorting. Upon validation of a full integrated chip and validation of control molecules for inhibiting stimulation, a "targeted library" will be screened against a desired ion channel to elucidate SAR around the controls from the which the "targeted library" is derived. The "targeted library" will be screened across 5 concentrations. Analytical tools will be created to automate NGS analysis, decode "active" structures, rank active members by potency, and provide insights into SAR. A validation workflow will be established, to resynthesize the most potent candidate molecules for analysis and profiling using 's standard assays to verify $EC_{50}$.

Milestone: Positive control inhibitor beads will be sampled, and a dose-response measured across 6 concentrations. Data will be used to determine a relative $EC_{50}$ within system, which must be within 3× of the known $EC_{50}$. Sorting will also be demonstrated, capable of isolating positive control beads from negative controls with <10% false-sort events. The output from a "targeted library" screen will up to 10 visualizations of the raw data output from the screen. Methodology and Project Design:

Definitions

Probe=$DiSBAC_6$ or analog, with CC2-DMPE unless otherwise stated
Toxin=Veratridine, OD-1 or other stimulatory molecule
Model cell line=HEK293 (Human Embryonic Kidney cells) unless otherwise stated.
Inhibitor=provided control compounds for system testing.
ChR=Channel rhodopsin or variant with tuned optical properties.
Fluorescent nuclear stains=DAPI, DRAQ5, PicoGreen, etc.
IC chip=Ion Channel chip to initiate stimulation of sodium ion channels in droplets.
ICES=Ion Channel chip designed for electrical stimulation of cells-in-droplet.
ICTS=Ion Channel chip designed for toxin stimulation of cells-in-droplet.
ICOS=Ion Channel chip designed for optogenetic stimulation of cells-in-droplet Stage 1: Detection of Droplet-Cell-Assay for Ion Channel Inhibition 1A) A model cell-line expressing a relevant ion channel will be used and a simple set of basic controls established to verify all reagents and to understand the dynamic activity of toxin stimulation by probe emission.
 1) well-plate control assay using model cell line, with probe, +/− inhibitor control using toxin stimulation.
 2) Fluorescence microscopy will determine cell-line uniformity, and steady-state behavior for probe emission, +/− inhibitor.
 3) FRET emission profiles of bulk population in plates collected to understand toxin kinetics, steady-state, and $EC_{50}$, +/− inhibitor.

1B) A simple microfluidic droplet generator will be used to introduce model cells with fluor-labels (Nuclear stain, fluor-Anti-ion channel) or probe to test cell detection in droplets in flow.
 1) Fluor-Anti-ion channel or similar label will be ideal to determine cell-expression uniformity, and to tune optical detection in flow using photo-stable fluorophores to determine the optical sensitivity for the system, without the variable of probe leeching or photo-bleaching.
 2) Membrane bound probe emission (CC2-DMPE) detection in droplet will then finalize the sensitivity required to observe probe emission in droplet in a flow channel.
 3) Model cell line biocompatibility and toxicity measurements inside droplets using fluorogenic live or dead stains.

1C) Develop $IC_{TS}$ Chip v1.0) to merge cells+probe (+/− inhibitor), with stimulatory toxin, just prior to droplet formation then capture probe emission from cells at set time points
 1) Flow-velocity in addition to the spatial position of excitation and detection dictates the time-delay post stimulation for assay observation.
 2) Toxin stimulation generates a depolarization pulse followed by a persistent tail current. Detection position can isolate specific points on this curve and can determine the best location for differentiating+/− inhibitor cell populations.
 3) Probe emission profiles for cells +/− inhibitor will be compared, and a statistical confidence (Z'-score) determined at various time points following toxin stimulation.

1D) Channelrhodopsin expression cell line generation to prove out optogenetic stimulation
 1) Ion channel expression in HEK cell line for electrical stim (or sced from)
 2) Ion Channel+ChR (ChrimsonR or other variant, DOI. 10.1038/nmeth.2836) expression in model cell line for optical stimulation.

1E) Cell stimulation control in electrophysiology microplates, +/− inhibitor.
 1) Electrode stimulation in well-plate using ion channel expression cell line, observing emission from fluorogenic probe ($DiSBAC_6$+CC2-DMPE) as a control for cell line quality.
 2) Optical stimulation in electrode well-plate using ion channel+ChR to detect current.
  A) Require >99% spike occurrence from ChrimsonR stimulation at 10 Hz using 660-nm light at 500 $mJ/s/cm^2$.
 3) Optical stimulation in well-plate using ion channel+ ChR+probe to detect probe emission response.

Stage 2: Stimulation of Droplet-Cell-Assay with Spatio-Temporal Control and Design and Construction of a 10K Member "Targeted Library" Against Ion Channel 2A) Covalent, photo-cleavable attachment of control inhibitors to beads (positive control bead.
 1) to collaborate and provide control inhibitors to contain reactive handles for attachment to photo-cleavable linker.
  a) Ideally suited are free primary or secondary amine, carboxylic acid, terminal amide, or phenol.
 2) Full product cleavage and LC-MS to verify photolabile-compound linkage.
 3) Photocleavage of inhibitor in well-plate to verify activity after UV release.

2B) Design and fabrication of IC chips for cell-in-droplet stimulation, monitoring probe emission by PMT or imaging.

This stage is a significant engineering effort with multiple strategies to prove out the most viable candidates for Stage 3.
1) $IC_{ES}$—Electrical stimulation in droplet will be examined using two approaches, with frequency of stimulation dictated by geometry (10 Hz).
   A) Non-contact electrodes to generate electric fields or dielectrophoretic forces.
2) $IC_{TS}$—Toxin stimulation in droplet will be examined using a pico-injection, droplet fusion, or a pre-injected architecture, which allows for stimulatory toxin to be injected into droplet post compound dosing in Stage 3.
3) $IC_{OS}$—Optical stimulation in droplet will be examined using an embedded fiber-optic waveguide illuminating cells with either UV, VIS or NIR wavelengths at geometry defined frequencies (10 Hz).

2C) IC chip demonstrations showing clear differentiation between cell populations+/− inhibitor. See FIG. 8 for strategy overview.
1) $IC_{ES}$ and $IC_{OS}$ chips will be designed for 10 Hz stimulation pulses, and probe-emission monitored at spatially controlled time-delays post stimulation to evaluate the assay Z'-score between +/− inhibitor cell populations at different time-points.
   A) Inhibitor titration (5-point) and detection will create an end-point dose-response profile to compare the approximate potency to's standard assays.
2) $IC_{TS}$ chip design will be tested using the time-interval post stimulatory toxin-injection determined in Stage 1C-2 to evaluate the assay Z'-score between +/− inhibitor cell populations in dose response to compare potency to 's standard assays.
   A) Inhibitor titration (5-point) and detection will create an end-point dose-response profile to compare the approximate potency to's standard assays.

2D) Design of 10K member "targeted library" and validation of synthetic methodologies used to construct the library.
1) The design of the library will utilize chemistries, as desired to permute the chemical structure of control compounds of known activity. The library will be designed so as to maximize the interpolation of structure-activity-relationships (SAR) of individual library members.
2) The synthetic methodologies used to construct the library will be validated with "building blocks" representative of "building block" classes used to construct the library. The yields of reactions with individual building blocks will be quantified with LC/MS to validate the reactivity of individual building blocks.
3) Individual beads from the "targeted library" will be subjected to photo-cleavage to verify that library members are cleaved from beads in the library.

Stage 3: Complete Integrated Chip Design for POC Screen Using Controls and a Subsequent Screen of a 10K Member "Targeted Library 3A) Candidate IC chip designs with qualifying Z'-scores will be incorporated into a complete integrated system.
1) $IC_{xx}$ chip 2.0 designed, fabricated, and tuned for inhibitor-bead delivery, compound dosing, incubation, cell-in-droplet stimulation, assay detection, and droplet sorting.
2) POC of IC chip 2.0 devices using positive control beads, releasing high-concentrations of inhibitor to optimize Z'-score within the integrated system.
3) Demonstration of inhibitor-bead isolation from negative-bead control by droplet sorting with <10% false-sort events (droplets not containing inhibitor-bead and cells.

3B) Compound-release trio-calibration curve to enable predictive compound dosing.
1) Fluorophore concentration vs PMT detection calibration in droplet.
2) Fluorophore release from bead by UV exposure vs PMT detection calibration in droplet.
3) UV exposure vs calibrant dye emission calibration.

3C) Control-bead titration with cell-population analysis to showcase dose-response and approximation of $EC_{50}$ for control inhibitor
1) Bead-released inhibitor titration and assay detection across 4Ln (i.e. 10 µM, 3 µM, 1 µM, 300 nM, <100 nM).
2) The inferred $IC_{50}$ of bead released compound in IC chip needs to be <3× from that shown using standard plate methods with the same model cell line.

3D) "Targeted Library" screen against ion channel using the designed library from Stage 2.
1) The "targeted" library will be screened, using 7 library equivalents, against ion channel with "spiked-in" positive control compounds on beads used in 3C.
2) Data will be analyzed with chemoinformatic tools and will be presented at the conclusion of the screen within 1 month of the screen being performed.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

The invention claimed is:

1. A method for amplifying a primer to maximize cellular nucleic acid barcoding, the method comprising:
   (a) providing an encapsulation encapsulating a scaffold comprising a nucleic acid encoding bound thereto, one or more cells, and an amplification mix;
   (b) lysing the one or more cells to release one or more cellular nucleic acids;
   (c) nicking the nucleic acid encoding at a nicking site, thereby creating a first encoded nucleic acid primer;
   (d) amplifying the first encoded nucleic acid primer via the nicking site and amplification mix; and
   (e) barcoding the one or more cellular nucleic acids with the first encoded nucleic acid primer.

2. The method of claim 1, wherein the nicking site comprises a specific nucleotide sequence in the nucleic acid encoding that is targeted by a nicking enzyme.

3. The method of claim 1, wherein the amplifying of d) comprises i) creating a copy of the nucleic acid encoding that extends from the nicking site; and ii) nicking the copy of the nucleic acid encoding to create a second encoded nucleic acid primer.

4. The method of claim 1, wherein the amplifying of d) comprises simultaneously i) creating a copy of the nucleic acid encoding that extends from the nicking site; and ii) displacing the copy of the nucleic acid encoding to create a second encoded nucleic acid primer.

5. The method of claim 4, wherein the amplification mix comprises an amplification enzyme, such that the amplification enzyme enables the copy of the nucleic acid encoding to be simultaneously created and displaced.

6. The method of claim 5, wherein the amplification enzyme comprises a polymerase.

7. The method of claim 1, wherein the nucleic acid encoding comprises a capture site for interacting with a target cellular nucleic acid to barcode the one or more cellular nucleic acids.

8. The method of claim 7, wherein the target cellular nucleic acid is a target mRNA.

9. The method of claim 1, wherein the scaffold comprises a bead, and the first encoded nucleic acid primer comprises a unique bead barcode and an encoding corresponding to an encoded effector.

10. The method of claim 1, wherein the scaffold comprises an encoded effector bound thereto by a cleavable linker.

11. The method of claim 1, wherein the barcoding of e) comprises barcoding the one or more cellular nucleic acids.

12. The method of claim 1, further comprising performing an effector screen, wherein the one or more cells are being screened against an encoded effector.

13. The method of claim 1, wherein the encapsulation comprises a droplet.

14. The method of claim 8, wherein the target mRNA encodes a protein of interest.

15. The method of claim 8, wherein target mRNA capture is increased by at least 10%, at least 25%, at least 50%, at least 100%, or at least 200%.

16. The method of claim 1, wherein the encapsulation further comprises a cell lysis buffer.

17. The method of claim 10, further comprising cleaving the cleavable linker using electromagnetic radiation.

18. The method of claim 10, further comprising cleaving the cleavable linker using a cleavage reagent or an enzyme.

19. The method of claim 1, wherein nicking the nucleic acid encoding at step (c) is via a nicking enzyme.

* * * * *